(12) United States Patent
Thuring et al.

(10) Patent No.: US 12,404,260 B2
(45) Date of Patent: Sep. 2, 2025

(54) PYRIDINE RINGS CONTAINING DERIVATIVES AS MALT1 INHIBITORS

(71) Applicant: Janssen Pharmaceutica NV, Beerse (BE)

(72) Inventors: Johannes Wilhelmus J. Thuring, Antwerp (BE); Tianbao Lu, Churchville, PA (US); Tongfei Wu, Boortmeerbeek (BE); Gaston Stanislas M. Diels, Turnhout (BE); Didier Jean-Claude Berthelot, La Neuville Chant d'Oisel (FR); Berthold Wroblowski, Vosselaar (BE)

(73) Assignee: Janssen Pharmaceutica NV, Beerse (BE)

( * ) Notice: Subject to any disclaimer, the term of this patent is extended or adjusted under 35 U.S.C. 154(b) by 749 days.

(21) Appl. No.: 17/602,885

(22) PCT Filed: Apr. 10, 2020

(86) PCT No.: PCT/EP2020/060307
§ 371 (c)(1),
(2) Date: Oct. 11, 2021

(87) PCT Pub. No.: WO2020/208222
PCT Pub. Date: Oct. 15, 2020

(65) Prior Publication Data
US 2022/0162187 A1    May 26, 2022

Related U.S. Application Data

(60) Provisional application No. 62/832,608, filed on Apr. 11, 2019.

(30) Foreign Application Priority Data

Jun. 7, 2019  (EP) .................................. 19178959

(51) Int. Cl.
| C07D 401/14 | (2006.01) |
| C07D 401/12 | (2006.01) |
| C07D 405/14 | (2006.01) |

(52) U.S. Cl.
CPC ......... C07D 401/14 (2013.01); C07D 401/12 (2013.01); C07D 405/14 (2013.01)

(58) Field of Classification Search
CPC .. C07D 401/14; C07D 401/12; C07D 405/14; A61P 35/00; A61P 37/02; A61P 19/02
See application file for complete search history.

(56) References Cited

U.S. PATENT DOCUMENTS

| 6,339,099 | B1 | 1/2002 | Lam et al. |
| 6,391,342 | B1 | 5/2002 | Henriksen et al. |
| 7,151,113 | B2 | 12/2006 | Dyckman et al. |
| 7,223,782 | B2 | 5/2007 | Atkinson et al. |
| 7,253,170 | B2 | 8/2007 | Dyckman et al. |
| 7,390,810 | B2 | 6/2008 | Dyckman et al. |
| 7,396,935 | B2 | 7/2008 | Dyckman et al. |
| 7,414,056 | B2 | 8/2008 | Dyckman et al. |
| 7,592,338 | B2 | 9/2009 | Dyckman et al. |
| 7,605,273 | B2 | 10/2009 | Dyckman et al. |
| 8,389,544 | B2 | 3/2013 | Wong et al. |
| 8,716,487 | B2 | 5/2014 | Maywald et al. |
| 9,375,008 | B2 | 6/2016 | Gross et al. |
| 9,730,938 | B2 | 8/2017 | Kuo et al. |
| 9,814,721 | B2 | 11/2017 | Buggy et al. |
| 9,815,842 | B2 | 11/2017 | Soldermann et al. |
| 10,882,841 | B2 | 1/2021 | Xue et al. |
| 10,888,550 | B2 * | 1/2021 | Lu ..................... C07K 16/2887 |
| 10,954,214 | B2 | 3/2021 | Lu et al. |
| 11,040,031 | B2 * | 6/2021 | Lu ..................... C07D 491/056 |
| 2007/0254868 | A1 | 11/2007 | Lauffer et al. |
| 2010/0260837 | A1 | 10/2010 | Chandran et al. |

(Continued)

FOREIGN PATENT DOCUMENTS

| CN | 104507933 B | 10/2017 |
| EA | 201590916 A1 | 2/2016 |

(Continued)

OTHER PUBLICATIONS

Hailfinger, S.; et al. "Targeting B-cell lymphomas with inhibitors of the MALT1 paracaspase" 2014, Current Opinion in Chemical Biology, vol. 23, pp. 47-55. (Year: 2014).*
Staal, J.; et al. "Regulation of NF-κB signaling by caspases and MALT1 paracaspase" 2011, Cell Research, vol. 21, pp. 40-54. (Year: 2011).*
Bornancin, F., et al., "Deficiency of MALT1 Paracaspase Activity Results in Unbalanced Regulatory and Effector T and B Cell Responses Leading to Multiorgan Inflammation", J. Immunology, (2015), vol. 194, No. 8, pp. 3723-3734.
Fontan, L., et al., "MALT1 Small Molecule Inhibitors Specifically Suppress ABC-DLBCL In Vitro and In Vivo", Cancer Cell, (2012), vol. 22, No. 6, pp. 812-824.

(Continued)

*Primary Examiner* — Eric Olson
*Assistant Examiner* — Benjamin M Brandsen

(57) ABSTRACT

Disclosed are compounds, compositions and methods for treating of diseases, syndromes, conditions, and disorders that are affected by the modulation of MALT1. Such compounds are represented by Formula (I) as follows:

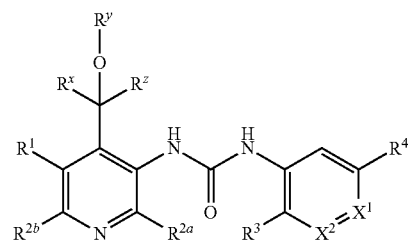

Formula (I)

wherein the variables are defined herein.

9 Claims, No Drawings

(56) References Cited

U.S. PATENT DOCUMENTS

| | | | |
|---|---|---|---|
| 2011/0269765 | A1 | 11/2011 | Dorsch et al. |
| 2013/0109682 | A1 | 5/2013 | Burger et al. |
| 2014/0194443 | A1 | 7/2014 | Nordhoff et al. |
| 2015/0225373 | A1 | 8/2015 | Fyfe et al. |
| 2017/0129899 | A1 | 5/2017 | Shvartsbart et al. |
| 2017/0283430 | A1 | 10/2017 | Arora et al. |
| 2018/0071295 | A1 | 3/2018 | Kuo et al. |
| 2018/0099976 | A1 | 4/2018 | Cheung et al. |
| 2018/0170909 | A1 | 6/2018 | Lu et al. |
| 2018/0177776 | A1 | 6/2018 | Zajac-Kaye et al. |
| 2018/0311153 | A1 | 11/2018 | Buggy et al. |
| 2019/0016721 | A1 | 1/2019 | Chen et al. |
| 2019/0160045 | A1* | 5/2019 | Kukreja ............... A61P 35/02 |
| 2019/0276471 | A1 | 9/2019 | Arora et al. |
| 2020/0009135 | A1 | 1/2020 | Albertella et al. |
| 2020/0385405 | A1* | 12/2020 | Gray .................. A61P 37/04 |
| 2021/0001733 | A1 | 1/2021 | Meins et al. |
| 2021/0052596 | A1 | 2/2021 | Mempel et al. |
| 2022/0056012 | A1 | 2/2022 | Kimpe et al. |

FOREIGN PATENT DOCUMENTS

| | | | | |
|---|---|---|---|---|
| WO | WO 2001/002385 | A1 | 1/2001 | |
| WO | WO 2001/30351 | A1 | 5/2001 | |
| WO | WO 2003/037274 | A2 | 5/2003 | |
| WO | WO 2003/037274 | A3 | 5/2003 | |
| WO | WO 2004/098515 | A2 | 11/2004 | |
| WO | WO 2004/098518 | A2 | 11/2004 | |
| WO | WO 2004/098518 | A3 | 11/2004 | |
| WO | WO 2006/085685 | A1 | 8/2006 | |
| WO | WO 2008/008286 | A2 | 1/2008 | |
| WO | WO 2008/008286 | A3 | 1/2008 | |
| WO | WO 2008/110196 | A1 | 9/2008 | |
| WO | WO 2009/065897 | A2 | 5/2009 | |
| WO | WO-2009146555 | A1 * | 12/2009 | ........... C07D 213/81 |
| WO | WO 2010/039039 | A1 | 4/2010 | |
| WO | WO 2010/064875 | A2 | 6/2010 | |
| WO | WO 2011/036885 | A1 | 3/2011 | |
| WO | WO 2012/063896 | A1 | 5/2012 | |
| WO | WO 2013/178591 | A1 | 12/2013 | |
| WO | WO 2014/074815 | A1 | 5/2014 | |
| WO | WO 2014/086478 | A1 | 6/2014 | |
| WO | WO 2015/181747 | A1 | 12/2015 | |
| WO | WO 2015/192081 | A1 | 12/2015 | |
| WO | WO 2016/005994 | A2 | 1/2016 | |
| WO | WO 2016/090382 | A1 | 6/2016 | |
| WO | WO 2017/081641 | A1 | 5/2017 | |
| WO | WO 2017/100662 | A1 | 6/2017 | |
| WO | WO 2018/020474 | A1 | 2/2018 | |
| WO | WO 2018/103060 | A1 | 6/2018 | |
| WO | WO 2018/114501 | A1 | 6/2018 | |
| WO | WO 2018/114503 | A1 | 6/2018 | |
| WO | WO 2018/115880 | A1 | 6/2018 | |
| WO | WO 2018/116201 | A1 | 6/2018 | |
| WO | WO 2018/116259 | A1 | 6/2018 | |
| WO | WO 2018/119036 | A1 | 6/2018 | |
| WO | WO 2018/141749 | A1 | 8/2018 | |
| WO | WO 2018/165385 | A1 | 9/2018 | |
| WO | WO 2018/226150 | A1 | 12/2018 | |
| WO | WO 2019/243964 | A1 | 12/2019 | |
| WO | WO 2019/243965 | A1 | 12/2019 | |
| WO | WO 2020/169736 | A1 | 8/2020 | |
| WO | WO 2020/169738 | A1 | 8/2020 | |
| WO | WO 2020/208222 | A1 | 10/2020 | |
| WO | WO 2022/037661 | A1 | 2/2021 | |
| WO | WO 2021/099609 | A1 | 5/2021 | |
| WO | WO 2021/099612 | A1 | 5/2021 | |
| WO | WO 2021/138298 | A2 | 7/2021 | |
| WO | WO 2022/038252 | A1 | 2/2022 | |
| WO | WO 2022/184716 | A1 | 9/2022 | |
| WO | WO 2022/185097 | A1 | 9/2022 | |

OTHER PUBLICATIONS

Gewies, A., et al., "Uncoupling Malt1 Threshold Function from Paracaspase Activity Results in Destructive Autoimmune Inflammation", Cell Reports, (2014), vol. 9, pp. 1292-1305.

Jabara, H.H., et al., "A homozygous mucosa-associated lymphoid tissue 1 (*MALT1*) mutation in a family with combined immunodeficiency", J. Allergy Clin. Immunol., (2013), vol. 132, pp. 151-158.

Jaworski, M., et al., "Malt1 protease inactivation efficiently dampens immune responses but causes spontaneous autoimmunity", The EMBO Journal, (2014), vol. 33, No. 23, pp. 2765-2781.

Jaworski, M., et al., "The paracaspase MALT1: biological function and potential for therapeutic inhibition", Cell. Mol. Life Sci., (2016), vol. 73, pp. 459-473.

Lim, K., et al., "Pathogentic importance and therapeutica implications of NF-κß in lymphoid malignancies", Immunological Reviews, (2012), vol. 246, pp. 359-378.

Mc Guire, C., et al., "Pharmacological inhibition of MALT1 protease activity protects mice in a mouse model of multiple sclerosis", Journal of Neuroinflammation, (2014), vol. 11, No. 124, pp. 1-12.

McKinnon et al., "Combined immunodeficiency associated with homozygous MALT1 mutations", J. Allergy Clin. Immunol. (2014), vol. 133, No. 5, pp. 1458-1462.e7.

Nagel, D., et al., "Pharmacologic Inhibition of MALT1 Protease by Phenothiazines as a Therapeutic Approach for the Treatment of Aggressive ABC-DLBCL", Cancer Cell, (2012), vol. 22, pp. 825-837.

Punwani, D., et al., "Combined Immunodeficiency Due to MALT1 Mutations, Treated by Hematopoietic Cell Transplantation", J Clin Immunol, (2015), vol. 35, pp. 135-146.

Rosebeck, S., et al., "Cleavage of NIK by the API2-MALT1 Fusion Oncoprotein Leads to Noncanonical NF-KκB Activation", Science, (2011), vol. 331, pp. 468-472.

Rosebeck, S., et al., "API2-MALT1 oncoprotein promotes lymphomagenesis via unique program of substrate ubiquitination and proteolysis", World J Biol Chem, (2016), vol. 7, No. 1, pp. 128-137.

Yu, J.W., et al., "MALT1 Protease Activity is Required for Innate and Adaptive Immune Responses", PLOS One, (2015), pp. 1-20.

Bundgaard, H., "Design of Prodrugs", (1985), Table of Contents.

McOmie, J., "Protective Groups in Organic Chemistry", (1973), Title Page and Table of Contents.

T.W. Greene & P.G.M. Wutz (eds.), Protective Groups in Organic Synthesis, $2^{nd}$ edition, John Wiley & Sons, Inc., (1991), Table of Contents.

T.W. Greene & P.G.M. Wutz (eds.), Protective Groups in Organic Synthesis, $3^{rd}$ edition, John Wiley & Sons, Inc., (1999), Table of Contents.

Hughes, J.P., et al., "Principles of early drug discovery", British Journal of Pharmacology, (2011), vol. 162, pp. 1239-1249.

International Search Report from PCT/IB2019/054964 mailed Oct. 18, 2019.

Bernstein, J., "Polymorphism in Molecular Crystals", (2002), Clarendon Press Oxford, pp. 115-118 & 272.

Braga, D., et al., "Making crystals from crystals: a green route to crystal engineering and polymorphism", (2005), J. Royal Soc. Chem. Commun., pp. 3635-3645.

Davidovich, M., et al., "Detection of Polymorphism by Powder X-Ray Diffraction: Interference by Preferred Orientation", (2004), Am. Pharm. Rev, vol. 7, No. 1, pp. 10, 12, 14, 16, 100.

Guillory, J.K., "Polymorphism in Pharmaceutical Solids", (in Brittain ed.), (1999), NY: Mercel Dekker, Inc., 1-2, 125-181, 183-226.

Ivanisevic, I., et al., "Uses of X-Ray Powder Diffraction in the Pharmaceutical Industry", (2010), Pharm. Sci. Encycl., pp. 1-42.

Jain, N.K., et al., "Polymorphism in Pharmacy", (1986), Indian Drugs, vol. 23, No. 6, pp. 315-329.

Jordan, V.C., "Tamoxifen: A Most Unlikely Pioneering Medicine", (2003), Nature Reviews, vol. 2, pp. 205-213.

Kirk-Othmer, "Crystallization", (2002), Encyclopedia of Chemical, vol. 8, pp. 95-147.

Seddon, K.R., "Pseudopolymorph: A Polemic", (2004), Crystal Growth & Design, vol. 4, No. 6, p. 108 (two pages from internet).

Vippagunta, S.R., et al., "Crystalline solids", (2001), Advanced Drug Delivery Review, vol. 48, pp. 3-26.

(56) References Cited

OTHER PUBLICATIONS

Yu, L., et al., "Physical characterization of polymorphic drugs: an integrated characterization strategy", (1998), PSTT, vol. 1, No. 3, pp. 118-127.
Boldron, C., et al., "N-[6-(4-Butanoyl-5-methyl-1H-pyrazol-1-yl)pyridazine-3-yl]-5-chloro-1-[2-(4-methylpiperazin-1-yl)-2-oxoethyl]-1H-indole-3-carboxamide(SAR216471), a Novel Intravenous and Oral, Reversible, and Directly Acting P2Y12 Antagonist", (2014), J.Med.Chem, vol. 57, pp. 7293-7316.
Mauger, C., et al., "The Synthesis of Important Pharmaceutical Building Blocks by Palladium-Catalyzed Coupling Reaction: Access to Various Arylhydrazines", (2005), Adv. Synth. Catal., vol. 347, pp. 773-782.
Nagel, D., et al., "Pharmacologic Inhibition of MALT1 Protease by Phenothiazines as a Therapeutic Approach for the Treatment of Aggressive ABC-DLBCL", (2012), Cancer Cell, vol. 22, pp. 825-837.
CHEMCATS Registry No. 1907875-04-0, 1H-Pyrazole-4-carboxamide, N-(2-chloro-3-pyridinyl)-5-methyl-1-(2-quinolinyl)—May 11, 2016—Ref. 1.
CHEMCATS Registry No. 1907028-26-5, 1H-Pyrazole-4-carboxamide, N-(3-chloro-4-methoxphenyl)-5-methyl-1-(2-quinolinyl)—May 10, 2016—Ref. 2.
CHEMCATS Registry No. 1898933-19-1, 1H-Pyrazole-4-carboxamide, 5-methyl-N-3-pyridinyl-1-(2-quinolinyl)—Apr. 27, 2016—Ref. 3.
Nagel, D., et al., "Combinatorial BTK and MALT1 inhibition augments killing of CD79 mutant diffuse large B cell lymphoma", (2015), Oncotarget, vol. 6, No. 39, pp. 42232-42242.
Bardet, M., et al., "The T-cell fingerprint of MALT1 paracaspase revealed by selective inhibition", (2018), Immunology & Cell Biology, vol. 96, pp. 81-99.
Burgess, D., "Assault on MALT1", (2013), Nature Reviews Cancer, vol. 13, No. 2, pp. 80-81.
Demeyer, A., et al., "Targeting MALT1 Proteolytic Activity in Immunity, Inflammation and Disease: Good or Bad?", (2016), Trends in Molecular Medicine, vol. 22, No. 2, pp. 135-150.
Jahangiri, A., et al., "Biomarkers predicting tumor response and evasion to anti-angiogenic therapy", (2011), Biochimica et Biophysica Acta, vol. 1825, No. 1, pp. 86-100.
Lorena, F., et al., "RNA Interference Screen Implicates TNFAIP2 and FOX01 in MALT1 Inhibition Resistance", (2016), BLOOD, 128 (22):837 retrieved from internet: URL:https://doi.org/10.1182/blood.V128.22.837.837.
Lorena, F., et al., "Mapping MALT1 Signaling Connectivity Unveils Novel B-Cell Feedback Mechanisms Directing Assembly of Potent Anti-Lymphoma Regimens", (2019), BLOOD, vol. 134, No. Supplement 1, pp. 173 retrieved from internet: URL:https://ashpublications.org/bloodarticle/134/Supplement_1/173/426129/Mapping-MALT1-Signaling-Connectivity-Unveils-Novel.
Makhov, P., et al., "Resistance to Systemic Therapies in Clear Cell Renal Cell Carcinoma: Mechanisms and Management Strategies", (2018), Molecular Cancer Therapeutics, vol. 17, No. 7, pp. 1355-1364.
Pahl, H.L., "Activators and target genes of Rel/NF-κB transcription factors", (1999), Oncogene, vol. 18, pp. 6853-6866.
Pan, D., et al., "MALT1 is required for EGFR-induced NF-κb activation and contributes to EGFR-driven lung cancer progression", (2016), Oncogene, vol. 35, pp. 919-928.
Trask, O.J., "Nuclear Factor Kappa B (NF-κB) Translocation Assay Development and Validation for High Content Screening" (2012), retrieved from internet: URL:https://www.ncbi.nlm.nih.gov/books/NBK100914/pdf/Bookshelf_NBK100914.pdf pp. 1-39.
Yang, Y., et al., "A database and functional annotation of NF-κB target genes", (2016), Int J Clin Exp Med, vol. 9, No. 5, pp. 7986-7995.
Philippar, U., et al., "Abstract 5690: Discovery of JNJ-67856633: A novel, first-in-class MALT1 protease inhibitor for the treatment of B cell lymphomas", (2020), Cancer Research, Proceedings: AACR Annual Meeting 2020; Apr. 27-28, 2020 and Jun. 22-24, 2020, Philadelphia, PA, vol. 80(16 Suppl):Abstract nr 5690, pp. 1-5.
International Search Report from PCT/EP2020/082968 mailed Jan. 21, 2021.
International Search Report from PCT/EP2020/082974 mailed Feb. 24, 2021.
Abdalla, M.J., et al., "Bruton's tyrosine kinase (Btk): function, regulation, and transformation with special emphasis on the PH domain", (2009), Immunological Reviews, vol. 228, No. 1, pp. 58-73.
Ahn, I.E., et al., "Clonal evolution leading to ibrutinib resistance in chronic lymphocytic leukemia", (2017), Blood, vol. 129, No. 11, pp. 1469-1479.
Berge, S.M., et al., "Pharmaceutical Salts", (1977), Journal of Pharmaceutical Sciences, vol. 66, No. 1, pp. 1-19.
Cao, S., et al., "NF-$_{78}$ B1 (p50) Homodimers Differentially Regulate Pro- and Anti-inflammatory Cytokines in Macrophages", (2006), Journal of Biological Chemistry, vol. 281, No. 36, pp. 26041-26050.
Chiappella, A., et al., "Ongoing Trials", (2017), Hematological Oncology, 35(S2), p. 419.
Coiffier, B., et al., "Diffuse large B-cell lymphoma: R-CHOP failure-what to do?", (2016), American Society of Hematology, vol. 1, pp. 366-378.
Crump, M., et al., "Outcomes in refractory diffuse large B-cell lymphoma: results from the international SCHOLAR-1 study", (2017), Blood, vol. 130, No. 16, pp. 1800-1808.
Gisselbrecht, C., et al., "Salvage Regimens With Autologous Transplantation for Relapsed Large B-Cell Lymphoma in the Rituximab Era", (2010), J Clin Oncol, vol. 28, No. 27, pp. 4184-4190.
Goy, A., et al., "Succeeding in Breaking the R-CHOP Ceiling in DLBCL: Learning From Negative Trials", (2017), Journal of Clinical Oncology, vol. 35, No. 31, pp. 3519-3522.
Hailfinger, S., et al., "Essential role of MALT1 protease activity in activated B cell-like diffuse large B-cell lymphoma", (2009), PNAS, vol. 106, No. 47, pp. 19946-19951.
Hermansky, S.J., et al., "Effects of Polyethylene Glycol 400 (PEG 400) Following 13 Weeks of Gavage Treatment in Fischer-344 Rats", (1995), Fd Chem. Toxic, vol. 33, No. 2, pp. 139-149.
Johnson, J.I., et al., "Relationships between drug activity in NCI preclinical in vitro and in vitro models and early clinical trials", (2001), British Journal of Cancer, vol. 84, No. 10, pp. 1424-1431.
Jang, S.W., et al., "Preparation of Solid Dispersion of Everolimus in Gelucire 50/13 using Melt Granulation Technique for Enhanced Drug Release", (2014), Bull. Korean Chem. Soc., vol. 35, No. 7, pp. 1939-1943.
Libermann, T.A., et al., "Activation of Interleukin-6 Gene Expression through the NF-κB Transcription Factor", (1990), Molecular and Cellular Biology, vol. 10, No. 5, pp. 2327-2334.
Libermann, T.A., et al., "Involvement of a Second Lymphoid-Specific Enhancer Element in the Regulation of Immunoglobulin Heavy-Chain Gene Expression", (1990), Molecular and Cellular Biology, vol. 10, No. 6, pp. 3155-3162.
Panigrahi, K.C., et al., "Gelucire: A versatile polymer for modified release drug delivery system", (2018), Future Journal of of Pharmaceutical Sciences, vol. 4, pp. 102-108.
Patel, N., et al., "Development of solid Sedds, III: application of Acconon C-50 and Gelucire 50/13 as both solidifying and emulsifying agents for medium chain triglycerides", (2012), J. Excipients and Food Chem, vol. 3, No. 2, pp. 83-92.
Pouton, C.W., "Formulation of poorly water-soluble drugs for oral administration: Physicochemical and physiological issues and the lipid formulation classification system", (2006), European Journal of Pharmaceutical Sciences, vol. 29, pp. 278-287.
Hendriks, R.W., et al., "Targeting Bruton's tyrosine kinase in B cell malignancies", (2014), Nature Reviews Cancer, vol. 14, pp. 219-232.
Shah, B., et al., "Resistance to Ibrutinib in B Cell Malignancies: One Size Does Not Fit All", (2018), Trends in Cancer, vol. 4, No. 3, pp. 197-206.
Sehn, L.H., et al., "Diffuse large B-cell lymphoma: optimizing outcome in the context of clinical and biologic heterogeneity", (2015), Blood, vol. 125, No. 1, pp. 22-32.

(56) References Cited

OTHER PUBLICATIONS

Sofi, S.H., "Gelucire: A Versatile Formulation Excipient", (2017), International Journal of Pharmacy & Pharmaceutical Research, vol. 10, No. 3, pp. 56-73.
Younes, A., et al., "Combination of ibrutinib with rituximab, cyclophosphamide, doxorubicin, vincristine, and prednisone (R-CHOP) for treatment-naïve patients with CD20-postive B-cell non-Hodgkin lymphoma: a non-randomised, phase 1b study", (2014), Lancet Oncology, vol. 15, pp. 1019-1026.
Davies, J.T., "A Quantitative Kinetic Theory of Emulsion Type. I. Physical Chemistry of the Emulsifying Agent", (1957), Gas/Liquid and Liquid/Liquid Interfaces. Proceedings of $2^{nd}$ International Congress Surface Activity, pp. 426-438.
Griffin, W.C., "Calculation of HLB Values of Non-Ionic Surfactants", (1954), Journal of the Society of Cosmetic Chemists, vol. 5, No. 1, pp. 248-256.
2.2.17 of the European Pharmacopoeia 9.6, (2019), pp. 5819-5821.
2.4.22 of the European Pharmacopoeia 10.0, (2008), pp. 118-120.
European Pharmacopeia 10.0 "Macrogol stearate", (2019), p. 3142.
European Pharmacopeia 5.0 "Stearoly Macrogolglycerides", (2017), pp. 2491-2492.
European Pharmacopoeia 10.0, "Macrogols", (2017), pp. 3145-3147.
Lauroyl macrogolglycerides monographs of the European Pharmacopoeia 10.0, (2017), pp. 3210-3211.
European Pharmacopeia 10.0 "Lauroly Macrogolglycerides", (2017), pp. 3068-3069.
US Pharmacopoeia Official Monographs, (2020), page information USP42-NF37-5882 "Polyethylene Glycol, Assay, Average Molecular Weight".
USP-NF in USP42-NF37-6010 "Stearoyl polyoxylglycerides" (2019), pp. 6010-6011.
USP-NF USP42-NF37-5904 polyoxyl stearate type I, (2019), pp. 5904-5905.
USP42-NF37-5799 polyoxylglycerides lauroyl, (2019), pp. 5799-5800.
The Pharmacopeia of the United States of America, in the chapter "General notices and Requirements" (2022), USP42-NF37 2S—9081; Section 5.30 Description and Solubility, pp. 1-15.
Mangin, D., et al., "Polymorphism in Processes of Crystallization in Solution: A Practical Review", (2009), Organic Process Research & Development, vol. 13, No. 6, pp. 1241-1253.
Hirayama, R., "Handbook of Organic Compound Crystal Preparation", (2008), Maruzen Co., Ltd., 2008, pp. 17-23, 37-40, 45-51, 57-65.
Serizawa, K., "Physico-Chemical Stuides on the Molecular Details of Drug Crystals", (2002), Pharm Tech Japan, vol. 18, No. 10, pp. 81-96.
The Chemical Society of Japan (ed.), (1996), Lectures on Experimental Chemistry, 4th ed. 1 Basic Operations I, Maruzen Co, pp. 184-189.
Japanese Pharmacopoeia, Sixteenth Edition, (2011), pp. 64-68.
Yang, L.V., et al., Polymorphic drugs, 1st edition, (2009), People's Health publishing house, pp. 6, 24-26, 138.
Fang, L., et al., Textbook for the Fourth Round of Planning for National Higher Medical College Pharmacy Subjects: Pharmaceutics 3rd Edition, (2016), p. 57.
Kummerer, K., "Pharmaceuticals in the Environment", (2010), Annu. Rev. Environ. Resour., vol. 35, pp. 57-75.

* cited by examiner

PYRIDINE RINGS CONTAINING DERIVATIVES AS MALT1 INHIBITORS

CROSS REFERENCE TO RELATED APPLICATIONS

This application is a national stage of PCT Application No. PCT/EP2020/060307, filed Apr. 10, 2020, which claims priority to U.S. Provisional Application No. 62/832,608, filed Apr. 11, 2019 and EP Application No. 19178959.3 filed Jun. 7, 2019, all of which are hereby incorporated by reference in their entirety.

FIELD OF THE INVENTION

The present invention relates to novel compounds that are MALT1 (mucosa-associated lymphoid tissue lymphoma translocation protein 1) inhibitors. These compounds may be useful for the treatment of a disease, syndrome, condition, or disorder, particularly a MALT1-related disease, syndrome, condition, or disorder, including but not limited to, cancer and immunological diseases. The invention also relates to pharmaceutical compositions comprising one or more of such compounds, to processes to prepare such compounds and compositions, and to the use of such compounds or pharmaceutical compositions for the treatment of cancer and autoimmunological diseases, syndromes, disorders, or conditions associated with MALT1 inhibitors.

BACKGROUND OF THE INVENTION

MALT1 (mucosa-associated lymphoid tissue lymphoma translocation 1) is a key mediator of the classical $NF_{\kappa}B$ signaling pathway. MALT1 is the only human paracaspase and transduces signals from the B cell receptor (BCR) and T cell receptor (TCR). MALT1 is the active subunit of the CBM complex which is formed upon receptor activation. The CBM complex consists of multiple subunits of three proteins: CARD11 (caspase recruitment domain family member 11), BCL10 (B-cell CLL/Lymphoma 10) and MALT1. MALT1 affects $NF_{\kappa}B$ signaling by two mechanisms: firstly, MALT1 functions as a scaffolding protein and recruits $NF_{\kappa}B$ signaling proteins such as TRAF6, TAB-TAK1 or NEMO-IKKα/β; and secondly, MALT1, as a cysteine protease, cleaves and thereby deactivates negative regulators of $NF_{\kappa}B$ signaling, such as RelB, A20 or CYLD. The ultimate endpoint of MALT1 activity is the nuclear translocation of the $NF_{\kappa}B$ transcription factor complex and activation of $NF_{\kappa}B$ signaling (Jaworski et al., Cell Mol Life Science 2016. 73, 459-473).

Constitutive activation of $NF_{\kappa}B$ signaling is the hallmark of ABC-DLBCL (Diffuse Large B cell Lymphoma of the Activated B Cell-like subtype), the more aggressive form of DLBCL. DLBCL is the most common form of non-Hodgkin's lymphoma (NHL), accounting for approximately 25% of lymphoma cases while ABC-DLBCL comprises approximately 40% of DLBCL. $NF_{\kappa}B$ pathway activation is driven by mutations of signaling components, such as CD79AB, CARD11, MYD88 or A20, in ABC-DLBCL patients (Staudt, Cold Spring Harb Perspect Biol 2010, 2; Lim et al, Immunol Rev 2012, 246, 359-378).

The use of BTK inhibitors, for example Ibrutinib, provides clinical proof-of-concept that inhibiting $NF_{\kappa}B$ signaling in ABC-DLBCL is efficacious. MALT1 is downstream of BTK in the $NF_{\kappa}B$ signaling pathway and a MALT1 inhibitor could target ABC-DLBCL patients not responding to Ibrutinib, mainly patients with CARD11 mutations, as well as treat patients that acquired resistance to Ibrutinib.

Small molecule tool compound inhibitors of MALT1 protease have demonstrated efficacy in preclinical models of ABC-DLBCL (Fontan et al., Cancer Cell 2012, 22, 812-824; Nagel et al., Cancer Cell 2012, 22, 825-837). Interestingly, covalent catalytic site and allosteric inhibitors of MALT1 protease function have been described, suggesting that inhibitors of this protease may be useful as pharmaceutical agents (Demeyer et al., Trends Mol Med 2016, 22, 135-150).

The chromosomal translocation creating the API2-MALT1 fusion oncoprotein is the most common mutation identified in MALT (mucosa-associated lymphoid tissue) lymphoma. API2-MALT1 is a potent activator of the $NF_{\kappa}B$ pathway (Rosebeck et al., World J Biol Chem 2016, 7, 128-137). API2-MALT1 mimics ligand-bound TNF receptor, promotes TRAF2-dependent ubiquitination of RIP1 which acts as a scaffold for activating canonical $NF_{\kappa}B$ signaling. Furthermore, API2-MALT1 has been shown to cleave and generate a stable, constitutively active fragment of $NF_{\kappa}B$-inducing kinase (NIK) thereby activating the non-canonical $NF_{\kappa}B$ pathway (Rosebeck et al., Science, 2011, 331, 468-472).

In addition to lymphomas, MALT1 has been shown to play a critical role in innate and adaptive immunity (Jaworski M, et al., Cell Mol Life Sci. 2016). MALT1 protease inhibitor can attenuate disease onset and progression of mouse experimental allergic encephalomyelitis, a mouse model of multiple sclerosis (Mc Guire et al., J. Neuroinflammation 2014, 11, 124). Mice expressing catalytically inactive MALT1 mutant showed loss of marginal zone B cells and B1 B cells and general immune deficiency characterized as decreased T and B cell activation and proliferation. However, those mice also developed spontaneous multi-organ autoimmune inflammation at the age of 9 to 10 weeks. It is still poorly understood why MALT1 protease dead knock-in mice show a break of tolerance while conventional MALT1 KO mice do not. One hypothesis suggests the unbalanced immune homeostasis in MALT1 protease dead knock-in mice may be caused by incomplete deficiency in T and B cell but severe deficiency of immunoregulatory cells (Jaworski et al., EMBO J. 2014; Gewies et al., Cell Reports 2014; Bornancin et al., J. Immunology 2015; Yu et al., PLOS One 2015). Similarly, MALT deficiency in humans has been associated with combined immunodeficiency disorder (McKinnon et al., J. Allergy Clin. Immunol. 2014, 133, 1458-1462; Jabara et al., J. Allergy Clin. Immunol. 2013, 132, 151-158; Punwani et al., J. Clin. Immunol. 2015, 35, 135-146). Given the difference between genetic mutation and pharmacological inhibition, a phenotype of MALT1 protease dead knock-in mice might not resemble that of patients treated with MALT1 protease inhibitors. A reduction of immunosuppressive T cells by MALT1 protease inhibition may be beneficial to cancer patients by potentially increasing antitumor immunity.

Thus, MALT1 inhibitors of the present invention may provide a therapeutic benefit to patients suffering from cancer and/or immunological diseases.

WO2018020474 describes substituted thiazolo-pyridine compounds as MALT1 inhibitors.

WO2015181747 describes pyrazolo pyrimidine derivatives and their use as MALT1 inhibitors.

WO2017081641 describes pyrazolo pyrimidine derivatives.

WO2018226150 describes pyrazolopyrimidine as MALT1 inhibitors.

WO2018119036 describes pyrazole derivatives as MALT1 inhibitors.
WO2019243964 describes pyrazole derivatives as MALT1 inhibitors.
WO2019243965 describes pyrazole derivatives as MALT1 inhibitors.

SUMMARY OF THE INVENTION

The present invention is directed to compounds of Formula (I)

Formula (I)

wherein
$R^x$ represents hydrogen, $C_{1-4}$alkyl, or $C_{3-6}$cycloalkyl;
$R^y$ represents hydrogen, $C_{1-4}$alkyl, or $C_{3-6}$cycloalkyl; and
$R^z$ represents hydrogen;
or
$R^x$ and $R^y$ are taken together to form a bivalent radical —$R^x$—$R^y$— wherein —$R^x$—$R^y$— represents —$(CH_2)_n$— or —$CH_2$—O—$(CH_2)_2$—; wherein n represents 2, 3, 4 or 5; and
$R^z$ represents hydrogen;
or
$R^y$ represents hydrogen, $C_{1-4}$alkyl, or $C_{3-6}$cycloalkyl;
$R^x$ and $R^z$ are taken together to form together with the carbon atom to which they are attached a $C_{3-6}$cycloalkyl;
$R^1$ is selected from the group consisting of hydrogen, —$OR^5$, $C_{1-4}$alkyl, $C_{2-4}$alkenyl, halo, —CN, $C_{3-6}$cycloalkyl, Het$^a$, —C(=O)—OH, —C(=O)—O—$C_{1-4}$alkyl, —$NR^{6a}R^{7a}$ and —C(=O)—$NR^{6b}R^{7b}$;
$R^{2a}$ and $R^{2b}$ are each independently selected from the group consisting of hydrogen, —O—$C_{1-4}$alkyl, halo, —$NR^{6c}R^{7c}$, $C_{3-6}$cycloalkyl, $C_{1-4}$alkyl, and $C_{1-4}$alkyl substituted with 1, 2 or 3 halo atoms;
$X^1$ represents N or $CR^a$;
$X^2$ represents N or $CR^b$;
such that only one of $X^1$ and $X^2$ are N in any instance;
$R^3$ represents hydrogen, $C_{1-4}$alkyl or —O—$C_{1-4}$alkyl;
$R^4$ represents halo, cyano or trifluoromethyl;
$R^5$ is selected from the group consisting of hydrogen, $C_{1-4}$alkyl, $C_{3-6}$cycloalkyl, Het$^b$, and $C_{1-4}$alkyl substituted with one or two substituents each independently selected from the group consisting of —OH, halo, —C(=O)—$NR^8R^9$, —C(=O)—OH, —C(=O)—O—$C_{1-4}$alkyl, $C_{3-6}$cycloalkyl and phenyl;
$R^{6a}$, $R^{6b}$, $R^{6c}$, $R^{7a}$, $R^{7b}$, $R^{7c}$, $R^8$ and $R^9$ each independently are selected from the group consisting of hydrogen and Cr-alkyl;
Het$^a$ represents a monocyclic 4- to 7-membered non-aromatic heterocyclyl containing one or two heteroatoms selected from nitrogen, oxygen and sulfur;
Het$^b$ represents a monocyclic 4- to 7-membered non-aromatic heterocyclyl containing one or two heteroatoms selected from nitrogen, oxygen and sulfur;
$R^a$ represents $C_{1-4}$alkyl or —O—$C_{1-4}$alkyl, each optionally substituted with one, two or three halo substituents; or
$R^a$ represents 2H-1,2,3-triazol-2-yl or $C_{3-6}$cycloalkyl; each optionally substituted on one or two carbon atoms with a substituent each independently selected from the group consisting of $C_{1-4}$alkyl, and $C_{1-4}$alkyl substituted with one —OH;
$R^b$ represents hydrogen;
or an enantiomer, diastereomer, solvate or pharmaceutically acceptable salt form thereof.

A skilled person will understand that all references below to Formula (I), in the context of this invention, might also refer to an enantiomer, diastereomer, solvate or pharmaceutically acceptable salt form thereof, even if not explicitly referred to, and that they are also included in the scope of the present invention.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I), or a pharmaceutically acceptable salt form thereof.

Also provided are processes for making a pharmaceutical composition comprising, consisting of, and/or consisting essentially of admixing a compound of Formula (I), and a pharmaceutically acceptable carrier, a pharmaceutically acceptable excipient, and/or a pharmaceutically acceptable diluent.

The present invention further provides methods for treating or ameliorating a disease, syndrome, condition, or disorder in a subject, including a mammal and/or human in which the disease, syndrome, or condition is affected by the inhibition of MALT1, including but not limited to, cancer and/or immunological diseases, using a compound of Formula (I).

The present invention also is directed to the use of any of the compounds described herein in the preparation of a medicament wherein the medicament is prepared for treating a disease, syndrome, condition, or disorder that is affected by the inhibition of MALT1, such as cancer and/or immunological diseases.

The present invention is also directed to the preparation of Compounds of Formula (I) that act as an inhibitor of MALT1.

Exemplifying the invention are methods of treating a disease, syndrome, condition, or disorder mediated by MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulva) cancer, esophageal cancer, salivary gland cancer, nasopharangeal cancer, buccal cancer, cancer of the mouth, and GIST (gastrointestinal stromal tumor), comprising, consisting of, and/or consisting essentially of, administering to a subject in need thereof a therapeutically effective amount of any of the compounds or pharmaceutical compositions described in the present invention.

In another embodiment, the present invention is directed to a compound of Formula (I) for use in the treatment of a disease, syndrome, condition, or disorder affected by the inhibition of MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the present invention is directed to a composition comprising a compound of Formula (I) for the treatment of a disease, syndrome, condition, or disorder affected by inhibition of MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulva) cancer, esophageal cancer, salivary gland cancer, nasopharangeal cancer, buccal cancer, cancer of the mouth, and GIST (gastrointestinal stromal tumor).

In another embodiment, the present invention is directed to a composition comprising a compound of Formula (I) for the treatment of a disease, syndrome, condition, or disorder affected by inhibition of MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the present invention is directed to a composition comprising a compound of Formula (I) for the treatment of a disease, syndrome, condition, or disorder affected by inhibition of MALT1, selected from the group consisting of diffuse large B-cell lymphoma (DLBCL), mantle cell lymphoma (MCL), follicular lymphoma (FL), and mucosa-associated lymphoid tissue (MALT) lymphoma.

An embodiment of the present invention is directed to a composition comprising a compound of Formula (I) for the treatment of immunological diseases that are affected by the inhibition of MALT1, including but not limited to, autoimmune and inflammatory disorders, e.g. arthritis, inflammatory bowel disease, gastritis, ankylosing spondylitis, ulcerative colitis, pancreatits, Crohn's disease, celiac disease, multiple sclerosis, systemic lupus erythematosus, lupus nephritis, rheumatic fever, gout, organ or transplact rejection, chronic allograft rejection, acute or chronic graft-versus-host disease, dermatitis including atopic, dermatomyositis, psoriasis, Behcet's diseases, uveitis, myasthenia gravis, Grave's disease, Hashimoto thyroiditis, Sjoergen's syndrome, blistering disorders, antibody-mediated vasculitis syndromes, immune-complex vasculitides, allergic disorders, asthma, bronchitis, chronic obstructive pulmonary disease (COPD), cystic fibrosis, pneumonia, pulmonary diseases including oedema, embolism, fibrosis, sarcoidosis, hypertension and emphysema, silicosis, respiratory failure, acute respiratory distress syndrome, BENTA disease, berylliosis, and polymyositis.

In another embodiment, the present invention is directed to a composition comprising a compound of Formula (I) for the treatment of a disease, syndrome, condition, or disorder affected by inhibition of MALT1, selected from the group consisting of rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

Another embodiment of the present invention is directed to a pharmaceutical composition comprising a compound of Formula (I).

DETAILED DESCRIPTION OF THE INVENTION

With reference to substituents, the term "independently" refers to the situation where several substituents are selected independently from each other and may be the same or different from each other.

The prefix '$C_{x-y}$' (where x and y are integers) as used herein refers to the number of carbon atoms in a given group. Thus, a $C_{1-4}$alkyl group contains from 1 to 4 carbon atoms, and so on.

The term '$C_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, 1-butyl and the like.

The term "$C_{2-4}$alkenyl" as used herein as a group or part of a group represents a straight or branched chain hydrocarbon group containing from 2 to 4 carbon atoms and containing a carbon carbon double bond such as, but not limited to, ethenyl, propenyl, butenyl and the like.

A 'non-aromatic heterocyclyl' embraces unsaturated heterocyclic ring systems without aromatic character, partially saturated and fully saturated heterocyclic ring systems. The term 'partially saturated' refers to rings wherein the ring structure(s) contain(s) at least one multiple bond e.g. a C=C, N=C bond. The term 'fully saturated' refers to rings where there are no multiple bonds between ring atoms. The skilled person will understand that a 'non-aromatic heterocyclyl' contains at least one heteroatom such as N, O or S, if not otherwise specified or is clear from the context.

Non-limiting examples of monocyclic 4- to 7-membered non-aromatic heterocyclyls containing one or two heteroatoms selected from nitrogen, oxygen and sulfur, include, but are not limited to azetidinyl, oxetanyl, pyrrolidinyl, tetrahydrofuranyl, piperidinyl, piperazinyl, pyranyl, dihydropyranyl, tetrahydropyranyl, morpholinyl, and thiomorpholinyl.

The term '$C_{3-6}$cycloalkyl' as used herein as a group or part of a group defines a saturated, cyclic hydrocarbon radical having from 3 to 6 carbon atoms, such as cyclopropyl, cyclobutyl, cyclopentyl and cyclohexyl.

The term "halogen" or "halo" refers to fluorine, chlorine, bromine and iodine atoms.

The label "R" at a stereocenter designates that the stereocenter is purely of the R-configuration as defined in the art; likewise, the label "S" means that the stereocenter is purely of the S-configuration. As used herein, the labels "*R" or "*S" at a stereocenter are used to designate that the stereocenter is of pure but unknown absolute configuration. As used herein, the label "RS" refers to a stereocenter that exists as a mixture of the R- and S-configurations.

A compound containing one stereocenter drawn without a stereo bond designation is a mixture of two enantiomers. A compound containing two stereocenters both drawn without stereo bond designations is a mixture of four diastereomers.

Unlabeled stereocenters drawn without stereo bond designations are mixtures of the R- and S-configurations. For unlabeled stereocenters drawn with stereo bond designations, the relative and absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, including reduction or inhibition of an enzyme or a protein activity, or ameliorating symptoms, alleviating conditions, slowing or delaying disease progression, or preventing a disease.

In one embodiment, the term "therapeutically effective amount" refers to the amount of a compound of the present invention that, when administered to a subject, is effective to (1) at least partially alleviate, inhibit, prevent, and/or ameliorate a condition, or a disorder or a disease (i) mediated by MALT1; or (ii) associated with MALT1 activity; or (iii) characterized by activity (normal or abnormal) of MALT1; or (2) reduce or inhibit the activity of MALT1; or (3) reduce or inhibit the expression of MALT1; or (4) modify the protein levels of MALT1.

The term "composition" refers to a product that includes the specified ingredients in therapeutically effective amounts, as well as any product that results, directly, or indirectly, from combinations of the specified ingredients in the specified amounts.

The term "MALT1-mediated" refers to any disease, syndrome, condition, or disorder that might occur in the absence of MALT1 but can occur in the presence of MALT1. Suitable examples of a disease, syndrome, condition, or disorder mediated by MALT1 include, but are not limited to, lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stoma tumor).

As used herein, the term "MALT1 inhibitor" refers to an agent that inhibits or reduces at least one condition, symptom, disorder, and/or disease of MALT1.

As used herein, unless otherwise noted, the term "affect" or "affected" (when referring to a disease, syndrome, condition or disorder that is affected by the inhibition of MALT1) includes a reduction in the frequency and/or severity of one or more symptoms or manifestations of said disease, syndrome, condition or disorder; and/or includes the prevention of the development of one or more symptoms or manifestations of said disease, syndrome, condition or disorder or the development of the disease, condition, syndrome or disorder.

As used herein, the term "treat", "treating", or "treatment" of any disease, condition, syndrome or disorder refers, in one embodiment, to ameliorating the disease, condition, syndrome or disorder (i.e. slowing or arresting or reducing the development of the disease or at least one of the clinical symptoms thereof). In another embodiment, "treat", "treating", or "treatment" refers to alleviating or ameliorating at lease one physical parameter including those which may not be discernible by the patient. In a further embodiment, "treat", "treating", or "treatment" refers to modulating the disease, condition, syndrome or disorder either physically (e.g. stabilization of a discernible symptom), physiologically, (e.g. stabilization of a physical parameter), or both. In yet another embodiment, "treat", "treating", or "treatment" refers to preventing or delaying the onset or development or progression of the disease, condition, syndrome or disorder.

The compounds of the instant invention are useful in methods for treating or ameliorating a disease, a syndrome, a condition or a disorder that is affected by the inhibition of MALT1. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

One embodiment of the present invention is directed to a method of treating a MALT1-dependent or MALT1-mediated disease or condition in a subject in need thereof, including an animal, a mammal, and a human in need of such treatment, comprising administering to the subject a therapeutically effective amount of a compound of Formula (I).

In another embodiment, the MALT1-dependent or MALT1-mediated disease or condition is selected from cancers of hematopoietic origin or solid tumors such as chonic myelogenous leukemia, myeloid leukemia, non-Hodgkin lymphoma, and other B cell lymphomas.

In particular, the compounds of Formula (I), or an enantiomer, diastereomer, solvate or pharmaceutically acceptable salt form thereof are useful for treating or ameliorating diseases, syndromes, conditions, or disorders such as diffuse large B-cell lymphoma (DLBCL), mantle cell lymphoma (MCL), follicular lymphoma (FL), and mucosa-associated lymphoid tissue (MALT) lymphoma.

More particularly, the compounds of Formula (I), or an enantiomer, diastereomer, solvate or pharmaceutically acceptable salt form thereof, are useful for treating or ameliorating diffuse large B-cell lymphoma (DLBCL), mantle cell lymphoma (MCL), follicular lymphoma (FL), and mucosa-associated lymphoid tissue (MALT) lymphoma, comprising administering to a subject in need thereof a therapeutically effective amount of a compound of Formula (I), or an enantiomer, diastereomer, solvate or pharmaceutically acceptable salt form thereof as herein defined.

Further, the compounds of Formula (I), or an enantiomer, diastereomer, solvate or pharmaceutically acceptable salt form thereof, are useful for treating or ameliorating an immunological disease, syndrome, disorder, or condition selected from the group consisting of rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

Embodiments of the present invention include a compound of Formula (I), wherein $R^x$ represents $C_{1-4}$alkyl, or $C_{3-6}$cycloalkyl;

$R^y$ represents $C_{1-4}$alkyl; and $R^z$ represents hydrogen;

$R^1$ is selected from the group consisting of hydrogen, —$OR^5$, $C_{1-4}$alkyl, $C_{2-4}$alkenyl, halo, —CN, $C_{3-6}$cycloalkyl, Het$^a$, —C(=O)—OH, —C(=O)—O—$C_{1-4}$alkyl, —$NR^{6a}R^{7a}$ and —C(=O)—$NR^{6b}R^{7b}$;

$R^{2a}$ and $R^{2b}$ are each independently selected from the group consisting of hydrogen, —$NR^{6c}R^{7c}$, $C_{3-6}$cycloalkyl, $C_{1-4}$alkyl, and $C_{1-4}$alkyl substituted with 1, 2 or 3 halo atoms;

$X^1$ represents N or $CR^a$;

$X^2$ represents N or $CR^b$;

such that only one of $X^1$ and $X^2$ are N in any instance;

$R^3$ represents hydrogen, $C_{1-4}$alkyl or —O—$C_{1-4}$alkyl;

$R^4$ represents halo, cyano or trifluoromethyl;

$R^5$ is selected from the group consisting of hydrogen, $C_{1-4}$alkyl, $C_{3-6}$cycloalkyl, Het$^b$, and $C_{1-4}$alkyl substituted with one or two substituents each independently selected from the group consisting of —C(=O)—$NR^8R^9$, —C(=O)—OH, —C(=O)—O—$C_{1-4}$alkyl, $C_{3-6}$cycloalkyl and phenyl;

$R^{6a}$, $R^{6b}$, $R^{6c}$, $R^{7a}$, $R^{7b}$, $R^{7c}$, $R^8$ and $R^9$ each independently are selected from the group consisting of hydrogen and $C_{1-4}$alkyl;

Het$^a$ represents a monocyclic 4- to 7-membered non-aromatic heterocyclyl containing one or two heteroatoms selected from nitrogen, oxygen and sulfur;

Het$^b$ represents a monocyclic 4- to 7-membered non-aromatic heterocyclyl containing one or two heteroatoms selected from nitrogen, oxygen and sulfur;

$R^a$ represents —O—$C_{1-4}$alkyl, each optionally substituted with one, two or three halo substituents;

or $R^a$ represents 2H-1,2,3-triazol-2-yl or $C_{3-6}$cycloalkyl; each optionally substituted on one carbon atom with a substituent each independently selected from the group consisting of $C_{1-4}$alkyl, and $C_{1-4}$alkyl substituted with one —OH;

$R^b$ represents hydrogen;

or an enantiomer, diastereomer, solvate or pharmaceutically acceptable salt form thereof.

Embodiments of the present invention include a compound of Formula (I), wherein $R^x$ represents $C_{1-4}$alkyl;

$R^y$ represents $C_{1-4}$alkyl; and $R^z$ represents hydrogen;

$R^1$ is selected from the group consisting of —$OR^5$, halo, and —CN;

$R^{2a}$ represents hydrogen;

$R^{2b}$ is selected from the group consisting of hydrogen, —$NR^{6c}R^{7c}$, and $C_{1-4}$alkyl;

$X^1$ represents $CR^a$;

$X^2$ represents N;

R³ represents hydrogen;
R⁴ represents trifluoromethyl;
R⁵ represents $C_{1-4}$alkyl;
$R^{6c}$ and $R^{7c}$ represent hydrogen;
$R^a$ represents 2H-1,2,3-triazol-2-yl;
or an enantiomer, diastereomer, solvate or pharmaceutically acceptable salt form thereof.

Embodiments of the present invention include a compound of Formula (I), wherein
$R^x$ represents $C_{1-4}$alkyl;
$R^y$ represents $C_{1-4}$alkyl; and
$R^z$ represents hydrogen;
R¹ is selected from the group consisting of halo and —CN;
$R^{2a}$ represents hydrogen;
$R^{2b}$ represents hydrogen, $—NR^{6c}R^{7c}$, $C_{1-4}$alkyl, and $C_{1-4}$alkyl substituted with 1, 2 or 3 halo atoms;
X¹ represents $CR^a$;
X² represents N;
R³ represents hydrogen or —O—$C_{1-4}$alkyl;
R⁴ represents halo or trifluoromethyl;
$R^{6c}$ and $R^{7c}$ represent hydrogen;
$R^a$ represents 2H-1,2,3-triazol-2-yl;
or an enantiomer, diastereomer, solvate or pharmaceutically acceptable salt form thereof.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
$R^x$ represents hydrogen, $C_{1-4}$alkyl, or $C_{3-6}$cycloalkyl;
$R^y$ represents hydrogen, $C_{1-4}$alkyl, or $C_{3-6}$cycloalkyl; and
$R^z$ represents hydrogen.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
$R^x$ and $R^y$ are taken together to form a bivalent radical $—R^x—R^y—$ wherein $—R^x—R^y—$ represents $—(CH_2)_n—$ or $—CH_2—O—(CH_2)_z—$; wherein n represents 2, 3, 4 or 5; and
$R^z$ represents hydrogen.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
$R^y$ represents hydrogen, $C_{1-4}$alkyl, or $C_{3-6}$cycloalkyl;
$R^x$ and $R^z$ are taken together to form together with the carbon atom to which they are attached a $C_{3-6}$cycloalkyl.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
R¹ is selected from the group consisting of —OR⁵, $C_{1-4}$alkyl, $C_{2-4}$alkenyl, halo, —CN, $C_{3-6}$cycloalkyl, $Het^a$, —C(=O)—OH, —C(=O)—O—$C_{1-4}$alkyl, $—NR^{6a}R^{7a}$ and $—C(=O)—NR^{6b}R^{7b}$.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
$R^{2a}$ represents hydrogen.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
$R^{2a}$ represents hydrogen; and
$R^{2b}$ represents hydrogen, $—NR^{6c}R^{7c}$, $C_{1-4}$alkyl, and $C_{1-4}$alkyl substituted with 1, 2 or 3 halo atoms.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
$R^a$ represents $C_{1-4}$alkyl or —O—$C_{1-4}$alkyl, each optionally substituted with one, two or three halo substituents.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
$R^a$ represents 2H-1,2,3-triazol-2-yl or $C_{3-6}$cycloalkyl; each optionally substituted on one or two carbon atoms with a substituent each independently selected from the group consisting of $C_{1-4}$alkyl, and Ct-alkyl substituted with one —OH.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
$R^a$ represents 2H-1,2,3-triazol-2-yl or $C_{3-6}$cycloalkyl; each optionally substituted on one or two carbon atoms with a substituent each independently selected from the group consisting of $C_{1-4}$alkyl, and —CH(OH)—$C_{0-3}$alkyl.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
$R^a$ represents $C_{1-4}$alkyl or —O—$C_{1-4}$alkyl, each optionally substituted with one, two or three halo substituents; or
$R^a$ represents 2H-1,2,3-triazol-2-yl or $C_{3-6}$cycloalkyl; each optionally substituted on one or two carbon atoms with a substituent each independently selected from the group consisting of $C_{1-4}$alkyl, and —CH(OH)—$C_{0-3}$alkyl.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
$R^a$ represents 2H-1,2,3-triazol-2-yl.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
X¹ represents N; and
X² represents $CR^b$.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein
X¹ represents $CR^a$; and
X² represents N.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein $X^1$ represents $CR^a$; and
$X^2$ represents $CR^b$.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein $R^{6c}$ and $R^{7c}$ represent hydrogen.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein Het$^a$ represents a monocyclic 4- to 7-membered fully saturated heterocyclyl containing one or two heteroatoms selected from nitrogen, oxygen and sulfur;
Het$^b$ represents a monocyclic 4- to 7-membered fully saturated heterocyclyl containing one or two heteroatoms selected from nitrogen, oxygen and sulfur.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein Het$^a$ represents a monocyclic 4- to 7-membered fully saturated heterocyclyl containing one oxygen atom;
Het$^b$ represents a monocyclic 4- to 7-membered fully saturated heterocyclyl containing one oxygen atom.

In an embodiment, the present invention relates to those compounds of Formula (I) or an enantiomer, diastereomer, solvate or pharmaceutically acceptable salt form thereof, or any subgroup thereof as mentioned in any of the other embodiments, wherein Het$^a$ and Het$^b$ represent oxetanyl, in particular 3-oxetanyl.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mutate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

A person of ordinary skill in the art would recognize that the compounds described herein may exist as tautomers and that other tautomeric arrangements of the structures depicted herein are possible. Tautomers are constitutional isomers that readily interconvert. It is understood that all tautomeric forms are encompassed by a structure where one possible tautomeric arrangement of the groups of the compound is described, even if not specifically indicated.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorph and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)-\text{enantiomer} = \frac{(\text{mass}(+)-\text{enantiomer})}{(\text{mass}(+)-\text{enantiomer}) + (\text{mass}(-)-\text{enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(+)-\text{enantiomer} = \frac{(\text{mass}(+)-\text{enantiomer})}{(\text{mass}(+)-\text{enantiomer}) + (\text{mass}(-)-\text{enantiomer})} \times 100.$$

It is intended that within the scope of the present invention, any one or more element(s), in particular when mentioned in relation to a compound of Formula (I), shall comprise all isotopes and isotopic mixtures of said element(s), either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of formula (I) may comprise one or more radioactive isotope(s) selected from the group of $^3$H, $^{11}$C, $^{18}$F, $^{122}$I, $^{123}$I, $^{125}$I, $^{131}$I, $^{73}$Br, $^{76}$Br, $^{77}$Br and $^{82}$Br. Preferably, the isotope is selected from the group of $^2$H, $^3$H, $^{11}$C and $^{18}$F. In particular, deuterated compounds are intended to be included within the scope of the present invention.

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry*, Second Edition, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis*, Third Edition, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein; although, it is apparent to one skilled in the art that the therapeutically effective amount for a compound of Formula (I) will vary as will the diseases, syndromes, conditions, and disorders being treated.

Optimal dosages of a compound of Formula (I) to be administered may be readily determined and will vary with the particular compound used, the mode of administration, the strength of the preparation, and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

It has been found that the compounds of the present invention inhibit MALT1 activity.

In some embodiments, the inhibition of MALT1 by a provided compound may be useful in treating or preventing, in particular treating, the non-limiting list of cancers described herein.

The invention relates to compounds of Formula (I) or an enantiomer, diastereomer, solvate or pharmaceutically acceptable salt form thereof, for use as a medicament.

The invention relates to compounds of Formula (I) or an enantiomer, diastereomer, solvate or pharmaceutically acceptable salt form thereof, for use in the inhibition of MALT1 activity.

The invention relates to compounds of Formula (I) or an enantiomer, diastereomer, solvate or pharmaceutically acceptable salt form thereof, for use in the treatment of diseases mentioned herein.

The invention relates to compounds of Formula (I) or an enantiomer, diastereomer, solvate or pharmaceutically acceptable salt form thereof, for the treatment or prevention, in particular for the treatment, of said diseases.

The invention relates to compounds of Formula (I) or an enantiomer, diastereomer, solvate or pharmaceutically acceptable salt form thereof, for the treatment or prevention, in particular in the treatment, of MALT1 mediated diseases or conditions.

The invention relates to compounds of Formula (I) or an enantiomer, diastereomer, solvate or pharmaceutically acceptable salt form thereof, for the manufacture of a medicament.

The invention relates to compounds of Formula (I) or an enantiomer, diastereomer, solvate or pharmaceutically acceptable salt form thereof, for the manufacture of a medicament for the inhibition of MALT1.

The invention relates to compounds of Formula (I) or an enantiomer, diastereomer, solvate or pharmaceutically acceptable salt form thereof, for the manufacture of a medicament for the treatment or prevention, in particular for the treatment, of any one of the disease conditions mentioned herein.

The invention relates to compounds of Formula (I) or an enantiomer, diastereomer, solvate or pharmaceutically acceptable salt form thereof, for the manufacture of a medicament for the treatment of any one of the disease conditions mentioned herein.

The invention relates to compounds of Formula (I) or an enantiomer, diastereomer, solvate or pharmaceutically acceptable salt form thereof, can be administered to mammals, preferably humans, for the treatment or prevention of any one of the diseases mentioned herein.

In view of the utility of the compounds of Formula (I) or an enantiomer, diastereomer, solvate or pharmaceutically acceptable salt form thereof, there is provided a method of treating warm-blooded animals, including humans, suffering from or a method of preventing warm-blooded animals, including humans, to suffer from any one of the diseases mentioned herein.

In an embodiment, cancers that may benefit from a treatment with MALT1 inhibitors of the present invention include, but are not limited to, lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head&neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, MALT1 inhibitors of the present invention may be used for the treatment of immunological diseases including, but not limited to, autoimmune and inflammatory disorders, e.g. arthritis, inflammatory bowel disease, gastritis, ankylosing spondylitis, ulcerative colitis, pancreatits, Crohn's disease, celiac disease, multiple sclerosis, systemic lupus erythematosus, lupus nephritis, rheumatic fever, gout, organ or transplact rejection, chonic allograft rejection, acute or chonic graft-versus-host disease, dermatitis including atopic, dermatomyositis, psoriasis, Behcet's diseases, uveitis, myasthenia gravis, Grave's disease, Hashimoto thyroiditis, Sjoergen's syndrome, blistering disorders, antibody-mediated vasculitis syndromes, immune-complex vasculitides, allergic disorders, asthma, bronchitis, chonic obstructive pulmonary disease (COPD), cystic fibrosis, pneumonia, pulmonary diseases including oedema, embolism, fibrosis, sarcoidosis, hypertension and emphysema, silicosis, respiratory failure, acute respiratory distress syndrome, BENTA disease, berylliosis, and polymyositis.

In another embodiment of the present invention, the compounds of the present invention may be employed in combination with one or more other medicinal agents, more particularly with other anti-cancer agents, e.g. chemotherapeutic, anti-proliferative or immunomodulating agents, or with adjuvants in cancer therapy, e.g. immunosuppressive or anti-inflammatory agents.

General Synthetic Methods

In this section, as in all other sections unless the context indicates otherwise, references to Formula (I) also include all other sub-groups and examples thereof as defined herein.

The general preparation of some typical examples of the compounds of Formula (I) is described hereunder and in the specific examples and are generally prepared from starting materials which are either commercially available or prepared by standard synthetic processes commonly used by those skilled in the art of organic chemistry. The following schemes are only meant to represent examples of the invention and are in no way meant to be a limit of the invention.

Alternatively, intermediates or compounds of the present invention may also be prepared by analogous reaction protocols as described in the general schemes below and the specific examples, combined with standard synthetic processes commonly used by those skilled in the art including also analogous reaction protocols as described in WO2018020474, WO2015181747 and WO2017081641.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. In general, conventional protecting groups can be used in accordance with standard practice. The protecting groups may be removed at a convenient subsequent stage using methods known from the art.

The skilled person will realize that in the reactions described in the Schemes, it may be advisable or necessary to perform the reaction under an inert atmosphere, such as for example under $N_2$-gas atmosphere, for example when NaH, LDA or MeMgBr is used in the reaction.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and final compounds shown in the Schemes below may be further functionalized according to methods well-known by the person skilled in the art. The intermediates and compounds described herein can be isolated in free form or as a salt, or a solvate thereof. The intermediates and compounds described herein may be synthesized in the form of mixtures of tautomers and stereoisomeric forms that can be separated from one another following art-known resolution procedures.

For abbreviations used in the Schemes below, check the table with abbreviations in the part 'Examples'.

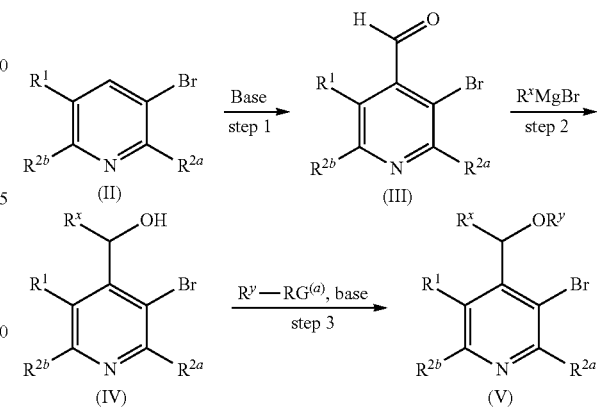

General Scheme 1

In scheme 1, '$RG^{(a)}$' is defined as a suitable reactive group such as for example iodo, bromo, or tosyl. In particular Scheme 1 can be used to prepare intermediates wherein $R^x$ and $R^y$ are not taken together. All other variables in Scheme 1 are defined according to the scope of the present invention.

In scheme 1, the following reaction conditions typically apply:
1: An intermediate of Formula (II) is reacted with a base, such as lithium diisopropyl amide (LDA), typically in an aprotic solvent, such as for example anhydrous THF in a suitable temperature range such as for example −70° C. to room temperature, and in the presence of a formyl donor, such as DMF;

2: An intermediate of Formula (III) is reacted with a Grignard reagent R$^x$MgBr, typically in an aprotic solvent, such as for example anhydrous THF in a suitable temperature range such as for example 0° C. to room temperature;

3: An intermediate of Formula (IV) is reacted with an alkylating agent R$^y$—RG$^{(a)}$, typically in an aprotic solvent, such as for example anhydrous THF, and in the presence of a suitable base such as sodium hydride (NaH) or potassium tert. Butoxide (KOtBu) or the like in a suitable temperature range such as for example 0° C. to room temperature.

All variables in Scheme 2 are defined according to the scope of the present invention.

In Scheme 2, the following reaction conditions typically apply:

An intermediate of Formula (V-a) is reacted with an amine source, such as aqueous ammonia, typically in a solvent, such as for example DMSO in the presence of a copper catalyst such as copper (I) iodide (Cu), an additive such as L-proline and a base, such as potassium carbonate in a suitable temperature range such as for example 60° C. to 120° C.

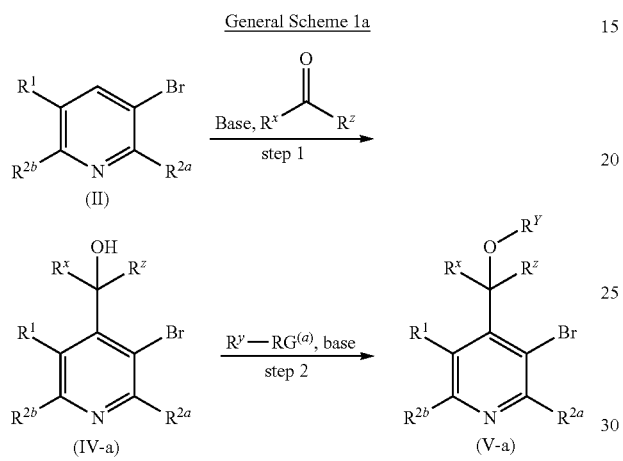

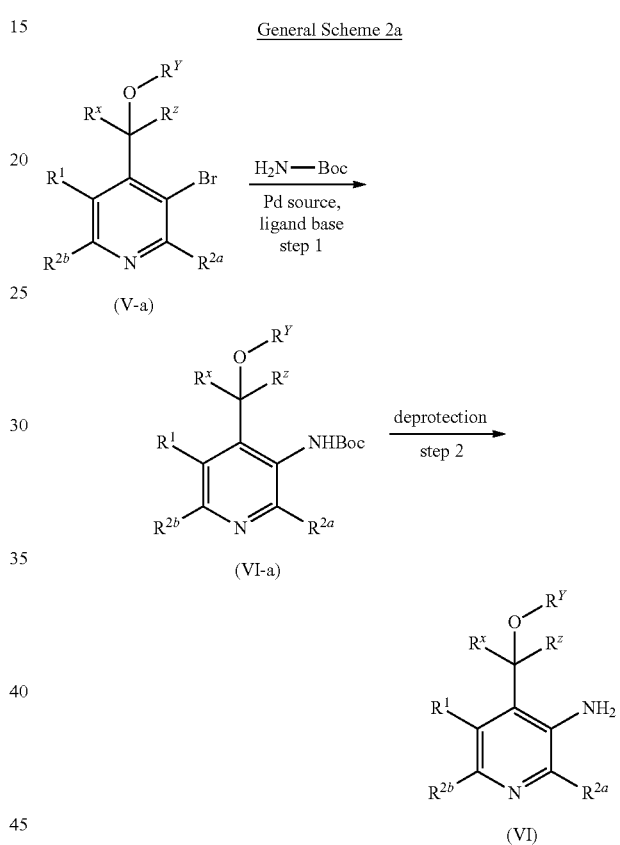

In scheme 1a, 'RG$^{(a)}$' is defined as a suitable reactive group such as for example iodo, bromo, tosyl. In particular Scheme 1a can be used to prepare intermediates wherein R$^x$ and R$^y$ are not taken together. All other variables in Scheme 1a are defined according to the scope of the present invention.

In scheme 1a, the following reaction conditions typically apply:

1: An intermediate of Formula (II) is reacted with a base, such as LDA, typically in an aprotic solvent, such as for example anhydrous THF in a suitable temperature range such as for example −70° C. to room temperature, and in the presence of a carbonyl source, R$^x$—C(O)—R$^y$;

2: An intermediate of Formula (IV-a) is reacted with an alkylating agent R$^y$—RG$^{(a)}$, typically in an aprotic solvent, such as for example anhydrous THF, and in the presence of a suitable base such as (NaH) or the like in a suitable temperature range such as for example 0° C. to room temperature.

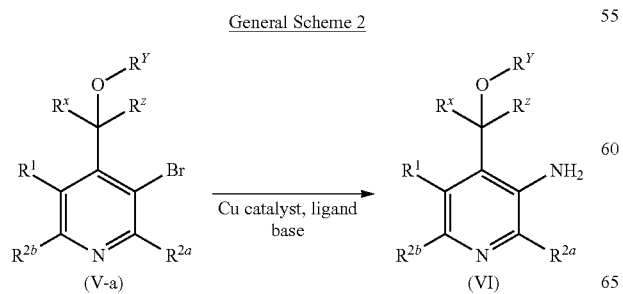

All variables in Scheme 2a are defined according to the scope of the present invention.

In Scheme 2a, the following reaction conditions typically apply:

1: An intermediate of Formula (Va) is reacted with an amine source, such as H$_2$N—Boc ("Boc" means tert-butyloxycarbonyl), typically in a solvent such as for example toluene or 1,4-dioxane in the presence of a palladium catalyst such as palladium acetate (Pd(OAc)$_2$) or tris(dibenzylideneacetone)dipalladium(0) (Pd$_2$(dba)$_3$), a ligand such as 4,5-bis(diphenylphosphino)-9,9-dimethylxanthene (xantphos) and a base, such as cesium carbonate in a suitable temperature range such as for example 100° C. to 125° C.;

2: in the presence of a suitable acid, such as for example trifluoroacetic acid (TFA) in dichloromethane (DCM), at a suitable temperature range such as for example 0° C. to room temperature.

General Scheme 2b

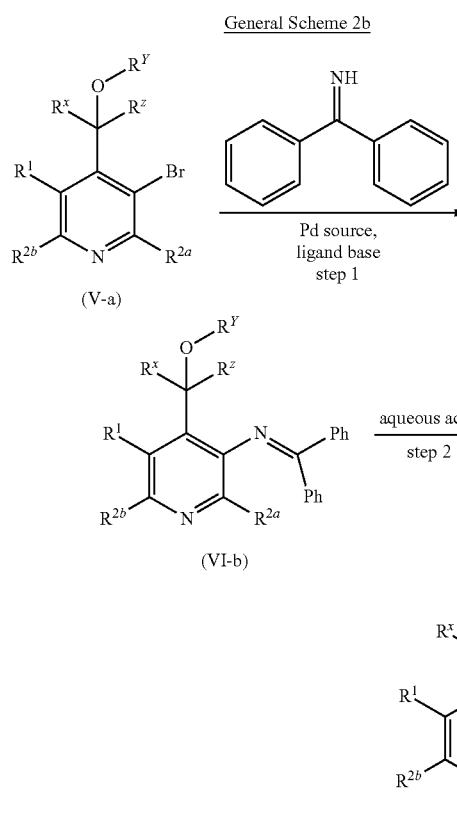

All variables in Scheme 2b are defined according to the scope of the present invention.

In Scheme 2b, the following reaction conditions typically apply:
1: An intermediate of Formula (Va) is reacted with an amine source, such as diphenylmethanimine, typically in a solvent, such as for example 1,4-dioxane in the presence of a palladium catalyst such as $Pd_2(dba)_3$, a ligand such as xantphos or BINAP, and a base, such as sodium tert-butoxide in a suitable temperature range such as for example 80° C. to 125° C.
2: in the presence of a suitable acid, such as for example aqueous HCl at a concentration of 1M to 4M in dichloromethane (DCM), at a suitable temperature range such as for example 20° C. to 40° C.

General Scheme 3

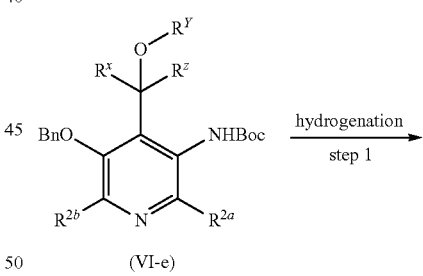

All variables in Scheme 3 are defined according to the scope of the present invention.

In Scheme 3, the following reaction conditions typically apply:

An intermediate of Formula (VI-c) is reacted with a cyanide source such as zinc cyanide in the presence of zinc, typically in a solvent, such as for example DMF in the presence of a palladium catalyst such as $Pd_2(dba)_3$, or $Pd(dppf)Cl_2$, in the presence of a ligand, such as dppf, in a suitable temperature range such as for example 100° C.-120° C.

General Scheme 4

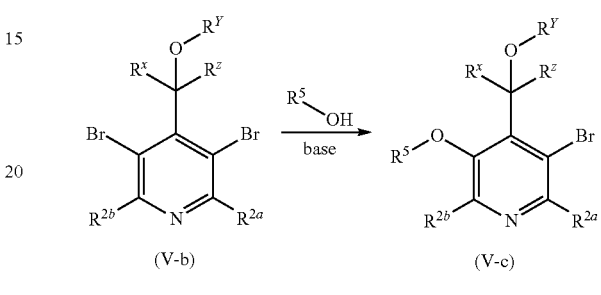

All variables in Scheme 4 are defined according to the scope of the present invention. However, a skilled person will understand that $R^5$ is not hydrogen.

In Scheme 4, the following reaction conditions typically apply:

An intermediate of Formula (V-b) is reacted with an alcohol $R^5$—OH and a base, such as sodium hydride in the presence of a catalyst such as copper powder, typically in a solvent, such as for example DMF in a suitable temperature range such as for example 20° C. to 80° C.

General Scheme 4a

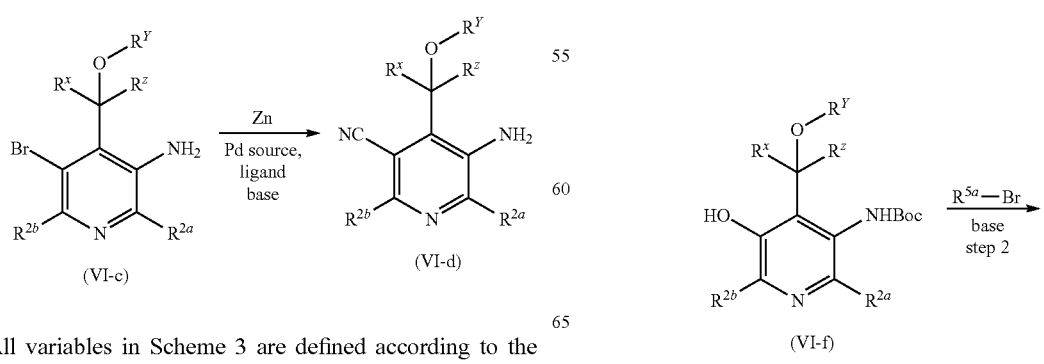

-continued

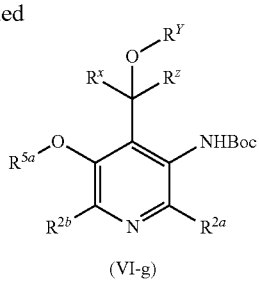

(VI-g)

In scheme 4a, '$R^{5a}$' is defined as $C_{1-4}$alkyl (optionally substituted) or $C_{3-6}$cycloalkyl; All other variables in Scheme 4a are defined according to the scope of the present invention In scheme 4a, the following reaction conditions typically apply:
1: An intermediate of Formula (VI-e) is reacted with hydrogen gas, typically at a pressure of 15 psi in the presence of a palladium catalyst such as palladium on carbon, optionally in the presence of an acid, such as hydrochloric acid, in a suitable solvent such as methanol or THF, at a suitable temperature of 25° C.
2: in the presence of a suitable alkylating agent, such as $R^{5a}$—Br, in the presence of an additive such as sodium iodide and a suitable base, such as cesium carbonate in a suitable solvent such as DMF or DMA, in a suitable temperature range such as for example 20° C. to 140° C.

General Scheme 5

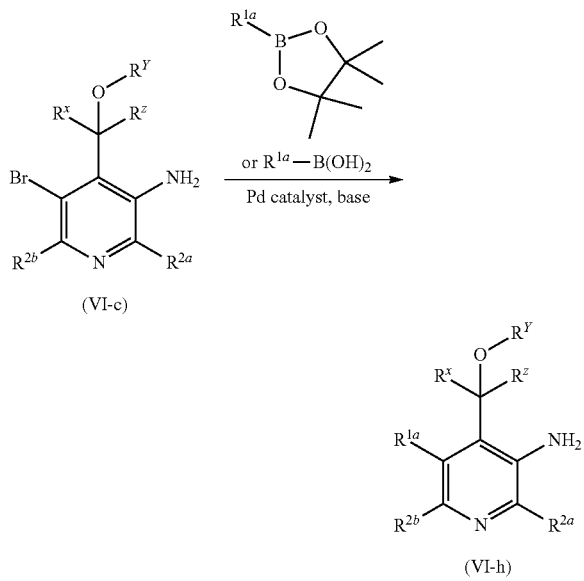

(VI-c)

(VI-h)

In scheme 5, '$R^{1a}$' is defined as $C_{1-4}$alkyl, $C_{2-4}$alkenyl or $C_{3-6}$cycloalkyl. All other variables in Scheme 5 are defined according to the scope of the present invention In scheme 5, the following reaction conditions typically apply:
An intermediate of Formula (VI-c) is reacted with a boronate ester, typically in a solvent, such as for example 1,4-dioxane or toluene, optionally in the presence of water, and in the presence of a palladium catalyst such as [1,1'-bis(di-tert-butylphosphino)ferrocene]dichloropalladium(II) (Pd(dtbpf)Cl$_2$ (CAS 95408-45-0)) and a suitable base, such as potassium phosphate, in a suitable temperature range such as for example 90° C.-120° C. Alternatively, the reaction can be performed using a suitable boronic acid $R^{1a}$—B(OH)$_2$, in the presence of a palladium catalyst such as Pd(OAc)$_2$ and a suitable ligand, such as tricyclohexylphosphine, in the presence of a base such as potassium phosphate in a suitable solvent such as for example 1,4-dioxane or toluene, optionally in the presence of water, in a suitable temperature range such as for example 100° C.-140° C.

General Scheme 5a

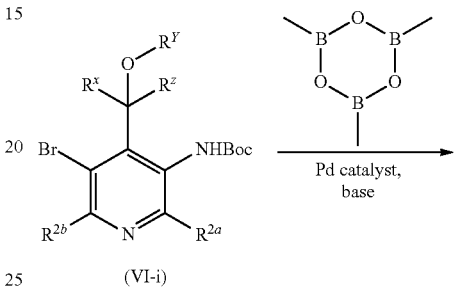

(VI-i)

(VI-j)

In scheme 5a all variables are defined according to the scope of the present invention.

In scheme 5a, the following reaction conditions typically apply:
An intermediate of Formula (VI-i) is reacted with 2,4,6-trimethyl-1,3,5,2,4,6-trioxatriborinane (CAS 823-96-1) typically in a solvent, such as for example 1,4-dioxane or toluene, optionally in the presence of water, and in the presence of a palladium catalyst such as tetrakis(triphenylphosphine)palladium(0) (Pd(PPh$_3$)$_4$), and a suitable base, such as potassium carbonate, in a suitable temperature range such as for example 90° C.-120° C.

General Scheme 5b

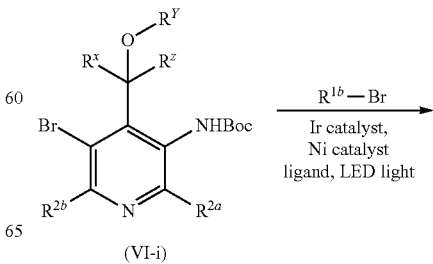

(VI-i)

-continued

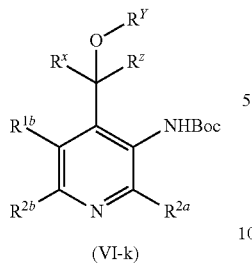

(VI-k)

In scheme 5b, '$R^{1b}$' is defined as $C_{1-4}$alkyl, $C_{3-6}$cycloalkyl, or Het (e.g. oxetane). All other variables in Scheme 5b are defined according to the scope of the present invention In scheme 5b, the following reaction conditions typically apply:

An intermediate of Formula (VI-i) is reacted with a compound $R^{1b}$—Br in the presence of a catalytic system consisting of an iridium catalyst, such as [4,4'-Bis(tert-butyl)-2,2'-bipyridine]bis[3,5-difluoro-2-[5-(trifluoromethyl)-2-pyridinyl]phenyl]iridium(III) hexafluorophosphate ((Ir[dF(CF$_3$)ppy]$_2$(dtbpy))PF$_6$ (CAS 870987-63-6)), and a nickel catalyst complex, such as NiCl$_2$·glyme in the presence of a ligand, such 4,4'-di-tert-butyl-2,2'-dipyridyl (CAS 72914-19-3). The reaction also requires the presence of tris(trimethylsilyl)silane and occurs under irradiation, eg using a blue LED light, in a solvent like DME at a suitable temperature, such as 25° C.

General Scheme 6

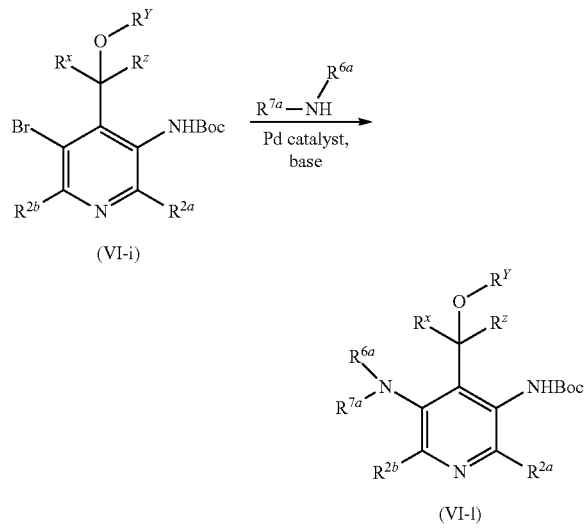

In scheme 6 all variables are defined according to the scope of the present invention.

In scheme 6, the following reaction conditions typically apply:

An intermediate of Formula (VI-i) is reacted with an amine $R^{7a}$—NH—$R^{6a}$, typically in a solvent, such as for example toluene in the presence of a palladium catalyst such as Pd$_2$(dba)$_3$, and a suitable base, such as sodium tert. butoxide, in a suitable temperature range such as for example 100° C.-140° C.

General Scheme 7

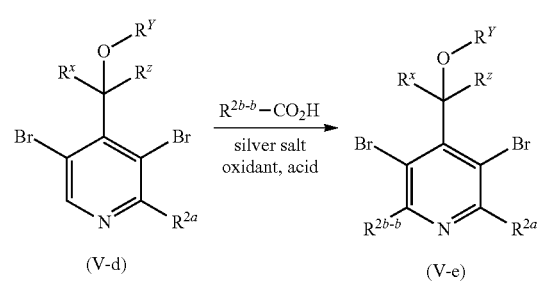

In scheme 7, '$R^{2b-b}$' is defined $C_{1-4}$alkyl, optionally substituted with 1, 2 or 3 halo atoms, or $C_{3-6}$cycloalkyl. All other variables in Scheme 7 are defined according to the scope of the present invention.

In scheme 7, the following reaction conditions typically apply:

An intermediate of Formula (V-d) is reacted with a carboxylic acid $R^{2b-b}$—CO$_2$H in the presence of an oxidant, such as ammonium persulfate, a silver salt such as silver nitrate, optionally in the presence of a strong acid such as sulfuric acid. The reaction occurs in a solvent like acetonitrile or DMSO in a suitable temperature range, such as 60° C.-100° C.

A skilled person will understand that in case $R^{2a}$ represents hydrogen, the reaction described in Scheme 7 might occur twice.

General Scheme 8

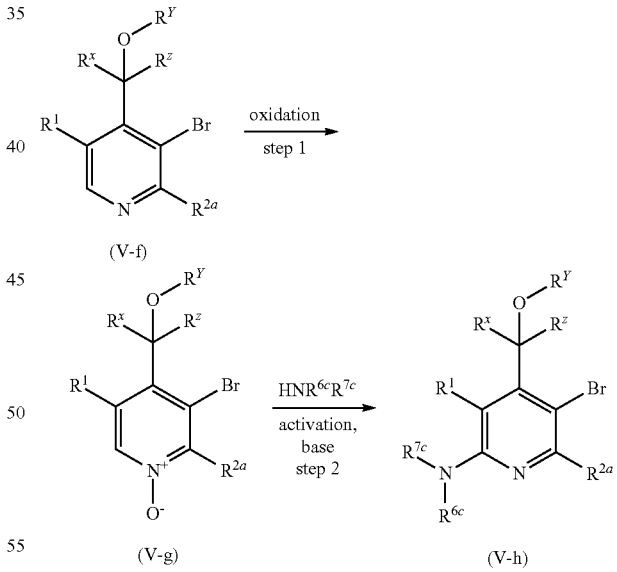

In scheme 8 all variables are defined according to the scope of the present invention.

In scheme 8, the following reaction conditions typically apply:
1: An intermediate of Formula (V-f) is reacted with an oxidant, such as mCPBA, in a suitable solvent such as dichloro methane, at a suitable temperature of 0° C.-25° C.
2: in the presence of an amine HNR$^{6c}$R$^{7c}$, in the presence of an activating agent such as PyBrOP and a suitable base, such as DIPEA in a suitable solvent such as THF, in a suitable temperature range such as for example 60° C. to 80° C.

General Scheme 9

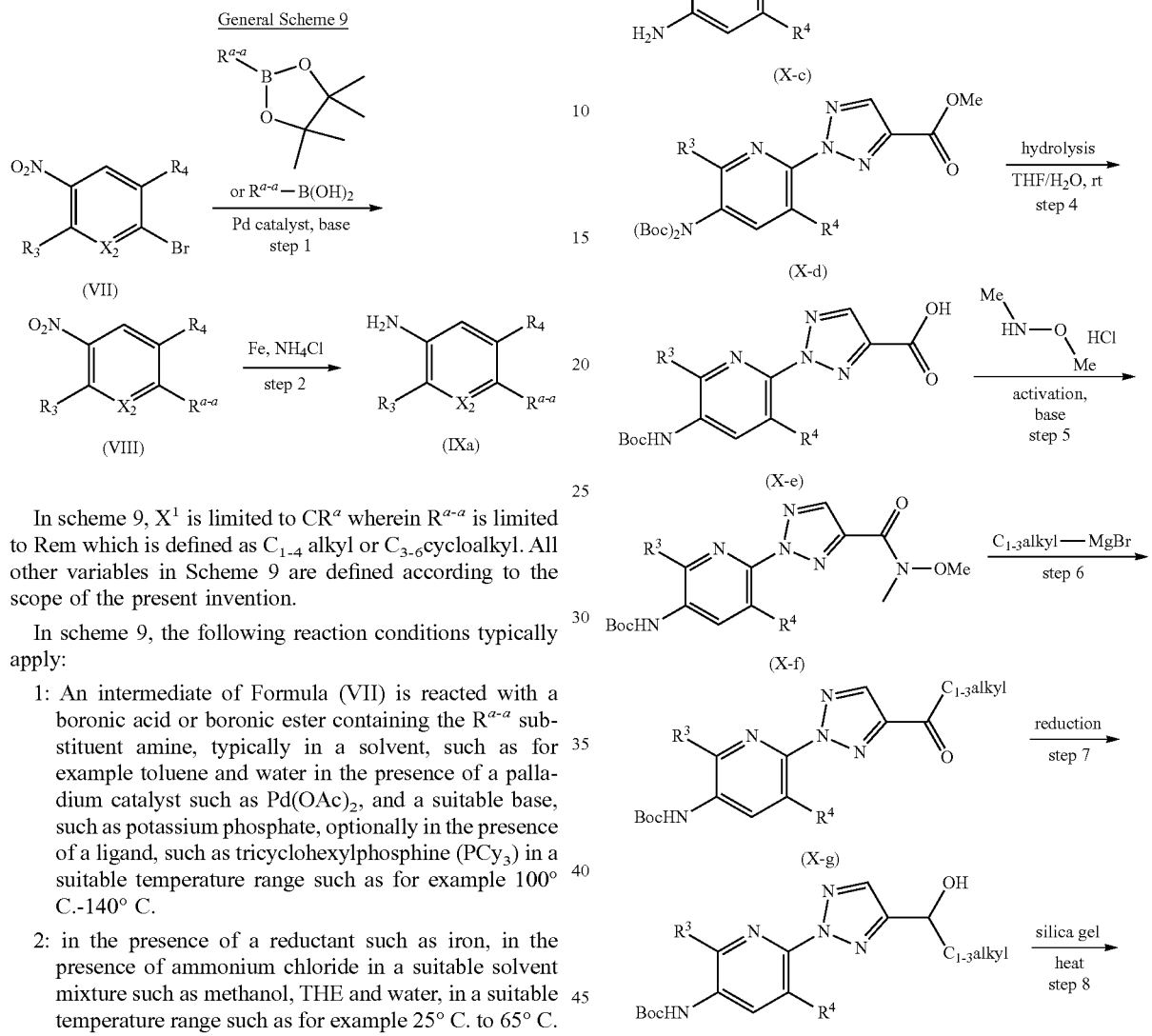

In scheme 9, $X^1$ is limited to $CR^a$ wherein $R^{a-a}$ is limited to Rem which is defined as $C_{1-4}$ alkyl or $C_{3-6}$ cycloalkyl. All other variables in Scheme 9 are defined according to the scope of the present invention.

In scheme 9, the following reaction conditions typically apply:

1: An intermediate of Formula (VII) is reacted with a boronic acid or boronic ester containing the $R^{a-a}$ substituent amine, typically in a solvent, such as for example toluene and water in the presence of a palladium catalyst such as $Pd(OAc)_2$, and a suitable base, such as potassium phosphate, optionally in the presence of a ligand, such as tricyclohexylphosphine ($PCy_3$) in a suitable temperature range such as for example 100° C.-140° C.

2: in the presence of a reductant such as iron, in the presence of ammonium chloride in a suitable solvent mixture such as methanol, THF and water, in a suitable temperature range such as for example 25° C. to 65° C.

General Scheme 10

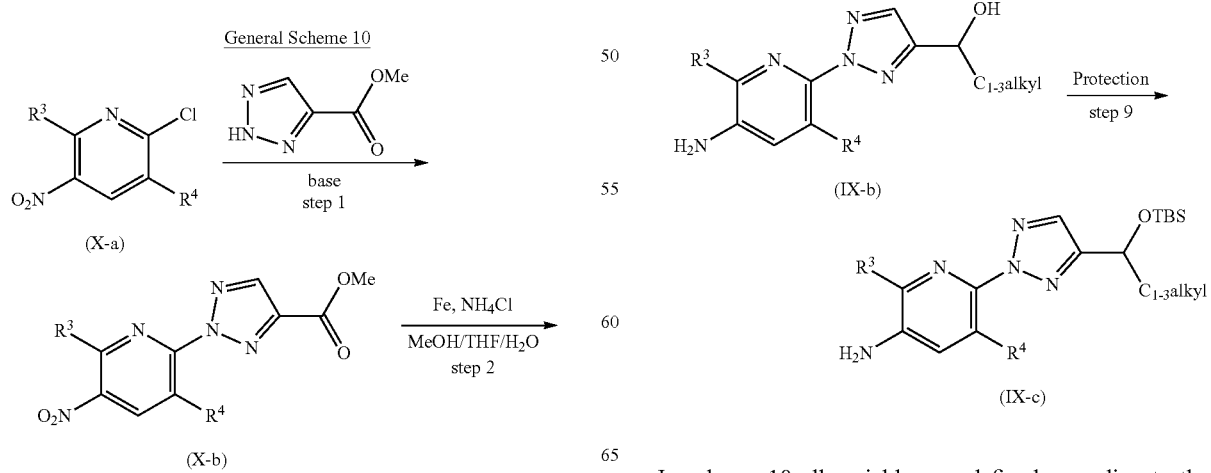

In scheme 10 all variables are defined according to the scope of the present invention.

In scheme 10, the following reaction conditions typically apply:
1: An intermediate of Formula (X-a) is reacted with methyl 2H-1,2,3-triazole-4-carboxylate, typically in a solvent, such as for example acetonitrile in the presence of a suitable base, such as potassium carbonate, temperature range such as for example 25° C.-50° C.
2: in the presence of a reductant such as iron, in the presence of ammonium chloride in a suitable solvent mixture such as methanol, THF and water, in a suitable temperature range such as for example 25° C. to 65° C.
3: Protection using Boc$_2$O, using a suitable base such as DMAP optionally in the presence of triethyl amine in a suitable solvent such as THF, at a suitable temperature such as for example room temperature.
4: Hydrolysis using lithium hydroxide in a suitable solvent mixture such as THF and water, at a suitable temperature such as for example room temperature.
5: Formation of the Weinreb amide using N,O-dimethylhydroxylamine hydrochloride in the presence of an activating agent such as HATU and a suitable base, such as DIPEA in a suitable solvent such as DMF, at a suitable temperature such as for example room temperature.
6: An intermediate of Formula (X-f) is reacted with a Grignard reagent $C_{1-3}$alkyl-MgBr, typically in an aprotic solvent, such as for example anhydrous THF in a suitable temperature range such as for example 0° C. to room temperature.
7: Reduction using for example sodium borohydride in a suitable solvent such as methanol, at a suitable temperature such as for example room temperature.
8: Deprotection using a weak acid such as for example silica gel in a suitable solvent such as toluene, at a suitable temperature such as 100° C. to 120° C.

General Scheme 10a

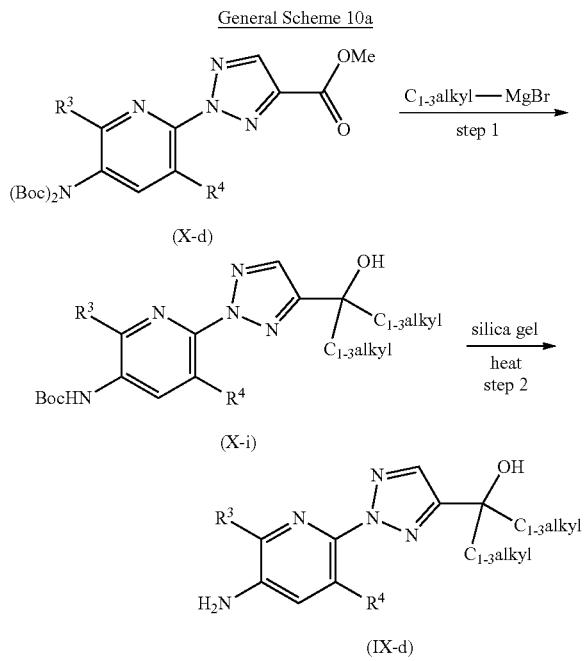

In scheme 10a all variables are defined according to the scope of the present invention.

In scheme 10a, the following reaction conditions typically apply:
1: An intermediate of Formula (X-d) is reacted with a Grignard reagent $C_{1-3}$alkyl-MgBr, typically in an aprotic solvent, such as for example anhydrous THF in a suitable temperature range such as for example 0° C. to room temperature.
2: Deprotection using a weak acid such as for example silica gel in a suitable solvent such as toluene, at a suitable temperature such as 100° C. to 120° C.

General Scheme 11

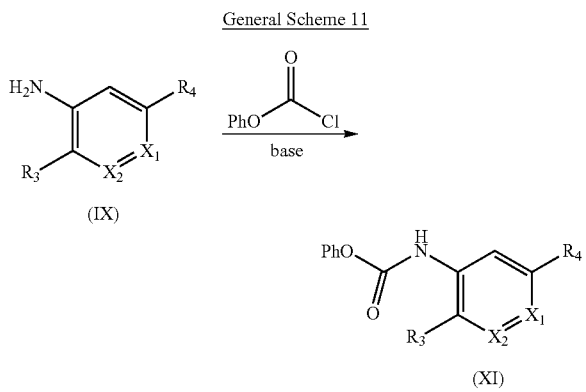

In scheme 11 all variables are defined according to the scope of the present invention.

In scheme 11, the following reaction conditions typically apply:
An intermediate of Formula (IX) is reacted with phenyl chloroformate, typically in a solvent, such as for example THF in the presence of a suitable base, such as pyridine, in a suitable temperature range such as for example 0° C.-20° C.

A skilled person will understand that alternative activating groups than phenyl formate can also be used such as for example isocyanate.

General Scheme 12

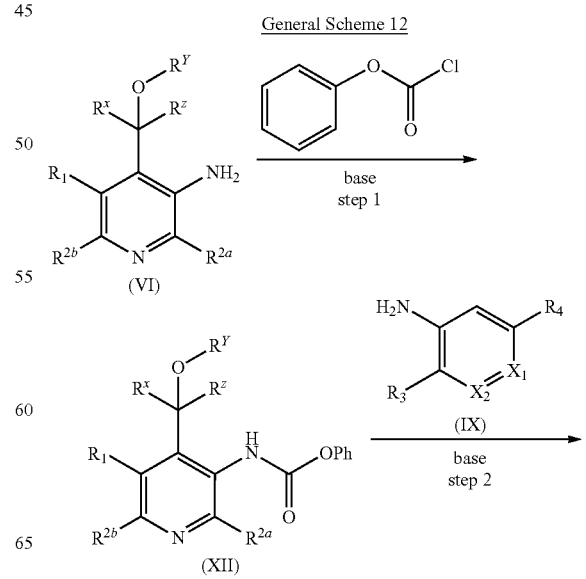

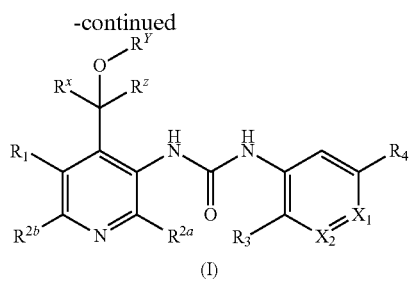

In scheme 12 all variables are defined according to the scope of the present invention.

In scheme 12, the following reaction conditions typically apply:
1: An intermediate of Formula (VI) is reacted with phenyl chloroformate, typically in a solvent, such as for example THE in the presence of a suitable base, such as pyridine, in a suitable temperature range such as for example 0° C.-20° C.
2: An intermediate of Formula (XII) is reacted with an intermediate of Formula (IX) in a suitable solvent such as THF, in the presence of a suitable base, such as triethyl amine or DMAP or the like in a suitable temperature range such as 20° C. to 80° C.

A skilled person will understand that alternative activating groups than phenyl formate can also be used such as for example isocyanate.

General Scheme 13

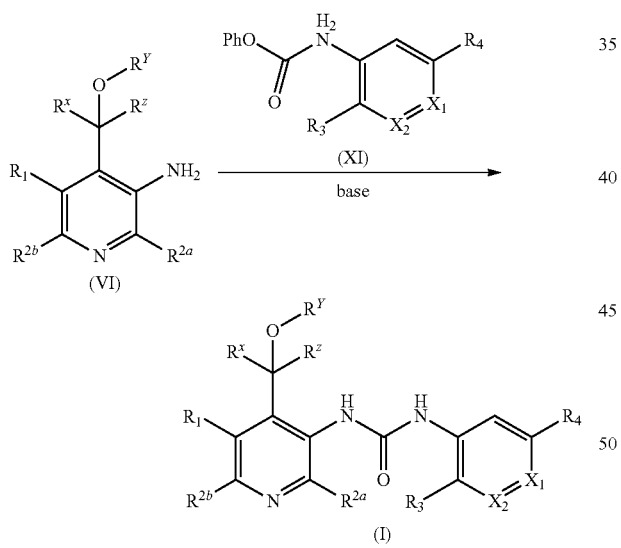

In scheme 13 all variables are defined according to the scope of the present invention.

In scheme 13, the following reaction conditions typically apply:
An intermediate of Formula (VI) is reacted with an intermediate of Formula (XI) in a suitable solvent such as THF, in the presence of a suitable base, such as triethyl amine or DMAP or the like, in a suitable temperature range such as 20° C. to 80° C.

A skilled person will understand that alternative activating groups than phenyl formate can also be used such as for example isocyanate.

General Scheme 14

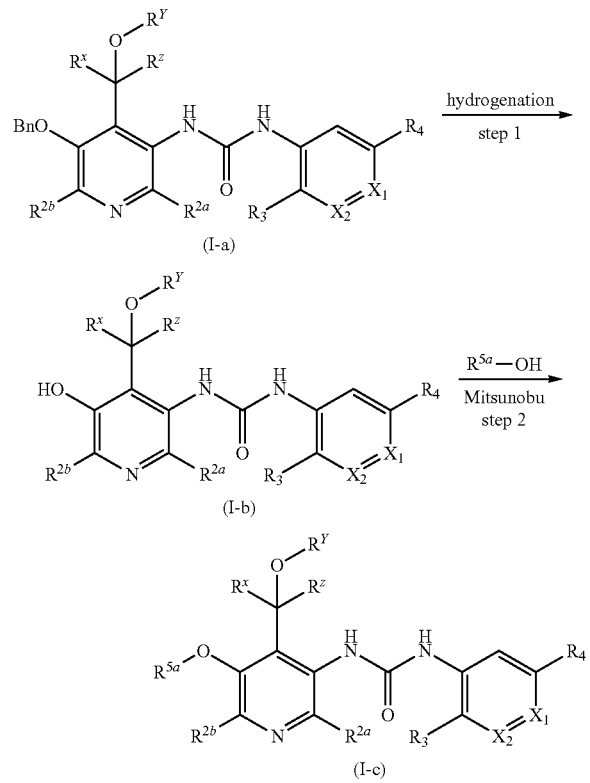

In scheme 14, '$R^{5a}$' is defined as $C_{1-4}$alkyl (optionally substituted) or $C_{3-6}$cycloalkyl. All other variables in Scheme 14 are defined according to the scope of the present invention.

In scheme 14, the following reaction conditions typically apply:
1: A Compound of Formula (I-a) is reacted with hydrogen gas, typically at a pressure of 15 psi (pounds per square inch) in the presence of a palladium catalyst such as palladium on carbon, optionally in the presence of an acid, such as hydrochloric acid, in a suitable solvent such as methanol or THF, at a suitable temperature of 25° C.
2: in the presence of an alcohol $R^{5a}$—OH, in the presence of (E)-diisopropyl diazene-1,2-dicarboxylate (DIAD) and triphenyl phosphine (PPh$_3$) in a suitable solvent such as THF or DMF or the like, in a suitable temperature range such as for example 0° C. to 40° C.

General Scheme 15

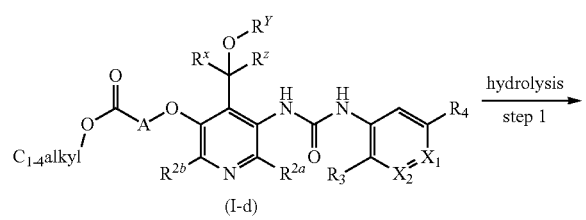

-continued

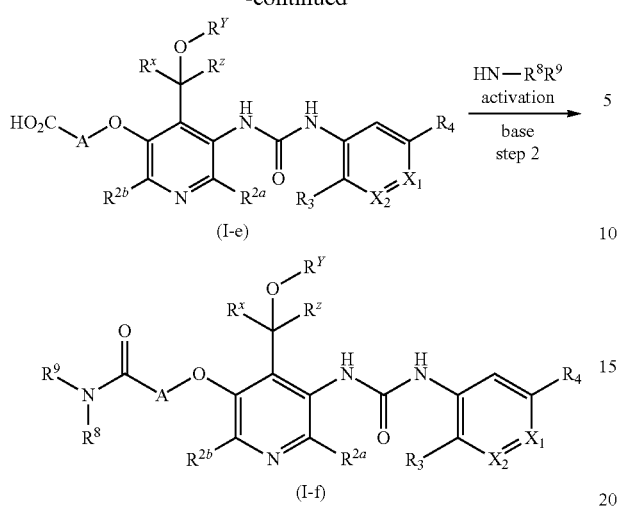

(I-e)

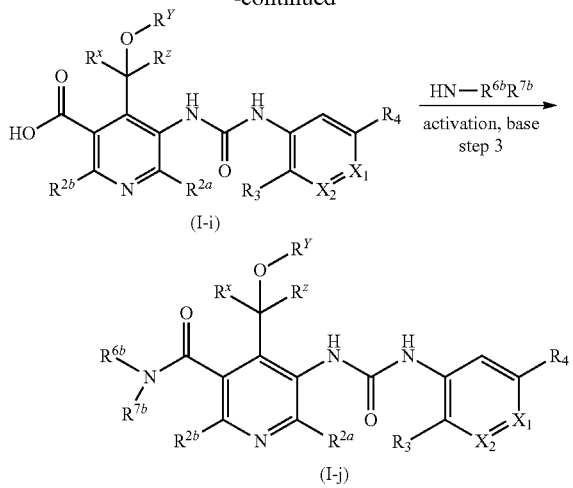

(I-i)

(I-f)

(I-j)

A = C$_{1-4}$alkyl

In scheme 15, 'A' is defined as C$_{1-4}$alkyl. All other variables in Scheme 15 are defined according to the scope of the present invention In scheme 15, the following reaction conditions typically apply:
1: Hydrolysis using lithium hydroxide in a suitable solvent mixture such as THF and water and an alcohol such as ethanol, at a suitable temperature such as for example room temperature.
2: Formation of an amide from a Compound (I-c), using an amine of the general formula HNR$^8$R$^9$ in the presence of an activating agent such as HATU and a suitable base, such as diisopropyl ethylamine (DIPEA) in a suitable solvent such as DMF, at a suitable temperature such as for example room temperature.

General Scheme

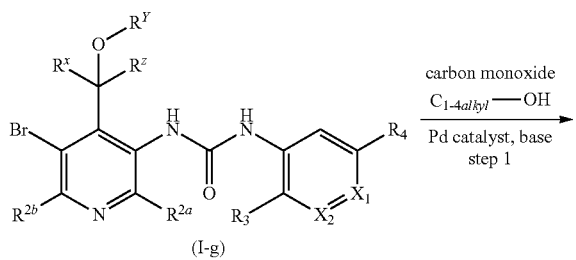

(I-g)

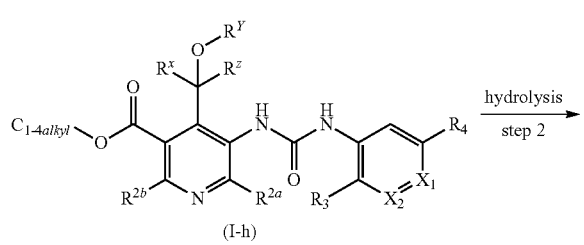

(I-h)

All variables in Scheme 16 are defined according to the scope of the present invention In scheme 16, the following reaction conditions typically apply:
1: A Compound of Formula (I-g) is treated under a carbon monoxide atmosphere at a suitable pressure, eg 60 Psi, in the presence of a catalyst such as Pd(dppf)Cl$_2$, in a suitable solvent such as C$_{1-4}$alkyl-OH optionally in the presence of THF, in a suitable temperature range of 60° C. to 100° C.
2: Hydrolysis using lithium hydroxide in a suitable solvent mixture such as water and an alcohol such as methanol or ethanol, optionally in the presence of THF, in a suitable temperature range of 20° C. to 40° C.
3: Formation of an amide from a Compound (I-c), using an amine of the general formula HNR$^{6b}$R$^{7b}$ in the presence of an activating agent such as HATU and a suitable base, such as diisopropyl ethylamine (DIPEA) in a suitable solvent such as DMF, at a suitable temperature such as for example room temperature.

In the preparation of compounds of the present invention, protection of remote functionality (e.g., primary amine) of intermediates may be necessary. The need for such protection will vary depending on the nature of the remote functionality and the conditions of the preparations methods. Suitable amino-protecting groups (NH-Pg) include t-butoxycarbonyl (Boc), acetyl .... The need for such protection is readily determined by one skilled in the art.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated there-from by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, New Jersey, 2007.

SPECIFIC EXAMPLES

In the following Examples, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

| Abbreviation | Meaning |
| --- | --- |
| ACN or MeCN | acetonitrile |
| aq. | aqueous |
| DINAP | (±)-2,2'-Bis(diphenylphosphino)-1,1'-binaphthalene |
| Boc | tert-butyloxycarbonyl |
| Boc$_2$O | tert-butoxycarbonyl anhydride |
| tBu | Tert-butyl |
| tBuONa or NaOtBu | sodium 2-methylpropan-2-olate |
| DCM | dichloromethane |
| DIAD | diisopropyl azodicarboxylate |
| DIEA or DIPEA | N,N-diisopropylethylamine |
| DMA | N,N-dimethylacetamide |
| DMAP | 4-(dimethylamino)pyridine |
| DME | 1,2-dimethoxyethane |
| DMF | N,N-dimethylformamide |
| DMSO | dimethyl sulfoxide |
| dppf | 1,1'-ferrocenediyl-bis(diphenylphosphine) |
| dtbbp | 4,4'-di-tert-butyl-2,2'-dipyridyl |
| Et | ethyl |
| EtOAc or EA | ethyl acetate |
| EtOH | ethanol |
| H or hrs | hour(s) |
| HATU | 1-[bis(dimethylamino)methylene]-1H-1,2,3-triazolo[4,5-b]pyridinium 3-oxid hexafluorophosphate |
| HPLC | high performance liquid chromatography |
| Ir[dF(CF$_3$)ppy]$_2$(dtbbpy)PF$_6$ | [4,4'-Bis(tert-butyl)-2,2'-bipyridine]bis[3,5-difluoro-2-[5-(trifluoromethyl)-2-pyridinyl]phenyl]iridium(III) hexafluorophosphate |
| LDA | lithium diisopropylamine |
| Me | methyl |
| MeI | methyl iodide |
| MeMgBr | methylmagnesium bromide |
| MeOH | methanol |
| mL | milliliters |
| mCPBA or m-CPBA | 3-chlorobenzenecarboperoxoic acid |
| mmol | millimoles |
| mg | milligram |
| min | minute(s) |
| NiCl$_2$•glyme | nickel(II) chloride ethylene glycol dimethyl ether complex |
| Pd/C | palladium on carbon |
| PCy$_3$ | tricyclohexylphosphine |
| Pd(dtbpf)Cl$_2$ | [1,1'-bis(di-tert-butylphosphino)ferrocene] dichloropalladium(II) |
| Pd(dppf)Cl$_2$ | [1,1'-bis(diphenylphosphino)ferrocene]dichloropalladium(II) |
| Pd(OAc)$_2$ | palladium(II) acetate |
| Pd$_2$(dba)$_3$ | tris(dibenzylideneacetone)dipalladium(0) |
| PPh$_3$ | triphenylphosphine |
| Pd(PPh$_3$)$_4$ | tetrakis(triphenylphosphine)palladium(0) |
| Psi | Pounds per square inch |
| PyBroP | bromotripyrrolidinophosphonium hexafluorophosphate |
| R$_t$ | retention time |
| RT or rt | room temperature |
| sat. | saturated |
| SFC | super critical fluid chromatography |
| TBS | tert-butyldimethylsilyl |
| TBSCl | tert-butyldimethylsilyl chloride |
| TEA or Et$_3$N | triethylamine |
| TFA | trifluoroacetic acid |
| THF | tetrahydrofuran |
| TLC | thin layer chromatography |
| Prep-TLC | preparative thin layer chromatography |
| Xanthpos | 4,5-bis(diphenylphosphino)-9,9-dimethylxanthene |

The skilled person will realize that in the examples described below, it may be advisable or necessary (even if not explicitly mentioned) to perform the reaction under an inert atmosphere, such as for example under N$_2$-gas atmosphere, for example when NaH, LDA or MeMgBr is used in the reaction (for example the synthesis of intermediate 55 or 56 was performed under inert atmosphere).

Synthesis of Compounds 1, 2 and 3

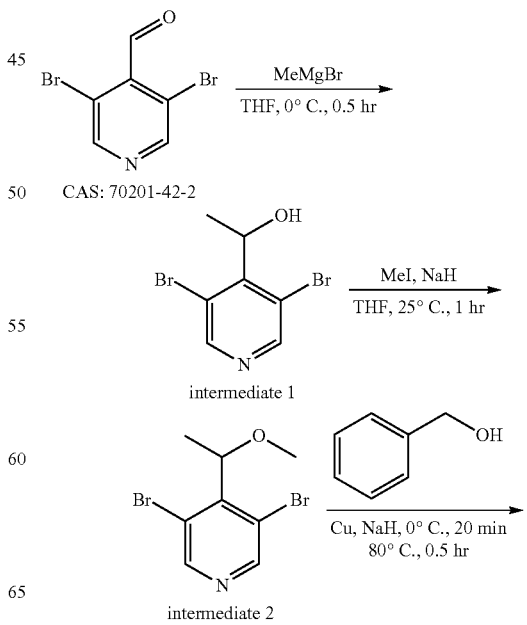

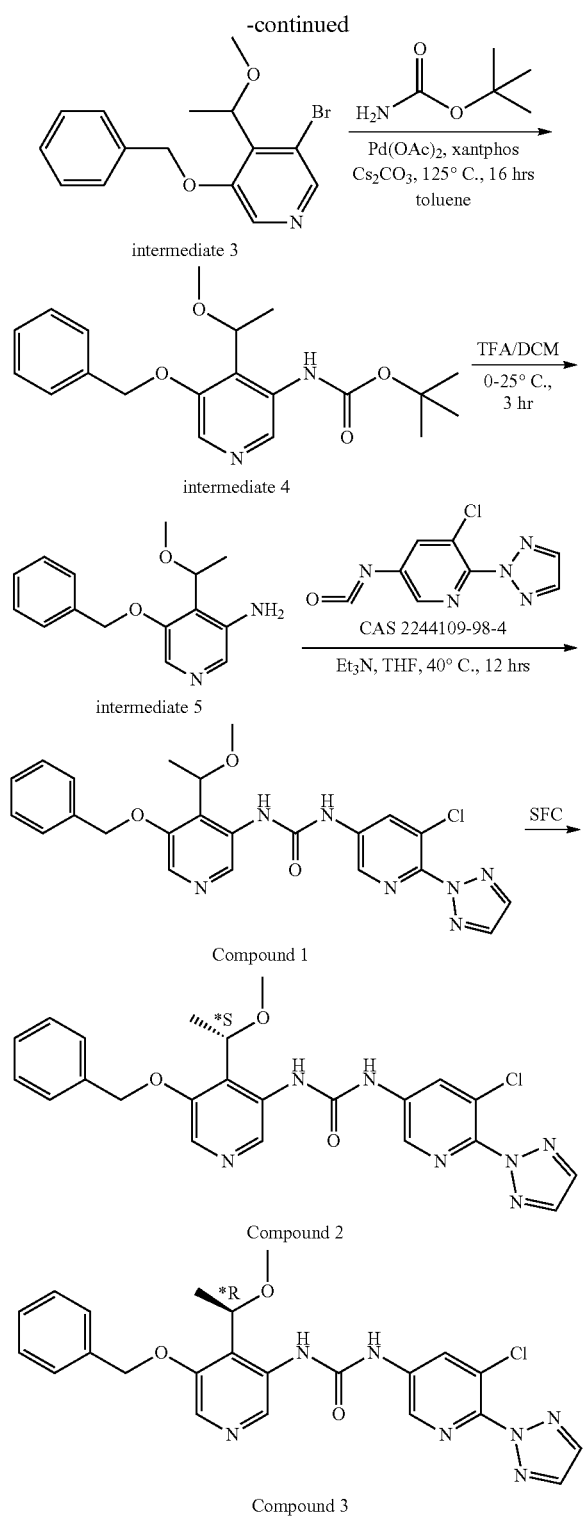

Preparation of Intermediate 1

To a solution of 3,5-dibromoisonicotinaldehyde (50 g, 189 mmol) in THF (200 mL) was added methylmagnesium bromide (3M in THF, 189 mL, 566 mmol) at 0° C. The mixture was allowed to warm to 20° C. and stirred at 20° C. for 1 hour. The mixture was quenched with sat.NH$_4$Cl aq. The mixture was extracted with EtOAc twice. The combined organic layers were washed with brine and dried with Na$_2$SO$_4$, filtered and the filtrate was concentrated in vacuum to give a crude product. The crude product was purified by flash column chromatography over silica gel (gradient elution: 0~15% EtOAc in petroleum ether). The desired fractions were collected and the solvent was concentrated under vacuum to afford intermediate 1 (40 g, yield: 75%) as light yellow solid.

Preparation of Intermediate 2

Intermediate 1 (40 g, 142 mmol) was dissolved in THF (150 mL) and sodium hydride (60% in mineral oil 8.5 g, 214 mmol) was added at 0° C. The mixture was stirred at 0° C. for 10 min. Then MeI (50.5 g, 356 mmol) was added and the mixture was stirred at 25° C. for 1 hour. Sat.NH$_4$Cl aq was added and extracted with EtOAc twice. The combined organic layers were washed with brine, dried over Na$_2$SO$_4$, filtered and concentrated under vacuum to give a crude product. The crude product was purified by column chromatography over silica gel (gradient elution: 0~10% EtOAc in petroleum ether). The desired fractions were collected and the solvent was concentrated under vacuum to afford intermediate 2 (39 g, yield: 93%) as white solid.

Preparation of Intermediate 3

To a mixture of benzyl alcohol (7.3 g, 69 mmol) in DMF (125 mL) was added sodium hydride (60% in mineral oil 2.7 g, 68 mmol) at 0° C. The mixture was stirred at 0° C. for 20 min. A solution of intermediate 2 (5.0 g, 17 mmol) in DMF (25 mL) was added dropwise. Then Cu powder (108 mg, 1.7 mmol) was added to the mixture and the reaction mixture was stirred at 80° C. for 0.5 hour. The mixture was allowed to warm to 25° C. and then brine was added. The mixture was extracted with EtOAc twice. The combined organic layers were washed with brine and dried over Na$_2$SO$_4$, filtered and the filtrate was concentrated in vacuum to give a crude product. The crude product was purified by flash column chromatography over silica gel (gradient elution: 0~5% EtOAc in petroleum ether). The desired fractions were collected and the solvent was concentrated in vacuum to give intermediate 3 (3.8 g, yield: 66%) as white solid.

Preparation of Intermediate 4

To a mixture of intermediate 3 (3.8 g, 11 mmol), and tert-butyl carbamate (2.6 g, 23 mmol) in toluene (150 mL) was added Cs$_2$CO$_3$ (14.7 g, 45.1 mmol). The mixture was degassed and then charged with N$_2$ for 10 min. Then Pd(OAc)$_2$ (380 mg, 1.7 mmol), and xantphos (652 mg, 1.1 mmol) were added and the mixture was stirred at 125° C. for 16 hours under N$_2$. The mixture was allowed to cool to 25° C. and filtered. The filtrate was concentrated to afford a crude product as yellow oil. The crude product was purified by flash column chromatography over silica gel (gradient elution: 0~27% EtOAc in petroleum ether). The desired fractions were collected and the solvent was concentrated in vacuum to give intermediate 4 (2.8 g, yield: 68%) as white solid.

Preparation of Intermediate 5

To a mixture of intermediate 4 (2.8 g, 7.7 mmol) in CH$_2$Cl$_2$ (45 mL) was added TFA (9 mL) at 0° C. The mixture was warmed to 25° C. and stirred for 3 hours. The mixture was neutralized with sat.Na$_2$CO$_3$ aq and extracted with CH$_2$Cl$_2$ twice. The combined organic layers were washed with brine, dried over Na$_2$SO$_4$, filtered and concentrated in vacuum to give a crude product. The crude product was purified by flash column chromatography over silica gel (gradient elution: 0~70% EtOAc in petroleum ether). The desired fractions were collected and the solvent was concentrated in vacuum to give intermediate 5 (1.8 g, yield: 90%) as light yellow solid.

Preparation of Compound 1

To a mixture of 3-chloro-5-isocyanato-2-(2H-1,2,3-triazol-2-yl)-pyridine CAS 2244109-98-4 (1.1 g, 4.9 mmol) and trimethylamine (1.4 mL, 10 mmol) in THF (20 mL) was added intermediate 5 (0.6 g, 2.3 mmol) at 25° C. The mixture was warmed to 40° C. and stirred for 12 hours. The reaction mixture was filtered and the filtrate was concentrated in vacuum to give a crude product as light yellow solid. To the crude product was added MeOH and the mixture was stirred at 25° C. for 15 min. Then the mixture was filtered, the filter cake was collected and dried in vacuum to give Compound 1 (1.0 g, yield: 89%) as white solid.

LC/MS: m/z 480.0 [M+H]⁺ method: B, purity: 99.5%, retention time: 0.727 min.

Preparation of Compounds 2 and 3

Compound 1 (100 mg, 0.2 mmol) was separated by SFC. [Column: DAICEL CHIRALCEL OJ-H (250 mm*30 mm, 5 μm), Condition: A: Supercritical CO₂, B: 0.1% NH₃H₂O EtOH; at the beginning: A (55%) and B (45%), at the end: A (55%) and B (45%), Flow Rate (ml/min) 40]. The pure fractions were collected and the organic solvent was evaporated under vacuum. MeCN and H₂O were added to the residue and it was lyophilized to dryness to give Compound 2 (42 mg, yield: 43%) and Compound 3 (46 mg, yield: 46%) as white solid.

Compound 2:

LC/MS: m/z 480.2 [M+H]⁺, rt 3.47 min. Purity 100%, method K

SFC: purity 100%, rt 5.66 min. method: SFC1

Compound 3:

LC/MS: m/z 480.2 [M+H]⁺, rt 3.47 min. Purity 100%, method K

SFC: purity 100%, rt 6.76 min. method: SFC1

Synthesis of Compounds 4, 5 and 6

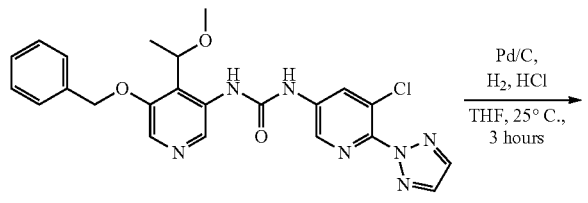

Compound 1

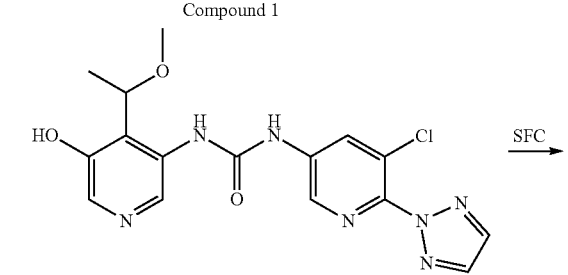

Compound 4

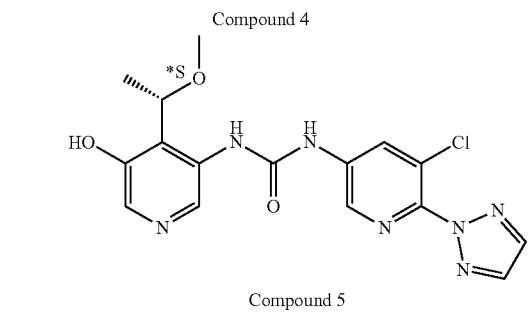

Compound 5

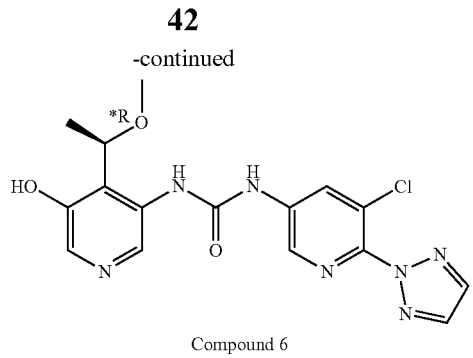

Compound 6

Preparation of Compound 4

A mixture of Compound 1 (500 mg, 1.1 mmol) in THF (100 mL) in the presence of concentrated HCl (1 mL) was hydrogenated at 25° C. (15 Psi) with Pd/C (500 mg, 10% wet) as a catalyst. The reaction mixture was stirred at 25° C. for 3 hours. After uptake of H₂ (1 equiv), the catalyst was filtered off and the filtrates were neutralized with sat. NaHCO₃ aq. and extracted with EtOAc twice. The combined organic layers were washed with brine, dried over Na₂SO₄, filtered and concentrated in vacuum to give Compound 4 (330 mg, yield: 75.9%) as white solid.

LC/MS: m/z 390.0 [M+H]⁺, rt: 0.77 min, purity: 93%, method: A

Preparation of Compounds 5 and 6

Compound 4 (100 mg, 0.2 mmol) was separated by SFC. [Column: DAICEL CHIRALPAK AD-H (250 mm*30 mm, 5 μm), Condition: solvent, A: Supercritical CO₂. Solvent, B: 0.1% aqueous ammonia in EtOH. At the beginning: A (65%) and B (35%), at the end: A (65%) and B (35%), Flow Rate (ml/min) 70]. The pure fractions were collected and the organic solvent was evaporated under vacuum. MeCN and H₂O were added to the residue and the mixture was lyophilized to dryness to give Compound 5 (40 mg, yield: 42%) and Compound 6 (41 mg, yield: 43%) as white solid.

Compound 5:

HPLC-MS: m/z 390.1 [M+H]⁺, rt: 2.84 min, purity: 97.2%, method: M

SFC: purity 100%, rt: 1.87 min, method: SFC9

Compound 6:

HPLC-MS: m/z 390.1 [M+H]⁺, rt: 2.84 min, purity: 95.9%, method: M

SFC: purity 99.6%, rt: 2.13 min, method: SFC9

Synthesis of Compound 7

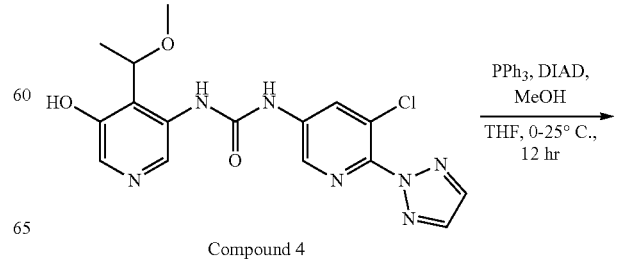

Compound 4

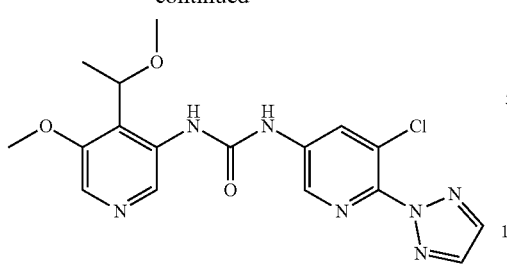

Compound 7

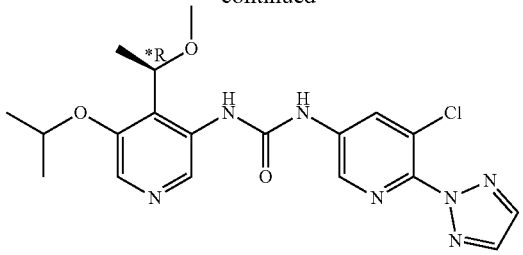

Compound 9

Preparation of Final Compound 7

To a mixture of Compound 4 (250 mg, 0.6 mmol), methanol (200 mg, 6.4 mmol) and triphenylphosphine (336 mg, 1.3 mmol) in THF (12 mL), was added (E)-diisopropyl diazene-1,2-dicarboxylate (259 mg, 1.3 mmol) at 0° C. The reaction mixture was stirred at 25° C. for 16 hours. The reaction mixture was concentrated in vacuum to give a crude product. The crude product was purified by preparative high-performance liquid chromatography. [Column: PhenomenexGemini 150*25 mm*10 um, Condition: A: water (0.04% aqueous ammonia+10 mM $NH_4HCO_3$), B: MeCN. At the beginning: A (82%) and B (18%), at the end: A (52%) and B (48%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 7 (146 mg, yield: 56.5%) as white solid.

Compound 7:

LC/MS: m/z 404.1 $[M+H]^+$, rt: 3.61 min, Purity: 99.7%, method: K.

SFC: purity 48.6%/51.4%, rt: 6.30 min/7.14 min, method: SFC6.

Synthesis of Compounds 8, 9 and 10

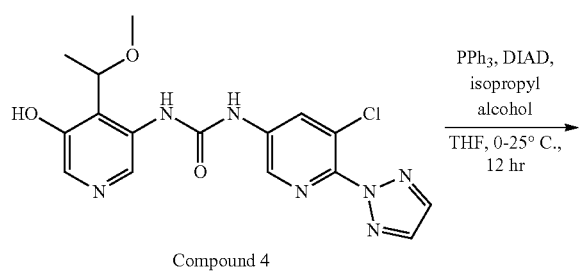

Compound 4

PPh₃, DIAD,
isopropyl
alcohol
THF, 0-25° C.,
12 hr

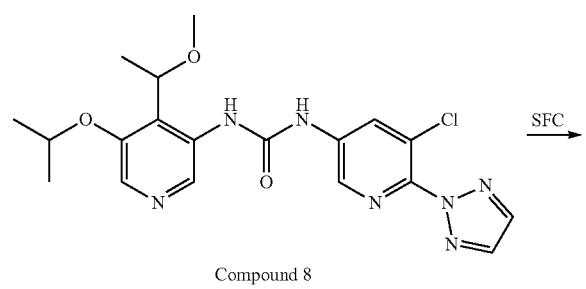

Compound 8

SFC

Compound 10

Preparation of Compound 8

Compound 8 was prepared by analogy to the procedure described for Compound 7, using isopropyl alcohol. The compound was purified by preparative high-performance liquid chromatography. [Column: PhenomenexGemini 150*25 mm*10 um, Condition: A: water (0.04% aqueous ammonia+10 mM $NH_4HCO_3$), B: MeCN. At the beginning: A (60%) and B (40%), at the end: A (30%) and B (70%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 8 (100 mg, yield: 29.5%) as white solid.

LC/MS: m/z 432.0 $[M+H]^+$, rt: 0.69 min, Purity: 100%, method: A.

SFC: purity 49.6%/50.4%, rt: 1.64 min/2.04 min, method: SFC9

Preparation of Compounds 9 and 10

Compound 8 (100 mg, 0.2 mmol) was separated by SFC. [Column: DAICEL CHIRALPAK AD-H (250 mm*30 mm, 5 μm), Condition: solvent, A: Supercritical $CO_2$. Solvent, B: 0.1% aqueous ammonia in EtOH. At the beginning: A (55%) and B (45%), at the end: A (55%) and B (45%), Flow Rate (ml/min) 50]. The pure fractions were collected and the organic solvent was evaporated under vacuum. MeCN and $H_2O$ was added to the residue and the mixture was lyophilized to dryness to give Compound 9 (37 mg, yield: 37%) and Compound 10 (36 mg, yield: 35%) as white solid.

Compound 9:

LC/MS ESI-MS: m/z 432.2 $[M+H]^+$, rt: 3.87 min, purity: 99.8%, method: K

SFC: purity 100%, rt: 1.66 min, method: SFC9

Compound 10:

LC/MS ESI-MS: m/z 432.2 $[M+H]^+$, rt: 3.88 min, purity: 98.4%, method: K

SFC: purity 99.8%, rt: 2.01 min, method: SFC9

Synthesis of Compound 11

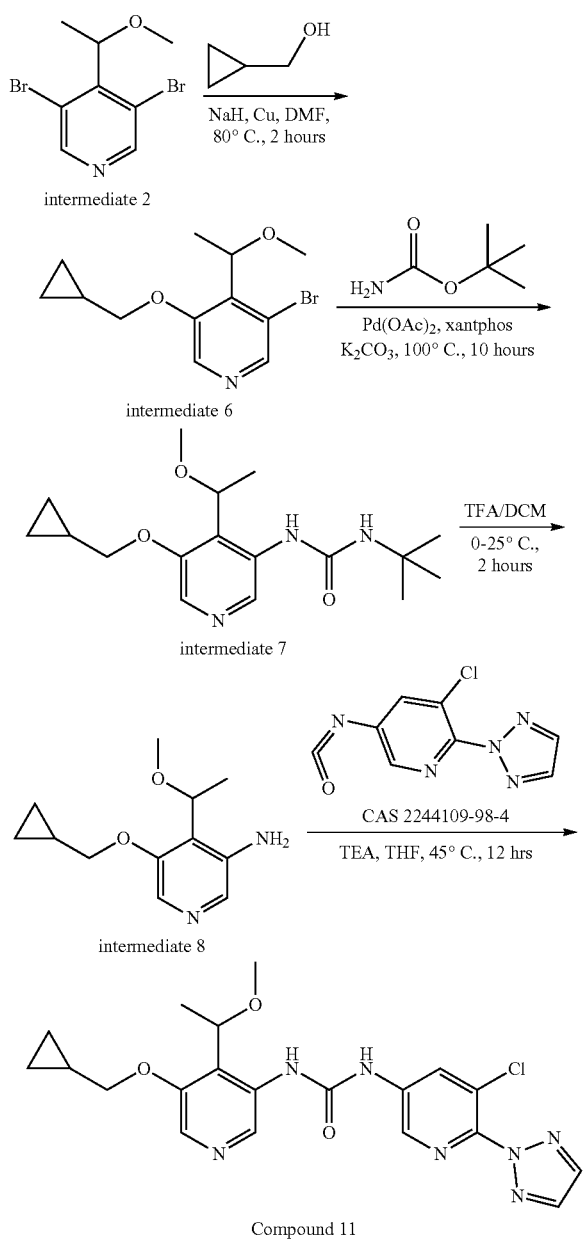

intermediate 2 intermediate 6 intermediate 7 intermediate 8

Compound 11

Preparation of Intermediate 6

To a mixture of cyclopropyl methanol (978 mg, 13.6 mmol) in DMF (20 mL) was added Sodium hydride (542 mg, 13.6 mmol, 60% in mineral oil) and the mixture was stirred at 25° C. for 1 hour. A solution of intermediate 2 (1.0 g, 3.4 mmol) in DMF (5 mL) was added dropwise. Then copper powder (22 mg, 0.34 mmol) was added and the mixture was stirred at 80° C. for 0.5 hour. The mixture was allowed to cool to 25° C. and was quenched with sat.NH$_4$Cl aq. The mixture was extracted with EtOAc twice. The combined organic layers were washed with brine, dried over Na$_2$SO$_4$, filtered and concentrated in vacuum to give a crude product. The crude product was purified by flash column chromatography over silica gel (gradient elution: 0~6% EtOAc in petroleum ether). The desired fractions were collected and the solvent was concentrated in vacuum to give intermediate 6 (600 mg, yield: 60%) as white solid.

Preparation of Intermediate 7

A mixture of intermediate 6 (0.5 g, 1.7 mmol), tert-butyl carbamate (0.4 g, 3.4 mmol) and Cs$_2$CO$_3$ (2.2 g, 6.8 mmol) in toluene (25 mL) was degassed with N$_2$ for 10 min. Then Pd(OAc)$_2$ (57 mg, 0.26 mmol) and xantphos (98 mg, 0.17 mmol) were added and the mixture was stirred at 120° C. for 12 hours under N$_2$. The mixture was cooled to 25° C. and was filtered. The filtrate was concentrated to afford a crude product. The crude product was purified by flash column chromatography over silica gel (gradient elution: 0~27% EtOAc in petroleum ether). The desired fractions were collected and the solvent was concentrated to dryness under vacuum to give intermediate 7 (0.5 g, yield: 89.3%) as colorless oil.

Preparation of Intermediate 8

To a solution of intermediate 7 (0.3 g, 0.9 mmol) in CH$_2$Cl$_2$ (5 mL) was added TFA (1 mL) at 25° C. The mixture was stirred at 25° C. for 2 hours. Sat.NaHCO$_3$ aq. was added and the mixture was extracted with CH$_2$Cl$_2$ twice. The combined organic layers were washed with brine, dried over Na$_2$SO$_4$, filtered and concentrated in vacuum to give a crude product. The crude product was purified by flash column chromatography over silica gel (gradient elution: 0~30% EtOAc in petroleum ether). The desired fractions were collected and the solvent was concentrated in vacuum to give intermediate 8 (0.3 g, yield: 96%) as light yellow solid.

Preparation of Compound 11

To a solution of 3-chloro-5-isocyanato-2-(2H-1,2,3-triazol-2-yl)pyridine (CAS 2244109-98-4) (540 mg, 2.4 mmol) and triethylamine (0.7 mL, 4.8 mmol) in THF (20 mL) was added a solution of intermediate 8 (200 mg, 0.9 mmol) in THF (5 mL) at 25° C. The reaction mixture was stirred at 40° C. for 12 hours. The mixture was allowed to reach 25° C. and was filtered. The filtrate was diluted with H$_2$O, and the resulting mixture was extracted with EtOAc twice. The combined organic layers were washed with brine, dried over Na$_2$SO$_4$, filtered and concentrated in vacuum to give a crude product. The crude product was purified by preparative high-performance liquid chromatography. [Column: PhenomenexGemini 150*25 mm*10 um, Condition: A: water (0.04% aqueous ammonia+10 mM NH$_4$HCO$_3$), B: MeCN. At the beginning: A (55%) and B (45%), at the end: A (25%) and B (75%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 11 (156 mg, yield: 40%) as white solid.

Compound 11:

LC/MS: m/z 444.2 [M+H]$^+$, rt: 3.97 min, method: K, Purity: 99.2%,

SFC: purity 49.1%/50.9%, rt: 2.99 min/3.29 min, method: SFC3

Synthesis of Compound 12

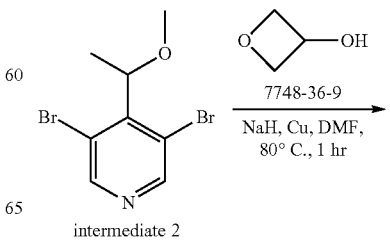

intermediate 2

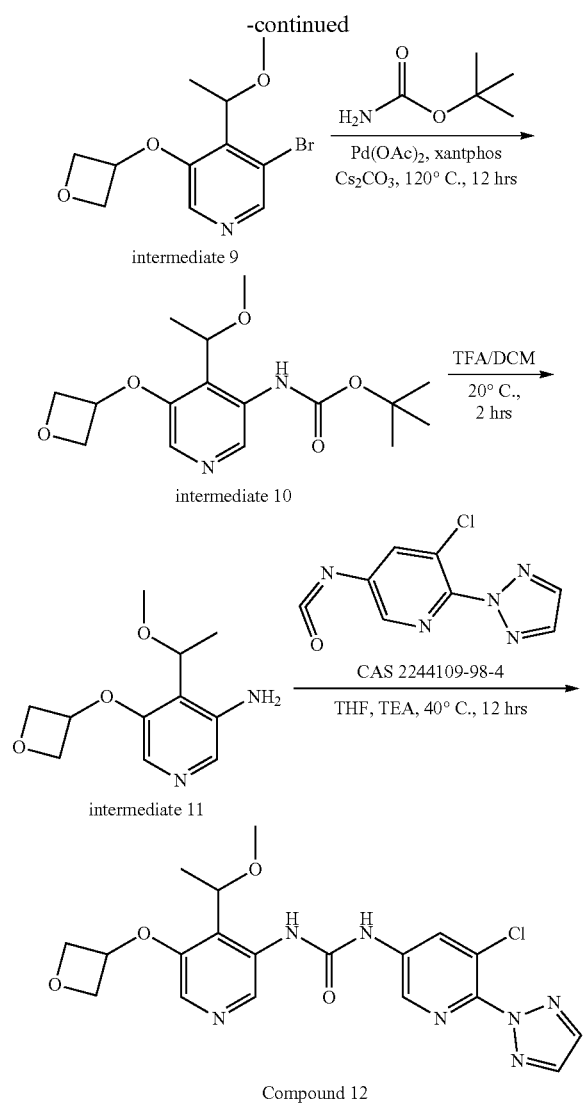

intermediate 9 intermediate 10 intermediate 11

Compound 12

Preparation of Intermediate 9

To a mixture of oxetan-3-ol (CAS 7748-36-9, 0.99 g, 13.3 mmol) in DMF (20 mL) was added sodium hydride (0.53 g, 13.3 mmol, 60% in mineral oil) and the mixture was stirred at 20° C. for 20 min. A solution of intermediate 2 (1.0 g, 3.3 mmol) in DMF (5 mL) was added dropwise. Then copper powder (22 mg, 0.34 mmol) was added and the mixture was stirred at 80° C. for 1 hour. The reaction mixture was allowed to cool to 25° C. and quenched with sat.NH$_4$Cl aq. The mixture was extracted with EtOAc twice. The combined organic layers were washed with brine, dried over Na$_2$SO$_4$, filtered and concentrated in vacuum to give a crude product. The crude product was purified by flash column chromatography over silica gel (gradient elution: 0~22% EtOAc in petroleum ether). The desired fractions were collected, and the solvent was concentrated in vacuum to give intermediate 9 (560 mg, yield: 56.7%) as white solid.

Preparation of Intermediate 10

A mixture of intermediate 9 (560 mg, 1.9 mmol), tert-butyl carbamate (442 mg, 3.8 mmol) and Cs$_2$CO$_3$ (2.5 g, 7.6 mmol) in toluene (35 mL) was degassed and then charged with N$_2$ for 10 min. Then Pd(OAc)$_2$ (64 mg, 0.28 mmol) and xantphos (109 mg, 0.19 mmol) were added and the mixture was stirred at 120° C. for 16 hours under N$_2$. The mixture was allowed to reach 25° C. and filtered. The filtrate was concentrated to afford a crude product. The crude product was purified by flash column chromatography over silica gel (gradient elution: 0~50% EtOAc in petroleum ether). The desired fractions were collected and the solvent was concentrated to dryness under vacuum to give intermediate 10 (600 mg, yield: 96%) as colorless oil.

Preparation of Intermediate 11

To a solution of intermediate 10 (300 mg, 0.9 mmol) in CH$_2$Cl$_2$ (5 mL) was added TFA (1 mL) at 25° C. The mixture was stirred at 25° C. for 2 hours. Sat.NaHCO$_3$ aq. was added and the mixture was extracted with CH$_2$Cl$_2$ twice. The combined organic layers were washed with brine, dried over Na$_2$SO$_4$, filtered and concentrated in vacuum to give a crude product. The crude product was purified by flash column chromatography over silica gel (gradient elution: 0~100% EtOAc in petroleum ether). The desired fractions were collected, and the solvent was concentrated in vacuum to give intermediate 11 (170 mg, yield: 83%) as white solid.

Preparation of Compound 12

To a solution of 3-chloro-5-isocyanato-2-(2H-1,2,3-triazol-2-yl)pyridine (CAS 2244109-98-4) (410 mg, 1.8 mmol) in THF (15 mL) was added triethylamine (0.5 mL, 3.6 mmol) at 25° C. A solution of intermediate 11 (150 mg, 0.7 mmol) in THF (5 mL) was added, the mixture was warmed to 40° C. and stirred for 12 hours. The reaction mixture was allowed to cool to 25° C. and filtered. The filtrate was washed with H$_2$O and extracted with EtOAc twice. The combined organic layers were washed with brine, dried over Na$_2$SO$_4$, filtered and concentrated in vacuum to give a crude product. The crude product was purified by preparative high-performance liquid chromatography. [Column: PhenomenexGemini 150*25 mm*10 um, Condition: A: water (0.04% aqueous ammonia+10 mM NH$_4$HCO$_3$), B: MeCN. At the beginning: A (77%) and B (23%), at the end: A (47%) and B (53%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 12 (113 mg, yield: 37%) as white solid.

Compound 12:

LC/MS: m/z 446.1 [M+H]$^+$, rt: 3.39 min, Purity: 97.8%, method: K.

SFC: purity 49.3%/50.7%, rt: 3.69 min/4.15 min, method: SFC2

Synthesis of Compound 13

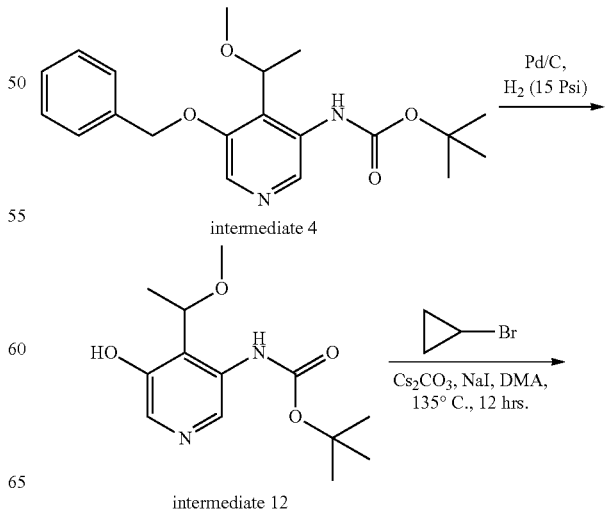

intermediate 4 intermediate 12

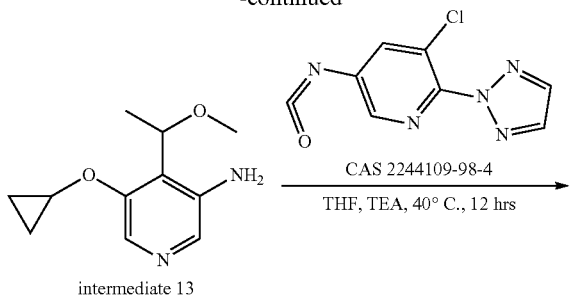

intermediate 13

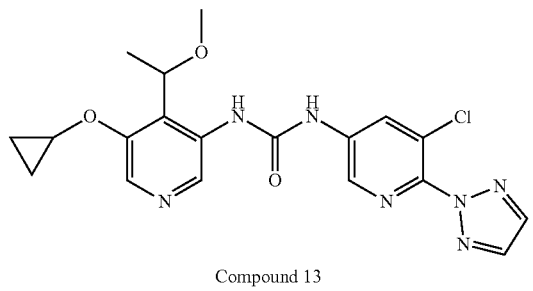

Compound 13

Preparation of Intermediate 12

A mixture of intermediate 4 (2 g, 5.6 mmol) in MeOH (100 mL) was hydrogenated at 25° C. (15 Psi) with Pd/C (1 g, 10% wet) as a catalyst. The reaction mixture was stirred at 25° C. for 2 hours. After uptake of $H_2$ (1 equiv), the catalyst was filtered off and the filtrate was concentrated in vacuum to give a crude product. The crude product was purified by flash column chromatography over silica gel (gradient elution: 0~30% EtOAc in petroleum ether). The desired fractions were collected and the solvent was concentrated under vacuum to afford intermediate 12 (1.4 g, yield: 92%) as white solid.

Preparation of Intermediate 13

To a mixture of intermediate 12 (0.5 g, 1.8 mmol), $Cs_2CO_3$ (1.8 g, 5.5 mmol) and NaI (28 mg, 0.2 mmol) in DMA (20 mL) was added bromocyclopropane (0.45 g, 3.7 mmol) at 25° C. The mixture was stirred at 135° C. for 12 hours. The reaction mixture was allowed to cool to 25° C. and filtered. To the filtrate was added $H_2O$ and the mixture was extracted with EtOAc twice. The combined organic layers were washed with brine, dried over $Na_2SO_4$, filtered and concentrated in vacuum to give a crude product. The crude product was purified by flash column chromatography over silica gel (gradient elution: 0~40% EtOAc in petroleum ether). The desired fractions were collected and the solvent was concentrated to dryness under vacuum to give intermediate 13 (100 mg, yield: 23.5%) as yellow solid.

Preparation of Compound 13

To a solution of 3-chloro-5-isocyanato-2-(2H-1,2,3-triazol-2-yl)pyridine (CAS 2244109-98-4) (287 mg, 1.3 mmol) in THF (15 mL) was added triethylamine (0.9 mL, 6.5 mmol). A solution of intermediate 13 (100 mg, 0.4 mmol) in THF (5 mL) was added to the reaction mixture at 25° C. The mixture was warmed to 40° C. and stirred for 12 hours. The reaction mixture was allowed to reach 25° C. and filtered. The filtrate was concentrated in vacuum to give a crude product. The crude product was purified by preparative high-performance liquid chromatography. [Column: PhenomenexGemini 150*25 mm*10 um, Condition: A: water (0.04% aqueous ammonia+10 mM $NH_4HCO_3$), B: MeCN. At the beginning: A (65%) and B (35%), at the end: A (35%) and B (65%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 13 (32 mg, yield: 17%) as white solid.

Compound 13:

LC/MS: m/z 430.1 $[M+H]^+$, rt: 3.66 min, Purity: 98.9%, method: K.

SFC: purity 49.9%/50.1%, rt: 3.72 min/4.02 min, method: SFC4

Synthesis of Compounds 14, 15 and 16

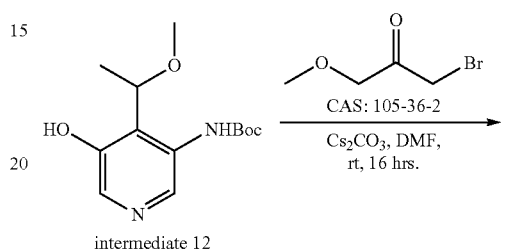

intermediate 12

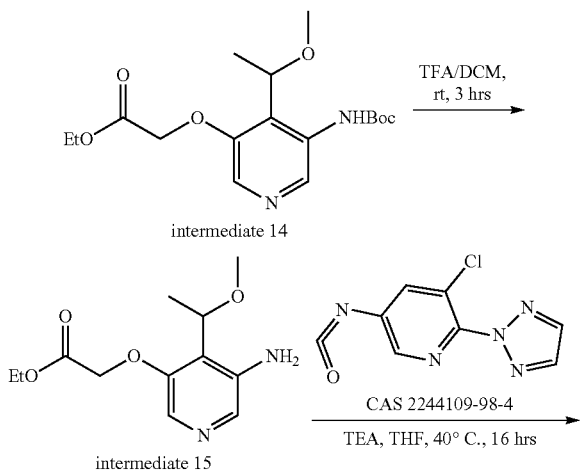

intermediate 14 intermediate 15

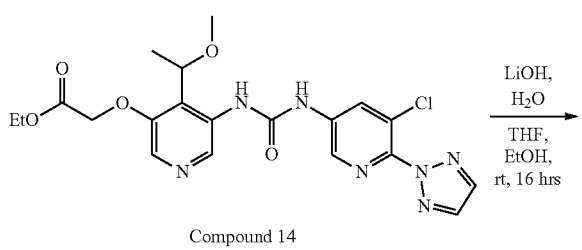

Compound 14

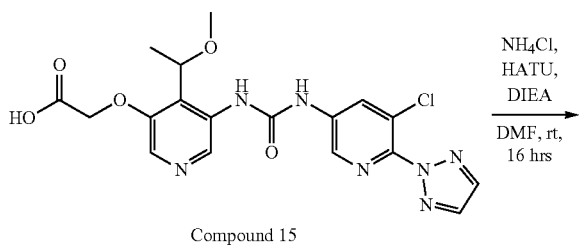

Compound 15

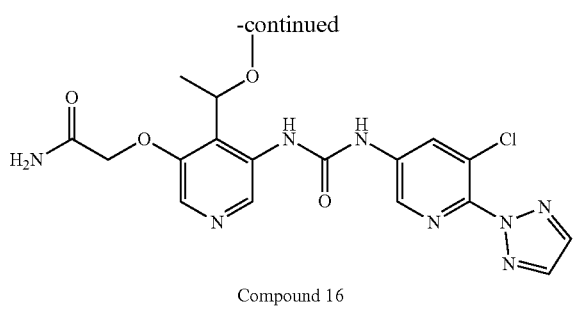

Compound 16

Preparation of Intermediate 14

To a mixture of intermediate 12 (200 mg, 0.74 mmol) and ethyl bromoacetate (249 mg, 1.5 mmol) in DMF (5 mL) was added Cs$_2$CO$_3$ (971 mg, 3 mmol). The mixture was stirred at 25° C. for 16 hours. The mixture was quenched with brine and extracted with EtOAc twice. The combined organic layers were washed with brine, dried over Na$_2$SO$_4$, filtered and the filtrate was concentrated in vacuum to give a crude product. The crude product was purified by a flash column chromatography over silica gel (gradient elution: 0~50% EtOAc in petroleum ether). The desired fractions were collected and the solvent was concentrated under vacuum to afford intermediate 14 (130 mg, yield: 42%) as yellow oil.

Preparation of Intermediate 15

To a solution of intermediate 14 (260 mg, 0.7 mmol) in DCM (10 mL) was added TFA (2 mL) at 0° C. The mixture was stirred at 25° C. for 3 hours. Most of the solvent was removed under vacuum to give a yellow gum. The yellow gum was dissolved in CH$_2$Cl$_2$. Sat. Na$_2$CO$_3$ aq. was added to the mixture and the mixture was extracted with CH$_2$Cl$_2$ twice. The combined organic layers were washed with brine, dried over Na$_2$SO$_4$, filtered and the filtrate was concentrated in vacuum to give a crude product. The crude product was purified by flash column chromatography over silica gel (gradient elution: 0~25% EtOAc in petroleum ether). The desired fractions were collected and the solvent was concentrated under vacuum to afford intermediate 15 (160 mg, yield: 86%) as yellow solid.

Preparation of Compound 14

To a solution of 3-chloro-5-isocyanato-2-(2H-1,2,3-triazol-2-yl)pyridine (CAS 2244109-98-4) (471 mg, 2.1 mmol) in THF (10 mL) was added triethylamine (1.6 mL, 11.8 mmol). Then a solution of intermediate 15 (150 mg, 0.6 mmol) in THF (5 mL) was added at 25° C. The mixture was stirred at 40° C. for 16 hours. The mixture was concentrated in vacuum to give a crude product. The crude product was stirred in (petroleum ether/ethyl acetate=1:1) for 10 min. The mixture was filtered and the filtrate was concentrated under vacuum to afford the crude product as yellow solid. The crude product was purified by preparative high-performance liquid chromatography. [Column: Xtimate C18 10μ 250 mm*50 mm, Condition: A: water (0.04% NH$_3$H$_2$O+10 mM NH$_4$HCO$_3$), B: MeCN. At the beginning: A (60%) and B (40%), at the end: A (30%) and B (70%), Gradient Time: 8 min; 100% B Hold Time: 0 min; Flow Rate: 25 ml/min]. The pure fractions were collected and the organic solvent was evaporated under vacuum. The aqueous layer was lyophilized to dryness to give Compound 14 (150 mg, yield: 33%) as white solid.

LC/MS: m/z 476.1 [M+H]$^+$, rt 3.77 min, purity 95.1%, method: K.

SFC: purity 49.9%/50.1%, rt: 4.26 min/4.56 min, method: SFC4

Preparation of Compound 15

To a solution of Compound 14 (200 mg, 0.2 mmol) in THF (4 mL), H$_2$O (1 mL), EtOH (0.2 mL) was added LiOH (50 mg, 1.2 mmol). The mixture was stirred at 25° C. for 16 hours. Water was added to the mixture and the mixture was extracted with EtOAc. The aqueous layer was adjusted to pH=6 with HCl (2 M in water). The aqueous layer was extracted with EtOAc twice. The combined organic layers were washed with brine, dried over Na$_2$SO$_4$, filtered and the filtrate was concentrated in vacuum to give Compound 15 (200 mg, crude) as white solid.

LC/MS: m/z 448.1 [M+H]$^+$, rt: 1.04 min, purity: 49.4%, method: E

Preparation of Compound 16

To a solution of Compound 15 (180 mg, 0.2 mmol) and NH$_4$Cl (32 mg, 0.59 mmol) in DMF (20 mL) was added HATU (113 mg, 0.3 mmol) and N,N-diisopropylethylamine (0.1 mL, 0.6 mmol) at 25° C. The mixture was stirred at 25° C. for 16 hours. The reaction mixture was filtered. The filtrates were concentrated under vacuum to afford crude product as brown oil. The crude product was purified by preparative high-performance liquid chromatography. [Column: Xtimate C18 10μ 250 mm*50 mm Condition: A: water (0.04% NH$_3$H$_2$O+10 mM NH$_4$HCO$_3$) B: MeCN. At the beginning: A (77%) and B (23%) At the end: A (47%) and B (53%). Gradient Time (min): 8; 100% B Hold Time (min) 0; Flow Rate (ml/min) 25]. The pure fractions were collected and the solvent was evaporated under vacuum, lyophilized to dryness to give Compound 16 (10 mg, 11% yield) as white solid.

HPLC-MS: m/z 447.1 [M+H]$^+$, rt: 3.63 min, purity: 98.5%, method: M.

SFC: purity: 50.6%/49.4%, rt: 4.98 min/5.49 min, method: SFC8

Synthesis of Compounds 17, 18 and 19

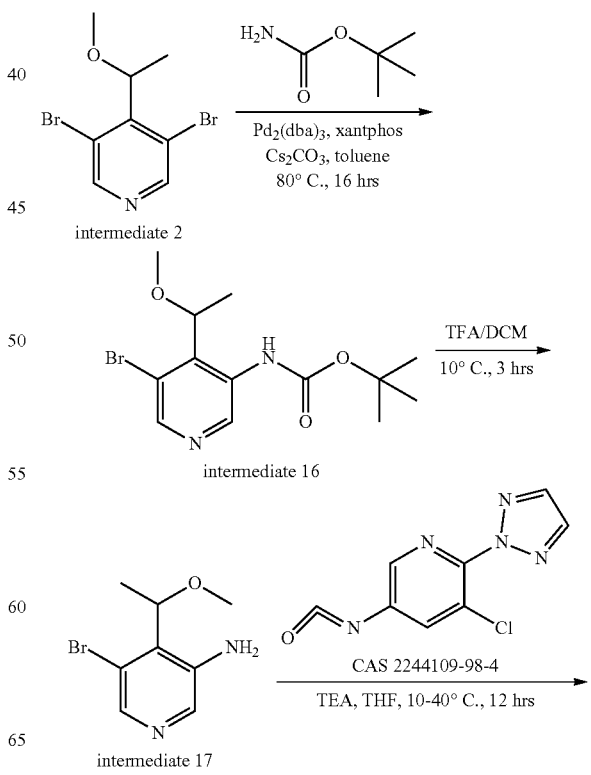

intermediate 2 intermediate 16 intermediate 17

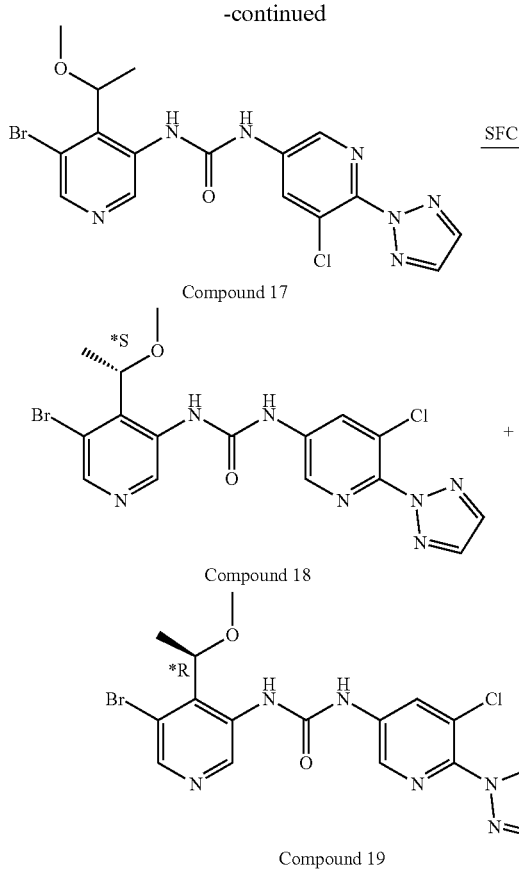

Compound 17

Compound 18

Compound 19

Preparation of Intermediate 16

A mixture of intermediate 2 (10 g, 33.9 mmol), tert-butyl carbamate (4 g, 33.9 mmol) and Cs$_2$CO$_3$ (22 g, 67.8 mmol) in toluene (50 mL) was degassed with N$_2$ for 10 min. Then Pd$_2$(dba)$_3$ (2.5 g, 2.9 mmol), xantphos (2.59 g, 5 mmol) was added and the mixture was stirred at 80° C. for 16 hours under N$_2$. The mixture was filtered and the filtrate was concentrated to afford a crude product as yellow oil. The crude product was purified by flash column chromatography over silica gel (gradient elution: 0~20% EtOAc in petroleum ether). The desired fractions were collected and the solvent was concentrated to dryness under vacuum to give intermediate 16 (6.5 g, yield: 58%) as white solid.

Preparation of Intermediate 17

To a solution of intermediate 16 (5.9 g, 17.8 mmol) in CH$_2$Cl$_2$ (100 mL) was added 2,2,2-trifluoroacetic acid (40 mL). The mixture was stirred at 10° C. for 3 hours. The majority of the solvent was removed under vacuum to give a yellow gum. The yellow gum was dissolved in CH$_2$Cl$_2$. NaHCO$_3$ was added to the mixture and the mixture was extracted with CH$_2$Cl$_2$ twice. The combined organic layers were washed with brine and dried with Na$_2$SO$_4$, filtered and the filtrate was concentrated in vacuum to give a yellow solid. The yellow solid was purified by flash column chromatography over silica gel (gradient elution: 0~25% EtOAc in petroleum ether). The desired fractions were collected and the solvent was concentrated in vacuum to give intermediate 17 (3.3 g, yield: 81%) as white solid.

Preparation of Compound 17

To a solution of 3-chloro-5-isocyanato-2-(2H-1,2,3-triazol-2-yl)pyridine (CAS 2244109-98-4) (3.5 g, 15.8 mmol) in THF (15 mL) was added trimethylamine (4 mL, 30 mmol) at 10° C. Then a solution of intermediate 17 (0.5 g, 2.1 mmol) in THF (15 mL) was added. The mixture was stirred at 40° C. for 12 hours. The mixture was cooled to 25° C. The mixture was evaporated under vacuum to give a yellow solid. The mixture was dissolved in methanol, and stirred at 10° C. for 0.5 hour. The mixture was filtered and the filtrate was evaporated under vacuum to give a yellow solid. The yellow solid was dissolved in methanol. The mixture was stirred at 10° C. for 0.5 hour to give a precipitate. The mixture was filtered and Compound 17 (420 mg, 0.9 mmol) was obtained as yellow solid.

LC/MS: m/z 452 [M+H]$^+$, rt 0.92 min, purity 96.9%, method A.

Preparation of Compounds 18 and 19

Compound 17 (124 mg, 0.26 mmol) was separated by SFC [Column: YMC CHIRAL Amylose-C (250 mm*30 mm, 5 μm), Condition: solvent A: Supercritical CO$_2$, solvent B: 0.1% aqueous ammonia in EtOH, at the beginning: A (55%) and B (45%), at the end: A (55%) and B (45%), Flow Rate (ml/min) 50]. The pure fractions were collected and the organic solvent was evaporated under vacuum. MeCN and H$_2$O were added to the residue and it was lyophilized to dryness to give Compound 18 (44 mg, yield: 36.3%) as white solid and Compound 19 (43 mg, yield: 35.9%) as white solid.

Compound 18:

LC/MS: m/z 452 [M+H]$^+$, rt 4.43 min. Purity 99.5%, method K

SFC: purity 100%, rt 1.73 min. method: SFC15

Compound 19:

LC/MS: m/z 452 [M+H]$^+$, rt 4.43 min. Purity 99.8%, method K

SFC: purity 99.2%, rt 2.36 min. method: SFC15

Synthesis of Compound 20

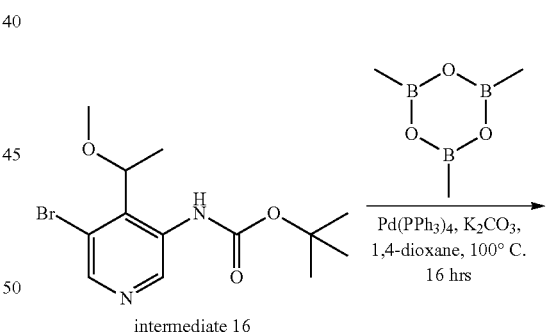

intermediate 16

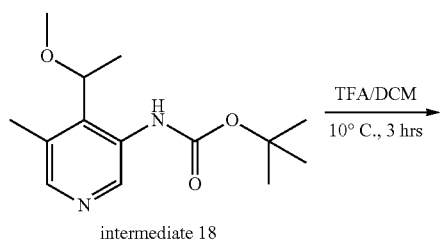

intermediate 18

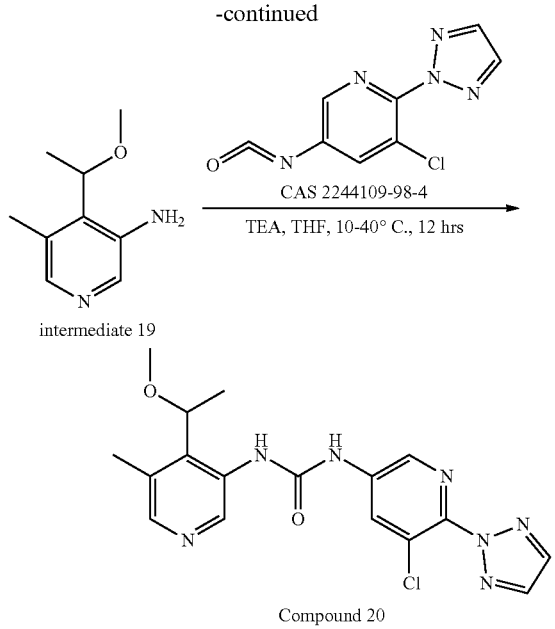

intermediate 19

Compound 20

Preparation of Intermediate 18

A mixture of intermediate 16 (500 mg, 1.5 mmol), 2,4,6-trimethyl-1,3,5,2,4,6-trioxatriborinane CAS 823-96-1 (417 mg, 1.7 mmol), Pd(PPh$_3$)$_4$ (174 mg, 0.1 mmol), potassium carbonate (417 mg, 3.0 mmol) in 1,4-dioxane (5 mL) was degassed and refilled with N$_2$ for three times. The mixture was stirred at 100° C. for 16 hours under N$_2$. The mixture was allowed to reach 25° C. The mixture was quenched with sat. NH$_4$Cl aq and the mixture was extracted with EtOAc twice. The combined organic layers were washed with brine, dried over Na$_2$SO$_4$, filtered and concentrated in vacuum to give a yellow solid. The yellow solid was purified by flash column chromatography over silica gel (gradient elution: 0~35% EtOAc in petroleum ether). The desired fractions were collected and the solvent was concentrated in vacuum to give intermediate 18 (330 mg, yield: 80.6%) as yellow solid.

Preparation of Intermediate 19

Intermediate 19 was prepared by analogy to the procedure described for intermediate 17. The compound was purified by flash column chromatography over silica gel (gradient elution: 0~45% EtOAc in petroleum ether). The desired fractions were collected and the solvent was concentrated in vacuum to give intermediate 19 (180 mg, yield: 89.7%) as yellow solid.

Preparation of Compound 20

To a solution of 3-chloro-5-isocyanato-2-(2H-1,2,3-triazol-2-yl)pyridine (CAS 2244109-98-4) (1.2 g, 5.3 mmol) and triethylamine (1.5 mL, 10.6 mmol) in THF (8 mL) was added intermediate 19 (130 mg, 0.76 mmol) at 25° C. The mixture was stirred at 40° C. for 12 hours. The mixture was cooled to 25° C. The mixture was evaporated under vacuum then dissolved in methanol and stirred at 25° C. for 0.5 hour. The mixture was filtered and the filtrate was evaporated under vacuum to give a yellow solid. The yellow solid was purified by preparative high-performance liquid chromatography [Column: Boston Prime C18 150*30 mm 5 um, Condition: A: water (0.05% ammonia hydroxide), B: MeCN, at the beginning: A (72%) and B (28%), at the end: A (42%) and B (58%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 20 (214 mg, yield: 71.1%) as white solid.

LC/MS: m/z 388.1 [M+H]$^+$, rt 3.28 min, purity 98.5%, method: K.

SFC: purity 50.1%/49.9%, rt 4.50 min/5.16 min. method: SFC5

Synthesis of Compound 21

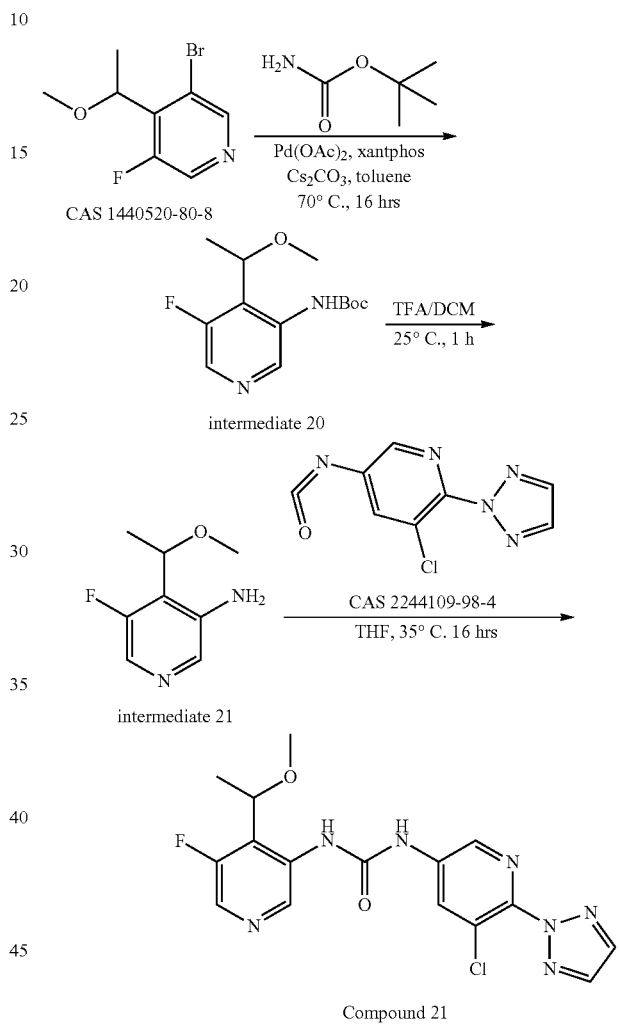

intermediate 20 intermediate 21

Compound 21

Preparation of Intermediate 20

A mixture consisting of CAS 1440520-80-8 (657 mg, 2.8 mmol), tert-butyl carbamate (395 mg, 3.4 mmol) and Cs$_2$CO$_3$ (1.8 g, 5.6 mmol) in dioxane (20 mL) was degassed with N$_2$ for 10 min. Then Pd(OAc)$_2$ (32 mg, 0.14 mmol) and xantphos (162 mg, 0.28 mmol) were added and the mixture was stirred at 100° C. for 16 hours under N$_2$. The mixture was filtered and the filtrate was concentrated to afford a crude product as yellow oil. The crude product was purified by flash column chromatography over silica gel (gradient elution: 0~30% EtOAc in petroleum ether). The desired fractions were collected and the solvent was concentrated to dryness under vacuum to give intermediate 20 (663 mg, yield: 87%) as yellow solid.

Preparation of Intermediate 21

To a solution of intermediate 20 (663 mg, 2.5 mmol) in CH$_2$Cl$_2$ (10 mL) was added TFA (1 mL) at 25° C. The mixture was stirred at 25° C. for 2 hours. Sat.NaHCO$_3$ aq.

was added to the mixture and the mixture was extracted with CH$_2$Cl$_2$ twice. The combined organic layers were washed with brine, dried over Na$_2$SO$_4$, filtered and concentrated in vacuum to give a crude product. The crude product was purified by flash column chromatography over silica gel (gradient elution: 0~70% EtOAc in petroleum ether). The desired fractions were collected and the solvent was concentrated in vacuum to give intermediate 21 (350 mg, yield: 68%) as yellow solid.

Preparation of Compound 21

Compound 21 was prepared by analogy to the procedure described for Compound 20. The compound was purified by preparative high-performance liquid chromatography. [Column: PhenomenexGemini 150*25 mm*10 um, Condition: A: water (0.05% ammonia hydroxide), B: MeCN. At the beginning: A (65%) and B (35%), at the end: A (35%) and B (65%), Gradient Time: 10 min; 100% B Hold Time: 3 min; Flow Rate: 25 ml/min]. The pure fractions were collected and the organic solvent was evaporated under vacuum. The aqueous layer was lyophilized to dryness to give Compound 21 (28 mg, yield: 23.2%) as white solid.

LC/MS: m/z 392.1 [M+H]$^+$, rt 4.06 min, purity 95.5%, method K

Synthesis of Compound 22

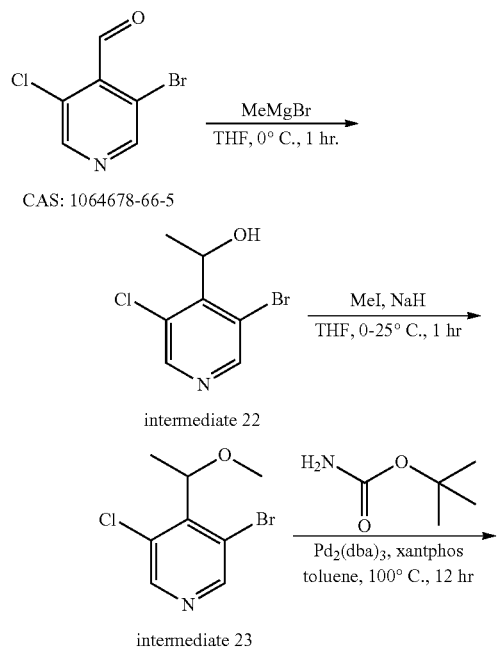

Preparation of Intermediate 22

To a solution of 3-bromo-5-chloroisonicotinaldehyde (1 g, 4.5 mmol) in THF (20 mL) was added methylmagnesium bromide (3 M in THF, 2.3 mL, 6.8 mmol) at 0° C. The mixture was stirred at 25° C. for 1 hour. The mixture was quenched with sat.NH$_4$Cl aq. and extracted with EtOAc twice. The combined organic layers were washed with brine, dried over Na$_2$SO$_4$, filtered and concentrated in vacuum to give a crude product. The crude product was purified by a flash column chromatography over silica gel (gradient elution: 0-15% EtOAc in petroleum ether). The desired fractions were collected and the solvent was concentrated under vacuum to afford intermediate 22 (0.9 g, yield: 84%) as white solid.

Preparation of Intermediate 23

To a mixture of intermediate 22 (0.9 g, 3.8 mmol) in THF (15 mL) was added sodium hydride (230 mg, 5.7 mmol, 60% in mineral oil) at 0° C. and the mixture was stirred for 10 min. Iodomethane (3.7 g, 25.7 mmol) was added and the mixture was stirred at 25° C. for 2 hours. The mixture was quenched with sat.NH$_4$Cl aq. and extracted with EtOAc twice. The combined organic layers were washed with brine, dried over Na$_2$SO$_4$, filtered and concentrated in vacuum to give a crude product. The crude product was purified by flash column chromatography over silica gel (gradient elution: 0~5% EtOAc in petroleum ether). The desired fractions were collected and the solvent was concentrated to dryness under vacuum to give intermediate 23 (0.8 g, yield: 84%) as white solid.

Preparation of Intermediate 24

A mixture of intermediate 23 (0.7 g, 2.8 mmol), tert-butyl carbamate (393 mg, 3.4 mmol) and Cs$_2$CO$_3$ (3.6 g, 11.2 mmol) in toluene (40 mL) was degassed with N$_2$ for 10 min. Then Pd(OAc)$_2$ (94 mg, 0.4 mmol) and xantphos (162 mg, 0.3 mmol) were added and the mixture was stirred at 100° C. for 12 hours under N$_2$. The mixture was cooled to 25° C. and was then filtered. The filtrate was concentrated to give a crude product. The crude product was purified by flash column chromatography over silica gel (gradient elution: 0~4% EtOAc in petroleum ether). The desired fractions were collected and the solvent was concentrated to dryness under vacuum to give intermediate 24 (0.60 g, yield: 71%) as white solid.

Preparation of Intermediate 25

To a solution of intermediate 24 (0.6 g, 2.0 mmol) in CH₂Cl₂ (15 mL) was added TFA (3 mL) at 25° C. The mixture was stirred at 25° C. for 2 hours. Sat. NaHCO₃ aq. was added to the mixture, and the mixture was extracted with CH₂Cl₂ twice. The combined organic layers were washed with brine, dried over Na₂SO₄, filtered and concentrated in vacuum to give the crude product. The crude product was purified by flash column chromatography over silica gel (gradient elution: 0~26% EtOAc in petroleum ether). The desired fractions were collected and the solvent was concentrated in vacuum to give intermediate 25 (360 mg, yield: 96%) as white solid.

Preparation of Compound 22

To a solution of 3-chloro-5-isocyanato-2-(2H-1,2,3-triazol-2-yl)pyridine (CAS 2244109-98-4) (328 mg, 1.5 mmol) and triethylamine (0.4 mL, 3 mmol) in THF (15 mL) was added to a solution of intermediate 25 (100 mg, 0.5 mmol) in THF (5 mL) at 25° C. The reaction mixture was stirred at 40° C. for 12 hours. The mixture was allowed to cool to 25° C. and filtered. The filtrate was concentrated in vacuum to give a crude product. The crude product was purified by preparative high-performance liquid chromatography. [Column: PhenomenexGemini 150*25 mm*10 um, Condition: A: water (0.04% aqueous ammonia+10 mM NH₄HCO₃), B: MeCN. At the beginning: A (65%) and B (35%), at the end: A (35%) and B (65%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 22 (55 mg, yield: 25%) as white solid.

Compound 22:

LC/MS: m/z 408.0 [M+H]⁺, rt: 4.29 min, Purity: 96.4%, method: K

SFC: purity 49.9%/50.1%, rt: 5.27 min/5.93 min, method: SFC1

Synthesis of Compounds 23 and 24

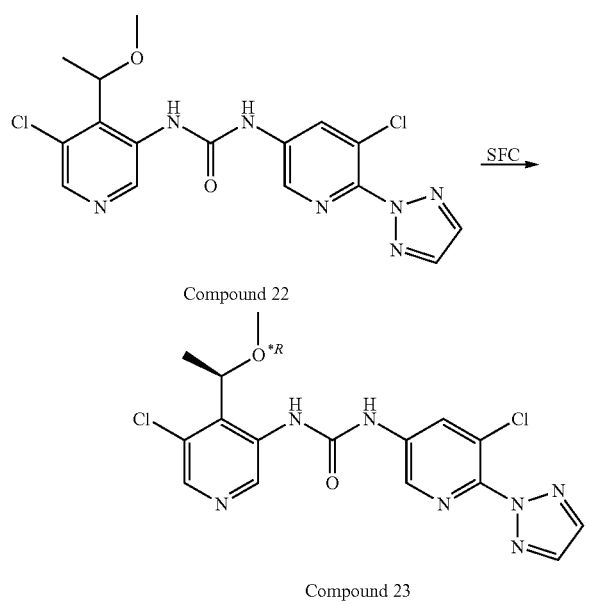

Compound 22

Compound 23

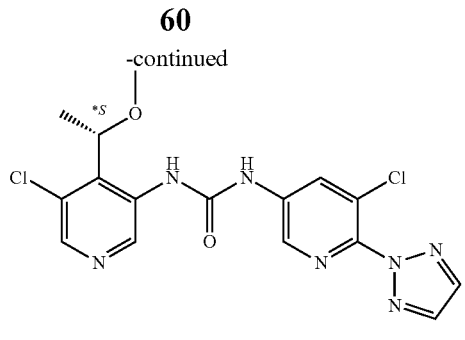

Compound 24

Compound 22 (300 mg, 0.7 mmol) was separated by SFC [Column: DAICEL CHIRALPAK AD-H (250 mm*30 mm, 5 μm), Condition: solvent, A: Supercritical CO₂. Solvent, B: 0.1% aqueous ammonia in EtOH. At the beginning: A (60%) and B (40%), at the end: A (60%) and B (40%), Flow Rate (ml/min): 50]. The pure fractions were collected and the organic solvent was evaporated under vacuum. MeCN and H₂O were added to the residue and the mixture was lyophilized to dryness to give Compound 23 (145 mg, yield: 48.3%) and Compound 24 (144 mg, yield: 47.8%) as white solid.

Compound 23:

LC/MS: m/z 408.1 [M+H]⁺, rt: 4.37 min, purity: 99.8%, method: K.

SFC: purity 100%, rt: 5.24 min, method: SFC1

Compound 24:

LC/MS: m/z 408.1 [M+H]⁺, rt: 4.38 min, purity: 100%, method: K

SFC: purity 100%, rt: 5.89 min, method: SFC1

Synthesis of Compound 25

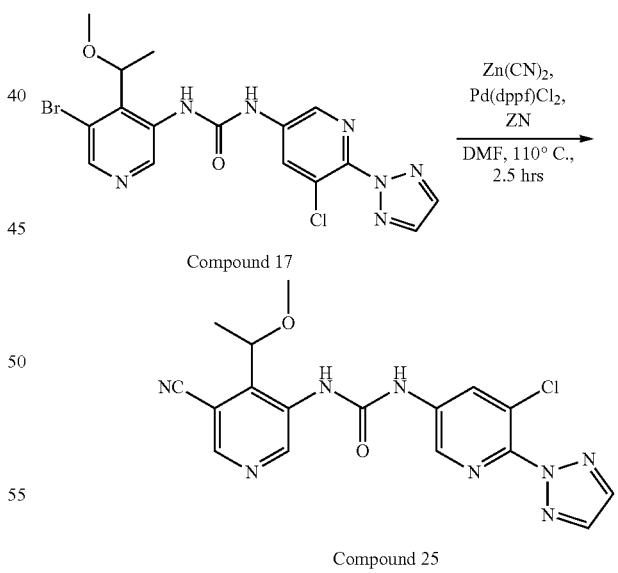

Compound 17

Compound 25

Preparation of Final Compound 25

To a mixture of Compound 17 (50 mg, 0.11 mmol), Zn(CN)₂ (16 mg, 0.14 mmol) and Zn (2 mg, 0.02 mmol) in DMF (5 mL) was added Pd(dppf)Cl₂ (12 mg, 0.02 mmol) at 25° C. The reaction mixture was stirred at 110° C. for 2.5 hours. The mixture was allowed to cool to 25° C. and filtered. The filtrate was concentrated to give a crude product. The crude product was purified by preparative high-performance liquid chromatography. [Column: PhenomenexGemini 150*25 mm*10 um, Condition: A: water (0.04% aqueous ammonia+10 mM NH4HCO3), B: MeCN. At the beginning: A (70%) and B (30%), at the end: A (40%) and B (60%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 25 (8 mg, yield: 18%) as white solid.

LC/MS: m/z 399.1 [M+H]+, rt: 4.06 min, Purity: 99.8%, method: K.

Synthesis of Compounds 25, 26 and 27

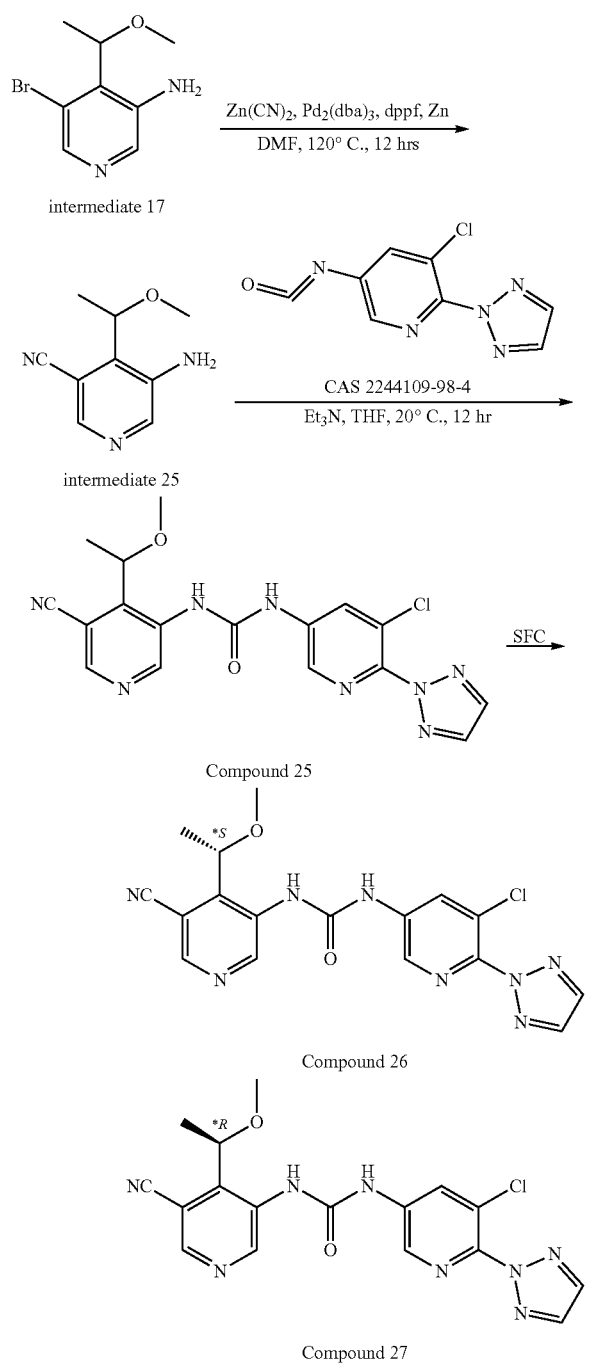

Preparation of Intermediate 26

A mixture of intermediate 17 (0.8 g, 3.5 mmol), Zn(CN)2 (0.25 g, 2.1 mmol) and Zn (68 mg, 1.1 mmol) in DMF (20 mL) was degassed with $N_2$ for 10 min. Then Pd2(dba)3 (159 mg, 0.17 mmol) and dppf (192 mg, 0.35 mmol) were added and the mixture was stirred at 120° C. for 12 hours under $N_2$. The mixture was allowed to cool to 25° C. and filtered. The filtrate was concentrated to give the crude product. The crude product was purified by flash column chromatography over silica gel (gradient elution: 0~30% EtOAc in petroleum ether). The desired fractions were collected and the solvent was concentrated to dryness under vacuum to give intermediate 26 (0.55 g, yield: 85%) as white solid.

Preparation of Compound 25 (Alternative Procedure)

To a solution of 3-chloro-5-isocyanato-2-(2H-1,2,3-triazol-2-yl)pyridine (CAS 2244109-98-4) (664 mg, 3.0 mmol) and triethylamine (0.8 mL, 6.0 mmol) in THF (30 mL) was added to a solution of intermediate 26 (200 mg, 1.1 mmol) in THF (10 mL) at 25° C. The reaction mixture was stirred at 40° C. for 12 hours. The mixture was allowed to reach 25° C. and filtered. The filtrate was concentrated in vacuum to give a crude product. The crude product was purified by preparative high-performance liquid chromatography. [Column: PhenomenexGemini 150*25 mm*10 um, Condition: A: water (0.04% aqueous ammonia+10 mM NH4HCO3), B: MeCN. At the beginning: A (65%) and B (35%), at the end: A (35%) and B (65%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 25 (120 mg, yield: 27.7%) as white solid.

Preparation of Compounds 26 and 27

Compound 25 (120 mg, 0.3 mmol) was separated by SFC [Column: DAICEL CHIRALPAK AD-H (250 mm*30 mm, 5 μm), Condition: solvent, A: Supercritical $CO_2$; Solvent, B: 0.1% aqueous ammonia in EtOH. At the beginning: A (60%) and B (40%), at the end: A (60%) and B (40%), Flow Rate (ml/min): 50]. The pure fractions were collected and the organic solvent was evaporated under vacuum. MeCN and $H_2O$ were added to the residue and the mixture was lyophilized to dryness to give Compound 26 (41 mg, yield: 34%) and Compound 27 (43 mg, yield: 36%) as white solid.

Compound 26:

1H NMR (400 MHz, DMSO-d6) δ ppm 1.52 (d, J=6.8 Hz, 3H), 3.27 (s, 3H), 4.82 (q, J=6.8 Hz, 1H), 8.15 (s, 2H), 8.47 (d, J=2.4 Hz, 1H), 8.55 (d, J=2.4 Hz, 1H), 8.77 (s, 1H), 9.24 (s, 1H);

HPLC/MS: m % z 399.1 [M+H]+, rt: 4.20 min, purity: 98%, method: M.

SFC: purity 99.8%, rt: 4.74 min, method: SFC7

Compound 27:

LC/MS: m/z 399.1 [M+H]+, rt: 4.12 min, purity: 100%, method: K

SFC: purity 99.5%, rt: 5.30 min, method: SFC7

Synthesis of Compound 28

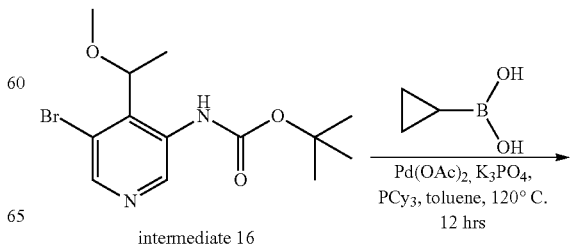

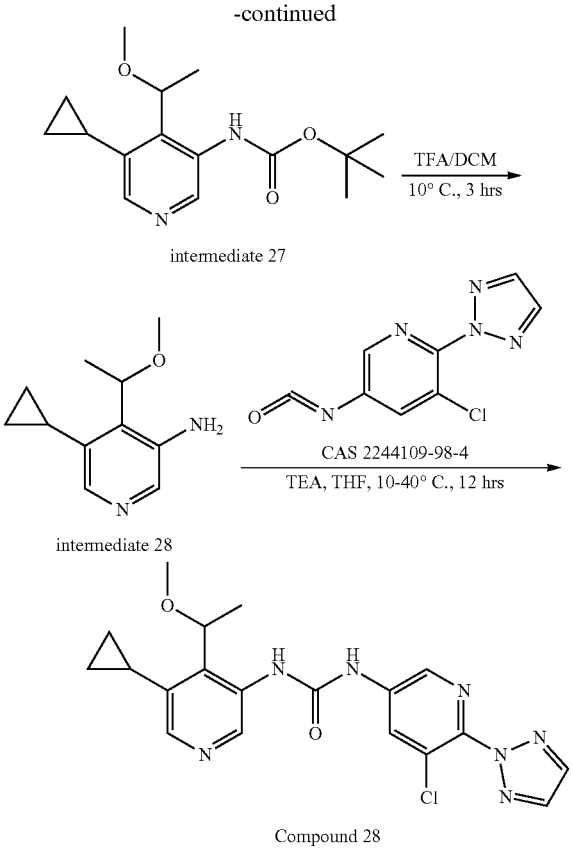

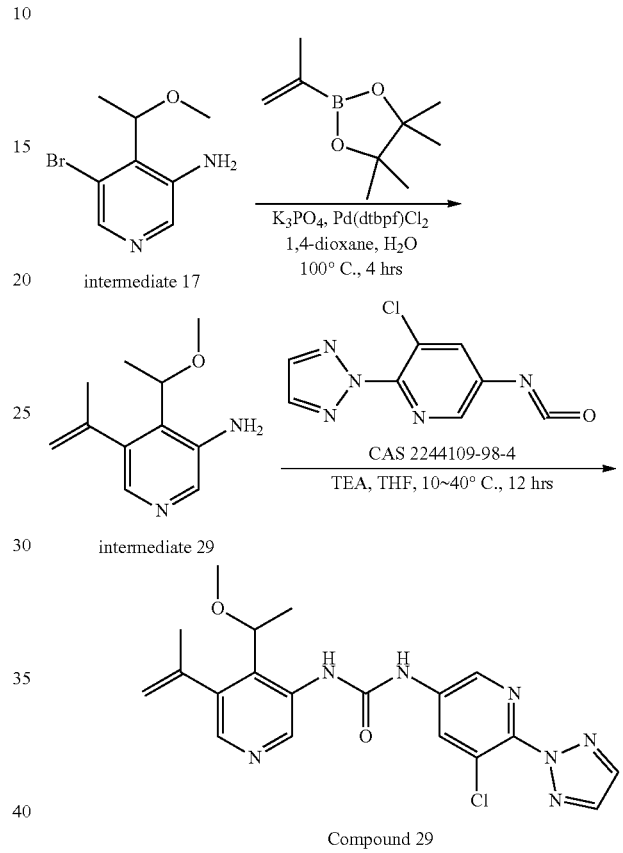

the organic solvent was evaporated under vacuum. The aqueous layer was lyophilized to dryness to give Compound 28 (75 mg, yield: 27%) as a white solid.

LC/MS: m/z 414.2 [M+H]$^+$, rt 3.54 min, purity 99.3%, method K.

SFC: purity 50.3%/49.7%, rt 4.78 min/5.40 min. method: SFC7

Synthesis of Compound 29

Preparation of Intermediate 27

To a solution of intermediate 16 (300 mg, 0.91 mmol), cyclopropylboronic acid (156 mg, 1.8 mmol), and potassium phosphate (385 mg, 1.8 mmol) in toluene (2 mL) and H$_2$O (0.5 mL) were added Pd(OAc)$_2$ (10 mg, 0.04 mmol) and tricyclohexylphosphine (25 mg, 0.09 mmol) under N$_2$. The reaction mixture was stirred at 120° C. for 12 hours under N$_2$. The mixture was cooled to 25° C. The mixture was extracted with EtOAc twice. The combined organic layers were washed with brine and dried with Na$_2$SO$_4$, filtered and the filtrate was concentrated under vacuum to give a gum. The yellow gum was purified by flash column chromatography over silica gel (gradient elution: 0~30% EtOAc in petroleum ether). The desired fractions were collected and the solvent was concentrated under vacuum to afford intermediate 27 (200 mg, yield: 71.9%) as light yellow oil.

Preparation of Intermediate 28

Intermediate 28 was prepared by an analogous procedure as was described for intermediate 17. The compound was purified by flash column chromatography over silica gel (gradient elution: 0~40% EtOAc in petroleum ether). The desired fractions were collected and the solvent was concentrated in vacuum to give intermediate 28 (111 mg, yield: 88.5%) as yellow solid.

Preparation of Compound 28

Compound 28 was prepared by analogy to the procedure described for Compound 20. The compound was purified by preparative high-performance liquid chromatography [Column: Boston Prime C18 150*30 mm 5 um, Condition: A: water (0.05% ammonia hydroxide), B: MeCN, at the beginning: A (70%) and B (30%), at the end: A (40%) and B (60%), Gradient Time 9 min; 100% B Hold Time 2 min; Flow Rate 25 ml/min]. The pure fractions were collected and Preparation of Intermediate 29

The mixture of intermediate 17 (300 mg, 1.3 mmol), 4,4,5,5-tetramethyl-2-(prop-1-en-2-yl)-1,3,2-dioxaborolane CAS 126726-62-3 (250 mg, 1.5 mmol), potassium phosphate (547 mg, 2.6 mmol) in 1,4-dioxane (20 mL) and H$_2$O (4 mL) was bubbled with N$_2$ for 5 minutes and then treated with Pd(dtbpf)Cl$_2$ CAS 95408-45-0 (84 mg, 0.1 mmol). The mixture was bubbled with N$_2$ for another 5 minutes and then stirred at 100° C. for 4 hours. The mixture was allowed to reach room temperature and quenched with H$_2$O and the mixture was extracted with EtOAc twice. The organic layers were separated, washed with brine, dried over Na$_2$SO$_4$ and evaporated under vacuum to give yellow gum. The yellow gum was purified by flash column chromatography over silica gel (gradient elution: 0~41% EtOAc in petroleum ether) to give intermediate 29 (205 mg, yield: 80.9%) as yellow solid.

Preparation of Compound 29

Compound 29 was prepared by analogy to the procedure described for Compound 20. The compound was purified by preparative high-performance liquid chromatography [Column: Boston Prime C18 150*30 mm 5 um, Condition: A: water (0.05% ammonia hydroxide), B: MeCN, at the beginning: A (70%) and B (30%), at the end: A (40%) and B (60%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 29 (83 mg, yield: 19%) as white solid.

LC/MS: m/z 414.2 [M+H]+, rt 3.74 min. Purity 99.8%, method K.

SFC: purity 48.8%; 51.2%, rt 1.84 min, 2.12 min. method: SFC9.

Synthesis of Compound 30

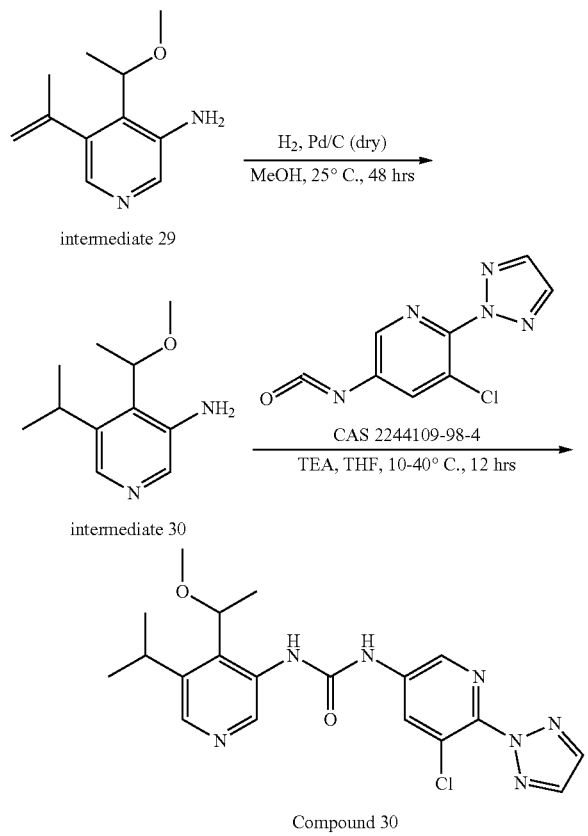

Preparation of Intermediate 30

A mixture of intermediate 29 (270 mg, 1.38 mmol) in methanol (50 mL) was hydrogenated at 25° C. (40 psi) with Pd/C (100 mg) as a catalyst. The reaction mixture was stirred for 48 hours. After uptake of H₂ (1 eq), the catalyst was filtered off and the filtrate was evaporated. The filtrates were concentrated under vacuum to afford a yellow gum. The yellow gum was purified by flash column chromatography over silica gel (gradient elution: 0-60% EtOAc in petroleum ether). The desired fractions were collected and the solvent was concentrated under vacuum to afford intermediate 30 (140 mg, yield: 51.9%) as light yellow solid.

Synthesis of Compound 30

Compound 30 was prepared by analogy to the procedure described for Compound 20. The compound was purified by preparative high-performance liquid chromatography [Column: Boston Prime C18 150*30 mm 5 um, Condition: A: water (0.05% ammonia hydroxide), B: MeCN, at the beginning: A (68%) and B (32%), at the end: A (38%) and B (62%), Gradient Time 9 min; 100% B Hold Time 2 min; Flow Rate 25 ml/min]. The pure fractions were collected and the organic solvent was evaporated under vacuum. The aqueous layer was lyophilized to dryness to give Compound 30 (73.5 mg, yield: 24.0%) as white solid.

LC/MS: m/z 416.2 [M+H]+, rt 3.63 min. Purity 97.2%, method K

SFC: purity 49.3%/50.7%, rt 4.42 min/4.71 min. method: SFC7.

Synthesis of Compound 31

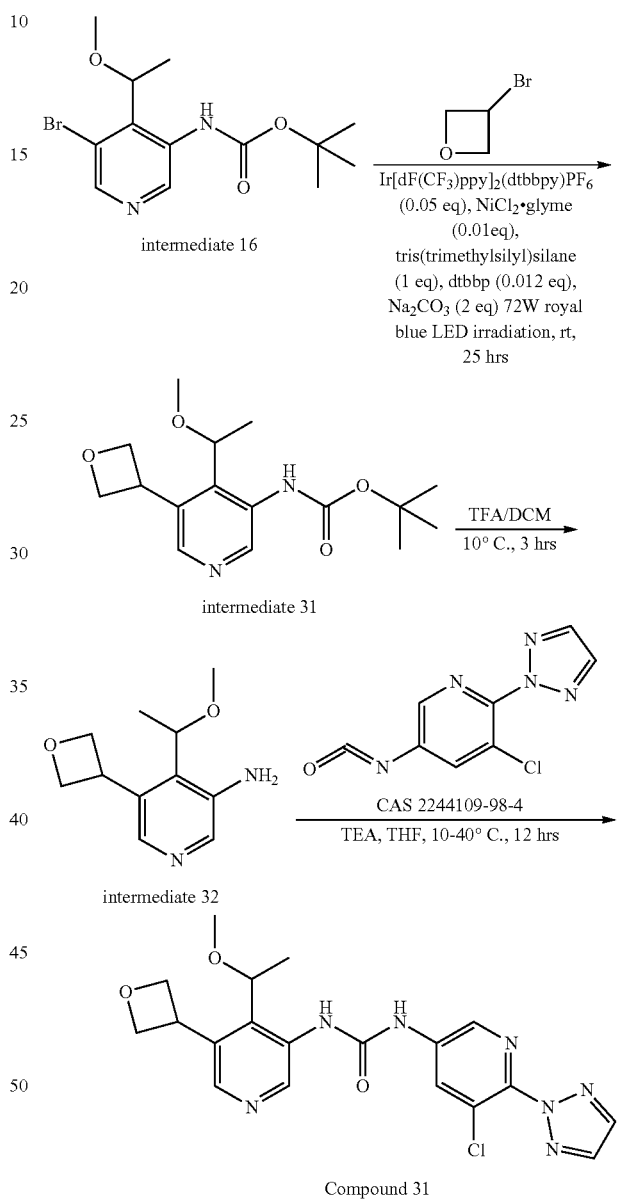

Preparation of Intermediate 31

To a yellow mixture of intermediate 16 (1100 mg, 3.3 mmol), 3-bromooxetane (478 mg, 3.5 mmol), tris(trimethylsilyl)silane (826 mg, 3.3 mmol), 4,4'-di-tert-butyl-2,2'-dipyridyl (CAS 72914-19-3) (10.7 mg, 0.04 mmol) and Na₂CO₃ (704 mg, 6.6 mmol) in DME (3 mL) were added NiCl₂·glyme (7.3 mg, 0.03 mmol) and (Ir[dF(CF₃)ppy]₂(dtbbpy))PF₆ (CAS 870987-63-6) (74 mg, 0.07 mmol). The mixture was bubbled with N₂ and stirred at RT under N₂ for 25 hours under 72 W royal blue LED irradiation. The mixture was filtered and the filtrate was evaporated under vacuum to give a yellow oil. The yellow oil was purified by flash column chromatography over silica gel (gradient elution: 0~50% EtOAc in petroleum ether). The desired fractions were collected and the solvent was concentrated under vacuum to afford intermediate 31 (380 mg, yield: 32.2%) as a yellow solid.

Preparation of Intermediate 32

Intermediate 32 was prepared by analogy to the procedure described for intermediate 17. The compound was purified by flash column chromatography over silica gel (gradient elution: 0~40% EtOAc in petroleum ether). The desired fractions were collected and the solvent was concentrated in vacuum to give intermediate 32 (140 mg, yield: 57.6%) as yellow solid.

Preparation of Compound 31

Compound 31 was prepared by analogy to the procedure described for Compound 20. The compound was purified by preparative high-performance liquid chromatography [Column: Boston Prime C18 150*30 mm 5 um, Condition: A: water (0.05% ammonia hydroxide), B: MeCN, at the beginning: A (77%) and B (23%), at the end: A (62%) and B (38%), Gradient Time 9 min; 100% B Hold Time 2 min; Flow Rate 25 ml/min]. The pure fractions were collected and the organic solvent was evaporated under vacuum. The aqueous layer was lyophilized to dryness to give Compound 31 (44 mg, yield: 38%) as a white solid.

HPLC/MS: m/z 430.1 [M+H]$^+$, rt 3.81 min, purity 96.6%, method M.

SFC: purity 49.6%/50.4%, rt 3.03 min/3.42 min. method: SFC16

Synthesis of Compound 32

Preparation of Intermediate 33

A mixture of intermediate 16 (100 mg, 0.3 mmol), xantphos (35 mg, 0.06 mmol), Pd$_2$(dba)$_3$ (28 mg, 0.03 mmol), and sodium tert-butoxide (87 mg, 0.9 mmol) in toluene (4 mL) was bubbled with N$_2$ for 1 min. Then propan-2-amine (125 mg, 2.1 mmol) in toluene (1 mL) was added to the above mixture. The resulting mixture was stirred at 120° C. for 16 hours under N$_2$. The mixture was cooled to 25° C. The mixture was filtered and the filtrate was evaporated under vacuum to give a yellow gum. The yellow gum was purified by prep-TLC (CH$_2$Cl$_2$/MeOH=10/1) to give intermediate 33 (25 mg, yield: 40%) as a yellow solid.

Synthesis of Compound 32

Compound 32 was prepared by analogy to the procedure described for Compound 20. The compound was purified by preparative high-performance liquid chromatography [Column: Waters Xbridge 150*25 5 um, Condition: A: water (10 mM NH$_4$HCO$_3$), B: MeCN, at the beginning: A (70%) and B (30%), at the end: A (52%) and B (48%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 32 (13.5 mg, yield: 14.2%) as white solid.

LC/MS: m/z 431.2 [M+H]$^+$, rt 3.78 min, purity 95.2%, method: K.

Synthesis of Compound 33

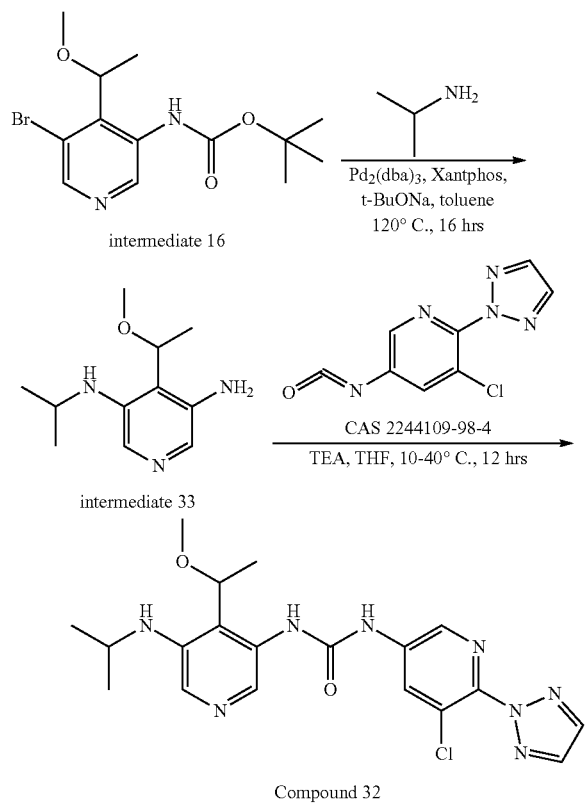

Compound 32

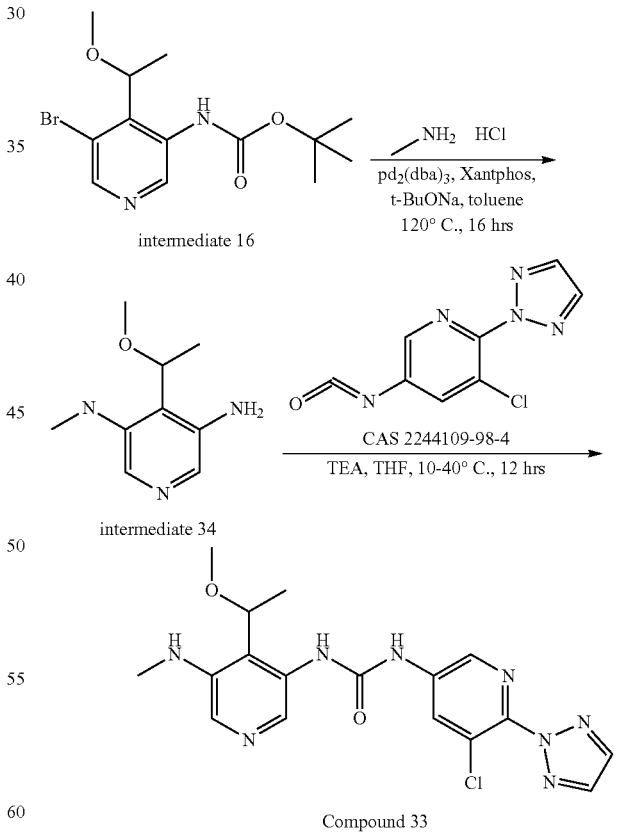

Compound 33

Preparation of Intermediate 34

Intermediate 34 was prepared by analogy to the procedure described for intermediate 33. The compound was purified by flash column chromatography over silica gel (gradient elution: 0~10% MeOH in DCM). The desired fractions were collected and the solvent was concentrated in vacuum to give intermediate 34 (270 mg, yield: 86.1%) as yellow solid.

Synthesis of Compound 33

Compound 33 was prepared by analogy to the procedure described for Compound 20. After reaction, the mixture was evaporated under vacuum to give a yellow solid. The yellow solid was dissolved in MeOH. The mixture was stirred at 20° C. for 1 hour. The mixture was filtered and filtrate was evaporated under vacuum to give yellow solid. The yellow solid was dissolved in DMSO and EtOAc. The mixture was stirred at 20° C. for 1 hour. The mixture was filtered and the filter cake was washed with EtOAc and MeOH. The filter cake was dissolved in H₂O and MeOH. The aqueous layer was lyophilized to dryness to give Compound 33 (192 mg, yield: 36.3%) as white solid.

HPLC/MS: m/z 403.2 [M+H]⁺, rt 3.89 min, purity 98.9%, method: M.

Synthesis of Compounds 34, 35, 36 and 37

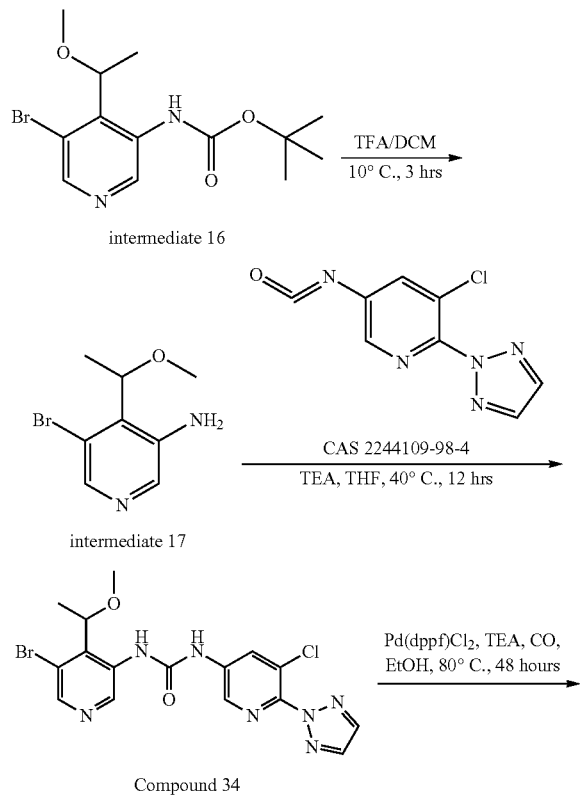

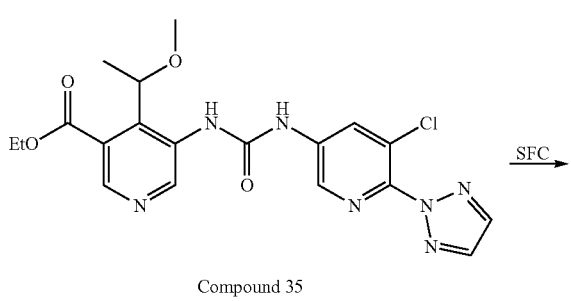

Compound 35

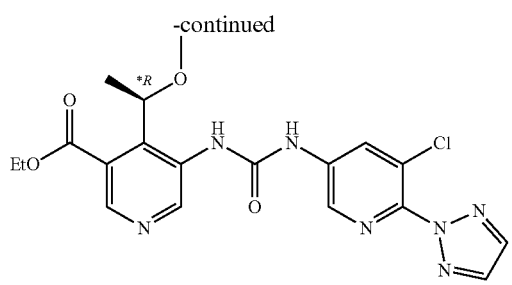

Compound 36

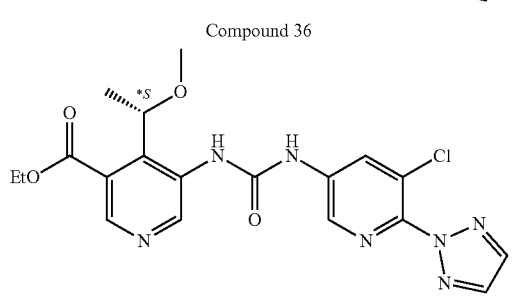

Compound 37

Preparation of Intermediate 17

To a solution of intermediate 16 (5.9 g, 17.8 mmol) in CH₂Cl₂ (100 mL) was added TFA (40 mL) at 10° C. The mixture was stirred at 10° C. for 3 hours. The mixture was treated with sat. NaHCO₃ aq and extracted with CH₂Cl₂ twice. The combined organic layers were washed with brine and dried with Na₂SO₄, filtered and the filtrate was concentrated in vacuum to give a crude product. The crude product was purified by flash column chromatography over silica gel (gradient elution: 0~25% EtOAc in petroleum ether). The desired fractions were collected and the solvent was concentrated in vacuum to give intermediate 17 (3.4 g, yield: 81%) as yellow solid.

Preparation of Compound 34

To a solution of 3-chloro-5-isocyanato-2-(2H-1,2,3-triazol-2-yl)-pyridine CAS 2244109-98-4 (2.3 g, 10.3 mmol) and triethylamine (2.8 mL, 20.6 mmol) in THF (80 mL) was added intermediate 17 (1 g, 4.3 mmol). The mixture was stirred at 40° C. for 12 hours. The mixture was concentrated in vacuum to give a crude product. The crude product was washed by MeOH/EtOAc, and the filter cake was dried to give Compound 34 (1.2 g, yield: 62%) as a white solid.

Preparation of Compound 35

A solution of Compound 34 (100 mg, 0.2 mmol) and TEA (154 uL, 1.1 mmol) in EtOH (20 mL) was treated under a CO atmosphere at 80° C. 50 psi with Pd(dppf)Cl₂ as a catalyst for 48 hours. The mixture was filtered and the filtrate was concentrated in vacuum to give a crude product. The crude product was purified by flash column chromatography over silica gel (gradient elution: 0~50% EtOAc in petroleum ether). The desired fractions were collected and the solvent was concentrated in vacuum to give Compound 35 (85 mg, yield: 86%) as yellow solid.

LC/MS: m/z 446.0 [M+H]⁺, rt 1.68 min, purity 94.2%, method C

Preparation of Compounds 36 and 37

Compound 35 (85 mg, 0.19 mmol) was separated by SFC. [Column: DAICEL CHIRALPAK AD-H (250 mm*30 mm, 5 μm), Condition: solvent A: Supercritical CO₂, solvent B: 0.1% aqueous ammonia in EtOH, at the beginning: A (60%) and B (40%), at the end: A (60%) and B (40%), Flow Rate (ml/min) 50]. The pure fractions were collected and the organic solvent was evaporated under vacuum. MeCN and H₂O was added to the residue and it was lyophilized to dryness to give Compound 36 (8.1 mg, yield: 7.9%) as white solid and Compound 37 (7.6 mg, yield: 7.5%) as white solid.
Compound 36:
  LC/MS: m/z 446.2 [M+H]⁺, rt 4.315 min. Purity 96.5%, method K
  SFC: purity 97.7%, rt 4.019 min. method: SFC17
Compound 37:
  HPLC/MS: m/z 446.1 [M+H]⁺, rt 4.404 min. Purity 97.7%, method M
  SFC: purity 95.8%, rt 4.471 min. method: SFC17
Synthesis of Compounds 38 and 39 ammonia hydroxide), B: MeCN, at the beginning: A (80%) and B (20%), at the end: A (60%) and B (40%), Gradient Time 9 min; 100% B Hold Time 2 min; Flow Rate 25 ml/min]. The pure fractions were collected and the organic solvent was evaporated under vacuum. The aqueous layer was lyophilized to dryness to give Compound 39 (56 mg, yield: 345%) as white solid.
  HPLC/MS: m/z 417.1 [M+H]⁺, rt 3.47 min, purity 95.2%, method M.
  SFC: purity 50.1%/49.9%, rt 4.82 min/5.03, method: SFC1

Synthesis of Compound 40

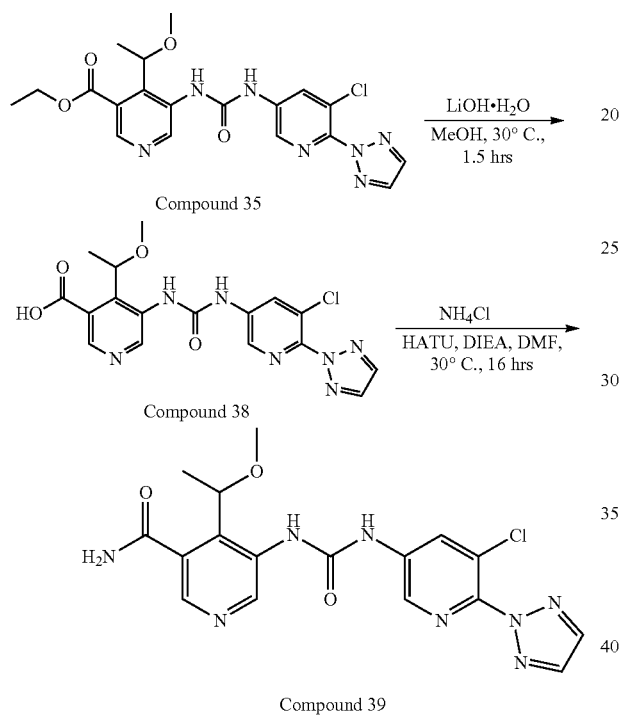

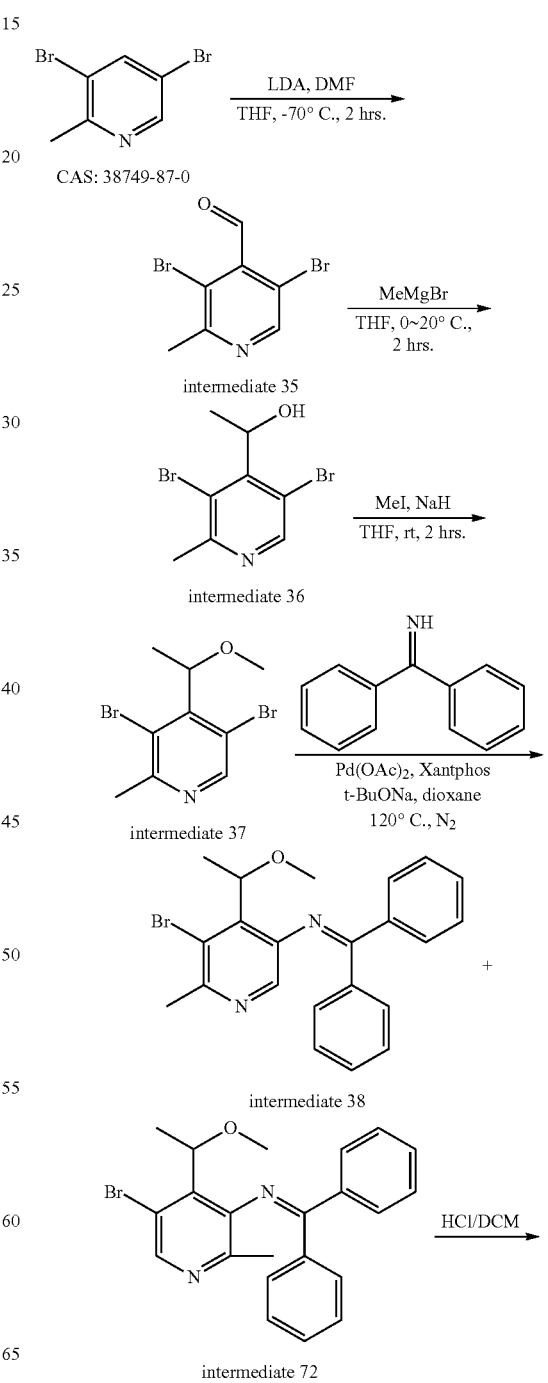

Preparation of Compound 38

To a solution of Compound 35 (160 mg, 0.4 mmol) in methanol (5 mL) was added LiOH·H₂O (1.8 mL, 3.7 mmol, 2 M). The mixture was stirred at 30° C. for 1.5 hours. The mixture was cooled to 25° C. The mixture was adjusted to pH=6 with HCl (1 N). The mixture was extracted with MeOH/DCM (v/v=1/3) (20 mL×5). The combined organic layers were washed with brine and dried with Na₂SO₄, filtered and the filtrate was concentrated under vacuum to afford Compound 38 as yellow solid. (160 mg, yield: 99.6%) as yellow solid.
  LC/MS: m/z 418.0 [M+H]⁺, rt 1.41 min, purity 96.4%, method C.

Preparation of Compound 39

A mixture of Compound 38 (160 mg, 0.4 mmol), HATU (210 mg, 0.5 mmol), N-ethyl-N-isopropylpropan-2-amine (191 mg, 1.5 mmol) in DMF (5 mL) was stirred at 30° C. for 10 minutes. NH₄Cl (30 mg, 0.5 mmol) was added to the mixture and stirred at 30° C. for 16 hours. The mixture was filtered and the filtrate was evaporated under vacuum to give a yellow gum. The yellow gum was purified by preparative high-performance liquid chromatography [Column: Xtimate C18 10µ 250 mm*50 mm, Condition: A: water (0.05%

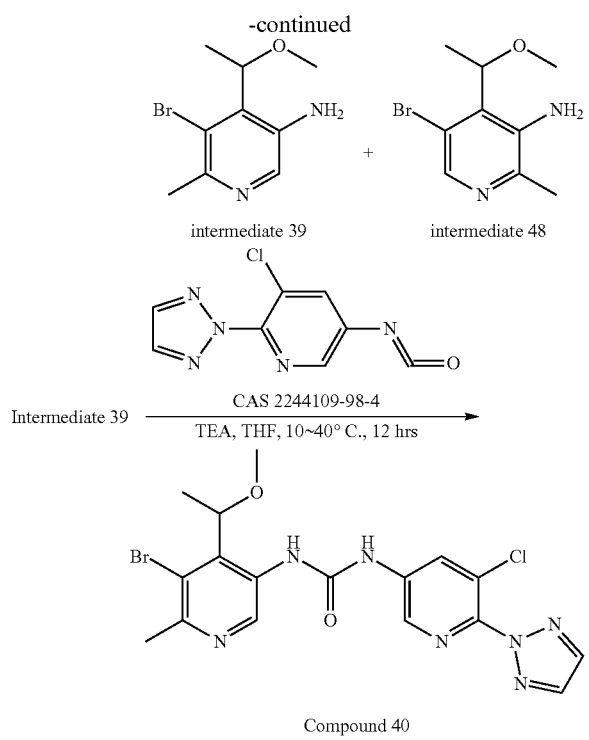

Compound 40

Preparation of Intermediate 35

3,5-dibromo-2-methylpyridine (15 g, 60 mmol) was dissolved in THF (300 mL) and the mixture was cooled to −70° C., LDA (2M in THF and heptanes 35.9 mL, 71.8 mmol) was added. The reaction mixture was stirred at −70° C. for 1 hour. DMF (6.9 mL, 90 mmol) was added to the mixture and the mixture was stirred at −70° C. for 1 hour. The reaction mixture was quenched with sat. $NH_4Cl$ aq. at a temperature between −20° C.~−70°, and then $H_2O$ was added and warmed to room temperature. The mixture was extracted with EtOAc twice. The combined organic layers were washed with brine and dried with $Na_2SO_4$, filtered and the filtrate was concentrated under vacuum to afford the crude product as yellow solid. The crude product was purified by flash column chromatography over silica gel (gradient elution: 0~7% EtOAc in petroleum ether). The desired fractions were collected and the solvent was concentrated under vacuum to afford intermediate 35 (9.5 g, yield: 57%) as light yellow solid.

Preparation of Intermediate 36

To a solution of intermediate 35 (16 g, 57 mmol) in THF (400 mL) was added methylmagnesium bromide (3 M in THF, 28.7 mL, 86 mmol) at 0° C. The mixture was allowed to warm to 20° C. and stirred at 20° C. for 1 hour. The mixture was quenched with sat.$NH_4Cl$ aq. The mixture was extracted with EtOAc twice. The combined organic layers were washed with brine and dried with $Na_2SO_4$, filtered and the filtrate was concentrated in vacuum to give a crude product. The crude product was purified by a flash column chromatography over silica gel (gradient elution: 0~15% EtOAc in petroleum ether). The desired fractions were collected and the solvent was concentrated under vacuum to afford intermediate 36 (15 g, yield: 89%) as light yellow solid.

Preparation of Intermediate 37

To a solution of intermediate 36 (15 g, 50 mmol) in THF (200 mL) was added NaH (60% in mineral oil, 3 g, 75 mmol) at 0° C. for 10 min. $CH_3I$ (26 g, 184 mmol) was added at 0° C. The mixture was allowed to warm to rt and stirred at rt for 2 hours. The mixture was quenched with sat.$NH_4Cl$ aq and the mixture was extracted with EtOAc twice. The combined organic layers were washed with brine and dried with $Na_2SO_4$, filtered and the filtrate was concentrated in vacuum to give a crude product. The crude product was purified by flash column chromatography over silica gel (gradient elution: 0~4% EtOAc in petroleum ether). The desired fractions were collected and the solvent was concentrated to dryness under vacuum to give intermediate 37 (14 g, yield: 90%) as white solid.

Preparation of Intermediate 38 and Intermediate 72

A mixture of intermediate 37 (6.0 g, 19 mmol), diphenylmethanimine (5.3 g, 29 mmol) and 1-BuONa (2.8 g, 29 mmol) in dioxane (120 mL) and purged with $N_2$ for 10 min. $Pd(OAc)_2$ (0.44 g, 1.9 mmol) and xantphos (2.2 g, 3.9 mmol) were added. The reaction mixture was stirred at 120° C. for 16 hours. The reaction was allowed to 25° C. and filtered. The residue was washed with EtOAc (400 mL). The filtrates were concentrated under vacuum to afford the crude product as yellow oil. The crude product was purified by flash column chromatography over silica gel (gradient elution: 0~10% EtOAc in petroleum ether). The desired fractions were collected and the solvent was concentrated in vacuum to give a mixture of intermediate 38 and intermediate 72 (5.2 g, purity: 73%) as yellow oil.

Preparation of Intermediate 39 and Intermediate 48

A mixture of Intermediates 38 and 72 (5.2 g, 73% purity), was dissolved in DCM (50 mL). Aqueous HCl (4 mL, 12 M) was added and the mixture was stirred at 40° C. for 18 hours. The reaction mixture was adjusted to pH=8 using sat. $NaHCO_3$ and extracted with EtOAc (100 mL*3). The combined organic layers were separated, washed with brine, dried over $Na_2SO_4$, filtered and the filtrates were evaporated under vacuum to give a yellow oil. The crude product was purified by flash column chromatography over silica gel (gradient elution: 0~30% EtOAc in petroleum ether). The desired fractions were collected and the solvent was concentrated in vacuum to give intermediate 39 (1.1 g) as yellow solid. and intermediate 48 (800 mg).

Alternative Procedure to Prepare Intermediate 38

A mixture of intermediate 37 (10 g, 32.4 mmol), diphenylmethanimine (6.5 g, 35.6 mmol) and 1-BuONa (3.1 g, 32.4 mmol) in toluene (200 mL) was purged with $N_2$ for 10 min. $Pd_2(dba)_3$ (1.5 g, 1.6 mmol) and BINAP (3.0 g, 4.8 mmol) were added. The reaction mixture was stirred at 120° C. for 16 hours. The reaction was allowed to 25° C. and filtered. The residue was washed with EtOAc (500 mL). The filtrates were concentrated under vacuum to afford the crude product as yellow oil. The crude product was purified by flash column chromatography over silica gel (gradient elution: 0~12% EtOAc in petroleum ether). The desired fractions were collected and the solvent was concentrated in vacuum to give crude intermediate 38 (20 g, purity: 39%) as yellow oil.

Alternative Procedure to Prepare Intermediate 39

The crude intermediate 38 (obtained via the alternative procedure to prepare intermediate 38) (20 g, 39% purity) was dissolved in DCM (60 mL). Aqueous HCl (10 mL, 2 M) was added and the mixture was stirred at 40° C. for 5 hours. The reaction mixture was adjusted to pH=8 using sat.$NaHCO_3$ and extracted with EtOAc (100 mL*3). The combined organic layers were separated, washed with brine, dried over $Na_2SO_4$, filtered and the filtrates were evaporated under vacuum to give a yellow oil. The crude product was purified by flash column chromatography over silica gel (gradient elution: 0~30% EtOAc in petroleum ether). The desired fractions were collected and the solvent was concentrated in vacuum to give intermediate 39 (4 g yield: 50.4% yield over two steps) as yellow solid.

Synthesis of Compound 40

Compound 40 was prepared by analogy to the procedure described for Compound 20. The crude product was purified by preparative high-performance liquid chromatography [Column: Xtimate C18 10μ 250 mm*50 mm, Condition: A: water (0.04% aqueous ammonia+10 mM NH₄HCO₃), B: MeCN, at the beginning: A (50%) and B (50%), at the end: A (20%) and B (80%), Gradient Time 8 min; 100% B Hold Time 0 min; Flow Rate 25 ml/min]. The pure fractions were collected and the organic solvent was evaporated under vacuum. The aqueous layer was lyophilized to dryness to give Compound 40 (6 mg, yield: 8.4%) as white solid.

HPLC/MS: m/z 466 [M+H]⁺, rt 4.716 min. Purity 98.7%, method M

SFC: purity 53.1%; 46.9%, rt 5.535 min, 6.995 min. method: SFC1

Synthesis of Compounds 41, 42 and 43

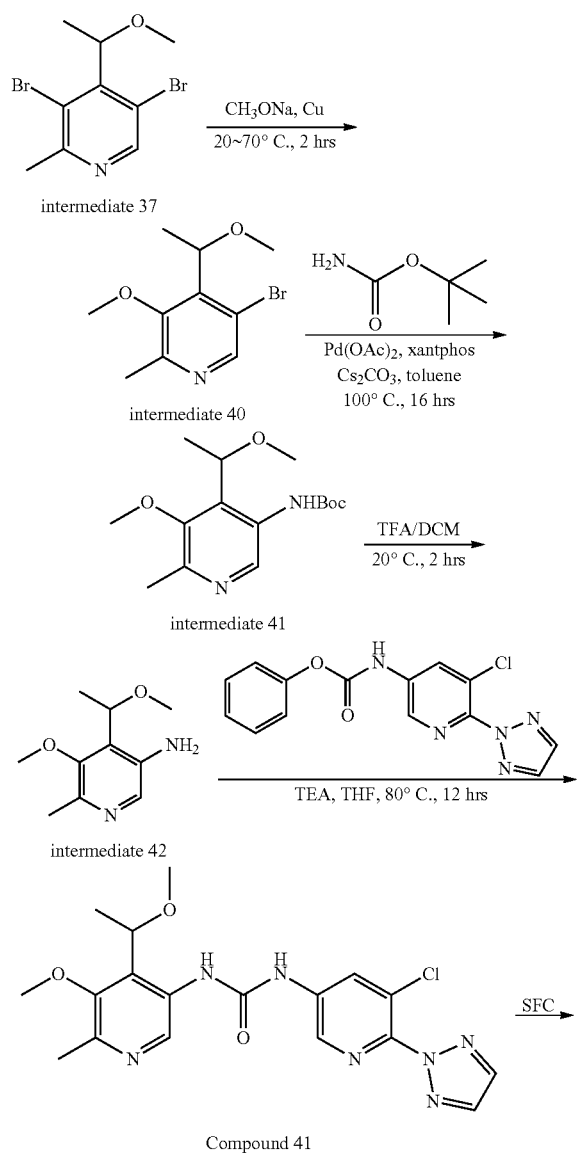

Compound 41

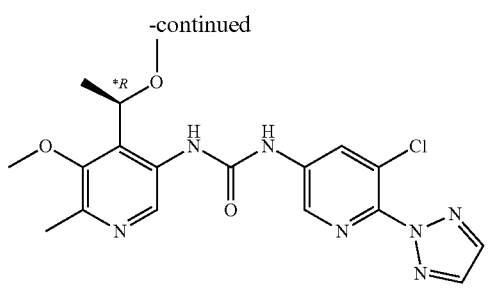

Compound 42

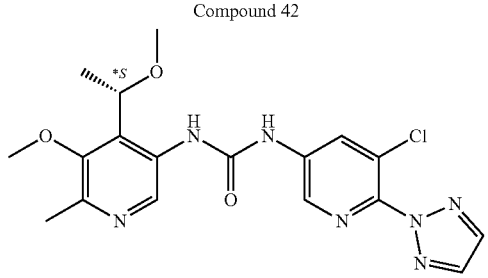

Compound 43

Preparation of Intermediate 40

To a mixture of intermediate 37 (1 g, 3 mmol) in DMF (10 mL) was added CH₃ONa (810 mg, 15 mmol) and Cu powder (20 mg, 0.3 mmol) at 20° C. The mixture was stirred at 70° C. for 2 hours. Brine was added to the mixture and the mixture was extracted with EtOAc twice. The combined organic layers were washed with brine and dried with Na₂SO₄, filtered and the filtrate was concentrated in vacuum to give a crude product. The crude product was purified by flash column chromatography over silica gel (gradient elution: 0~5% EtOAc in petroleum ether). The desired fractions were collected and the solvent was concentrated in vacuum to give intermediate 40 (520 mg, yield: 53.3%) as colorless oil.

Preparation of Intermediate 41

A mixture consisting of intermediate 40 (240 mg, 0.9 mmol), tert-butyl carbamate (162 mg, 1.4 mmol) and Cs₂CO₃ (1.2 g, 3.7 mmol) in toluene (6 mL) was degassed with N₂ for 10 min. Then Pd(OAc)₂ (31 mg, 0.14 mmol), xantphos (53 mg, 0.1 mmol) was added and the mixture was stirred at 100° C. for 16 hours under N₂. The mixture was filtered and the filtrate was concentrated to afford a crude product as yellow oil. The crude product was purified by flash column chromatography over silica gel (gradient elution: 0~10% EtOAc in petroleum ether). The desired fractions were collected and the solvent was concentrated to dryness under vacuum to give intermediate 41 (140 mg, yield: 48%) as white solid.

Preparation of Intermediate 42

To a solution of intermediate 41 (280 mg, 0.9 mmol) in CH₂Cl₂ (10 mL) was added TFA (2 mL) at 20° C. The mixture was stirred at 20° C. for 2 hours. The mixture was treated with sat. NaHCO₃ aq. and was extracted with CH₂Cl₂ twice. The combined organic layers were washed with brine and dried with Na₂SO₄, filtered and the filtrate was concentrated in vacuum to give a crude product. The crude product was purified by flash column chromatography over silica gel (gradient elution: 0~30% EtOAc in petroleum ether). The desired fractions were collected and the solvent was concentrated in vacuum to give intermediate 42 (130 mg, yield: 70.1%) as white solid.

Preparation of Compound 41

To a solution of intermediate 42 (110 mg, 0.6 mmol) and N-[5-chloro-6-(2H-1,2,3-triazol-2-yl)-3-pyridinyl]-Carbamic acid phenyl ester (CAS 2178988-79-7) (226 mg, 0.7 mmol) in THF (8 mL) was added TEA (233 uL, 1.68 mmol) at 20° C. The reaction mixture was stirred at 80° C. for 12 hours. The mixture was allowed to cool to room temperature and concentrated in vacuum to give a crude product. The crude product was purified by preparative high-performance liquid chromatography [Column: Phenomenex Gemini 150*25 mm*10 um, Condition: A: water (0.04% aqueous ammonia+10 mM $NH_4HCO_3$), B: MeCN, at the beginning: A (65%) and B (35%), at the end: A (35%) and B (65%), Gradient Time 8 min; 100% B Hold Time 8 min; Flow Rate 25 ml/min]. The pure fractions were collected and the organic solvent was evaporated under vacuum. The aqueous layer was lyophilized to dryness to give Compound 41 (150 mg, yield: 64%) as white solid.

Preparation of Compounds 42 and 43

Compound 41 (150 mg, 0.36 mmol) was separated by SFC [Column: DAICEL CHIRALPAK AD-H (250 mm*30 mm, 5 μm), Condition: solvent A: Supercritical $CO_2$, solvent B: 0.1% aqueous ammonia in EtOH, at the beginning: A (55%) and B (45%), at the end: A (55%) and B (45%), Flow Rate (ml/min) 70]. The pure fractions were collected and the organic solvent was evaporated under vacuum. MeCN and $H_2O$ was added to the residue and it was lyophilized to dryness to give Compound 42 (71 mg, yield: 48%) as white solid and Compound 43 (71 mg, yield: 48%) as white solid.

Compound 42:

LC/MS: m/z 418.1 $[M+H]^+$, rt 3.470 min. Purity 100%, method K

SFC: purity 100%, rt 5.66 min. method: SFC1

Compound 43:

LC/MS: m/z 418.1 $[M+H]^+$, rt 3.47 min. Purity 100%, method K

SFC: purity 100%, rt 6.76 min. method: SFC1 Synthesis of compounds 44, 45 and 46

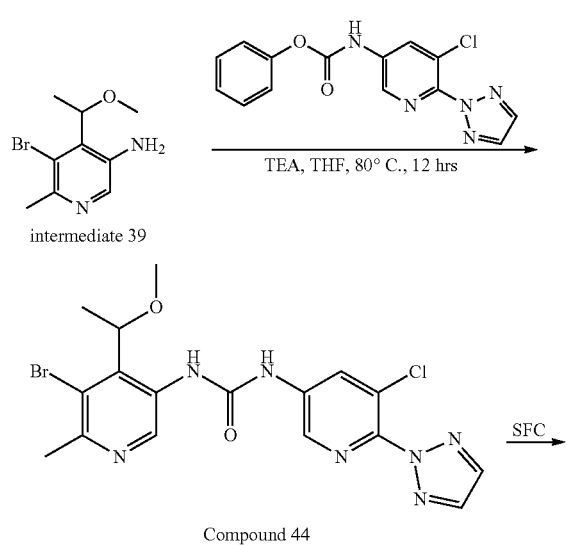

Compound 44

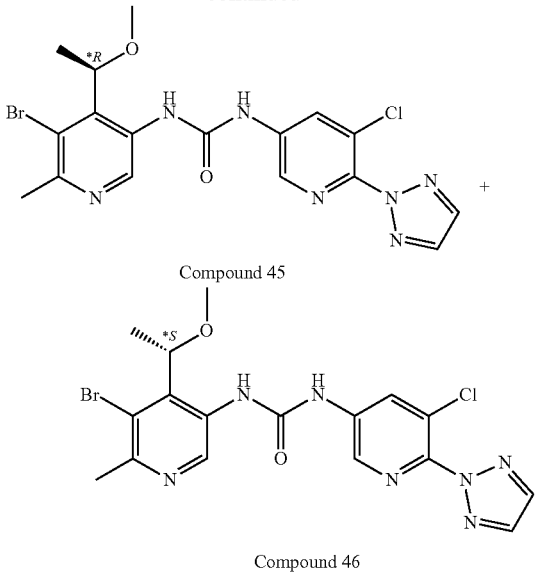

Compound 45

Compound 46

Preparation of Compound 44

Compound 44 was prepared by analogy to the procedure described for Compound 41, starting from intermediate 39 and N-[5-chloro-6-(2H-1,2,3-triazol-2-yl)-3-pyridinyl]-carbamic acid phenyl ester (CAS 2178988-79-7). The reaction mixture was concentrated under vacuum to afford crude product as a white solid. MeOH (100 mL) was added to the mixture and stirred at 70° C. for 1 h. Filtered and the filtrates were concentrated under vacuum to afford crude Compound 44 as yellow oil. The crude product was purified by preparative high-performance liquid chromatography [Column: Boston Prime C18 150*30 mm 5 um, Condition: A: water (0.04% aqueous ammonia+10 mM $NH_4HCO_3$), B: MeCN, at the beginning: A (55%) and B (45%), at the end: A (25%) and B (75%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 44 (460 mg, yield: 48%) as white solid.

LC/MS: m/z 466.1/468.1 $[M+H]^+$, rt 1.015 min, purity 99.4%, method G.

Preparation of Compounds 45 and 46

Compound 44 (500 mg, 1.07 mmol) was separated by SFC [Column: DAICEL CHIRALPAK AD (250 mm*30 mm, 10 μm), Condition: solvent A: Supercritical $CO_2$, solvent B: 0.1% aqueous ammonia in EtOH, at the beginning: A (55%) and B (45%), at the end: A (55%) and B (45%), Flow Rate (ml/min) 70]. The pure fractions were collected and the organic solvent was evaporated under vacuum. MeCN and $H_2O$ was added to the residue and it was lyophilized to dryness to give Compound 45 (235 mg, yield: 47.5%) as white solid and Compound 46 (235.8 mg, yield: 47.7%) as white solid.

Compound 45:

LC/MS: m/z 466.1/468.1 $[M+H]^+$, rt 4.338 min. Purity 99.8%, method K;

SFC: purity 100%, rt 1.880 min. method: SFC14.

Compound 46:

LC/MS: m/z 466.1/468.1 $[M+H]^+$, rt 4.326 min. Purity 100%, method K;

SFC: purity 100%, rt 2.347 min. method: SFC14.

Synthesis of Compounds 47 and 48

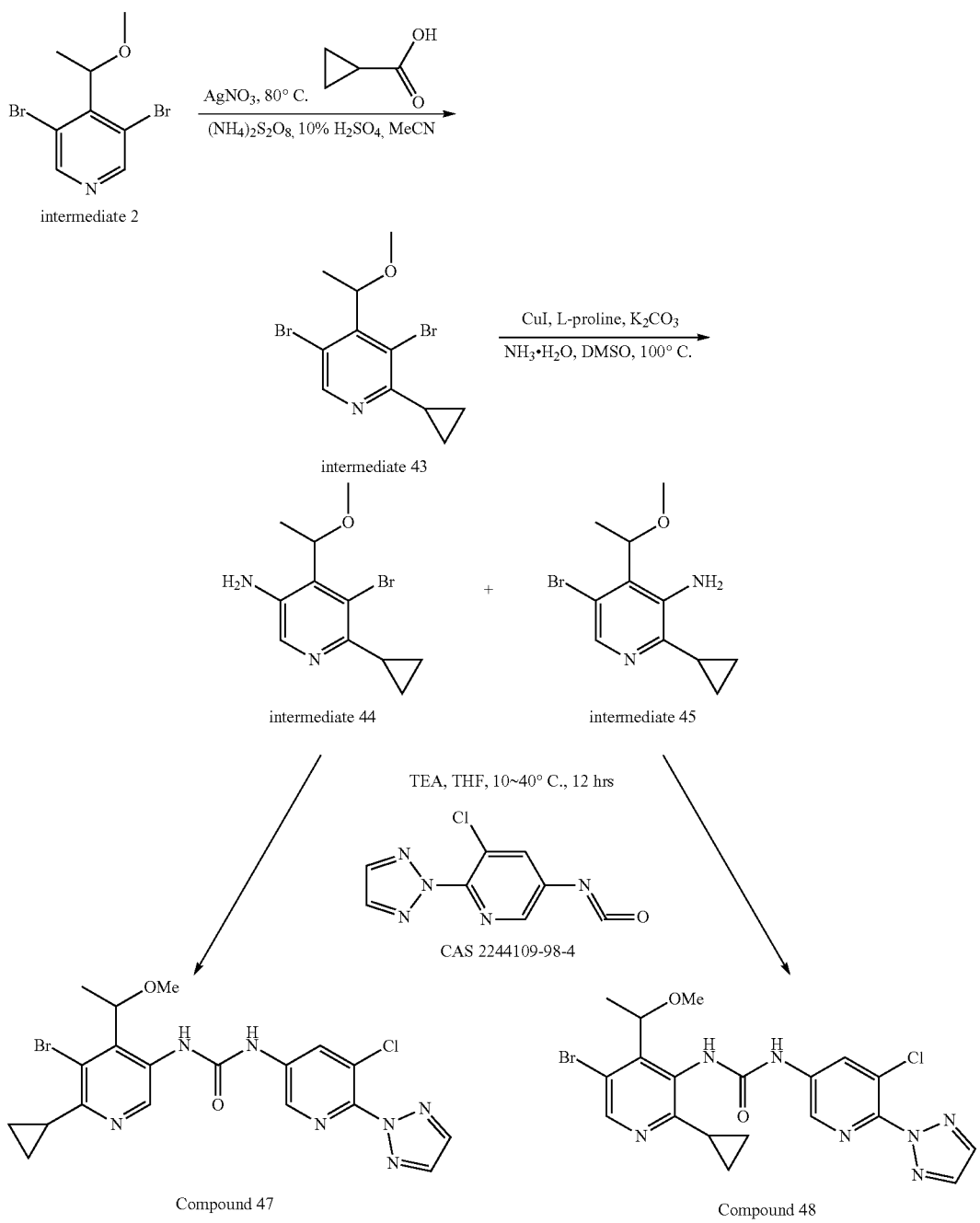

Preparation of Intermediate 43

AgNO₃ (3 g, 18 mmol) and cyclopropane carboxylic acid (4.6 g, 54 mmol) were added to a solution of intermediate 2 (5.4 g, 18 mmol) in a mixture of MeCN (90 mL) and 10% $H_2SO_4$ (90 mL). The reaction mixture was heated to a temperature between 70-80° C. A freshly prepared solution of $(NH_4)_2S_2O_8$ (12.3 g, 54 mmol) in $H_2O$ (150 mL) was added slowly to the mixture. The reaction mixture was stirred at 80° C. for 4 hours. The mixture was allowed to reach 25° C. and the pH was adjusted to 10 using $NH_3 \cdot H_2O$. The mixture was extracted with EtOAc thrice. The combined organic layers were separated, washed with brine, dried over $Na_2SO_4$, filtered and the filtrates were evaporated under vacuum to give a yellow oil. The crude product was purified by flash column chromatography over silica gel (gradient elution: 0~5% EtOAc in petroleum ether). The desired fractions were collected and the solvent was concentrated in vacuum to give crude (2 g, 60% purity), which was purified by preparative high-performance liquid chromatography [Column: Phenomenex Synergi Max-RP 250*50 mm*10 um, Condition: A: water (0.225% FA), B: MeCN, at the beginning: A (70%) and B (30%), at the end: A (15%) and B (85%), Gradient Time 24 min; 100% B Hold Time 8 min; Flow Rate 100 ml/min]. The pure fractions were collected and the organic solvent was evaporated under vacuum. The aqueous layer was lyophilized to dryness to give intermediate 43 (600 mg, yield: 7.5%) as colourless oil.

Preparation of Intermediates 44 and 45

A mixture of intermediate 43 (500 mg, 1.5 mmol), CuI (57 mg, 0.3 mol), L-proline (69 mg, 0.6 mmol), $K_2CO_3$ (311 mg, 2.25 mmol), $NH_3 \cdot H_2O$ (8 mL) in DMSO (5 mL) was purged with $N_2$. The mixture was stirred at 100° C. for 4 hours. $H_2O$ was added and the mixture was extracted with EtOAc thrice. The combined organic layers were separated, washed with brine, dried over $Na_2SO_4$, filtered and the filtrates were evaporated under vacuum to give a yellow oil. The crude product was purified by flash column chromatography over silica gel (gradient elution: 0~15% EtOAc in petroleum ether). The desired fractions were collected and the solvent was concentrated in vacuum to give intermediate 44 (30 mg, yield: 6%) as white solid and intermediate 45 (60 mg, yield: 12%) as yellow oil.

Synthesis of Compound 47

Compound 47 was prepared by analogy to the procedure described for Compound 20 using intermediate 44 and 3-chloro-5-isocyanato-2-(2H-1,2,3-triazol-2-yl)-pyridine (CAS 2244109-98-4). The crude product was purified by preparative high-performance liquid chromatography [Column: Xtimate C18 10μ 250 mm*50 mm, Condition: A: water (0.04% aqueous ammonia+10 mM $NH_4HCO_3$), B: MeCN, at the beginning: A (50%) and B (50%), at the end: A (20%) and B (80%), Gradient Time 8 min; 100% B Hold Time 0 min; Flow Rate 25 ml/min]. The pure fractions were collected and the organic solvent was evaporated under vacuum. The aqueous layer was lyophilized to dryness to give Compound 47 (6 mg, yield: 13%) as white solid.

LC/MS: m/z 492 [M+H]$^+$, rt 5.138 min. Purity 99.8%, method K

SFC: purity 50.7%; 49.3%, rt 4.758 min, 5.371 min. method: SFC1

Synthesis of Compound 48

Compound 48 was prepared by analogy to the procedure described for Compound 20 using intermediate 45 and 3-chloro-5-isocyanato-2-(2H-1,2,3-triazol-2-yl)-pyridine (CAS 2244109-98-4). The crude product was purified by preparative high-performance liquid chromatography [Column: Boston Prime C18 150*30 mm 5 um, Condition: A: water (0.04% aqueous ammonia+10 mM $NH_4HCO_3$), B: MeCN, at the beginning: A (50%) and B (50%), at the end: A (20%) and B (80%), Gradient Time 8 min; 100% B Hold Time 0 min; Flow Rate 25 ml/min]. The pure fractions were collected and the organic solvent was evaporated under vacuum. The aqueous layer was lyophilized to dryness to give Compound 48 (3 mg, yield: 5%) as white solid.

LC/MS: m/z 492 [M+H]$^+$, rt 4.772 min. Purity 98.9%, method K

SFC: purity 47.9%; 52.1%, rt 3.945 min, 4.493 min. method: SFC1.

Synthesis of Compounds 49 and 50

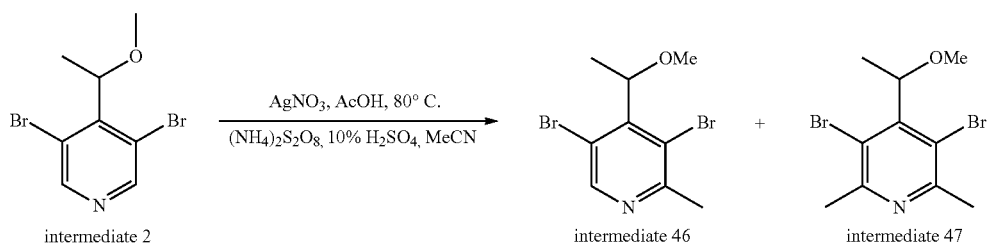

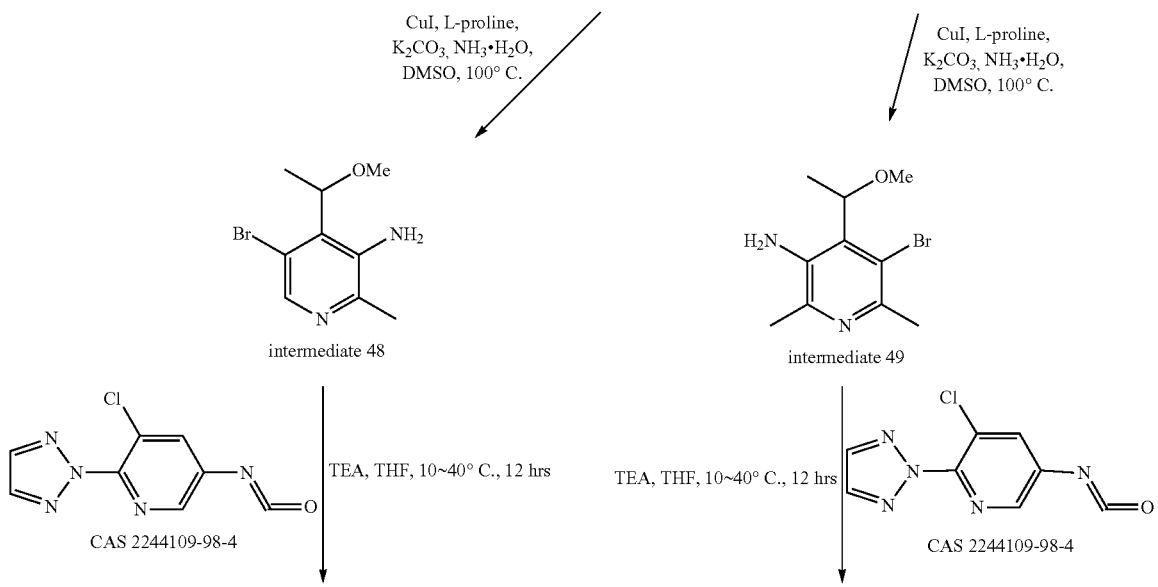

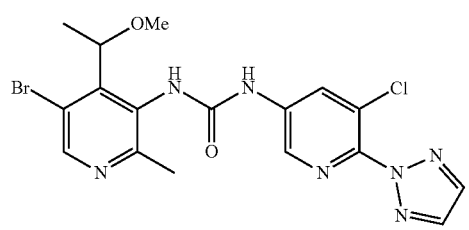

Compound 50

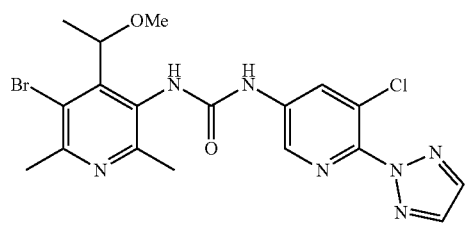

Compound 49

Preparation of Intermediates 46 and 47

Intermediates 46 and 47 were prepared by analogy to the procedure described for intermediate 43. The crude product was purified by flash column chromatography over silica gel (gradient elution: 0~5% EtOAc in petroleum ether). The desired fractions were collected and the solvent was concentrated in vacuum to give crude product, which was purified by preparative high-performance liquid chromatography [Column: Phenomenex Synergi Max-RP 250*50 mm*10 um, Condition: A: water (0.225% FA), B: MeCN, at the beginning: A (80%) and B (20%), at the end: A (25%) and B (75%), Gradient Time 24 min; 100% B Hold Time 3 min; Flow Rate 25 ml/min]. The pure fractions were collected and the organic solvent was evaporated under vacuum. The aqueous layer was lyophilized to dryness to give intermediate 47 (150 mg, yield: 2%) and intermediate 46 (650 mg, yield: 8%) as yellow solids.

Preparation of Intermediate 49

Intermediate 49 was prepared by analogy to the procedure described for intermediate 45. The crude product was purified by flash column chromatography over silica gel (gradient elution: 0~15% EtOAc in petroleum ether). The desired fractions were collected and the solvent was concentrated in vacuum to give intermediate 49 (20 mg, 25%) as white solid.

Synthesis of Compound 49

Compound 49 was prepared by analogy to the procedure described for Compound 20. The crude product was purified by preparative high-performance liquid chromatography [Column: Boston Prime C18 150*30 mm 5 um, Condition: A: water (0.04% aqueous ammonia+10 mM NH$_4$HCO$_3$), B: MeCN, at the beginning: A (55%) and B (45%), at the end: A (25%) and B (75%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 49 (4 mg, yield: 7%) as white solid.

LC/MS: m/z 480.0/482.0 [M+H]$^+$, rt 3.911 min. Purity 99.8%, method K

SFC: purity 51.7%; 48.3%, rt 4.483 min, 4.944 min. method: SFC1

Preparation of Intermediate 48

Intermediate 48 was prepared by analogy to the procedure described for intermediate 45; or as described in the experimental procedure in the preparation of compound 40. The crude product was purified by flash column chromatography over silica gel (gradient elution: 0~15% EtOAc in petroleum ether). The desired fractions were collected and the solvent was concentrated in vacuum to give intermediate 48 (40 mg, yield: 8%) as yellow solid.

Preparation of Compound 50

Compound 50 was prepared by analogy to the procedure described for Compound 20 starting from intermediate 48. The crude product was purified by preparative high-performance liquid chromatography [Column: Xtimate C18 10μ 250 mm*50 mm, Condition: A: water (0.04% aqueous ammonia+10 mM NH$_4$HCO$_3$), B: MeCN, at the beginning: A (60%) and B (40%), at the end: A (30%) and B (70%), Gradient Time 8 min; 100% B Hold Time 0 min; Flow Rate 25 ml/min]. The pure fractions were collected and the organic solvent was evaporated under vacuum. The aqueous layer was lyophilized to dryness to give Compound 50 (4 mg, yield: 5%) as white solid.

LC/MS: m/z 466 [M+H]$^+$, rt 4.255 min. Purity 97.3%, method K

SFC: purity 52.9%; 47.1%, rt 6.058 min, 7.033 min. method: SFC13

Synthesis of Compounds 51, 52 and 53

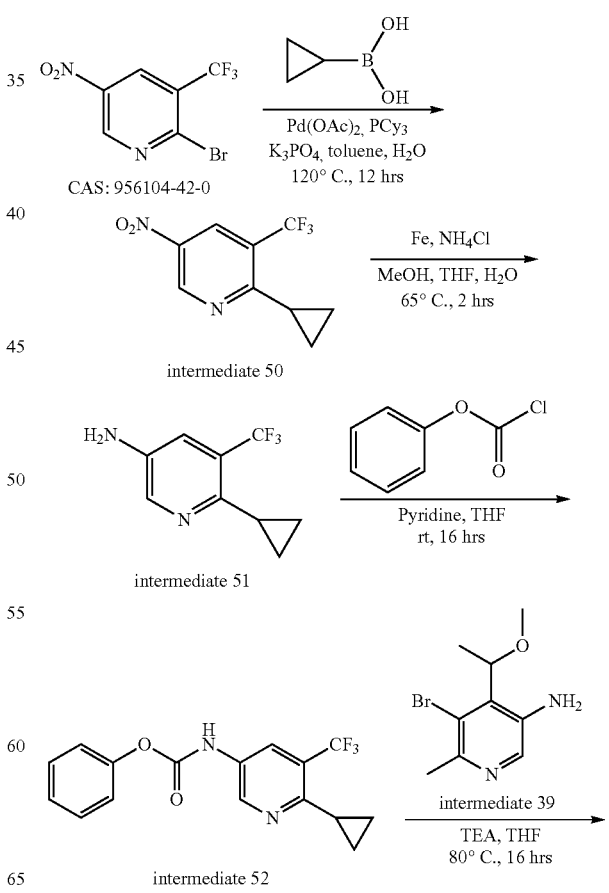

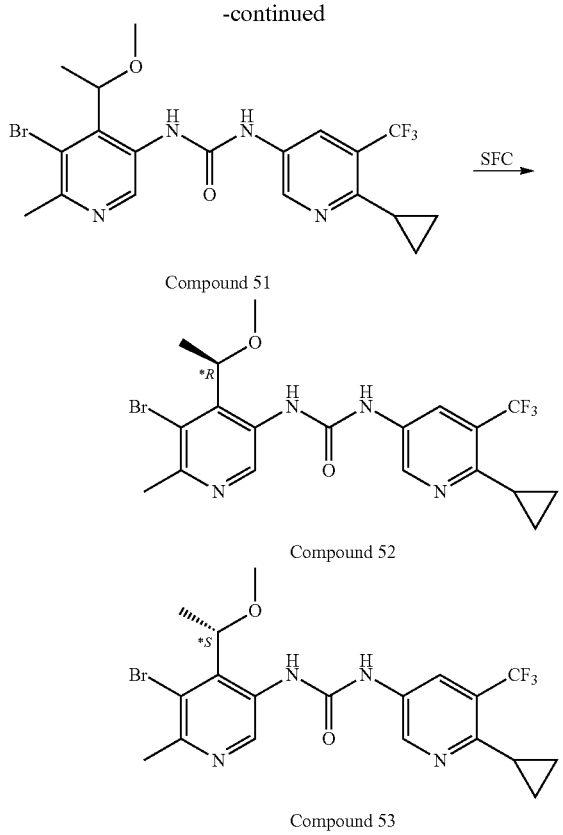

Compound 51

Compound 52

Compound 53

Preparation of Intermediate 50

2-Bromo-5-nitro-3-(trifluoromethyl)pyridine (20 g, 74 mmol) and cyclopropylboronic acid (13 g, 148 mmol) were dissolved in a solvent mixture of toluene (160 mL) and H₂O (40 mL), and then K₃PO₄ (31 g, 148 mmol), PCy₃ (3 g, 11 mmol), Pd(OAc)₂ (1 g, 5 mmol) were added under N₂. The reaction was stirred at 120° C. for 12 hours under N₂. After the solution was cooled to room temperature, the mixture was filtered and the residue was washed by 200 mL ethyl acetate twice. The organic layers were washed with brine and dried with Na₂SO₄, filtered and the filtrate was concentrated in vacuum to give a crude product. The crude product was purified by flash column chromatography over silica gel (gradient elution: 0~10% EtOAc in petroleum ether). The desired fractions were collected and the solvent was concentrated under vacuum to afford intermediate 50 (13 g, yield: 76%) as yellow solid.

Preparation of Intermediate 51

NH₄Cl (15 g, 280 mmol) was added at room temperature to a solution of intermediate 50 (13 g, 56 mmol) in MeOH (40 mL), THF (80 mL) and H₂O (20 mL). Iron powder (16 g, 280 mmol) was added slowly. The reaction was stirred at 65° C. for 2 hours. The mixture was allowed to cool to 25° C. and was then filtered. The residue was washed with 300 mL ethyl acetate twice. The organic layers were washed with brine and dried with Na₂SO₄, filtered and the filtrate was concentrated in vacuum to give a crude product. The crude product was purified by a flash column chromatography over silica gel (gradient elution: 0~30% EtOAc in petroleum ether). The desired fractions were collected and the solvent was concentrated under vacuum to afford intermediate 51 (10.5 g, yield: 89%) as a yellow solid.

Preparation of Intermediate 52

To a solution of intermediate 51 (2 g, 10 mmol) in THF (50 mL) was added pyridine (1.2 mL, 14.8 mmol) at room temperature. Phenyl chloroformate (2 g, 13 mmol) was added slowly. The reaction was stirred at room temperature for 16 hours. The mixture was quenched with sat. NH₄Cl aq. The mixture was extracted with EtOAc (100 mL) twice. The combined organic layers were washed with brine and dried with Na₂SO₄, filtered and the filtrate was concentrated in vacuum to give a crude product. The crude product was purified by flash column chromatography over silica gel (gradient elution: 0~30% EtOAc in petroleum ether). The desired fractions were collected and the solvent was concentrated under vacuum to afford intermediate 52 (3 g, yield: 75%) as white solid.

Preparation of Compound 51

To a solution of intermediate 52 (657 mg, 1.6 mmol) and intermediate 39 (200 mg, 0.8 mmol) in THF (5 mL) was added TEA (340 uL, 2.5 mmol) at 25° C. The reaction mixture was stirred at 80° C. for 16 hours. The mixture was allowed to reach room temperature and concentrated in vacuum to give a crude product. The crude product was purified by preparative high-performance liquid chromatography [Column: Xtimate C18 10μ 250 mm*50 mm, Condition: A: water (0.04% aqueous ammonia+10 mM NH₄HCO₃), B: MeCN, at the beginning: A (40%) and B (60%), at the end: A (10%) and B (90%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 51 (240 mg, yield: 57.3%) as white solid.

LC/MS: m/z 473.1 [M+H]⁺, rt 2.37 min, purity 92.2%, method: D

Preparation of Compounds 52 and 53

Compound 51 (240 mg, 0.43 mmol) was separated by SFC [Column: DAICEL CHIRALCEL OD-H (250 mm*30 mm, 5 μm), Condition: solvent A: Supercritical CO₂, solvent B: 0.1% aqueous ammonia in MeOH, at the beginning: A (70%) and B (30%), at the end: A (70%) and B (30%), Flow Rate (ml/min) 50]. The pure fractions were collected and the organic solvent was evaporated under vacuum. MeCN and H₂O were added to the residue and it was lyophilized to dryness to give Compound 52 (105 mg, yield: 46.8%) as white solid and Compound 53 (110 mg, yield: 49.7%) as white solid.

Compound 52:

LC/MS: m/z 473.1 [M+H]⁺, rt 5.15 min. Purity 98.7%, method: K

SFC: purity 100%, rt 3.98 min. method: SFC11

Compound 53:

LC/MS: m/z 473.1 [M+H]⁺, rt 5.15 min. Purity 99.9%, method: K

SFC: purity 99.7%, rt 4.56 min. method: SFC11

Synthesis of Compounds 54, 55 and 56

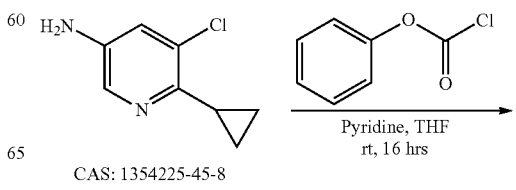

CAS: 1354225-45-8

Pyridine, THF
rt, 16 hrs

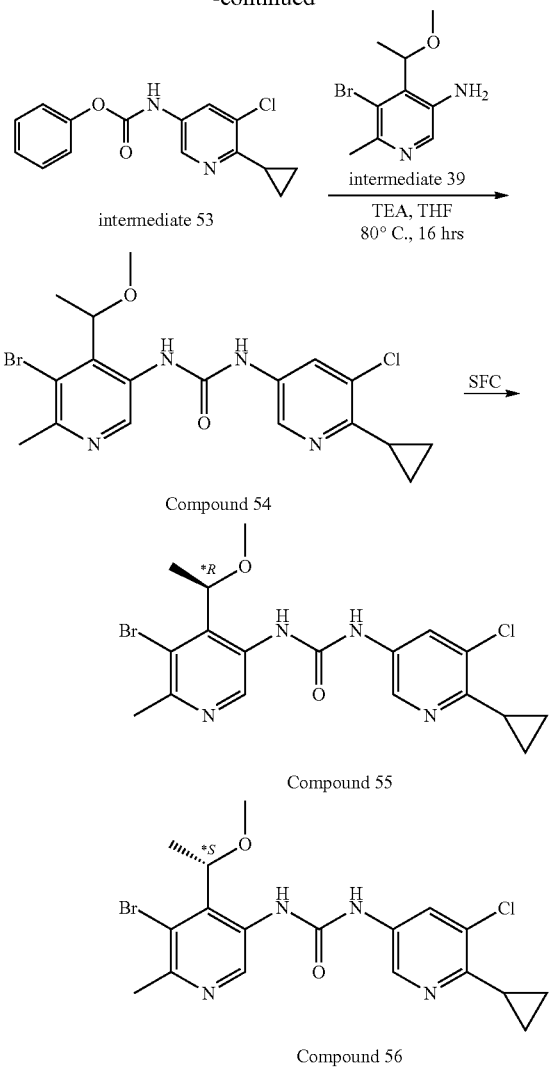

mm, Condition: A: water (0.04% aqueous ammonia+10 mM NH₄HCO₃), B: MeCN, at the beginning: A (40%) and B (60%), at the end: A (10%) and B (90%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 54 (186 mg, yield: 51.8%) as white solid.

LC/MS: m/z 439.1 [M+H]⁺, rt: 2.30 min, purity: 100%, method: B

Preparation of Compounds 55 and 56

Compound 54 (186 mg, 0.42 mmol) was separated by SFC [Column: DAICEL CHIRALCEL OD-H (250 mm*30 mm, 5 μm). Condition: solvent A: Supercritical CO₂, solvent B: 0.1% aqueous ammonia in MeOH. At the beginning: A (60%) and B (40%), at the end: A (60%) and B (40%), Flow Rate (ml/min) 50]. The pure fractions were collected and the organic solvent was evaporated under vacuum. MeCN and H₂O was added to the residue and it was lyophilized to dryness to give Compound 55 (79 mg, yield: 42%) as white solid and Compound 56 (90 mg, yield: 48%) as white solid.

Compound 55:

LC/MS: m/z 439.1 [M+H]⁺, rt: 4.85 min. Purity: 99.3%, method: K

SFC: purity 100%, rt: 5.01 min. method: SFC12

Compound 56:

LC/MS: m/z 439.1 [M+H]⁺, rt 4.84 min. Purity 99%, method: K

SFC: purity 98.9%, rt: 5.57 min. method: SFC12

Synthesis of Compounds 57, 58 and 59

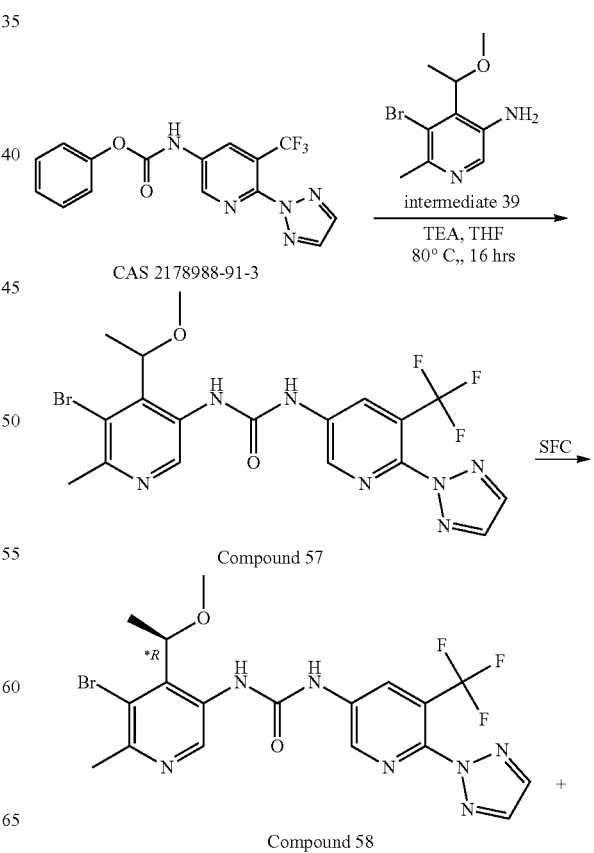

Preparation of Intermediate 53

To a solution of 5-chloro-6-cyclopropyl-3-pyridinamine (500 mg, 2.8 mmol) in THF (10 mL) was added pyridine (0.4 mL, 4.3 mmol) at room temperature. Phenyl chloroformate (0.5 mL, 3.7 mmol) was added slowly. The reaction was stirred at room temperature for 16 hours. The mixture was quenched with sat.NH₄Cl aq. The mixture was extracted with EtOAc twice. The combined organic layers were washed with brine and dried with Na₂SO₄, filtered and the filtrate was concentrated in vacuum to give a crude product. The crude product was purified by a flash column chromatography over silica gel (gradient elution: 0~33% EtOAc in petroleum ether). The desired fractions were collected and the solvent was concentrated under vacuum to afford intermediate 53 (755 mg, yield: 93%) as white solid.

Preparation of Compound 54

To a solution of intermediate 53 (353 mg, 1.2 mmol) and intermediate 39 (200 mg, 0.8 mmol) in THF (10 mL) was added triethylamine (340 uL, 2.5 mmol) at 25° C. The reaction mixture was stirred at 80° C. for 16 hours. The mixture was allowed to cool to room temperature and concentrated in vacuum to give a crude product. The crude product was purified by preparative high-performance liquid chromatography [Column: Xtimate C18 10μ 250 mm*50

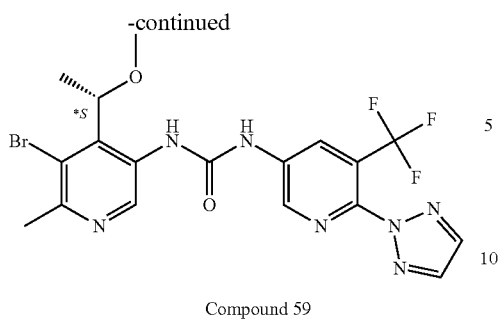

Compound 59

Preparation of Compound 57

To a solution of N-[6-(2H-1,2,3-triazol-2-yl)-5-(trifluoromethyl)-3-pyridinyl]-carbamic acid phenyl ester (CAS 2178988-91-3) (427 mg, 1.2 mmol) and intermediate 39 (200 mg, 0.8 mmol) in THF (5 mL) was added TEA (0.34 mL, 2.5 mmol) at 25° C. The reaction mixture was stirred at 80° C. for 16 hours. The mixture was allowed to reach room temperature and was concentrated in vacuum to give a crude product. The crude product was purified by preparative high-performance liquid chromatography [Column: Xtimate C18 10μ 250 mm*50 mm, Condition: A: water (0.04% aqueous ammonia+10 mM $NH_4HCO_3$), B: MeCN, at the beginning: A (48%) and B (52%), at the end: A (18%) and B (82%), Gradient Time 8 min; 100% B Hold Time 1 min; Flow Rate 25 ml/min]. The pure fractions were collected and the organic solvent was evaporated under vacuum. The aqueous layer was lyophilized to dryness to give Compound 57 (240 mg, yield: 58%) as white solid.

LC/MS: m/z 500 [M+H]$^+$, rt 2.08 min, purity 99.1%, method: D.

Preparation of Compounds 58 and 59

Compound 57 (240 mg, 0.48 mmol) was separated by SFC [Column: Phenomenex-Amylose-1 (250 mm*30 mm, 5 μm), Condition: solvent A: Supercritical $CO_2$, solvent B: 0.1% aqueous ammonia in EtOH, at the beginning: A (70%) and B (30%), at the end: A (70%) and B (30%), Flow Rate (ml/min) 50]. The pure fractions were collected and the organic solvent was evaporated under vacuum. MeCN and $H_2O$ were added to the residue and it was lyophilized to dryness to give Compound 58 (95 mg, yield: 39%) as white solid and Compound 59 (80 mg, yield: 33%) as white solid.

Compound 58:

LC/MS: m/z 500.1 [M+H]$^+$, rt 4.62 min. Purity 96.7%, method: K

SFC: purity 98.5%, rt 4.21 min. method: SFC1 Compound 59:

LC/MS: m/z 500.1 [M+H]$^+$, rt 4.62 min. Purity 99.3%, method: K

SFC: purity 99.6%, rt 3.77 min. method: SFC1

Synthesis of Compounds 60, 61 and 62

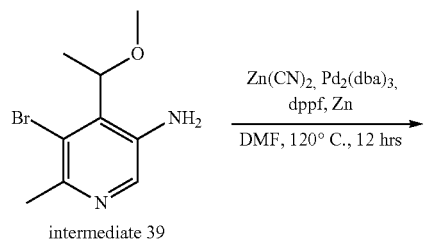

intermediate 39

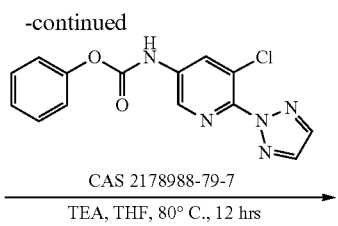

intermediate 54

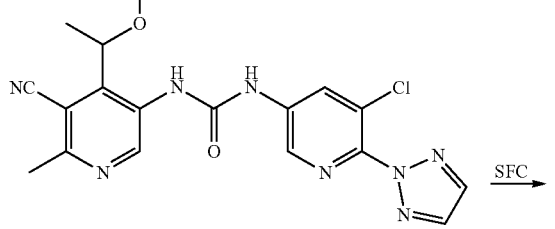

Compound 60

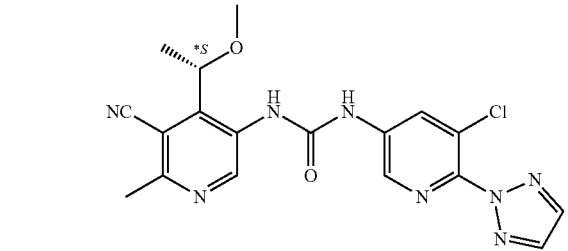

Compound 61

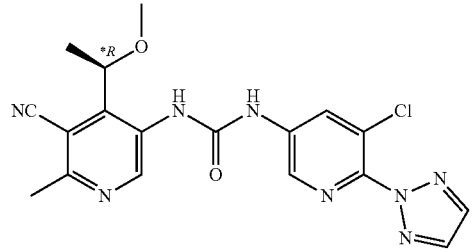

Compound 62

Preparation of Intermediate 54

A mixture of intermediate 39 (7.0 g, 28 mmol), $Zn(CN)_2$ (2.1 g, 18 mmol) and Zn (0.55 g, 8.4 mmol) in DMF (150 mL) was degassed with $N_2$ for 5 min. $Pd_2(dba)_3$ (1.3 g, 1.4 mmol) and dppf (1.6 g, 2.8 mmol) were added. The mixture was stirred at 120° C. for 12 hours under $N_2$. The mixture was filtered and the filtrate was concentrated to afford a crude product as yellow oil. The crude product was purified by flash column chromatography over silica gel (gradient elution: 0~30% EtOAc in petroleum ether). The desired fractions were collected and the solvent was concentrated in vacuum to give intermediate 54 (5.0 g, purity: 90%) as yellow solid.

Preparation of Compound 60

To a mixture of intermediate 54 (150 mg, 0.78 mmol) and N-[5-chloro-6-(2H-1,2,3-triazol-2-yl)-3-pyridinyl]-carbamic acid phenyl ester (CAS 2178988-79-7) (316 mg, 0.94 mmol) in THF (6 mL) was added triethylamine (0.32 mL, 2.4 mmol) at 25° C. The reaction mixture was stirred at 80° C. for 12 hours. The mixture was allowed to cool to 25° C. and filtered. The filtrate was concentrated in vacuum to give the crude product as yellow solid. The crude product was purified by preparative high-performance liquid chromatography. [Column: PhenomenexGemini 150*25 mm*10 um, Condition: A: water (0.04% aqueous ammonia+10 mM $NH_4HCO_3$), B: MeCN. At the beginning: A (65%) and B (35%), at the end: A (35%) and B (65%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 60 (100 mg, yield: 30%) as white solid.

Preparation of Compounds 61 and 62

Compound 60 (100 mg, 0.24 mmol) was separated by SFC [Column: DAICEL CHIRALPAK AD-H (250 mm*30 mm, 5 μm), Condition: solvent, A: Supercritical $CO_2$; Solvent, B: 0.1% aqueous ammonia in EtOH. At the beginning: A (65%) and B (35%), at the end: A (65%) and B (35%), Flow Rate (ml/min): 50]. The pure fractions were collected and the organic solvent was evaporated under vacuum. MeCN and $H_2O$ was added to the residue and the mixture was lyophilized to dryness to give Compound 61 (27 mg, yield: 28%) and Compound 62 (27 mg, yield: 28%) as white solid.

Compound 61:
LC/MS: m/z 413.1 [M+H]$^+$, rt: 4.27 min, purity: 100%, method: K.
SFC: purity 99.8%, rt: 4.38 min, method: SFC10.

Compound 62:
LC/MS: m/z 413.2 [M+H]$^+$, rt: 4.26 min, purity: 98.4%, method: K
SFC: purity 99.2%, rt: 4.87 min, method: SFC10.

Alternative Preparation of Compound 60

To a solution of intermediate 54 (500 mg, 2.5 mmol) and N-[5-chloro-6-(2H-1,2,3-triazol-2-yl)-3-pyridinyl]-carbamic acid phenyl ester (CAS 2178988-79-7) (1.3 g, 3.8 mmol) in THF (20 mL) was added DMAP (619 mg, 5.1 mmol) at 20° C. The reaction mixture was stirred at 60° C. for 2 hours. The mixture was concentrated in vacuum to give the crude product. Petroleum ether:ethyl acetate=1:1 (50 mL) was added to the crude product, and the mixture was stirred at 25° C. for 10 min. The resulting solid was collected by filtration and washed with petroleum ether:ethyl acetate=1:1 (20 mL). The solid residue was collected, treated with MeCN (200 mL) and the suspension was stirred at 25° C. for 10 min. The mixture was filtered and the filtrate, containing the product, was concentrated in vacuo to afford Compound 60 (450 mg, yield: 43%) as a white solid.

LC/MS: m/z 413.0 [M+H]$^+$, rt 0.75 min, purity 100%, method A

Alternative Preparation of Compounds 61 and 62

Compound 60 (450 mg, 1.09 mmol) was separated by SFC [Column: Phenomenex-Amylose-1 (250 mm*30 mm, 5 μm), Condition: solvent A: Supercritical $CO_2$, solvent B: 0.1% aqueous ammonia in EtOH, at the beginning: A (70%) and B (30%), at the end: A (70%) and B (30%), Flow Rate (mL/min) 50]. The pure fractions were collected and the organic solvent was evaporated under vacuum. MeCN and $H_2O$ were added to the residues and they were lyophilized to dryness to give Compound 61 (166 mg, yield: 37%) as white solid, and Compound 62 (173.3 mg, yield: 38.3%) as white solid.

Compound 61:
HPLC-MS: m/z 413.1 [M+H]$^+$, rt 4.25 min. Purity 100%, method K;
SFC: purity 100%, rt 4.40 min. method: SFC10.

Compound 62:
HPLC-MS: m % z 413.1 [M+H]$^+$, rt 4.25 min. Purity 99.59%, method K;
SFC: purity 99.38%, rt 4.88 min. method: SFC10.

Synthesis of Compounds 63, 64 and 65

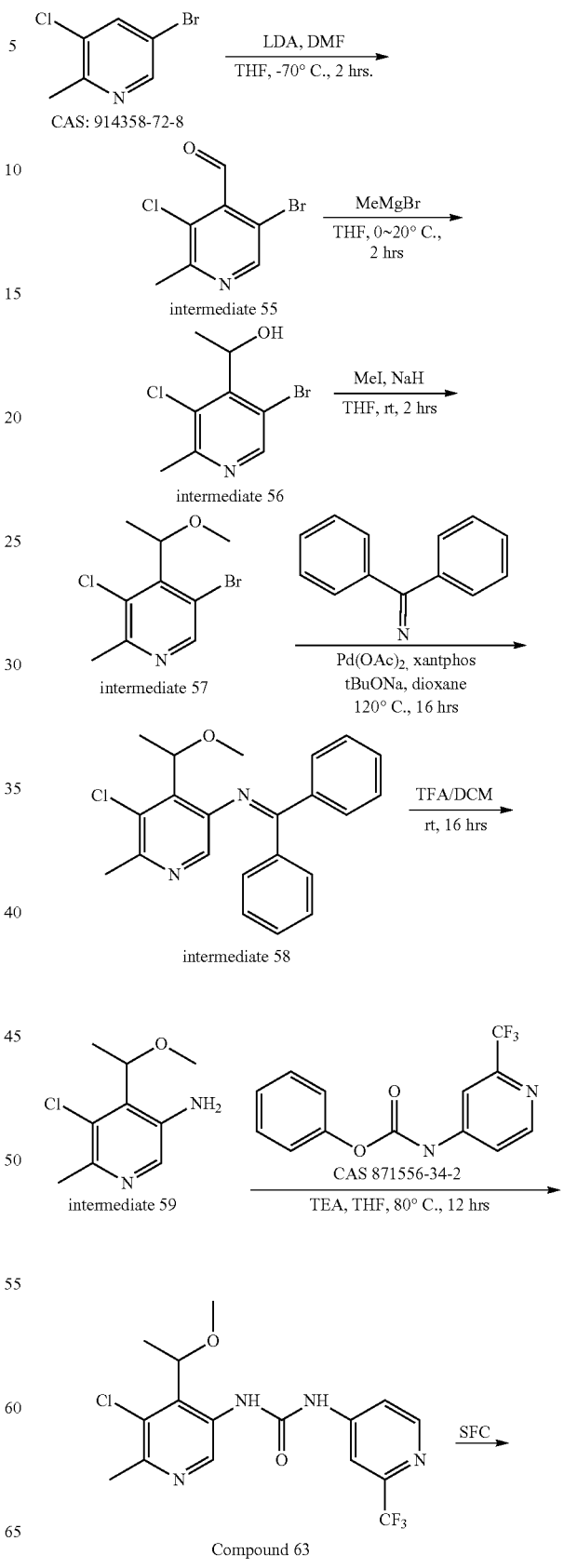

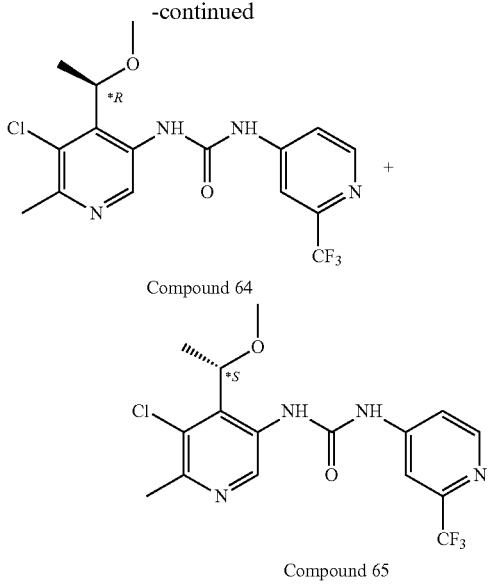

Compound 64

Compound 65

Preparation of Intermediate 55

5-bromo-3-chloro-2-methylpyridine (6.5 g, 31.5 mmol) was dissolved in THF (130 mL) and cooled to −70° C. LDA (2M in THF and heptanes, 19 mL, 38 mmol) was added dropwise. The reaction mixture was stirred at −70° C. for 1 h. DMF (4.9 mL, 63 mmol) was added to the mixture and stirred at −70° C. for 1 hours. The reaction mixture was quenched with sat. NH$_4$Cl aq at a temperature between −20° C.~−70°, and then H$_2$O was added and the mixture was warmed to room temperature. The mixture was extracted with EtOAc twice. The combined organic layers were washed with brine and dried with Na$_2$SO$_4$, filtered and the filtrate was concentrated under vacuum to afford the crude product as yellow solid. The crude product was purified by flash column chromatography over silica gel (gradient elution: 0~3% EtOAc in petroleum ether). The desired fractions were collected and the solvent was concentrated under vacuum to afford intermediate 55 (6 g, yield: 81%) as light yellow solid.

Preparation of Intermediate 56

Intermediate 55 (6 g, 26 mmol) was dissolved in THF (150 mL) and stirred at 0° C. A solution of methylmagnesium bromide (3 M in THF, 17.1 mL, 51 mmol) was added at 0° C. The mixture was allowed to warm to 20° C. and stirred at 20° C. for 1 hour. The mixture was quenched with sat.NH$_4$Cl aq. The mixture was extracted with EtOAc twice. The combined organic layers were washed with brine and dried with Na$_2$SO$_4$, filtered and the filtrate was concentrated in vacuum to give crude intermediate 56 (5.9 g, yield: 89%) as yellow solid.

Preparation of Intermediate 57

Intermediate 56 (6.3 g, 25 mmol) was dissolved in THF (65 mL) and stirred at 0° C. NaH (60% in mineral oil, 1.5 g, 38 mmol) was added and the mixture was stirred at 0° C. for 0.5 h. MeI (13 g, 93 mmol) was added and stirred at rt for another 16 hours. The mixture was quenched with sat. NH$_4$Cl aq. and the mixture was extracted with EtOAc twice. The combined organic layers were washed with brine and dried with Na$_2$SO$_4$, filtered and the filtrate was concentrated in vacuum to give a crude product. The crude product was purified by flash column chromatography over silica gel (gradient elution: 0~9% EtOAc in petroleum ether). The desired fractions were collected and the solvent was concentrated to dryness under vacuum to give intermediate 57 (6.1 g, yield: 91%) as yellow oil.

Preparation of Intermediate 58

Intermediate 57 (3.9 g, 19 mmol) and diphenylmethanimine (4.0 g, 22 mmol) were dissolved in dioxane (60 mL). Then Pd(OAc)$_2$ (329 mg, 1.5 mmol), xantphos (1.7 g, 2.9 mmol) and tBuONa (2 g, 22 mmol) were added and the mixture purged with N$_2$. The reaction mixture was stirred at 120° C. for 16 hours. Sat.NH$_4$Cl aq. was added to the mixture and the mixture was extracted with EtOAc twice. The combined organic layers were washed with brine and dried with Na$_2$SO$_4$, filtered and the filtrate was concentrated in vacuum to give a crude product. The crude product was purified by flash column chromatography over silica gel (gradient elution: 0~8% EtOAc in petroleum ether). The desired fractions were collected and the solvent was concentrated to dryness under vacuum to give intermediate 58 (6 g, yield 68.6%) as yellow oil.

Preparation of Intermediate 59

Intermediate 58 (2 g, 5.5 mmol) was dissolved in DCM (40 mL) and TFA (20 mL) was added. The reaction mixture was stirred at rt for 16 hours. The mixture was concentrated under vacuum to remove TFA. The crude product was diluted with EtOAc and sat. NaHCO$_3$ was added to obtain a pH=7. The aqueous phase was extracted with EtOAc twice. The organic layers were washed with brine and dried with MgSO$_4$, filtered and evaporated to give a yellow solid. The crude product was purified by flash column chromatography over silica gel (gradient elution: 0~40% EtOAc in petroleum ether). The desired fractions were collected and the solvent was concentrated to dryness under vacuum to give intermediate 59 (0.8 g, yield 73%) as yellow solid.

Preparation of Compound 63

To a solution of intermediate 59 (200 mg, 1.0 mmol) and N-[2-(trifluoromethyl)-4-pyridinyl]-Carbamic acid phenyl ester (CAS 871556-34-2) (445 mg, 1.5 mmol) in THF (10 mL) was added TEA (303 mg, 3.0 mmol) at 25° C. The reaction mixture was stirred at 80° C. for 12 hours. The mixture was concentrated in vacuum to give a crude product. The crude product was purified by flash column chromatography over silica gel (gradient elution: 0~60% EtOAc in petroleum ether). The desired fractions were collected and the solvent was concentrated in vacuum to give Compound 63 (265 mg, yield: 68%) as yellow solid.

LC/MS: m/z 389.1 [M+H]$^+$, rt 0.79 min, purity 100%, method A

Preparation of Compounds 64 and 65

Compounds 63 (265 mg, 0.68 mmol) was separated by SFC [Column: DAICEL CHIRALPAK AD-H (250 mm*30 mm, 5 μm), Condition: solvent A: Supercritical CO$_2$, solvent B: 0.1% aqueous ammonia in EtOH, at the beginning: A (85%) and B (15%), at the end: A (85%) and B (15%), Flow Rate (mL/min) 60]. The pure fractions were collected and the organic solvent was evaporated under vacuum. MeCN and H$_2$O was added to the residue and it was lyophilized to dryness to give Compound 64 (130 mg, yield: 49%) as white solid and Compound 65 (135 mg, yield: 51%) as white solid.

Compound 64:

LC/MS: m/z 389.1 [M+H]$^+$, rt 5.54 min. Purity 100%, method K

SFC: purity 100%, rt 2.82 min. method: SFC10 Compound 65:

LC/MS: m/z 389.1 [M+H]$^+$, rt 5.54 min. Purity 100%, method K

SFC: purity 100%, rt 3.02 min. method: SFC10

Synthesis of Compounds 66, 67 and 68

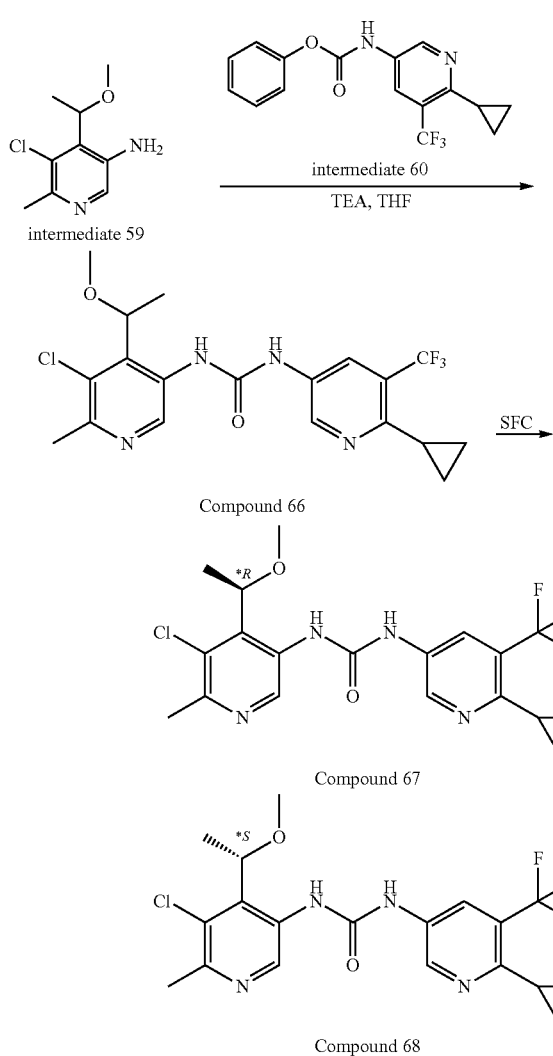

Compound 66

Compound 67

Compound 68

Preparation of Compound 66

To a mixture of intermediate 59 (200 mg, 1 mmol) and intermediate 60 (prepared by analogy to the protocols in WO2018020474) (385 mg, 1.2 mmol) in THF (5 mL) was added triethylamine (0.4 mL, 3 mmol) at 25° C. The reaction mixture was stirred at 80° C. for 12 hours. Then an additional amount of intermediate 60 (160 mg, 0.5 mmol) was added. The reaction mixture was stirred at 80° C. for 12 hours. The reaction mixture was allowed to reach 25° C. and concentrated under vacuum to afford the crude product as a yellow solid. The crude product was purified by flash column chromatography over silica gel (gradient elution: 0~50% EtOAc in petroleum ether). The desired fractions were collected and the solvent was concentrated to give the product as yellow solid. The yellow solid was washed by petroleum ether/ethyl acetate (5:1) to give white solid as Compound 66 (250 mg, yield: 58%).

LC/MS: m/z 429.1 [M+H]$^+$, rt: 2.33 min, purity: 100%, method: C

SFC: purity 49.9/50.1%, rt: 4.95/5.59, method: SFC6

Preparation of Compounds 67 and 68

Compound 66 (250 mg, 0.6 mmol) was separated by SFC [Column: DAICEL CHIRALPAK AD-H (250 mm*30 mm, 5 µm), Condition: solvent, A: Supercritical CO$_2$; Solvent, B: 0.1% aqueous ammonia in EtOH. At the beginning: A (60%) and B (40%), at the end: A (60%) and B (40%), Flow Rate (ml/min): 60]. The pure fractions were collected and the organic solvent was evaporated under vacuum. MeCN and H$_2$O was added to the residue and the mixture was lyophilized to dryness to give Compound 67 (100 mg, yield: 40%) and Compound 68 (103 mg, yield: 41%) as white solids.

Compound 67:

LC/MS: m/z 429.2 [M+H]$^+$, rt: 5.09 min, purity: 100%, method: K.

SFC: purity 100%, rt: 4.94 min, method: SFC6 Compound 68:

LC/MS: m/z 429.2 [M+H]$^+$, rt: 5.10 min, purity: 99.8%, method: K

SFC: purity 100%, rt: 5.57 min, method: SFC6

Synthesis of Compounds 69, 70 and 71

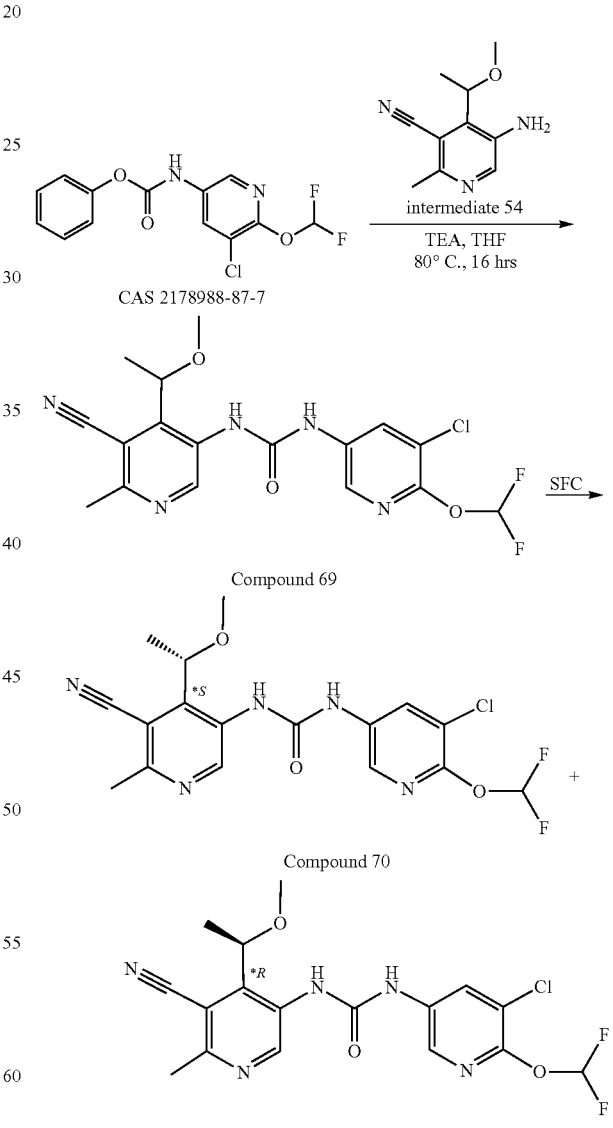

Compound 69

Compound 70

Compound 71

Preparation of Compound 69

Compound 69 was prepared by analogy to the procedure described for Compound 57 using N-[5-chloro-6-(difluoromethoxy)-3-pyridinyl]-carbamic acid phenyl ester (CAS 2178988-87-7) and intermediate 54. The mixture was allowed to reach room temperature and was concentrated in vacuum to give a crude product. The crude product was purified by preparative high-performance liquid chromatography [Column Boston Prime C18 150*30 mm 5 um, Condition: A: water (0.04% aqueous ammonia+10 mM $NH_4HCO_3$), B: MeCN, at the beginning: A (50%) and B (50%), at the end: A (20%) and B (80%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 69 (125 mg, yield: 39%) as white solid.

LC/MS: m/z 412.2 $[M+H]^+$, rt: 1.85 min, purity 99.9%, method: C.

Preparation of Compounds 70 and 71

Compound 69 (125 mg, 0.3 mmol) was separated by SFC [Column: Phenomenex-Amylose-1 (250 mm*30 mm, 5 μm), Condition: solvent A: Supercritical $CO_2$, solvent B: 0.1% aqueous ammonia in EtOH, at the beginning: A (85%) and B (15%), at the end: A (85%) and B (15%), Flow Rate (ml/min) 50]. The pure fractions were collected and the organic solvent was evaporated under vacuum. MeCN and $H_2O$ were added to the residue and it was lyophilized to dryness to give Compound 70 (42 mg, yield: 33%) as white solid and Compound 71 (48 mg, yield: 38.3%) as white solid.

Compound 70:

HPLC/MS: m/z 412.1 $[M+H]^+$, rt: 4.96 min, Purity 98.5%, method: K;

SFC: purity 99.8%, rt: 2.87 min, method: SFC1.

Compound 71:

HPLC/MS: m/z 412.1 $[M+H]^+$, rt: 4.96 min, Purity 99.7%, method: K;

SFC: purity 100%, rt: 3.12 min, method: SFC1.

Synthesis of Compounds 72, 73 and 74

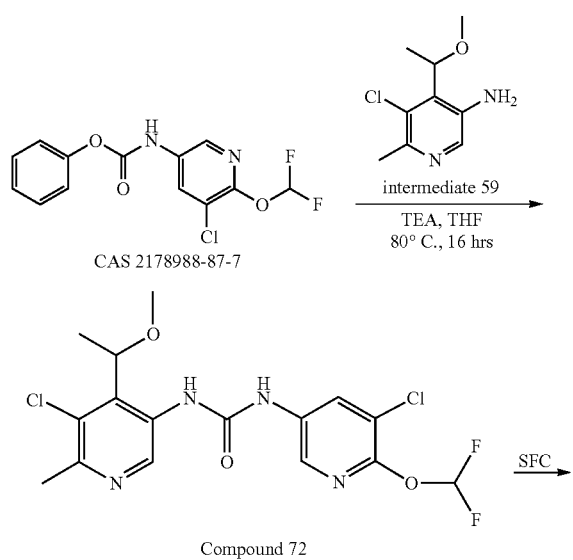

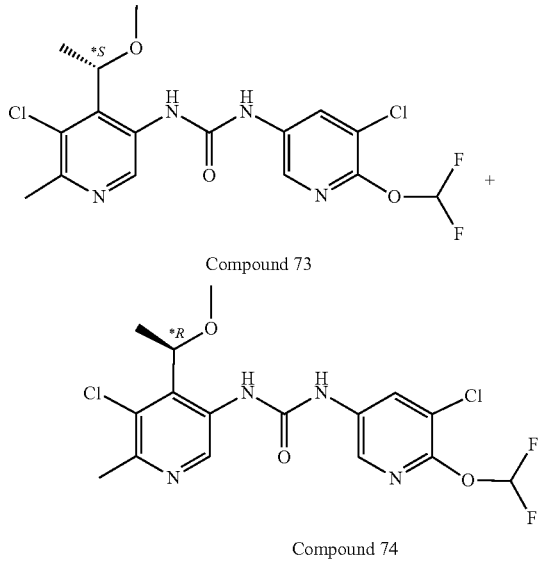

Compound 73

Compound 74

Preparation of Compound 72

Compound 72 was prepared by analogy to the procedure described for Compound 57 using carbamate CAS 2178988-87-7 and intermediate 59. The mixture was allowed to reach room temperature and was concentrated in vacuum to give a crude product. The crude product was purified by preparative high-performance liquid chromatography [Column: Xtimate C18 10μ 250 mm*50 mm, Condition: A: water (0.04% aqueous ammonia+10 mM $NH_4HCO_3$), B: MeCN, at the beginning: A (45%) and B (55%), at the end: A (15%) and B (85%), Gradient Time 15 min; 100% B Hold Time 0 min; Flow Rate 60 ml/min]. The pure fractions were collected and the organic solvent was evaporated under vacuum. The aqueous layer was lyophilized to dryness to give Compound 72 (170 mg, yield: 53.4%) as white solid.

LC/MS: m/z 421.1 $[M+H]^+$, rt: 1.96 min, purity 98.1%, method C.

Preparation of Compounds 73 and 74

Compound 72 (170 mg, 0.4 mmol) was separated by SFC [Column: Phenomenex-Amylose-1 (250 mm*30 mm, 5 μm), Condition: solvent A: Supercritical $CO_2$, solvent B: 0.1% aqueous ammonia in EtOH, at the beginning: A (75%) and B (25%), at the end: A (75%) and B (25%), Flow Rate (ml/min) 50]. The pure fractions were collected and the organic solvent was evaporated under vacuum. MeCN and $H_2O$ were added to the residue and it was lyophilized to dryness to give Compound 73 (70 mg, yield: 41.9%) as white solid, and Compound 74 (65 mg, yield: 38.5%) as white solid.

Compound 73:

HPLC/MS: m/z 421.1 $[M+H]^+$, rt: 4.88 min, Purity 99.9%, method: K;

SFC: purity 99.7%, rt: 3.53 min, method: SFC10.

Compound 74:

HPLC/MS: m % z 421.1 $[M+H]^+$, rt: 4.88 min, Purity 98.8%, method: K;

SFC: purity 98.1%, rt: 4.87 min, method: SFC10.

Synthesis of Compounds 75, 76 and 77

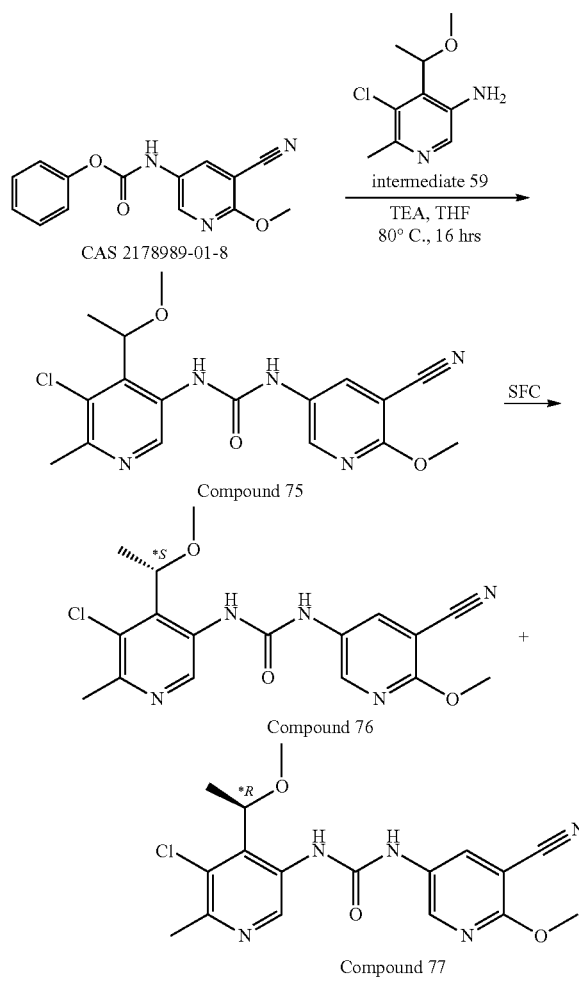

Preparation of Compound 75

Compound 75 was prepared by analogy to the procedure described for Compound 57 using carbamate CAS 2178989-01-8 and intermediate 59. The mixture was allowed to reach room temperature and was concentrated in vacuum to give a crude product. The crude product was purified by preparative high-performance liquid chromatography [Column: Boston Prime C18 150*30 mm 5 um, Condition: A: water (0.04% aqueous ammonia+10 mM $NH_4HCO_3$), B: MeCN, at the beginning: A (60%) and B (40%), at the end: A (30%) and B (70%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 75 (160 mg, yield: 42.1%) as white solid.

LC/MS: m/z 376.2 [M+H]$^+$, rt: 1.71 min, purity 97.7%, method: C.

Preparation of Compounds 76 and 77

Compound 75 (160 mg, 0.42 mmol) was separated by SFC [Column: Phenomenex-Amylose-1 (250 mm*30 mm, 5 μm), Condition: solvent A: Supercritical $CO_2$, solvent B: 0.1% aqueous ammonia in EtOH, at the beginning: A (70%) and B (30%), at the end: A (70%) and B (30%), Flow Rate (ml/min) 50]. The pure fractions were collected and the organic solvent was evaporated under vacuum. MeCN and $H_2O$ were added to the residue and it was lyophilized to dryness to give Compound 76 (52 mg, yield: 33.2%) as white solid, and Compound 77 (55 mg, yield: 35.2%) as white solid.

Compound 76:

HPLC/MS: m/z 376.1 [M+H]$^+$, rt: 4.17 min. Purity 99.7%, method: K.

SFC: purity 99.9%, rt: 4.39 min, method: SFC10.

Compound 77:

HPLC/MS: m/z 376.2 [M+H]$^+$, rt: 4.17 min. Purity 100%, method: K.

SFC: purity 99.1%, rt: 4.94 min, method: SFC10.

Synthesis of Compounds 78, 79 and 80

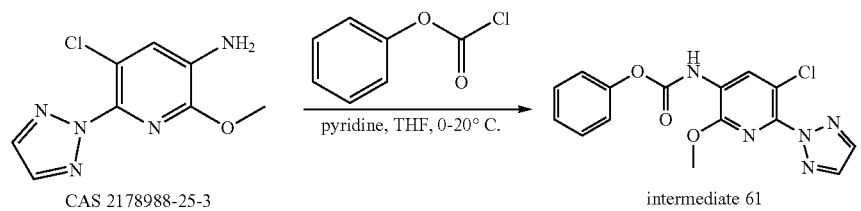

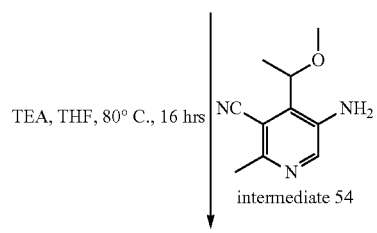

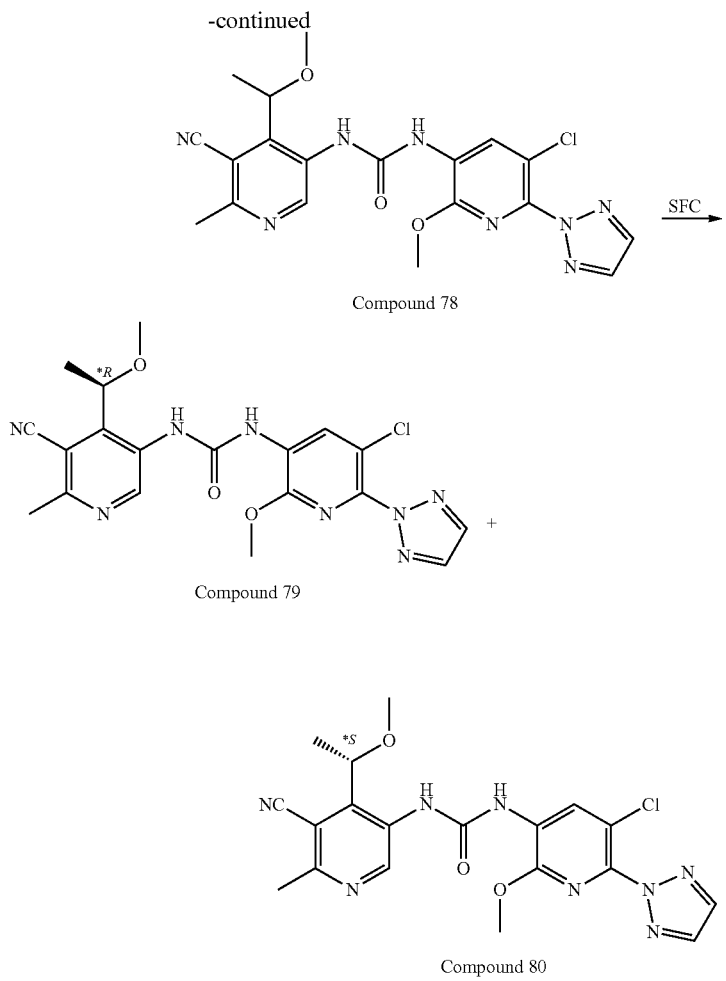

Compound 78

Compound 79

Compound 80

Preparation of Intermediate 61

To a mixture of amino pyridine CAS 2178988-25-3 (1.6 g, 7 mmol) in THF (30 mL) was added pyridine (1.1 mL, 14 mmol) at 20° C. and phenyl chloroformate (1.6 g, 10.5 mmol) at 0° C. The mixture was stirred at 20° C. for 16 hours. The mixture was quenched with sat. NH$_4$Cl aq. The mixture was extracted with EtOAc twice. The combined organic layers were washed with brine and dried with Na$_2$SO$_4$, filtered and the filtrate was concentrated in vacuum to give a crude product. The crude product was purified by flash column chromatography over silica gel (gradient elution: 0~30% EtOAc in petroleum ether). The desired fractions were collected and the solvent was concentrated under vacuum to afford intermediate 61 (2 g, yield: 82%) as white solid.

Preparation of Compound 78

Compound 78 was prepared by analogy to the procedure described for Compound 57, using intermediate 61 and intermediate 54. The mixture was allowed to reach room temperature and was concentrated in vacuum to give a crude product. The crude product was purified by flash column chromatography over silica gel (gradient elution: 0~50% EtOAc in petroleum ether). The desired fractions were collected and the solvent was concentrated under vacuum to afford Compound 78 (150 mg, yield: 32%) as white solid.

LC/MS: m/z 443.2 [M+H]$^+$, rt: 0.83 min, Purity 98.4%, method: B.

Preparation of Compounds 79 and 80

Compound 78 (150 mg, 0.3 mmol) was separated by SFC. [Column: DAICEL CHIRALPAK AD-H (250 mm*30 mm, 5 μm), Condition: solvent, A: Supercritical CO$_2$; Solvent, B: 0.1% aqueous ammonia in MeOH. At the beginning: A (45%) and B (55%), at the end: A (55%) and B (45%), Flow Rate (ml/min): 50]. The pure fractions were collected and the organic solvent was evaporated under vacuum. MeCN and H$_2$O were added to the residue and the mixture was lyophilized to dryness to give Compound 79 (65 mg, yield: 44%) as white solid and Compound 80 (65 mg, yield: 42%) as white solid.

Compound 79:

$^1$H NMR (400 MHz, DMSO-d$_6$) δ ppm 1.49 (d, J=6.8 Hz, 3H), 2.67 (s, 3H), 3.20 (s, 3H), 3.99 (s, 3H), 4.77 (q, J=6.8 Hz, 1H), 8.13 (s, 2H), 8.70 (s, 1H), 8.93 (s, 1H), 8.98 (br s, 1H), 9.51 (br s, 1H)

HPLC/MS: m/z 443.2 [M+H]$^+$, rt: 4.62 min, purity 99.3%, method: K;

SFC: purity 100%, rt: 4.43 min, method: SFC19.

Compound 80:

HPLC/MS: m % z 443.2 [M+H]$^+$, rt: 4.64 min, purity 95.1%, method: K;

SFC: purity 100%, rt: 3.53 min, method: SFC19.

Synthesis of Compounds 81, 82 and 83

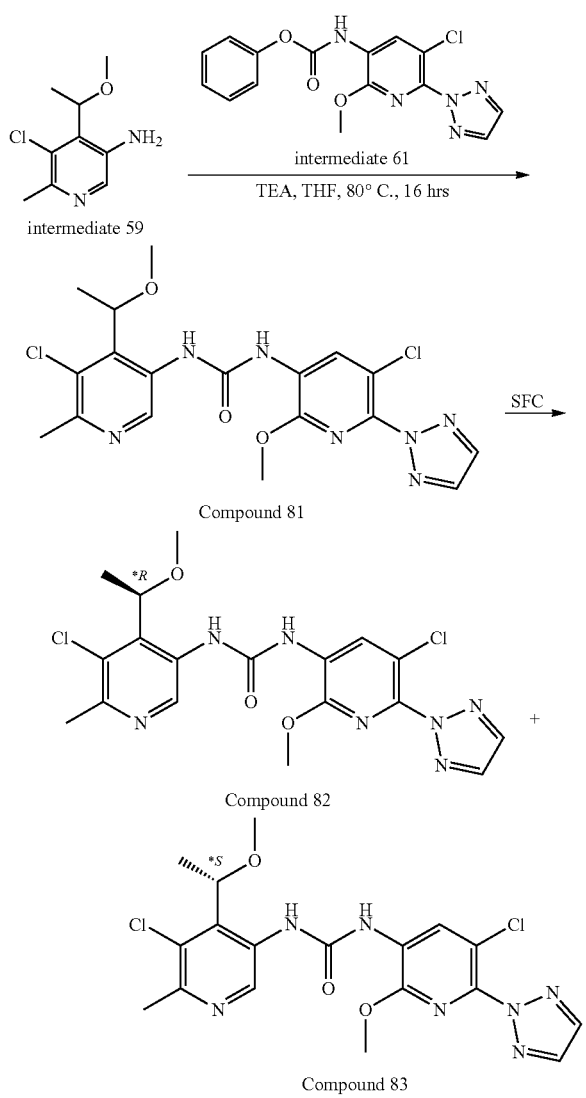

Compound 81

Compound 82

Compound 83

Preparation of Compound 81

Compound 81 was prepared by analogy to the procedure described for Compound 57 using intermediate 61 and intermediate 59. The mixture was allowed to reach room temperature and was concentrated in vacuum to give a crude product. The crude product was purified by flash column chromatography over silica gel (gradient elution: 0~50% EtOAc in petroleum ether). The desired fractions were collected and the solvent was concentrated under vacuum to afford Compound 81 (200 mg, yield: 45%) as white solid.

LC/MS: m/z 452.1 [M+H]$^+$, rt: 0.83 min, Purity 100%, method: B.

Preparation of Compounds 82 and 83

Compound 81 (200 mg, 0.4 mmol) was separated by SFC [Column: DAICEL CHIRALPAK AD-H (250 mm*30 mm, 5 μm), Condition: solvent, A: Supercritical CO$_2$; Solvent, B: 0.1% aqueous ammonia in MeOH. At the beginning: A (50%) and B (50%), at the end: A (50%) and B (50%), Flow Rate (ml/min): 70]. The pure fractions were collected and the organic solvent was evaporated under vacuum. MeCN and H$_2$O were added to the residue and the mixture was lyophilized to dryness to give Compound 82 (80 mg, yield: 40%) as white solid and Compound 83 (80 mg, yield: 40%) as white solid.

Compound 82:
HPLC/MS: m/z 452.0 [M+H]$^+$, rt: 4.7 min, purity 99.5%, method: K;
SFC: purity 98.8%, rt: 2.72 min, method: SFC19.

Compound 83:
HPLC/MS: m/z 452.0 [M+H]$^-$, rt: 4.7 min, purity 99.8%, method: K;
SFC: purity 100%, rt: 1.38 min, method: SFC19.

Synthesis of Compounds 84, 85 and 86

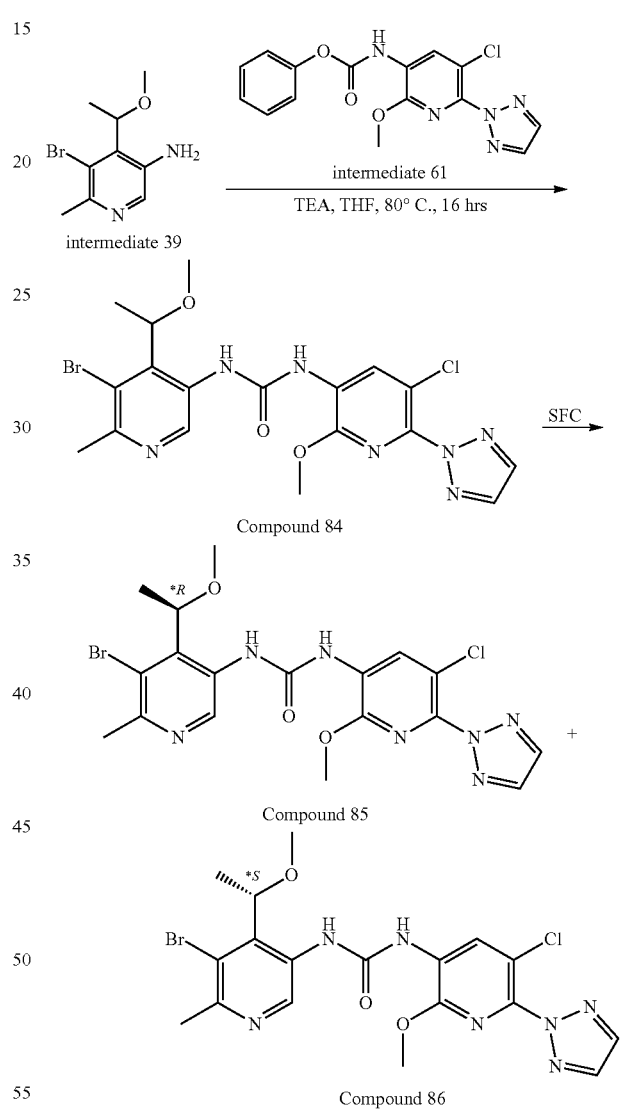

Compound 84

Compound 85

Compound 86

Preparation of Compound 84

Compound 84 was prepared by analogy to the procedure described for Compound 57 using intermediate 61 and intermediate 39. The mixture was allowed to reach room temperature and was concentrated in vacuum to give a crude product. The crude product was purified by flash column chromatography over silica gel (gradient elution: 0~50% EtOAc in petroleum ether). The desired fractions were collected and the solvent was concentrated under vacuum to afford Compound 84 (150 mg, yield: 36%) as white solid.

LC/MS: m/z 496 [M+H]⁺, rt: 0.84 min, Purity 98%, method: B.

Preparation of Compounds 85 and 86

Compound 84 (150 mg, 0.3 mmol) was separated by SFC [Column: DAICEL CHIRALPAK AD-H (250 mm*30 mm, 5 μm), Condition: solvent, A: Supercritical CO₂; Solvent, B: 0.1% aqueous ammonia in MeOH. At the beginning: A (50%) and B (50%), at the end: A (50%) and B (50%), Flow Rate (ml/min): 70]. The pure fractions were collected and the organic solvent was evaporated under vacuum. MeCN and H₂O were added to the residue and the mixture was lyophilized to dryness to give Compound 85 (60 mg, yield: 39%) as white solid and Compound 86 (60 mg, yield: 40.9%) as white solid.

Compound 85:

HPLC/MS: m/z 496 [M+H]⁺, rt: 4.79 min, purity 96.3%, method: K;

SFC: purity 100%, rt: 3.30 min, method: SFC19.

Compound 86:

HPLC/MS: m/z 496 [M+H]⁺, rt: 4.79 min, purity 100%, method: K;

SFC: purity 100%, rt: 1.55 min, method: SFC19.

Synthesis of Compounds 87, 88 and 89

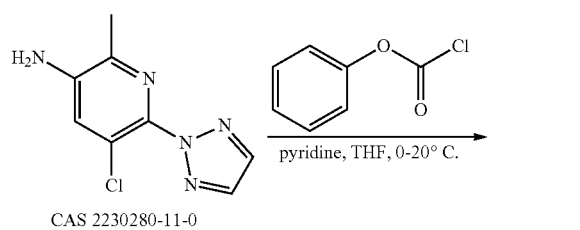

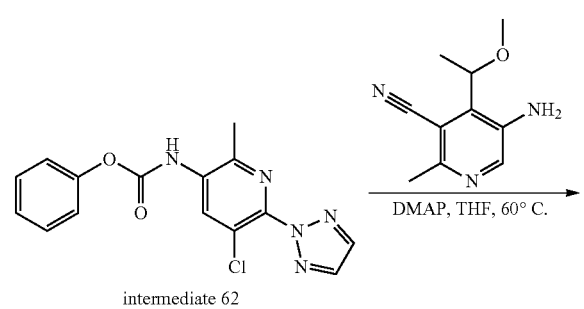

intermediate 62

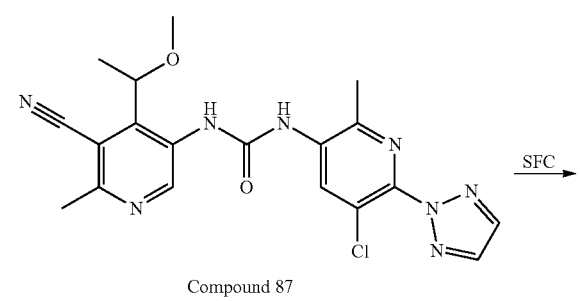

Compound 87

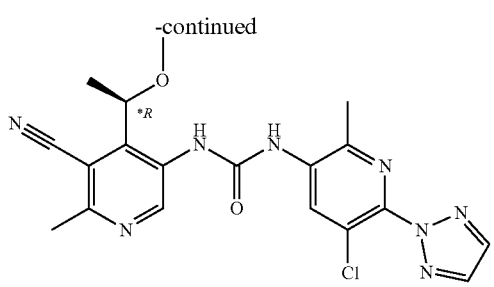

Compound 88

+

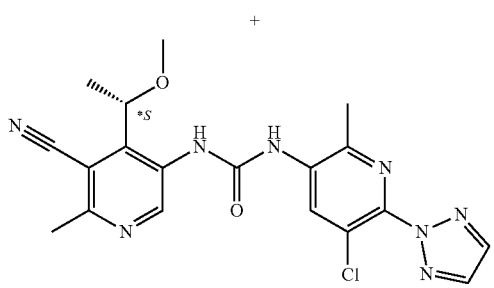

Compound 89

Preparation of Intermediate 62

To a mixture of CAS 2230280-11-0 (10 g, 47 mmol) in THF (200 mL) was added pyridine (11.5 mL, 143 mmol) at 20° C. and phenyl chloroformate (9 mL, 71 mmol) at 0° C. The mixture was stirred at 20° C. for 16 hours. The mixture was quenched with sat. NH₄Cl aq. The mixture was extracted with EtOAc twice. The combined organic layers were washed with brine and dried with Na₂SO₄, filtered and the filtrate was concentrated in vacuum to give a crude product. The crude product was purified by flash column chromatography over silica gel (gradient elution: 0~50% EtOAc in petroleum ether). The desired fractions were collected and the solvent was concentrated under vacuum to afford intermediate 62 (9 g, yield: 51%) as yellow solid.

Preparation of Compound 87

To a mixture of intermediate 54 (200 mg, 1 mmol) in THF (10 mL) was added intermediate 62 (561 mg, 1.5 mmol) and DMAP (247 mg, 2 mmol) at 25° C. The reaction mixture was stirred at 60° C. for 2 hours. The mixture was allowed to reach 25° C. and filtered. The filtrate was concentrated in vacuum to give a crude product as yellow solid. The crude product was purified by preparative high-performance liquid chromatography [Column: Phenomenex Gemini 150*25 mm*10 um, Condition: A: water (0.04% aqueous ammonia+ 10 mM NH₄HCO₃), B: MeCN. At the beginning: A (70%) and B (30%), at the end: A (40%) and B (60%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 87 (120 mg, yield: 27.4%) as yellow solid.

LC/MS: m/z 427.0 [M+H]⁺, rt: 0.75 min, Purity: 98.9%, method: A.

Preparation of Compounds 88 and 89

Compound 87 (120 mg, 0.28 mmol) was separated by SFC [Column: DAICEL CHIRALPAK IC (250 mm*30 mm, 10 μm), Condition: MeOH, A: Supercritical CO₂; Solvent, B: MeOH. At the beginning: A (45%) and B (55%), at the end: A (45%) and B (55%), Flow Rate (ml/min): 80]. The pure fractions were collected and the organic solvent was evaporated under vacuum. MeCN and H₂O were added to the residue and the mixture was lyophilized to dryness to give Compound 88 (41.3 mg, yield: 35%) as white solid and Compound 89 (44.1 mg, yield: 37%) as white solid.
Compound 88:
HPLC/MS: m/z 427.2, [M+H]+, rt: 4.25 min, purity: 100%, method: K.
SFC: purity 100%, rt: 1.93 min, method: SFC19.
Compound 89:
HPLC/MS: m/z 427.2, [M+H]+, rt: 4.25 min, purity: 99.9%, method: K.
SFC: purity 99.99%, rt: 4.40 min, method: SFC19.
Synthesis of Compounds 90, 91 and 92 concentrated in vacuum to give a crude product. The crude product was purified by flash column chromatography over silica gel (gradient elution: 0~40% EtOAc in petroleum ether). The pure fractions were collected and the solvent was evaporated under vacuum give intermediate 63 (13 g, yield: 70%) as white solid.
Preparation of Compound 90
To a solution of intermediate 39 (200 mg, 0.7 mmol) and intermediate 63 (300 mg, 1.0 mmol) in THF (10 mL) was added DMAP (159 mg, 1.3 mmol) at 20° C. The reaction mixture was stirred at 80° C. for 2 hours. The mixture was concentrated in vacuum to give a crude product. The crude

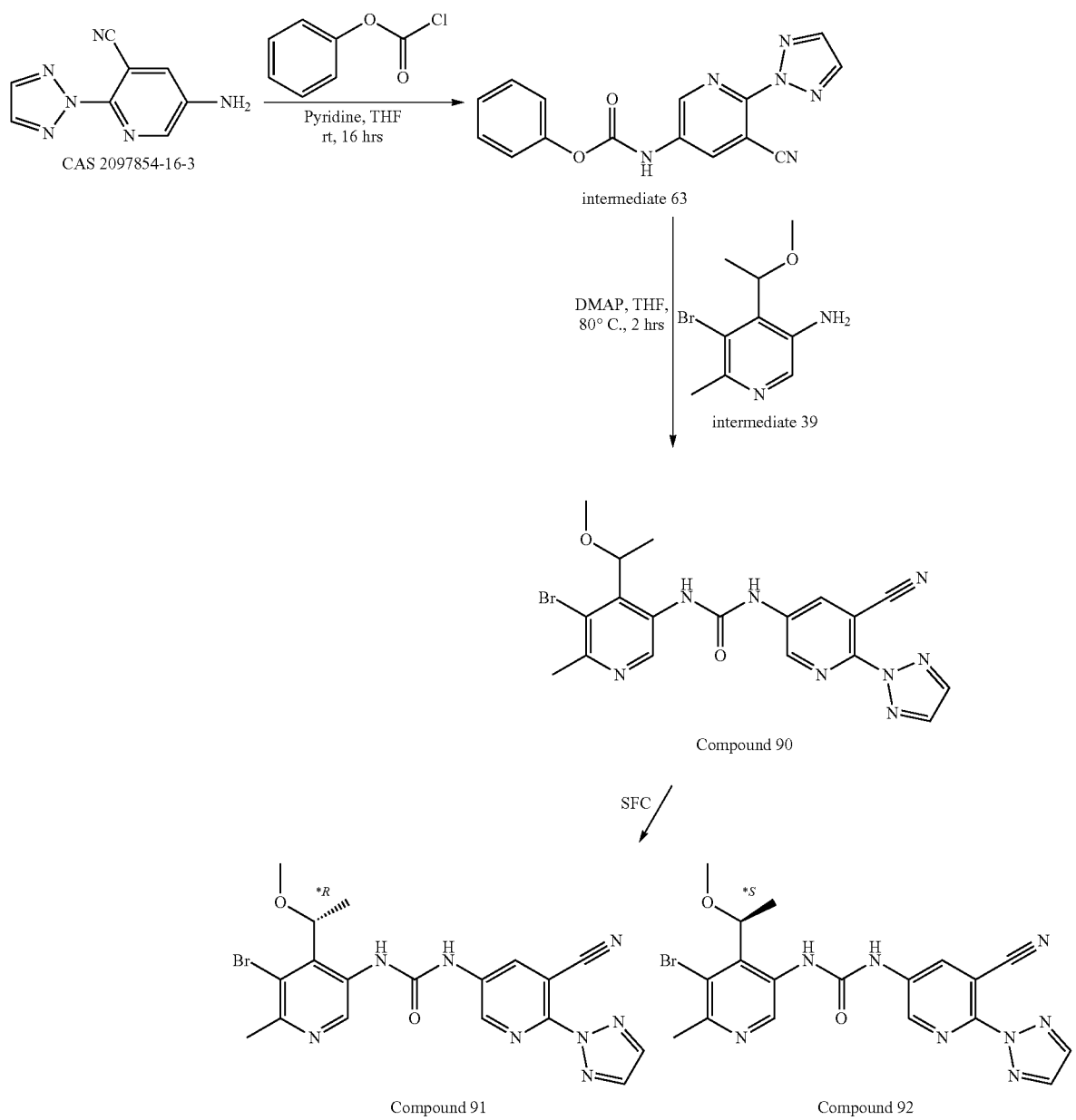

Preparation of Intermediate 63
To a solution of CAS 2097854-16-3 (10 g, 54 mmol) and pyridine (8.7 mL, 108 mmol) in THF (10 mL) was added phenyl chloroformate (11 g, 70 mmol) at 20° C. The reaction mixture was stirred at 20° C. for 16 hours. The mixture was product was purified by preparative high-performance liquid chromatography [Column: PhenomenexGemini 150*25 mm*10 um, Condition: A: water (0.04% $NH_3H_2O$+10 mM $NH_4HCO_3$), B: MeCN, at the beginning: A (64%) and B (36%), at the end: A (34%) and B (66%), Gradient Time 8.5 min; 100% B Hold Time 2 min; Flow Rate 25 ml/min]. The pure fractions were collected and the organic solvent was evaporated under vacuum. The aqueous layer was lyophilized to dryness to give Compound 90 (180 mg, yield: 60%) as white solid.

LC/MS: m/z 457.1 [M+H]$^+$, rt 1.0 min, purity 100%, method G

Preparation of Compounds 91 and 92

Compound 90 (180 mg, 0.39 mmol) was separated by SFC [Column: DAICEL CHIRALPAK AD-H (250 mm*30 mm, 10 μm), Condition: solvent A: Supercritical CO$_2$, solvent B: 0.1% aqueous ammonia in EtOH, at the beginning: A (50%) and B (50%), at the end: A (50%) and B (50%), Flow Rate (mL/min) 70]. The pure fractions were collected and the organic solvent was evaporated under vacuum. MeCN and H$_2$O were added to the residue and it was lyophilized to dryness to give Compound 91 (86 mg, yield: 47.5%) as white solid, and Compound 92 (86 mg, yield: 47.3%) as white solid.

Compound 91:

HPLC-MS: m/z 457.1 [M+H]$^+$, rt 4.10 min. Purity 99.5%, method K

SFC: purity 100%, rt 0.59 min. method: SFC18

Compound 92:

HPLC-MS: m % z 457 [M+H]$^+$, rt 4.10 min. Purity 99.1%, method K

SFC: purity 100%, rt 1.51 min. method: SFC18

Synthesis of Compounds 96, 97 and 98

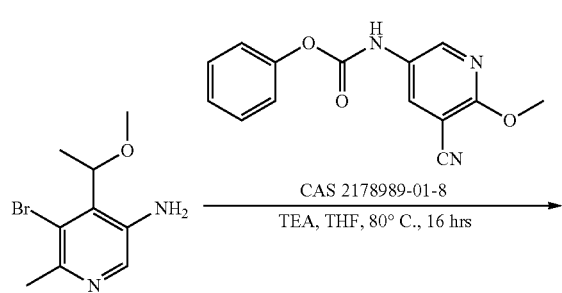

intermediate 39

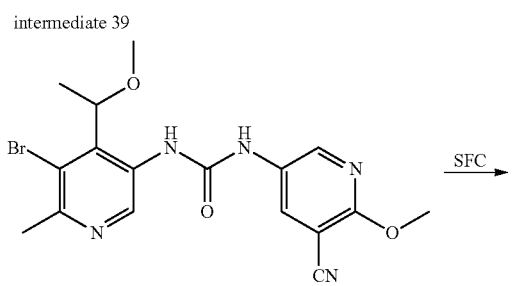

Compound 96

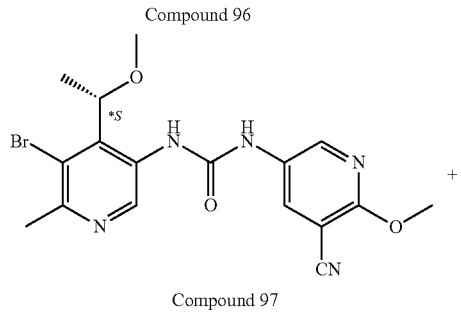

Compound 97

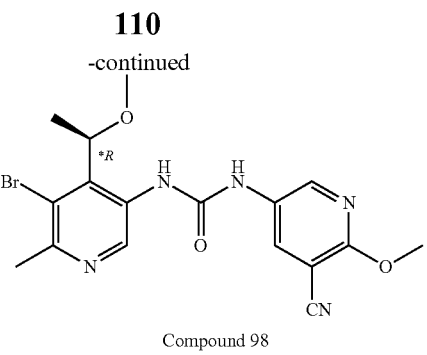

Compound 98

Preparation of Compound 96

Compound 96 was prepared by analogy to the procedure described for Compound 57 using CAS 2178989-01-8 and intermediate 39 as starting materials. The mixture was allowed to reach room temperature and was concentrated in vacuum to give a crude product. The crude product was purified by preparative high-performance liquid chromatography [Column: Boston Prime C18 150*30 mm 5 um, Condition: A: water (0.04% aqueous ammonia+10 mM NH$_4$HCO$_3$), B: MeCN, at the beginning: A (60%) and B (40%), at the end: A (30%) and B (70%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 96 (200 mg, yield: 57%) as white solid.

Preparation of Compounds 97 and 98

Compound 96 (200 mg, 0.47 mmol) was separated by SFC [Column: Phenomenex-Amylose-1 (250 mm*30 mm, 5 μm), Condition: solvent A: Supercritical CO$_2$, solvent B: 0.1% aqueous ammonia in EtOH, at the beginning: A (70%) and B (30%), at the end: A (70%) and B (30%), Flow Rate (ml/min) 50]. The pure fractions were collected and the organic solvent was evaporated under vacuum. MeCN and H$_2$O were added to the residue and it was lyophilized to dryness to give Compound 97 (66 mg, yield: 33.2%) as white solid, and Compound 98 (70 mg, yield: 35.6%).

Compound 97:

LC/MS: m/z 420.1 [M+H]$^+$, rt 4.24 min. Purity 99.2%, method K;

SFC: purity 99.7%, rt 4.68 min. method: SFC1 Compound 98:

LC/MS: m/z 420.1 [M+H]$^+$, rt 4.24 min. Purity 100%, method K;

SFC: purity 98.3%, rt 5.25 min. method: SFC1

Synthesis of Compounds 99, 100 and 101

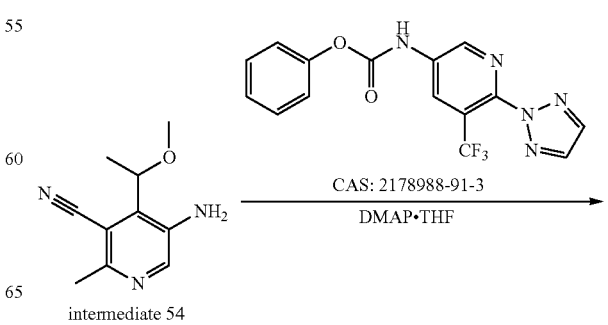

intermediate 54

-continued

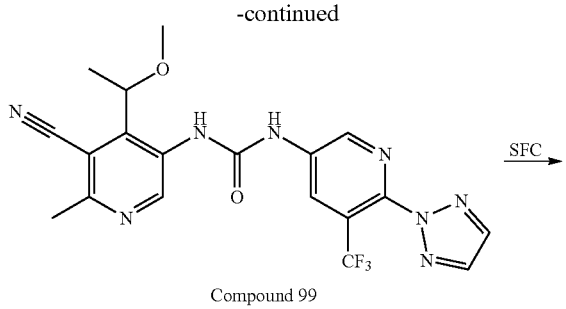

Compound 99

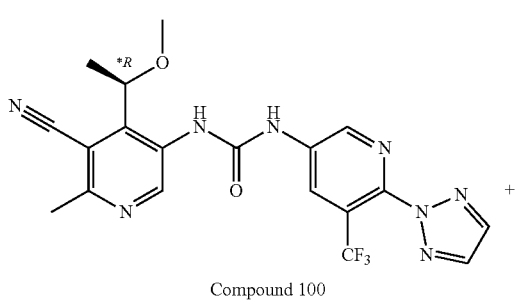

Compound 100

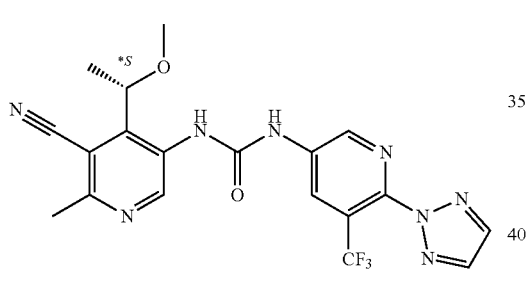

Compound 101

Preparation of Compound 99

A solution of intermediate 54 (1 g, 5.1 mmol) and CAS 2178988-91-3 (2.6 g, 7.6 mmol) in THF (30 mL) was added DMAP (1.2 g, 10 mmol) at 20° C. The reaction mixture was stirred at 80° C. for 3 hours. The mixture was concentrated in vacuum to give a crude product. The crude product was purified by flash column chromatography over silica gel (gradient elution: 0~55% EtOAc in petroleum ether). The pure fractions were collected and the solvent was evaporated under vacuum to give the product as white solid. The compound was purified by preparative high-performance liquid chromatography [Column: PhenomenexGemini 150*25 mm*10 um, Condition: A: water (0.225% FA)-ACN, B: MeCN, at the beginning: A (70%) and B (30%), at the end: A (40%) and B (60%), Gradient Time (min) 8; 100% B Hold Time (min) 2; Flow Rate (ml/min) 60]. The pure fractions were collected and the organic solvent was evaporated under vacuum. The aqueous layer was lyophilized to dryness to give Compound 99 (1.1 g, yield: 47%) as white solid.

LC/MS: m/z 447.0 [M+H]$^+$, rt 0.783 min. Purity 98.6%, method A

Preparation of Compounds 100 and 101

Compound 99 (1.1 g, 2.4 mmol) was separated by SFC. [Column: DAICEL CHIRALPAK AD-H (250 mm*30 mm, 5 μm), Condition: A: CO$_2$, B: 0.1% NH$_3$H$_2$O ETOH at the beginning: A (75%) and B (25%), at the end: A (75%) and B (25%), Flow Rate (ml/min) 50]. The pure fractions were collected and the organic solvent was evaporated under vacuum. The aqueous layers were lyophilized to dryness to give Compound 100 (502 mg, yield: 47%) and Compound 101 (505 mg, yield: 47%) as white solid.

Compound 100:

$^1$H NMR (400 MHz, DMSO-d$_6$) δ ppm 1.52 (d, J=6.8 Hz, 3H), 2.67 (s, 3H) 3.27 (s, 3H), 4.82 (q, J=6.8 Hz, 1H), 8.17 (s, 2H), 8.69 (d, J=2.4 Hz, 1H), 8.77 (br s, 1H), 8.84 (d, J=2.4 Hz, 1H), 9.10 (s, 1H), 10.46 (br s, 1H)

HPLC/MS: m/z 447.1 [M+H]$^+$, rt: 4.59 min. Purity: 99.9%, method: K;

SFC: purity 99.9%, rt: 4.85 min, method: SFC13.

Compound 101:

HPLC/MS: m/z 447.2 [M+H]$^+$, rt: 4.55 min. Purity: 100%, method: K;

SFC: purity 99.7%, rt: 5.36 min, method: SFC13.

Synthesis of Compounds 102, 103 and 104

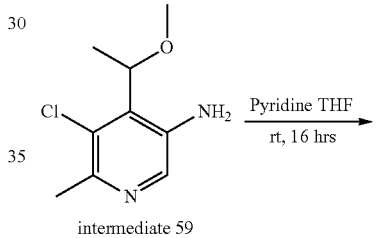

intermediate 59

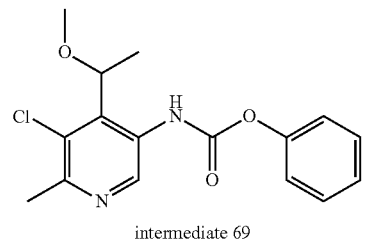

intermediate 69

Preparation of Intermediate 69

Intermediate 59 (350 mg, 1.74 mmol) and pyridine (0.21 mL, 2.8 mmol) were dissolved in THF (4 mL) and stirred at 0° C., phenyl chloroformate (0.4 mL, 3.5 mmol) was added dropwise to the mixture and allowed to warm to rt for 16 h. Sat. NH$_4$Cl was added and extracted with EtOAc twice. The combined organic layers were dried with Na$_2$SO$_4$, filtered and concentrated under vacuum to afford the crude product. The crude product was purified by column chromatography over silica gel (gradient elution: 10-30% EtOAc in petroleum ether). The desired fractions were collected and the solvent was concentrated under vacuum to afford intermediate 69 (450 mg, yield: 80.4%).

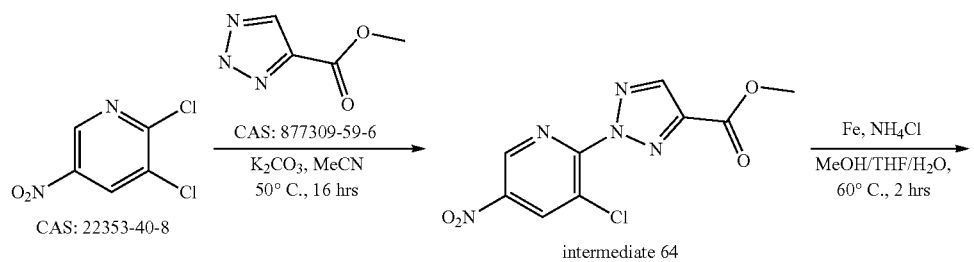
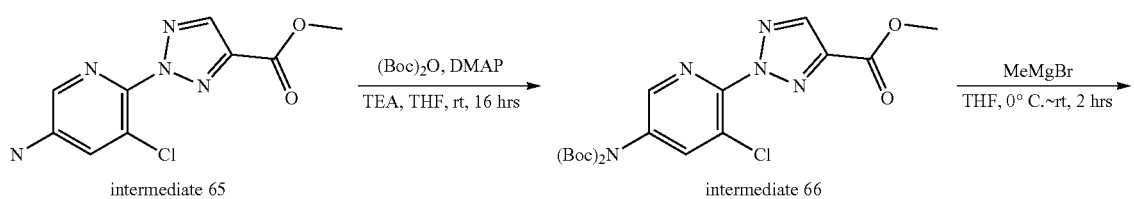
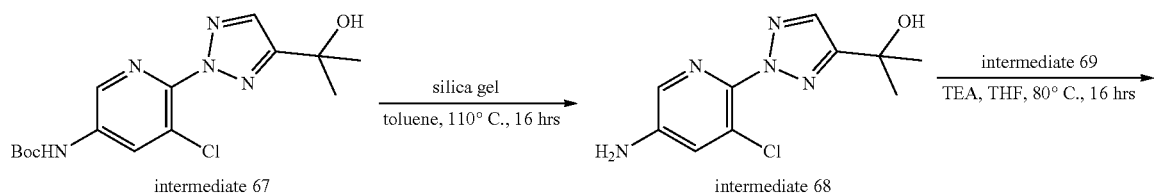
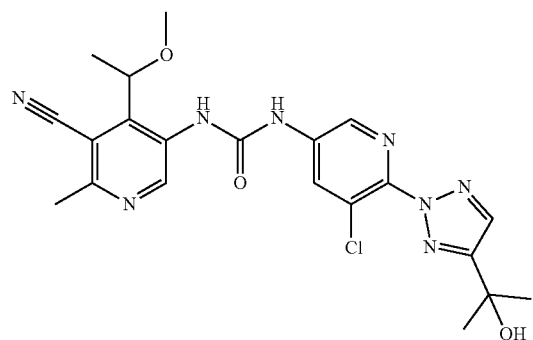
Compound 102
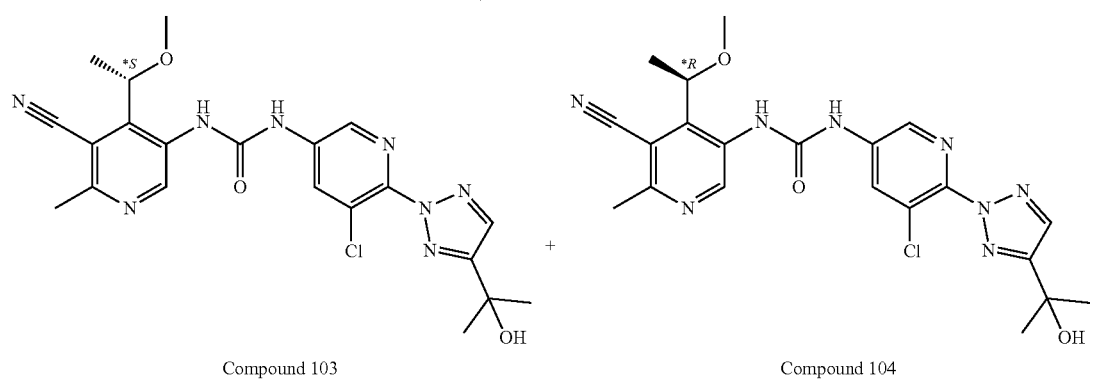
Compound 103 + Compound 104

Preparation of Intermediate 64

To a mixture of 2,3-dichloro-5-nitropyridine (16.7 g, 86.5 mmol) and methyl 2H-1,2,3-triazole-4-carboxylate (10.0 g, 78.7 mmol) in MeCN (200 mL) was added $K_2CO_3$ (32.6 g, 236.0 mmol) and the mixture was stirred at 50° C. for 16 hours. The mixture was cooled to 25° C. and filtered and the filtrate was concentrated to give intermediate 64 (22 g, yield:

Preparation of Intermediate 65

Fe powder (4.9 g, 88.1 mmol) and $NH_4Cl$ (4.7 g, 88.1 mmol) were added to a mixture of intermediate 64 (10 g, 17.6 mmol) in MeOH (40 mL), THF (80 mL) and $H_2O$ (20 mL) and the mixture was stirred at 60° C. for 2 hours. The mixture was cooled to 25° C. and filtered. The filtrate was concentrated to afford a crude product. The crude product was purified by flash column chromatography over silica gel (gradient elution: 0~60% EtOAc in petroleum ether). The desired fractions were collected and the solvent was concentrated to dryness under vacuum to give intermediate 65 (3.2 g, yield: 35.8%) as yellow solid.

Preparation of Intermediate 66

To a solution of intermediate 65 (6 g, 23.7 mmol), DMAP (289 mg, 2.4 mmol) and TEA (7.2 g, 70.9 mmol) in THF (100 mL) was slowly added $(Boc)_2O$ (25.8 g, 118.3 mmol) at 25° C. The reaction was stirred at 25° C. for 16 hours. The reaction mixture was concentrated in vacuum to give a crude product. The crude product was purified by flash column chromatography over silica gel (gradient elution: 0~30% EtOAc in petroleum ether). The desired fractions were collected and the solvent was concentrated in vacuum to give intermediate 66 (7.5 g, yield: 69.8%) as white solid.

Preparation of Intermediate 67

Intermediate 66 (2.9 g, 6.4 mmol) was dissolved in THF (40 mL) and methylmagnesium bromide (3M in THF, 8.9 mL, 26.8 mmol) was added at 0° C. The mixture was warmed to 25° C. and stirred at 25° C. for 2 hours. The mixture was quenched with sat. $NH_4Cl$ aq. The mixture was extracted with EtOAc twice. The combined organic layers were washed with brine and dried with $Na_2SO_4$, the filtrate was concentrated in vacuum to give a crude product. The crude product was purified by flash column chromatography over silica gel (gradient elution: 0~60% EtOAc in petroleum ether). The desired fractions were collected and the solvent was concentrated under vacuum to afford intermediate 67 (2.2 g, yield: 96%) as yellow solid.

Preparation of Intermediate 68

Silica gel (15 g) was added to a mixture of intermediate 67 (2.2 g, 6.1 mmol) in toluene (50 mL) was stirred at 110° C. for 16 hours. The mixture was cooled to 25° C. and filtered. The filtrate was concentrated to afford a crude product. The crude product was purified by flash column chromatography over silica gel (gradient elution: 0~100% EtOAc in petroleum ether). The desired fractions were collected and the solvent was concentrated to dryness under vacuum to give intermediate 68 (1.5 g, yield: 97%) as yellow solid.

Preparation of Compound 102

Compound 102 was prepared by analogy to the procedure described for Compound 57 using intermediate 68 and 69. The mixture was allowed to reach room temperature and was concentrated in vacuum to give a crude product. The crude product was purified by preparative high-performance liquid chromatography [Column: Boston Prime C18 150*30 mm 5 um, Condition: A: water (0.04% aqueous ammonia+ 10 mM $NH_4HCO_3$), B: MeCN. At the beginning: A (65%) and B (35%), at the end: A (35%) and B (65%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 102 (114.7 mg, yield: 30.3%).

LC/MS: m/z 480.1 $[M+H]^+$, rt: 1.87 min, Purity: 100%, method: C.

Preparation of Compounds 103 and 104

Compound 102 (114.7 mg, 0.24 mmol) was separated by SFC [Column: DAICEL CHIRALPAK AD (250 mm*30 mm, 10 μm), Condition: A: Supercritical $CO_2$, B: 0.1% $NH_3H_2O$ EtOH at the beginning: A (55%) and B (45%), at the end: A (55%) and B (45%), Flow Rate (ml/min) 70]. The pure fractions were collected and the organic solvent was evaporated under vacuum. MeCN and $H_2O$ were added to the residue and it was lyophilized to dryness to give Compound 103 (44 mg, yield: 38.3%) as a white solid, and Compound 104 (44 mg, yield: 40%) as a white solid.

Compound 103:

HPLC/MS: m/z 480.1 $[M+H]^+$, rt 4.21 min, Purity 99.8%, method K.

SFC: purity 100%, rt 5.57 min. method: SFC1.

Compound 104:

HPLC/MS: m/z 480.2 $[M+H]^-$, rt 4.21 min, Purity 100%, method K.

SFC: purity 100%, rt 7.02 min. method: SFC1.

Synthesis of Compound 105

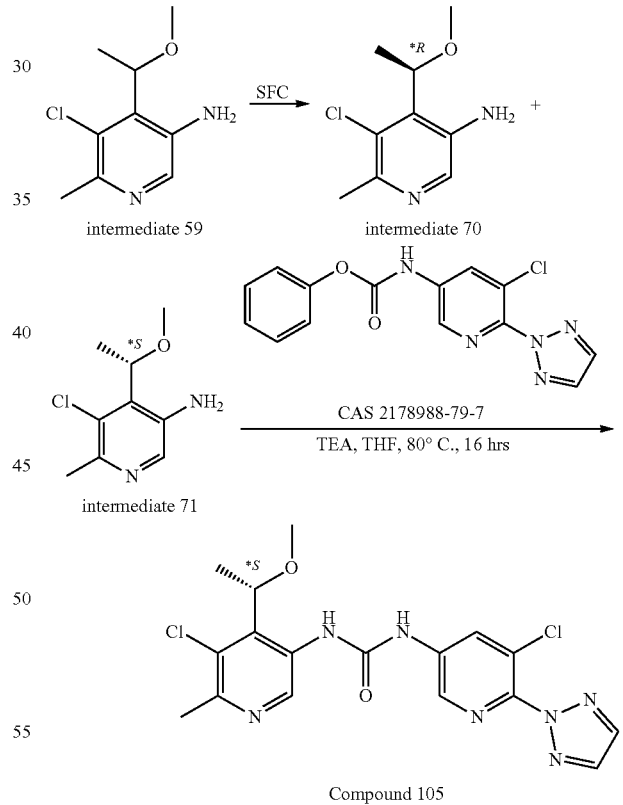

Compound 105

Preparation of Intermediates 70 and 71

Intermediate 59 (500 mg, 2.46 mmol) was separated by SFC [Column: DAICEL CHIRALPAK AD-H (250 mm*30 mm, 5 μm), Condition: solvent A: Supercritical $CO_2$, solvent B: 0.1% aqueous ammonia in MeOH, at the beginning: A (85%) and B (15%), at the end: A (85%) and B (15%), Flow Rate (ml/min) 50]. The pure fractions were collected and the organic solvent was evaporated under vacuum. MeCN and 1120 were added to the residue and it was lyophilized to dryness to give Intermediate 70 (220 mg, yield: 44%) as white solid and Intermediate 71 (210 mg, yield: 42%) as white solid.

Intermediate 70 SFC: purity 100%, rt 2.594 min. method: SFC10.

Intermediate 71 SFC: purity 99.87%, rt 2.848 min. method: SFC10.

Preparation of Compound 105

Compound 105 was prepared by analogy to the procedure described for Compound 57 using CAS 2178988-79-7 and intermediate 71. The mixture was concentrated in vacuum to give a crude product as light yellow solid. Petroleum ether: ethyl acetate=1:1 (50 mL) was added to the crude; the mixture was stirred at 25° C. for 10 min and filtered. The filter cake was washed by another 20 ml mixture solvent. The filter cake was collected and THF was added (20 mL) and the mixture was stirred at 25° C. for 10 min. The filtrate was concentrated in vacuum to give Compound 105 (164.4 mg, yield: 37%) as white solid.

HPLC/MS: m/z 422.2 [M+H]$^+$, rt 4.225 min. Purity 99.47%, method K;

SFC: purity 99.93%, rt 1.653 min. method: SFC18.

Synthesis of Compound 106

Preparation of Intermediate 73

A mixture of intermediate 48 (500 mg, 2 mmol; prepared by analogy to intermediate 39), tert-butyl nitrite (630 mg, 6.1 mmol) and CuCl$_2$ (55 mg, 0.4 mmol) in THF (15 mL) was stirred at 80° C. for 16 hours. The mixture was allowed to cool to 25° C. 1120 (30 mL) was added and extracted with EtOAc (20 mL*2). The combined organic layers were washed with brine, dried over Na$_2$SO$_4$, filtered and the filtrates were concentrated under vacuum to afford crude as yellow oil. The crude product was purified by flash column chromatography over silica gel (gradient elution: 0~10% EtOAc in petroleum ether). The desired fractions were collected and the solvent was concentrated in vacuo to give intermediate 73 (270 mg, purity 83%; yellow oil).

Preparation of Intermediate 74

A mixture of intermediate 73 (220 mg, 83% purity), CuI (15 mg, 0.08 mmol), L-proline (18 mg, 0.16 mmol), K$_2$CO$_3$ (165 mg, 1.2 mmol) NH$_3$·H$_2$O (5 mL) was dissolved in DMSO (5 mL). The mixture was stirred at 100° C. for 16 hours. The reaction was quenched with sat. NH$_4$Cl (20 mL), extracted with EtOAc (20 mL*2). The combined organic layers were separated, washed with brine, dried over Na$_2$SO$_4$, filtered and the filtrates were evaporated under vacuum to give a yellow oil. The crude product was purified by flash column chromatography over silica gel (gradient elution: 0~100% EtOAc in petroleum ether). The desired fractions were collected and the solvent was concentrated in vacuum to give intermediate 74 (40 mg, yield: 29.5%) as yellow oil.

Preparation of Compound 106

Compound 106 was prepared by analogy to the procedure described for Compound 57 using N-[5-chloro-6-(2H-1,2,3-triazol-2-yl)-3-pyridinyl]-Carbamic acid phenyl ester and intermediate 74. The reaction mixture was concentrated under vacuum to afford crude as white solid. MeOH (20 mL) was added to the mixture and stirred at 80° C. for 15 min. Filtered and the filtrates were concentrated under vacuum to afford crude as yellow oil. The crude product was purified by preparative high-performance liquid chromatography [Column: Boston Prime C18 150*30 mm 5 um, Condition: A: water (0.04% aqueous ammonia+10 mM NH$_4$HCO$_3$), B: MeCN, at the beginning: A (75%) and B (25%), at the end: A (45%) and B (55%), Gradient Time 8 min; 100% B Hold Time 2 min; Flow Rate 25 ml/min]. The pure fractions were collected and the organic solvent was evaporated under vacuum. The aqueous layer was lyophilized to dryness to give Compound 106 as a 1:1 mixture of 2 enantiomers (21 mg, yield: 23%) as white solid.

HPLC/MS: m/z 388.1 [M+H]$^+$, rt 3.903 min. Purity 100%, method M;

SFC: purity 49.79%; 50.21%, rt 5.813 min, 8.012 min. method: SFC1

Synthesis of Compounds 110, 111 and 112

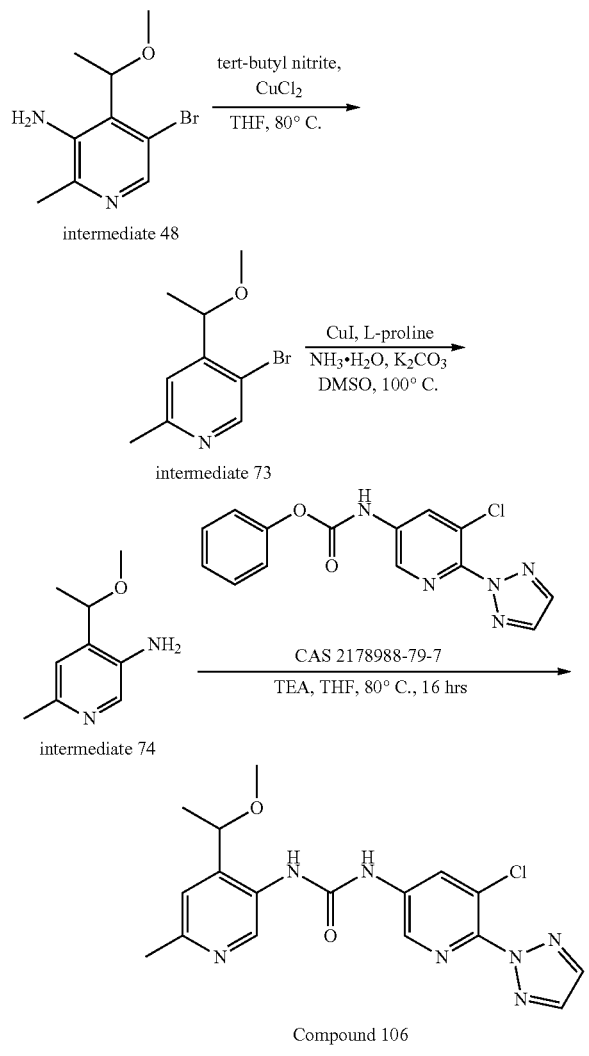

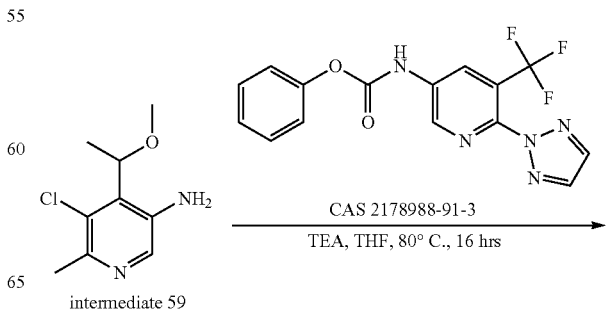

119

-continued

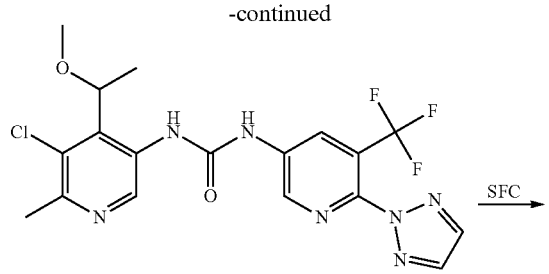

Compound 110

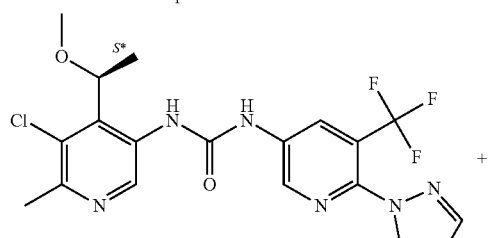

Compound 111

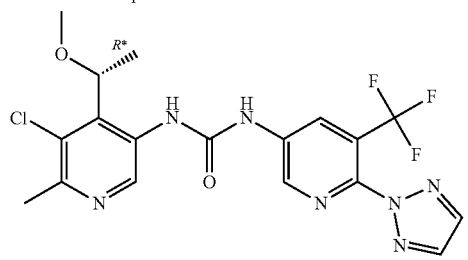

Compound 112

Preparation of Compound 110

Compound 110 was prepared by analogy to the procedure described for Compound 57 using CAS 2178988-91-3 and intermediate 59. The mixture was allowed to reach room temperature and was concentrated in vacuum to give a crude product. The crude product was purified by preparative high-performance liquid chromatography [Column: Boston Prime C18 150*30 mm 5 um, Condition: A: water (0.04% aqueous ammonia+10 mM NH$_4$HCO$_3$), B: MeCN. At the beginning: A (55%) and B (45%), at the end: A (25%) and B (75%), Gradient Time: 8 min; 100% B Hold Time: 2 min; Flow Rate: 25 ml/min]. The pure fractions were collected and the organic solvent was evaporated under vacuum. The aqueous layer was lyophilized to dryness to give Compound 110 (200 mg, yield: 44%) as white solid.

LC/MS: m/z 456.1 [M+H]$^+$, rt: 1.85 min, Purity: 100%, method: C.

Preparation of Compounds 111 and 112

Compound 110 (200 mg, 0.44 mmol) was separated by SFC [Column: DAICEL CHIRALPAK AD-H (250 mm*30 mm, 5 μm), Condition: A: Supercritical CO$_2$, B: 0.1% NH$_3$H$_2$O ETOH at the beginning: A (75%) and B (25%), at the end: A (75%) and B (25%), Flow Rate (ml/min) 60]. The pure fractions were collected and the organic solvent was evaporated under vacuum. MeCN and H$_2$O were added to the residue and it was lyophilized to dryness to give Compound 111 (89.5 mg, yield: 44.7%) as a white solid, and Compound 112 (98.2 mg, yield 47.5%).

Compound 111:

HPLC/MS: m/z 456.2 [M+H]$^+$, rt 4.55 min. Purity 100%, method K

120

SFC: purity 100%, rt 3.54 min. method: SFC1.

Compound 112:

HPLC/MS: m/z 456.0 [M+H]$^+$, rt 4.55 min. Purity 96.6%, method K

SFC: purity 100%, rt 3.92 min. method: SFC1.

Synthesis of Compounds 113, 114 and 115

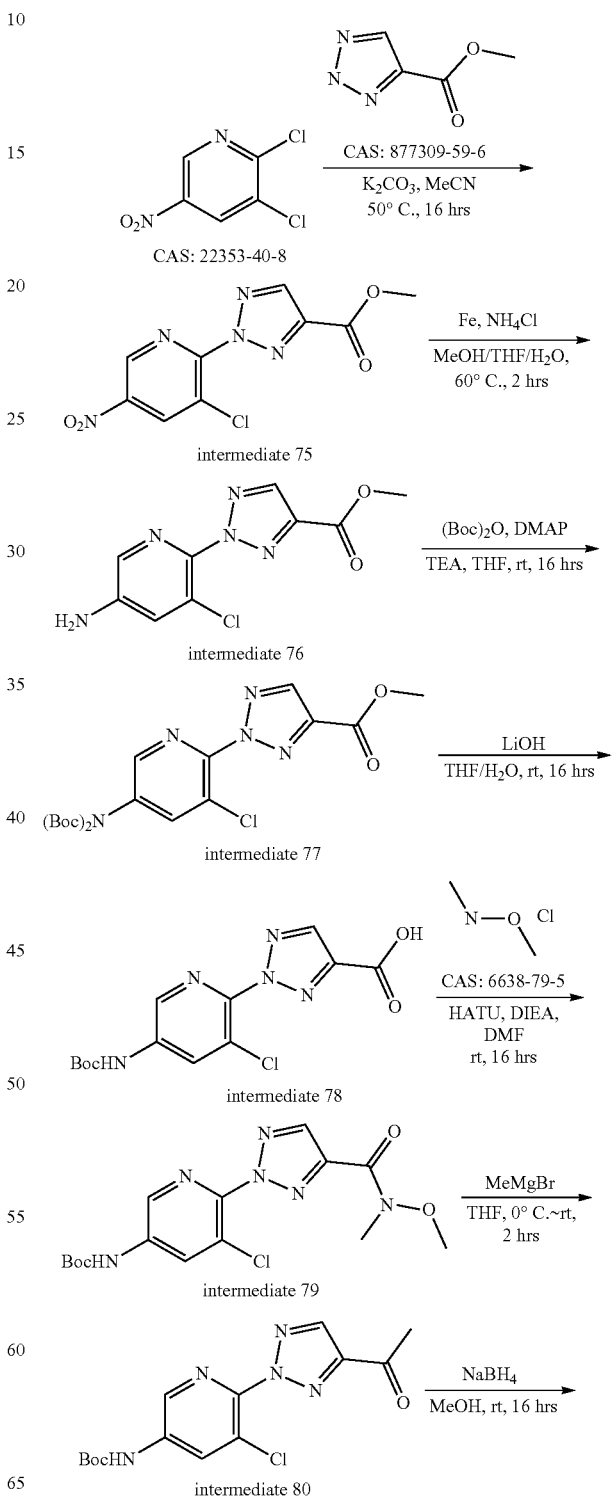

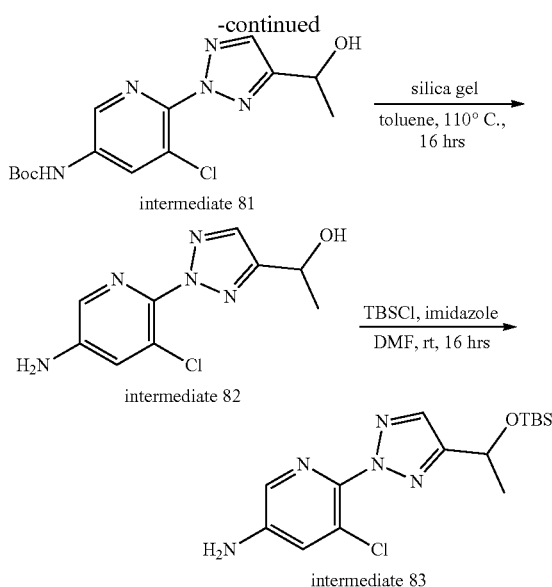

Preparation of Intermediate 75

To a mixture of 2,3-dichloro-5-nitropyridine (16.7 g, 86.5 mmol) and methyl 2H-1,2,3-triazole-4-carboxylate (10.0 g, 78.7 mmol) in MeCN (200 mL) was added $K_2CO_3$ (32.6 g, 236.0 mmol) and the mixture was stirred at 50° C. for 16 hours. The mixture was cooled to 25° C. and filtered and the filtrate was concentrated to give intermediate 75 (22 g, yield: 98.6%) as yellow solid.

Preparation of Intermediate 76

Fe powder (4.9 g, 88.1 mmol) and $NH_4Cl$ (4.7 g, 88.1 mmol) were added to a mixture of intermediate 75 (10 g, 17.6 mmol) in MeOH (40 mL), THF (80 mL) and $H_2O$ (20 mL). The mixture was stirred at 60° C. for 2 hours. The mixture was cooled to 25° C. and filtered. The filtrate was concentrated to afford a crude product. The crude product was purified by flash column chromatography over silica gel (gradient elution: 0~60% EtOAc in petroleum ether). The desired fractions were collected and the solvent was concentrated to dryness under vacuum to give intermediate 76 (3.2 g, yield: 35.8%) as yellow solid.

Preparation of Intermediate 77

To a solution of intermediate 76 (6 g, 23.7 mmol), DMAP (289 mg, 2.4 mmol) and TEA (7.2 g, 70.9 mmol) in THF (100 mL) was slowly added $(Boc)_2O$ (25.8 g, 118.3 mmol) at 25° C. The reaction was stirred at 25° C. for 16 hours. The reaction mixture was concentrated in vacuum to give a crude product. The crude product was purified by flash column chromatography over silica gel (gradient elution: 0~30% EtOAc in petroleum ether). The desired fractions were collected and the solvent was concentrated in vacuum to give intermediate 77 (7.5 g, yield: 69.8%) as white solid.

Preparation of Intermediate 78

To a solution of intermediate 77 (3 g, 6.6 mmol) in THF (24 mL) and $H_2O$ (6 mL) was added LiOH (2.8 g, 66.0 mmol) at 25° C. The reaction was stirred at 25° C. for 16 hours. The reaction mixture was adjusted to pH=3-4 using aqueous HCl (5 M) and extracted with EtOAc (50 mL*3). The combined organic layers were separated, washed with brine, dried over $Na_2SO_4$, filtered and concentrated in vacuum to give a crude intermediate 78 (2.2 g, yield: 97.3%) as white solid.

Preparation of Intermediate 79

To a solution of intermediate 78 (2.2 g, 6.4 mmol), N,O-dimethylhydroxylamine hydrochloride (0.94 g, 9.6 mmol) and DIEA (4.8 mL, 28.9 mmol) in DMF (30 mL) was slowly added HATU (3.7 g, 9.6 mmol) at 25° C. The reaction was stirred at 25° C. for 16 hours. The mixture was diluted with $H_2O$ and extracted with EtOAc twice. The combined organic layers were washed with brine, dried over $Na_2SO_4$, filtered and concentrated in vacuum to give a crude product. The crude product was purified by flash column chromatography over silica gel (gradient elution: 0~60% EtOAc in petroleum ether). The desired fractions were collected and the solvent was concentrated to dryness under vacuum to give intermediate 79 (2.4 g, yield: 96%) as white solid.

Preparation of Intermediate 80

Intermediate 79 (2.4 g, 6.2 mmol) was dissolved in THF (60 mL) and methyl magnesium bromide (3M in THF, 8.3 mL, 24.8 mmol) was added at 0° C. The mixture was warmed to 25° C. and stirred at 25° C. for 2 hours. The mixture was quenched with sat.$NH_4Cl$ aq. The mixture was extracted with EtOAc twice. The combined organic layers were washed with brine and dried with $Na_2SO_4$, filtered and the filtrate was concentrated in vacuum to give a crude product. The crude product was purified by flash column chromatography over silica gel (gradient elution: 0~50% EtOAc in petroleum ether). The desired fractions were collected and the solvent was concentrated under vacuum to afford Intermediate 80 (2 g, yield: 95%) as yellow solid.

Preparation of Intermediate 81

Intermediate 80 (2 g, 5.9 mmol) was dissolved in MeOH (30 mL) and $NaBH_4$ (1.1 g, 29.6 mmol) was slowly added at 25° C. The mixture was stirred at 25° C. for 16 hours. The mixture was quenched with sat. $NH_4Cl$ aq. The mixture was extracted with EtOAc twice. The combined organic layers were washed with brine and dried with $Na_2SO_4$, filtered and the filtrate was concentrated in vacuum to give a crude product. The crude product was purified by flash column chromatography over silica gel (gradient elution: 0~100% EtOAc in petroleum ether). The desired fractions were collected and the solvent was concentrated under vacuum to afford intermediate 81 (1.7 g, yield: 84%) as yellow solid.

Preparation of Intermediate 82

Silica gel (8 g) was added to a mixture of intermediate 81 (1.1 g, 3.2 mmol) in toluene (30 mL). The mixture was stirred at 110° C. for 18 hours. The mixture was cooled to 25° C. and filtered. The filtrate was concentrated to afford a crude product. The crude product was purified by flash column chromatography over silica gel (gradient elution: 0~100% EtOAc in petroleum ether). The desired fractions were collected and the solvent was concentrated to dryness under vacuum to give intermediate 82 (650 mg, yield: 82.3%) as yellow solid.

Preparation of Intermediate 83

Tert-butylchlorodimethylsilane was added to a mixture of intermediate 82 (650 mg, 2.7 mmol) and imidazole (910 mg, 13.3 mmol) in DMF (10 mL) at 0° C. under $N_2$. The reaction mixture was stirred at rt for 16 hours. The mixture was allowed to warm to 25° C. $H_2O$ (30 mL) was added and extracted with EtOAc (30 mL*2). The combined organic layers were washed with brine, dried over $Na_2SO_4$, filtered and the filtrates were concentrated under vacuum to afford crude as yellow solid. The crude product was purified by flash column chromatography over silica gel (gradient elution: 0~60% EtOAc in petroleum ether). The desired fractions were collected and the solvent was concentrated in vacuum to give intermediate 83 (700 mg, purity: 74%) as white solid.

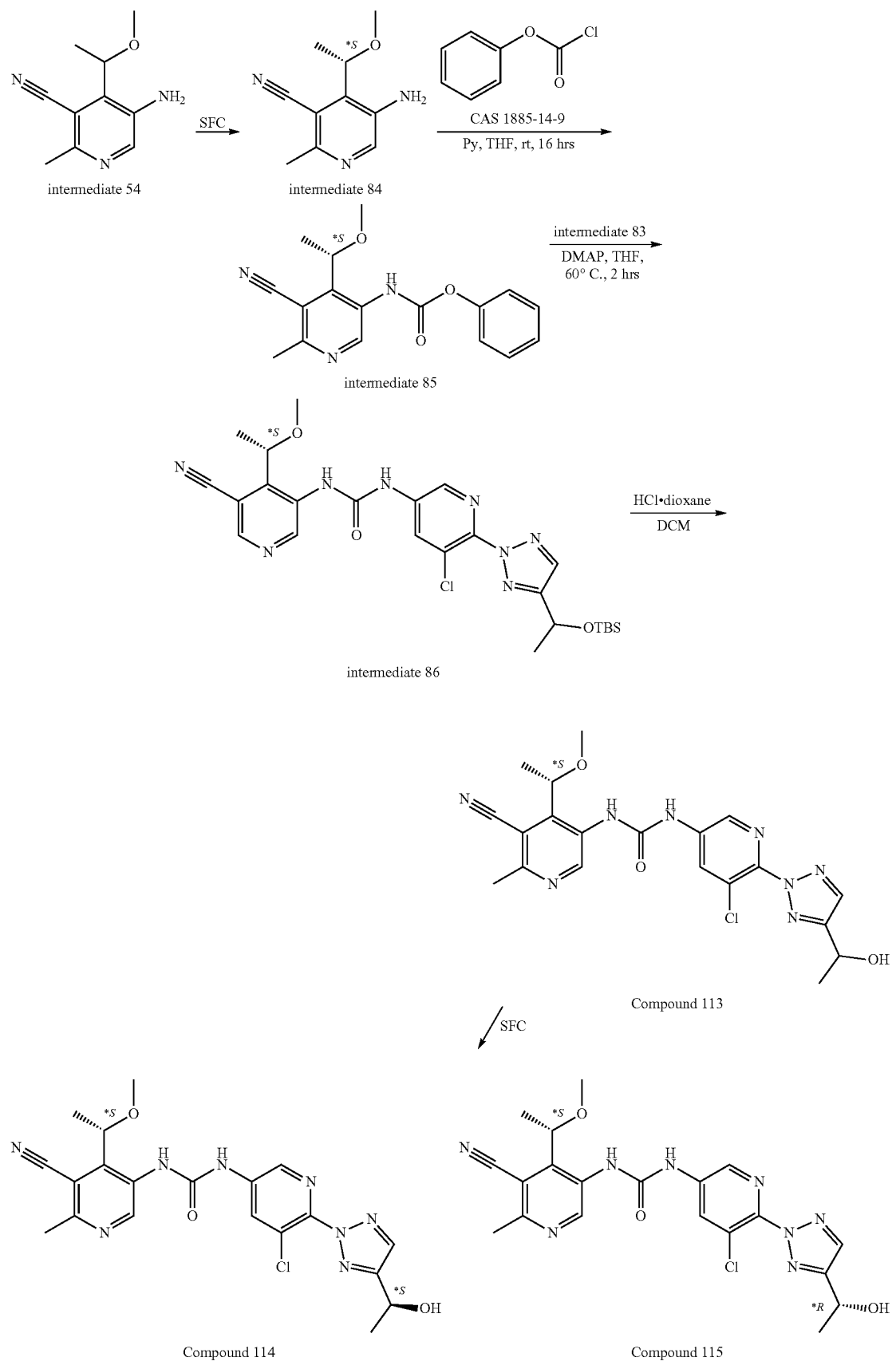

Preparation of Intermediate 84

Intermediate 54 (2.6 g, 13.6 mmol) was separated by SFC [Column: DAICEL CHIRALPAK AY (250 mm*50 mm, 10 µm), Condition: solvent A: Supercritical $CO_2$, solvent B: 0.1% aqueous ammonia in EtOH, at the beginning: A (85%) and B (15%), at the end: A (85%) and B (15%), Flow Rate (ml/min) 180]. The pure fractions were collected and concentrated in vacuum to give intermediate 84 (1.1 g, purity: 100%) as yellow solid.

SFC: purity 100%, rt: 3.36 min, method: SFC20

Preparation of Intermediate 85

To a solution of intermediate 84 (300 mg, 1.6 mmol) in THF (10 mL) was added pyridine (0.3 mL, 3.1 mmol) at room temperature. Phenyl chloroformate (320 mg, 2.0 mmol) was added slowly. The reaction was stirred at room temperature for 16 hours. The mixture was quenched with sat. $NH_4Cl$ aq, and then extracted with EtOAc twice. The combined organic layers were washed with brine and dried with anhydrous $Na_2SO_4$, filtered and the filtrate was concentrated in vacuum to give a crude product. The crude product was purified by flash column chromatography over silica gel (gradient elution: 0~50% EtOAc in petroleum ether). The desired fractions were collected and the solvent was concentrated under vacuum to afford intermediate 85 (450 mg, yield: 92%) as white solid.

Preparation of Intermediate 86

Intermediate 86 was prepared by analogy to the procedure described for Compound 87 starting from intermediate 85 and intermediate 83. The mixture was allowed to reach room temperature and was concentrated in vacuum to give a crude. The crude product was purified by flash column chromatography over silica gel (gradient elution: 0~60% EtOAc in petroleum ether). The desired fractions were collected and the solvent was concentrated under vacuum to afford intermediate 86 (420 mg, yield: 88%) as white solid.

Preparation of Compound 113

To a solution of intermediate 86 (350 mg, 0.6 mmol) in DCM (5 mL) was added HCl·dioxane (4 M) (5 mL) at 25° C. The reaction was stirred at 25° C. for 2 hours. The reaction mixture was adjusted to pH=8~9 using sat. $NaHCO_3$ and extracted with EtOAc (30 mL*3). The combined organic layers were separated, washed with brine, dried over $Na_2SO_4$, filtered and concentrated in vacuum to give a crude product. The crude product was purified by flash column chromatography over silica gel (gradient elution: 0~100% EtOAc in petroleum ether). The desired fractions were collected and the solvent was concentrated under vacuum to afford Compound 113 (260 mg, yield: 91%) as white solid.

LC/MS: m/z 457.2 $[M+H]^+$, rt: 0.82 min, purity 98.6%, method: B

SFC: purity 50.0%/50.0%, rt: 2.3 min/6.0 min, method: SFC21

Preparation of Compounds 114 and 115

Compound 113 (260 mg, 0.56 mmol) was separated by SFC [Column: DAICEL CHIRALPAK IC (250 mm*30 mm, 10 µm), Condition: solvent A: Supercritical $CO_2$, solvent B: 0.1% aqueous ammonia in EtOH, at the beginning: A (60%) and B (40%), at the end: A (60%) and B (40%), Flow Rate (ml/min) 70]. The pure fractions were collected and the organic solvent was evaporated under vacuum. MeCN and $H_2O$ were added to the residue and it was lyophilized to dryness to give Compound 114 (89.0 mg, yield: 34%) as white solid and Compound 115 (95.0 mg, yield: 36%)

Compound 114:

HPLC/MS: m % z 457.0 $[M+H]^+$, rt 4.60 min. Purity 98.2%, method M

SFC: purity 100%, rt: 5.57 min, method: SFC21

Compound 115:

HPLC/MS: m/z 457.0 $[M+H]^+$, rt 4.67 min. Purity 97.4%, method M.

SFC: purity 99.2%, rt: 6.3 min, method: SFC21

Synthesis of Compounds 116, 117, 118 and 119

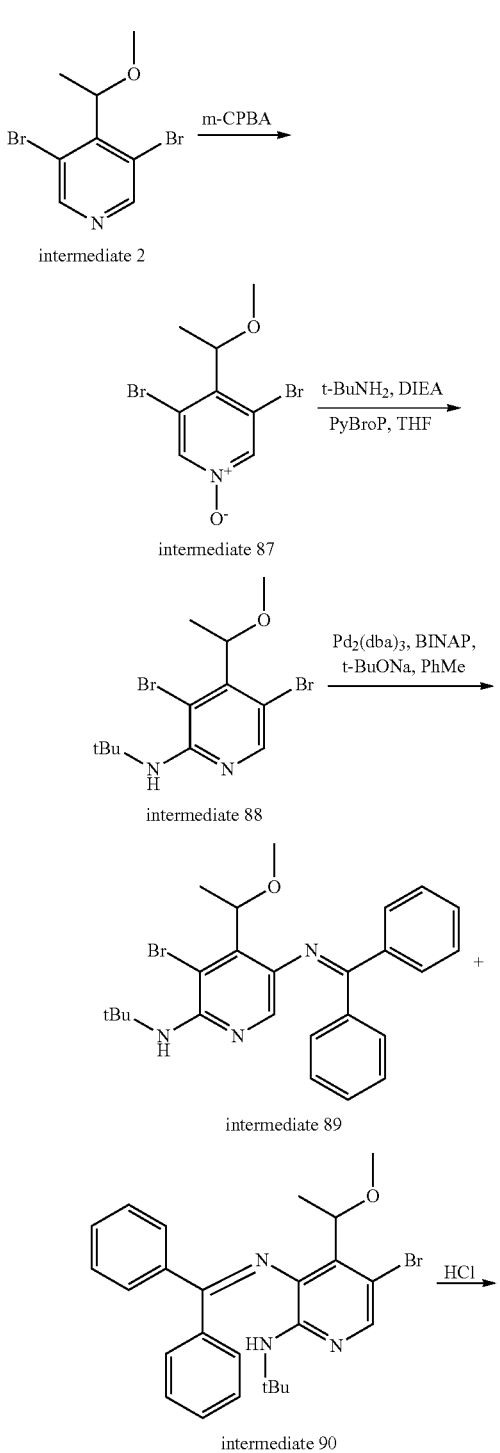

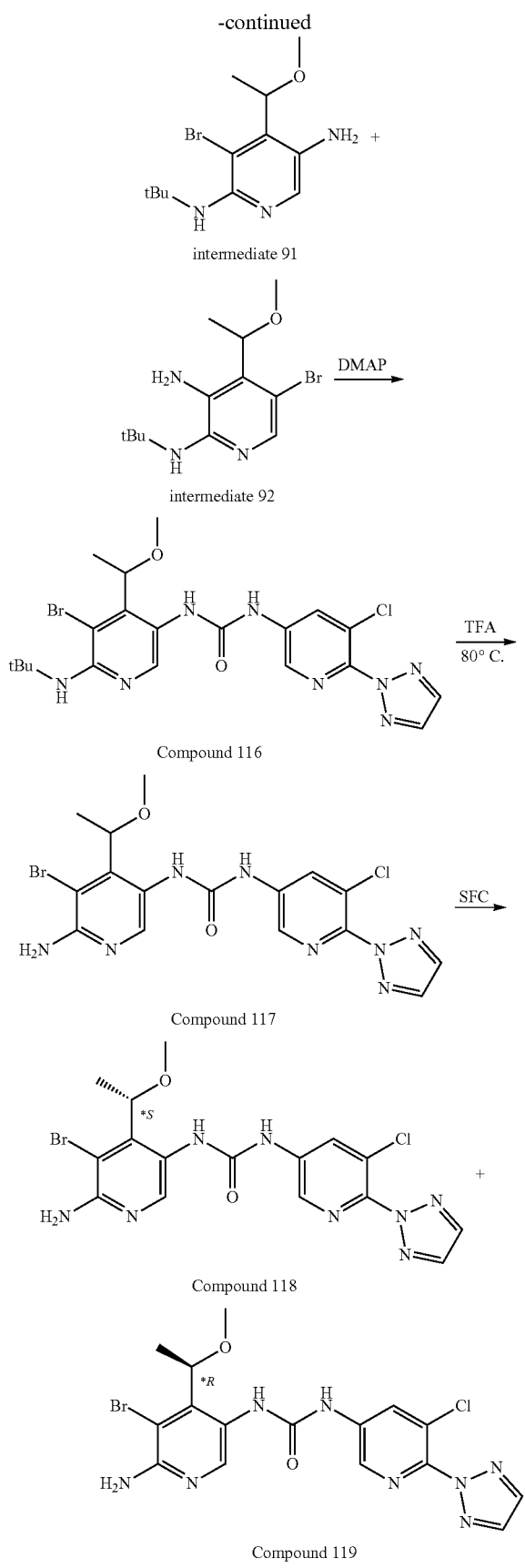

Preparation of Intermediate 87

Intermediate 87 (10 g, 40 mmol) was dissolved in DCM (100 mL) and m-CPBA (85%, 13.7 g, 688 mmol) was added. The mixture was stirred at 20° C. for 16 hours. The pH was adjusted to 12 using NaOH (5 M), water (100 mL) was added and the mixture was extracted with EtOAc twice. The combined organic layers were washed with brine, dried over anhydrous $Na_2SO_4$, filtered and concentrated under vacuum to give a crude product. The crude product was washed by 100 mL mixture solvent (petroleum ether/ethyl acetate=10: 1). The solid was collected and concentrated under vacuum to afford intermediate 87 (9.8 g, yield: 90%) as white solid.

Preparation of Intermediate 88

To a solution of intermediate 87 (30 g, 96.5 mmol) in THF (200 mL), Tert-butylamine (8.82 g, 120.6 mmol), PyBroP CAS 132705-51-2 (58.5 g, 125.4 mmol) and DIPEA (46.7 g, 361.8 mmol) were added. The reaction was stirred at 80° C. for 16 hours. The mixture was cooled to 25° C., and then filtered and the residue was washed with 150 mL ethyl acetate twice. Sat. $NH_4Cl$ (400 mL) was added, the combined organic layers were washed with brine and dried over anhydrous $Na_2SO_4$, filtered and the filtrate was concentrated in vacuum to give a crude product. The crude product was purified by flash column chromatography over silica gel (gradient elution: 0~10% EtOAc in petroleum ether). The desired fractions were collected and the solvent was concentrated under vacuum to afford intermediate 88 (12.5 g, yield: 35.4%) as white solid.

Preparation of a Mixture of Intermediates 89 and 90

A mixture of intermediates 89 and 90 was prepared by analogy to the procedure described for intermediate 38. The residue was washed with EtOAc (200 mL). The filtrates were concentrated under vacuum to afford the crude product as yellow oil. The crude product was purified by flash column chromatography over silica gel (gradient elution: 0~8% EtOAc in petroleum ether). The desired fractions were collected and the solvent was concentrated in vacuum to give a mixture of intermediate 89 and 90 (6 g crude) as yellow oil.

Preparation of Intermediates 91 and 92

A mixture of intermediates 89 and 90 (6 g crude) was dissolved in DCM (20 mL). Aqueous HCl (80 mL, 1 M) was added and the mixture was stirred at 25° C. for 16 hours. The reaction mixture was adjusted to pH=8 using aq. NaOH (5 M) and extracted with DCM (80 mL*2). The combined organic layers were separated, washed with brine, dried over $Na_2SO_4$, filtered and the filtrates were evaporated under vacuum to give yellow oil. The crude product was purified by flash column chromatography over silica gel (gradient elution: 0~10% EtOAc in petroleum ether). The desired fractions were collected and the solvent was concentrated in vacuum to give intermediate 91 (1.5 g, yield: 25% over two steps) as white solid and unreacted intermediate 90 (4 g crude) as yellow oil. Then intermediate 90 (4 g crude) was dissolved in DCM (10 mL). Aqueous HCl (30 mL, 3 M) was added and the mixture was stirred at 25° C. for 16 hours. The reaction mixture was adjusted to pH=8 using aq. NaOH (5 M) and extracted with DCM (50 mL*2). The combined organic layers were separated, washed with brine, dried over $Na_2SO_4$, filtered and the filtrates were evaporated under vacuum to give yellow oil. The crude product was purified by flash column chromatography over silica gel (gradient elution: 0~12% EtOAc in petroleum ether). The desired fractions were collected and the solvent was concentrated in vacuum to give intermediate 92 (700 mg, yield: 12% over three step) as yellow solid.

Preparation of Compound 116

Compound 116 was prepared by analogy to the procedure described for Compound 99. The reaction mixture was cooled to 25° C., filtered and the residue was washed with EtOAc (50 mL). The combined filtrates were concentrated under vacuum to afford crude as yellow oil. The crude product was purified by flash column chromatography over silica gel (gradient elution: 0~60% EtOAc in petroleum ether). The desired fractions were collected and the solvent was concentrated in vacuum to give Compound 116 (1.0 g, yield: 60%) as yellow solid.

LC/MS: m/z 523.1 [M+H]$^+$, rt 2.230 min, purity 99.3%, method C.

Preparation of Compound 117

Compound 116 (1.0 g, 1.9 mmol) was dissolved in DCM (10 mL), TFA (10 mL) was added. The reaction mixture was stirred at 80° C. for 16 hours. The reaction mixture was concentrated under vacuum to afford crude product as yellow oil. The reaction mixture was adjusted to pH=7 using sat. NaHCO$_3$, 50 mL water was added and stirred at rt for 30 min. The product was collected by filtration and the residue was collected and dried under vacuum to afford Compound 117 (700 mg, yield: 72%) as white solid.

LC/MS: m/z 467.0 [M+H]$^+$, rt 1.488 min, purity 90.8%, method C.

Preparation of Compounds 118 and 119

Compound 117 (600 mg, 1.165 mmol) was separated by SFC [Column: DAICEL CHIRALPAK IC (250 mm*30 mm, 10 μm), Condition: solvent A: Supercritical CO$_2$, solvent B: 0.1% aqueous ammonia in EtOH, at the beginning: A (45%) and B (55%), at the end: A (45%) and B (55%), Flow Rate (ml/min) 60]. The pure fractions were collected and the organic solvent was evaporated under vacuum. MeCN and H$_2$O were added to the residue and it was lyophilized to dryness to give Compound 118 (252 mg, yield: 46.3%) as white solid, and Compound 119 (255 mg, yield: 46.8%) as white solid.

Compound 118:

HPLC/MS: m/z 467 [M+H]$^+$, rt: 3.526 min, Purity 98.4%, method: K;

SFC: purity 100%, rt: 7.808 min, method: SFC22.

Compound 119:

$^1$H NMR (400 MHz, DMSO-d$_6$) δ ppm 1.37 (d, J=6.8 Hz, 3H) 3.21 (s, 3H) 4.89 (q, J=6.8 Hz, 1H) 6.14 (s, 2H) 8.11 (s, 2H) 8.20 (s, 1H) 8.25 (br s, 1H) 8.42-8.44 (m, 1H) 8.45-8.47 (m, 1H) 10.17 (br s, 1H)

HPLC/MS: m/z 467 [M+H]$^+$, rt: 3.536 min, Purity 98.8%, method: K;

SFC: purity 100%, rt: 9.907 min, method: SFC22.

Synthesis of Compounds 120,121 and 122

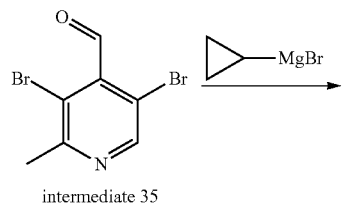

intermediate 35

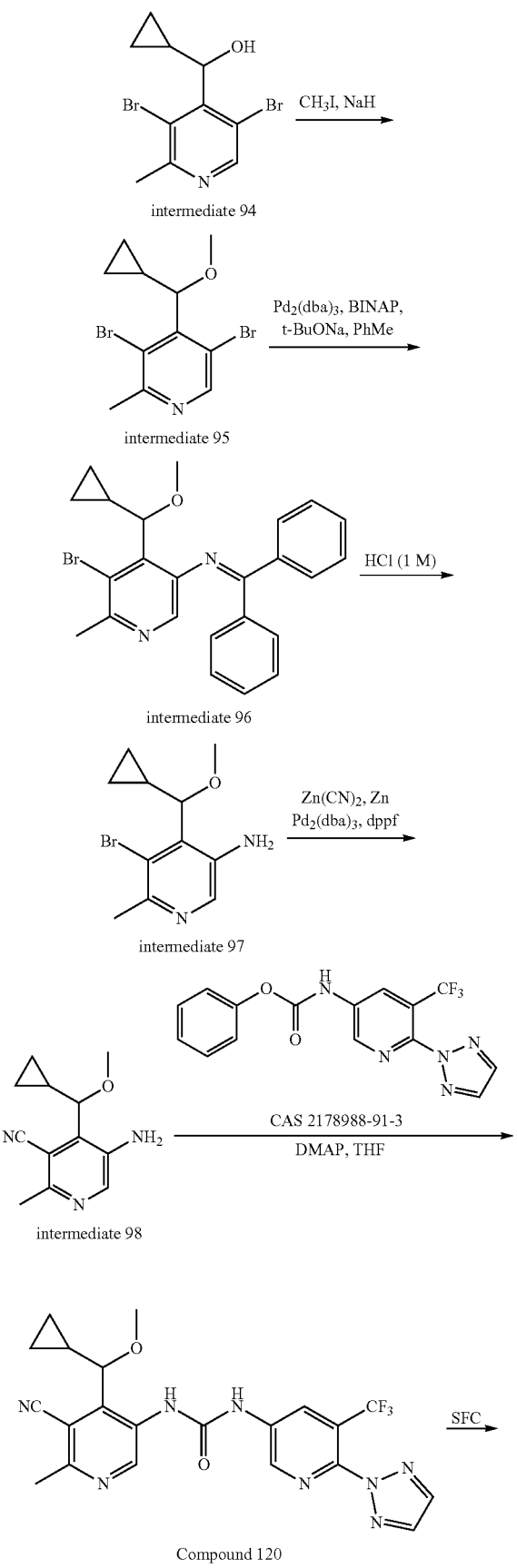

Compound 120

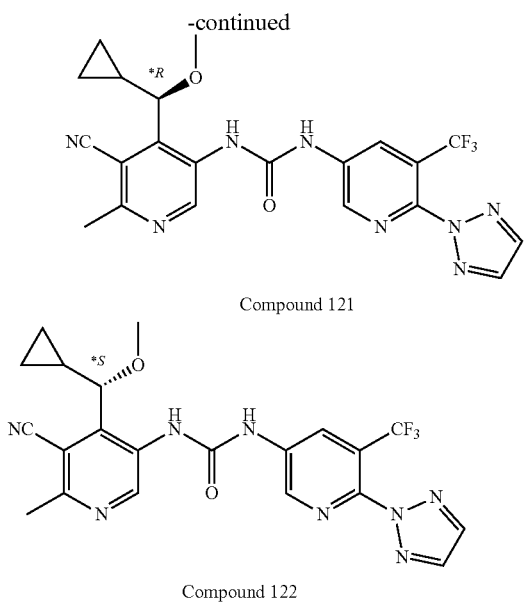

Compound 121

Compound 122

Preparation of Intermediate 94

Intermediate 35 (2.0 g, 7.2 mmol) was dissolved in THF (20 mL) and cyclopropylmagnesium bromide (28.7 mL, 14.3 mmol 0.5 M in THF) was added at −78° C. The reaction mixture was stirred at −78° C. for 2 hours. TLC showed the reaction was completed. The reaction mixture was quenched with Sat.NH$_4$Cl aq., then H$_2$O was added and the mixture was extracted with EtOAc twice. The combined organic layers were dried with Na$_2$SO$_4$, filtered and the filtrate was concentrated under vacuum to afford the crude product as yellow oil. The crude product was purified by flash column chromatography over silica gel (gradient elution: 0~20% EtOAc in petroleum ether). The desired fractions were collected and the solvent was concentrated under vacuum to afford intermediate 94 (1.8 g, yield: 78%) as yellow oil.

Preparation of Intermediate 95

To a solution of intermediate 94 (1.8 g, 5.6 mmol) in THF (20 mL) was added NaH (336 mg, 8.4 mmol 60% in mineral oil) at 0° C. The mixture was stirred at 0° C. for 0.5 hour. Then MeI (3.2 g, 22.4 mmol) was added. The mixture was stirred at 20° C. for 2 hours. The mixture was quenched with sat. NH$_4$Cl aq. and extracted with EtOAc twice. The combined organic layers were dried over Na$_2$SO$_4$, filtered and concentrated in vacuum to give a crude product. The crude product was purified by a flash column chromatography over silica gel (gradient elution: 0~20% EtOAc in petroleum ether). The desired fractions were collected and the solvent was concentrated under vacuum to afford intermediate 95 (1.4 g, yield: 74%) as yellow oil.

Preparation of Intermediate 96

To a mixture of intermediate 95 (1.4 g, 4.2 mmol) in toluene (16 mL), diphenylmethanimine (0.8 g, 4.6 mmol) and 1-BuONa (0.4 g, 4.2 mmol) were added and the mixture was purged with N$_2$ for 10 min. Pd$_2$(dba)$_3$ (0.2 g, 0.2 mmol) and BINAP (0.4 g, 0.6 mmol) were added. The reaction mixture was stirred at 120° C. for 12 hours. TLC showed the reaction was completed. The mixture was filtered and the filtrate was concentrated to afford a crude product as yellow oil. The crude product was purified by flash column chromatography over silica gel (gradient elution: 0~20% EtOAc in petroleum ether). The desired fractions were collected and the solvent was concentrated in vacuum to give intermediate 96 (1.0 g, yield: 36%) as yellow oil.

Preparation of Intermediate 97

To a solution of intermediate 96 (1.0 g, 1.5 mmol) in DCM (15 mL) was added HCl (3 mL, 1 M). The mixture was stirred at 40° C. for 2 hours. The reaction mixture was adjusted to pH=8 using sat. NaHCO$_3$ aq. and extracted with CH$_2$Cl$_2$ twice. The combined organic layers were washed with brine, dried over Na$_2$SO$_4$, filtered and evaporated under vacuum to give yellow oil. The crude product was purified by flash column chromatography over silica gel (gradient elution: 0~55% EtOAc in petroleum ether). The desired fractions were collected and the solvent was concentrated in vacuum to give intermediate 97 (330 mg) as a white solid.

Preparation of Intermediate 98

To a mixture of intermediate 97 (330 mg, 1.1 mmol), Zn(CN)$_2$ (82 mg, 0.7 mmol) and Zn (23 mg, 0.3 mmol) were added in DMF (10 mL). The mixture was purged with N$_2$ for 5 min. Pd$_2$(dba)$_3$ (53 mg, 0.1 mmol) and dppf CAS 12150-46-8 (65 mg, 0.1 mmol) were added. The reaction mixture was stirred at 120° C. for 12 hours. The mixture was filtered and the filtrate was concentrated to afford a crude product as yellow oil. The crude product was purified by flash column chromatography over silica gel (gradient elution: 0~52% EtOAc in petroleum ether). The desired fractions were collected and the solvent was concentrated in vacuum to give intermediate 98 (250 mg, yield: 88%) as yellow solid.

Preparation of Compound 120

To a solution of intermediate 98 (150 mg, 0.6 mmol) and CAS 2178988-91-3 (322 mg, 0.9 mmol) in THF (20 mL) was added DMAP (150 mg, 1.2 mmol) at 20° C. The reaction mixture was stirred at 80° C. for 3 hours. The mixture was concentrated in vacuum to give a crude. The crude product was purified by flash column chromatography over silica gel (gradient elution: 0~45% EtOAc in petroleum ether). The pure fractions were collected and the solvent was evaporated under vacuum to give the product as white solid. The compound was purified by preparative high-performance liquid chromatography [Column: PhenomenexGemini 150*25 mm*10 um, Condition: A: water (0.04% NH$_3$H$_2$O+10 mM NH$_4$HCO$_3$)-ACN, B: MeCN, at the beginning: A (58%) and B (42%), at the end: A (28%) and B (72%), Gradient Time (min) 8; 100% B Hold Time (min) 2; Flow Rate (ml/min) 25]. The pure fractions were collected and the organic solvent was evaporated under vacuum. The aqueous layer was lyophilized to dryness to give Compound 120 (70 mg, yield: 24%) as white solid.

LC/MS: m/z 473.1 [M+H]$^+$, rt: 0.96 min, Purity 100%, method: A.

SFC: purity 50.1%/49.9%, rt: 5.2 min/6.9 min, method: SFC13.

Preparation of Compounds 121 and 122

Compound 120 (70 mg, 0.1 mmol) was separated by SFC [Column: DAICEL CHIRALPAK AD-H (250 mm*30 mm, 5 μm), Condition: A: CO$_2$, B: 0.1% NH$_3$H$_2$O EtOH at the beginning: A (60%) and B (40%), at the end: A (60%) and B (40%), Flow Rate (ml/min) 70]. The pure fractions were collected and the organic solvent was evaporated under vacuum. The aqueous layers were lyophilized to dryness to give Compound 121 (29.5 mg, yield: 42%) and Compound 122 (28.6 mg, yield: 40%) as white solid.

Compound 121:

HPLC/MS: m/z 473.2 [M+H]$^+$, rt: 4.87 min. Purity 100%, method: K;

SFC: purity 100%, rt: 5.19 min, method: SFC13.

Compound 122:

HPLC/MS: m/z 473.2 [M+H]⁺, rt: 4.87 min. Purity: 100%, method: K;

SFC: purity 100%, rt: 6.87 min, method: SFC13.

Synthesis of Compounds 123, 124 and 125

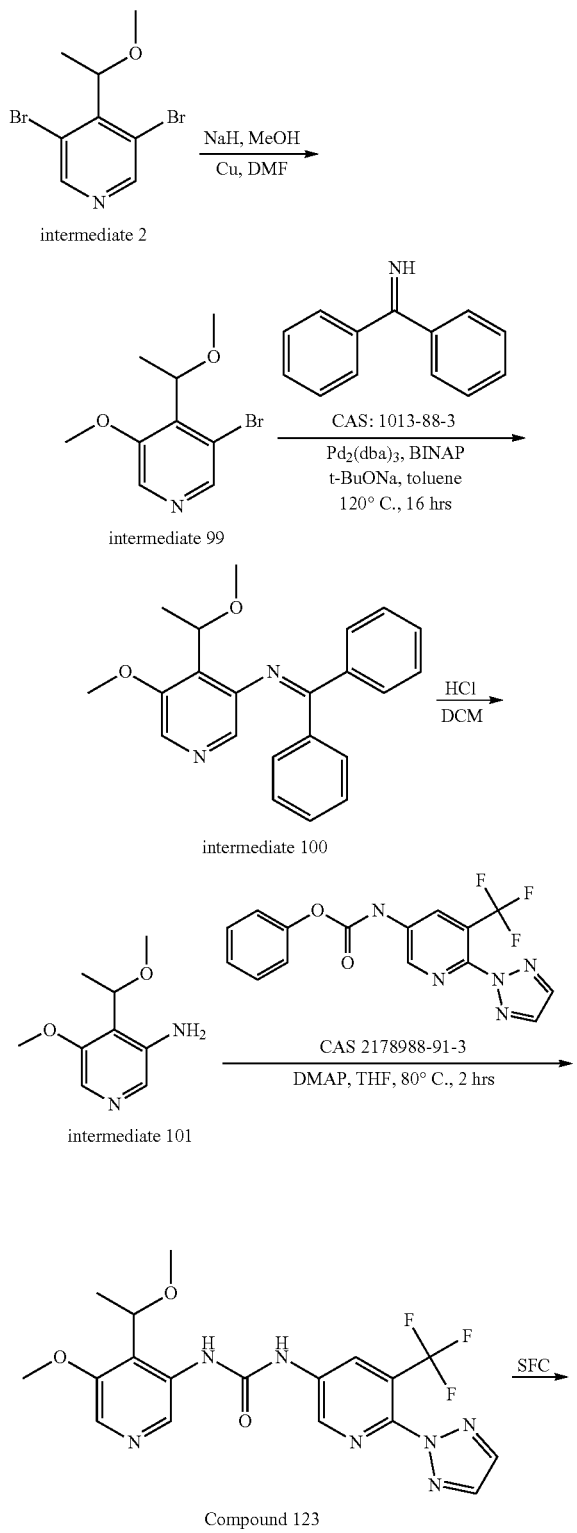

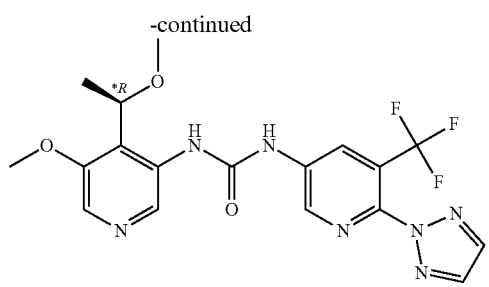

Compound 124

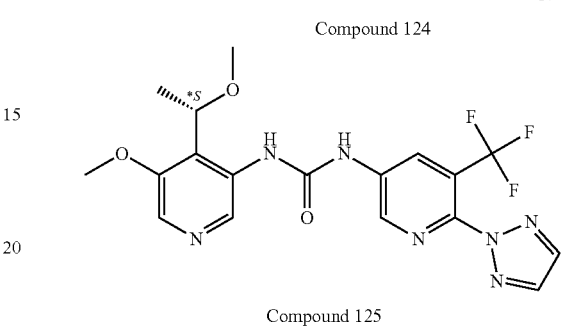

Compound 125

Preparation of Intermediate 99

Methanol (0.83 g, 26 mmol) was dissolved in DMF (30 mL) and NaH (1.0 g, 26 mmol, 60% in mineral oil) was added at 0° C. The mixture was stirred at room temperature for 1 hour. Then intermediate 2 (2.0 g, 6.5 mmol) and Cu powder (0.040 g, 0.65 mmol) were added slowly to the mixture. The mixture was stirred at 80° C. for 20 min. The reaction was cooled to 0° C. and quenched by dropwise addition of water (30 mL) and then extracted with EtOAc (50 mL×2) twice. The combined organic layers were washed with brine, dried over anhydrous Na₂SO₄, filtered and concentrated under vacuum to give a crude product. The crude product was purified by column chromatography over silica gel (gradient elution: 0~60% EtOAc in petroleum ether). The desired fractions were collected and the solvent was concentrated under vacuum to afford intermediate 99 (1.13 g, yield: 70.4%) as colorless liquid.

Preparation of Intermediate 100

A mixture of intermediate 99 (1.13 g, 4.58 mmol), diphenylmethanimine CAS 1013-88-3 (0.9 g, 5 mmol) and 1-BuONa (0.44 g, 4.58 mmol) in toluene (20 mL) was purged with N₂ for 10 min. Then Pd₂(dba)₃ (0.21 g, 0.23 mmol) and BINAP (0.43 g, 0.69 mmol) were added. The reaction mixture was stirred at 120° C. for 16 hours. The reaction was cooled to 25° C. and filtered. The residue was washed with EtOAc (50 mL). The filtrates were concentrated under vacuum to afford the crude product. The crude product was purified by flash column chromatography over silica gel (gradient elution: 0~70% EtOAc in petroleum ether). The desired fractions were collected and the solvent was concentrated in vacuum to give crude intermediate 100 (1.78 g, yield: 65.9%) as yellow oil.

Preparation of Intermediate 101

Crude intermediate 100 (1.78 g, 58.7% purity) was dissolved in DCM (20 mL). Aq. HCl (6 mL, 1 M) was added and the mixture was stirred at room temperature for 24 hours. The reaction mixture was adjusted to pH=8 using sat.NaHCO₃ and extracted with DCM (30 mL×2). The combined organic layers were washed with brine, dried over Na₂SO₄, filtered and the filtrates were evaporated under vacuum to give yellow oil. The crude product was purified by flash column chromatography over silica gel (gradient elution: 0~90% EtOAc in petroleum ether). The desired fractions were collected and the solvent was concentrated in vacuum to give intermediate 101 (0.47 g, yield: 56% over two steps) as white solid.

Preparation of Compound 123

To a solution of intermediate 101 (350 mg, 1.92 mmol) and CAS 2178988-91-3 (805 mg, 2.3 mmol) in THF (10 mL) was added DMAP (469 uL, 3.84 mmol) at 20° C. The reaction mixture was stirred at 80° C. for 2 hours. The mixture was allowed to cool to room temperature and concentrated in vacuum to give a crude product. The crude product was purified by flash column chromatography over silica gel (gradient elution: 0~90% EtOAc in petroleum ether). The desired fractions were collected and the solvent was concentrated in vacuum to give Compound 123 (0.6 g, yield: 66%) as white solid.

LC/MS: m/z 438.1 [M+H]$^+$, rt: 0.699 min, purity 92.8%, method: B.

Preparation of Compounds 124 and 125

Compound 123 (600 mg, 1.27 mmol) was separated by SFC [Column: DAICEL CHIRALPAK AD (250 mm*50 mm, 10 μm), Condition: solvent A: Supercritical CO$_2$, solvent B: 0.1% aq. ammonia in EtOH, at the beginning: A (65%) and B (35%), at the end: A (65%) and B (35%), Flow Rate (ml/min) 80]. The pure fractions were collected and the solvent was evaporated in vacuum to give a crude (260 mg, purity: 93.5%) as white solid. The crude was purified by flash column chromatography over silica gel (gradient elution: 0~90% EtOAc in petroleum ether). The pure fractions were collected and the organic solvent was evaporated under vacuum. MeCN and H$_2$O were added to the residue and it was lyophilized to dryness to give Compound 124 (207 mg, yield: 37%) and Compound 125 (253 mg, yield: 45%) as white solids.

Compound 124:

HPLC/MS: m/z 438.2 [M+H]$^+$, rt: 3.762 min, purity 99.9%, method: K.

SFC: purity 100%, rt: 0.928 min, method: SFC1.

Compound 125:

LC/MS: m/z 438.2 [M+H]$^+$, rt: 3.765 min, purity 100%, method: K.

SFC: purity 100%, rt: 1.163 min, method: SFC1.

Synthesis of Compounds 126, 127 and 128

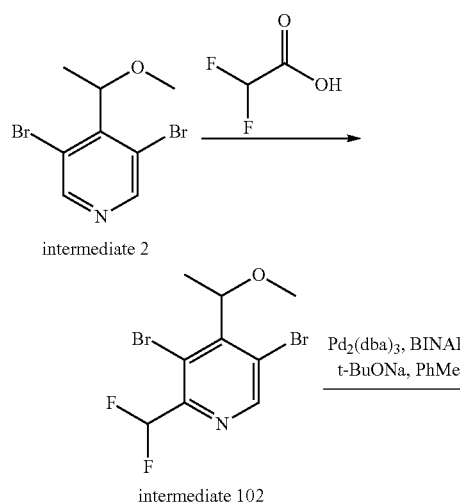

intermediate 2 intermediate 102

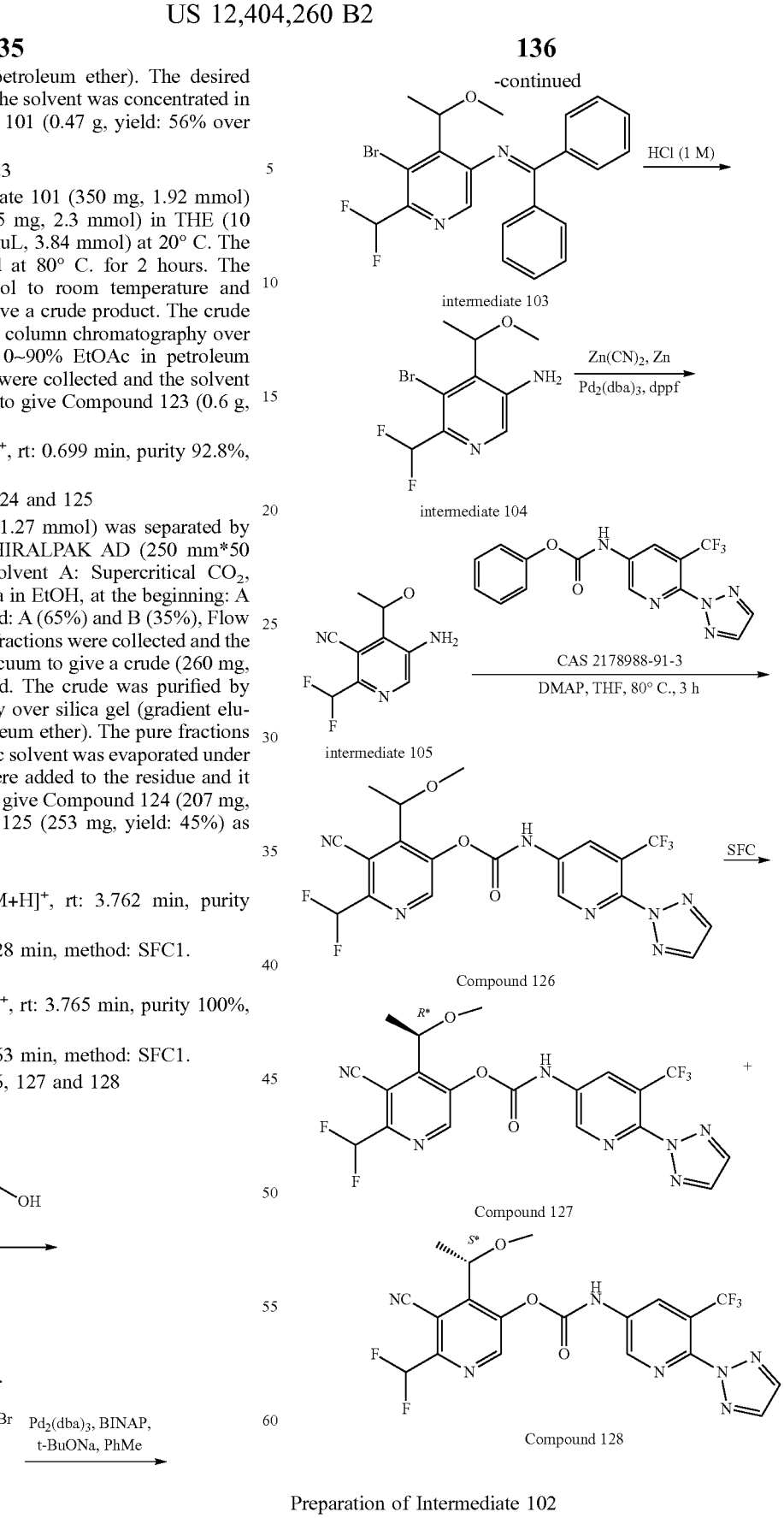

intermediate 103 intermediate 104 intermediate 105

Compound 126

Compound 127

Compound 128

Preparation of Intermediate 102

(NH$_4$)$_2$S$_2$O$_3$ (10 eq) was added to a mixture of intermediate 2 (5.0 g; 17 mmol)), 2,2-difluoroacetic acid (5 eq) and AgNO$_3$ (5 eq) in a mixture of CH$_3$CN (250 mL) and H$_2$O (125 mL). The reaction mixture was heated to 60° C. The reaction mixture was stirred at 60° C. for 36 hours. The reaction mixture was adjusted to pH=10 using $NH_3 \cdot H_2O$ and extracted with EtOAc (100 mL*3). The combined organic layers were dried with $Na_2SO_4$ filtered and the filtrates were concentrated under vacuum to afford as yellow oil. The crude was purified by flash column chromatography over silica gel (petroleum ether/ethyl acetate from 100/0 to 95/5). The desired fraction was collected and the solvent was concentrated under vacuum to give crude intermediate 102 (2.5 g) as yellow oil, which was purified by pre-HPLC: Column: Xtimate C18 150*25 mm*5 um Condition: A: water (0.225% FA)B: MeCN at the beginning: A (60%) and B (40%) at the end: A (30%) and B (70%) Gradient Time (min) 7 100% B Hold Time (min) 2; Flow Rate (ml/min) 30. The pure fractions were collected and the organic solvent was evaporated under vacuum. The aqueous layer was lyophilized to dryness to give intermediate 102 (800 mg, yield: 15.5%) as white solid.

Preparation of Intermediate 103

Intermediate 102 (800 mg, 2.32 mmol) and diphenylmethanimine (462 mg, 2.55 mmol) were dissolved in toluene (20 mL), $Pd_2(dba)_3$ CAS: 51364-51-3 (106 mg, 0.12 mmol). BINAP (216 mg, 0.35 mmol) and NaOtBu (223 mg, 2.32 mmol) were added to the solution, and the solution was purged with $N_2$. The reaction mixture was stirred at 120° C. for 16 hours. The reaction was cooled to rt and the mixture was filtered and the filter cake was washed with EtOAc (20 mL). The filtrates were concentrated under vacuum to afford the crude product. The crude was purified by flash column chromatography over silica gel (petroleum ether/ethyl acetate from 100/0 to 85/15). The desired fraction was collected and the solvent was concentrated under vacuum to give intermediate 103 (750 mg, yield: 72.3%) as yellow oil.

Preparation of Intermediate 104

Intermediate 103 (750 mg, 1.68 mmol) was dissolved in DCM (6 mL) and HCl (6 mL, 1 M aqueous solution) was added. The reaction mixture was stirred at rt for 16 hours. The reaction mixture was adjusted to pH=8 using sat.$NaHCO_3$, and extracted with DCM (30 mL*2). The combined organic layers were dried with $Na_2SO_4$, filtered and the filtrates were concentrated under vacuum to afford crude as yellow oil. The crude was purified by flash column chromatography over silica gel (eluent: petroleum ether/ethyl acetate from 100/0 to 45/55). The desired fractions were collected and the solvent was concentrated under vacuum to afford intermediate 104 (350 mg, yield: 73.9%) as yellow solid.

Preparation of Intermediate 105

A solution of intermediate 104 (350 mg, 1.24 mmol), $Zn(CN)_2$ (150 mg, 1.28 mmol) and Zn dust (49 mg, 0.75 mmol) in DMF (10 mL) was degassed for 5 min. Then $Pd_2(dba)_3$ (57 mg, 0.06 mmol), dppf (69 mg, 0.12 mmol) was added and the mixture was stirred at 120° C. for 16 hours under $N_2$. The mixture was filtered and the filtrate was concentrated in vacuum to give a crude product. The crude product was purified by flash column chromatography over silica gel (eluent: petroleum ether/EtOAc from 100/0 to 62/38). The desired fractions were collected and the solvent was concentrated to dryness under vacuum to give intermediate 105 (210 mg, yield: 65.6%) as yellow solid.

Preparation of Compound 126

To a solution of intermediate 105 (210 mg, 0.82 mmol) and CAS 2178988-91-3 (428 mg, 1.22 mmol) in THF (10 mL) was added DMAP (299 mg, 2.45 mmol) at rt. The reaction mixture was stirred at 80° C. for 16 hours. To the mixture was added MeCN (10 mL) and filtered. The filtrate was concentrated in vacuum to give a crude product. The crude product was purified by preparative high-performance liquid chromatography [Column: Waters Xbridge Prep OBD C18 150*40 mm*10 μm, Condition: A: water (10 mM $NH_4HCO_3$)B: MeCN, at the beginning: A (62%) and B (38%), at the end: A (32%) and B (68%), Gradient Time (min) 15; 100% B Hold Time (min) 1; Flow Rate (ml/min) 25]. The pure fractions were collected and the solvent was evaporated to dryness to give Compound 126 (80 mg, yield; 20%) as white solid.

LC/MS: m/z 483.1 $[M+H]^+$, rt: 0.98 min, purity 99.2%, method: A.

Preparation of Compounds 127 and 128

Compound 126 (80 mg, 0.16 mmol) was separated by SFC [Column: DAICEL CHIRALCEL OD (250 mm*30 mm, 10 μm), Condition: Mobile phase: A: Supercritical $CO_2$, B: 0.1% $NH_3H_2O$ IPA. at the beginning: B (40%), at the end: B (40%), Flow Rate (ml/min) 50]. The pure fractions were collected and the organic solvent was evaporated under vacuum. 2 mL of $CH_3CN$ and 20 mL of $H_2O$ was added and the mixture was lyophilized to dryness to give Compound 127 (35 mg, purity: 99%, yield: 43.8%) and Compound 128 (35 mg, purity: 100%, yield: 44.1%) as white solids.

Compound 127:

$^1H$ NMR (400 MHz, DMSO-$d_6$) δ ppm 1.54 (d, J=6.8 Hz, 3H), 3.30 (s, 3H), 4.93 (q, J=6.8 Hz, 1H), 6.94-7.31 (m, 1H), 8.15 (s, 2H), 8.67 (d, J=2.4 Hz, 1H), 8.83 (d, J=2.4 Hz, 1H), 9.07 (br s, 1H), 9.44 (s, 1H), 10.71 (br s, 1H)

LC/MS: m/z 483.1 $[M+H]^+$, rt: 5.04 min, Purity 99.3%, method: K;

SFC: purity 100%, rt: 5.43 min, method: SFC23

Compound 128:

LC/MS: m/z 483.2 $[M+H]^+$, rt: 5.04 min, Purity 100%, method: K;

SFC: purity 99.6%, rt: 5.90 min, method: SFC23.

The compounds in the Table below were prepared by analogy to one of the previously described compounds. In the Table below for the 'Synthesis', reference is made to the procedures described in the General Schemes.

| Compound | Structure | Synthesis (ref to General Schemes) |
|---|---|---|
| 129 | 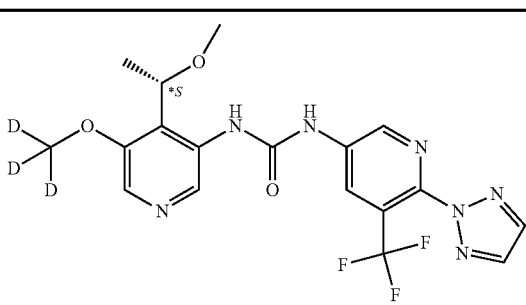 | 1 4 2a 13 |

| Compound | Structure | Synthesis (ref to General Schemes) |
|---|---|---|
| 130 | 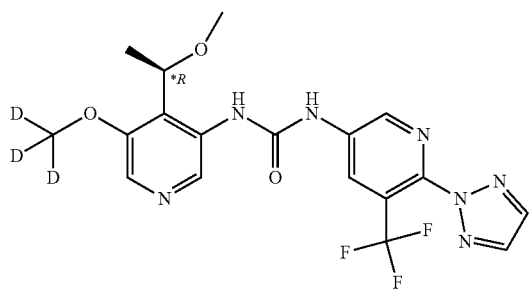 [SMILES: [2H]C([2H])([2H])Oc1cncc(NC(=O)Nc2cnc(-n3nccn3)c(C(F)(F)F)c2)c1[C@@H](C)OC] | 1 4 2a 13 |
| 131 | 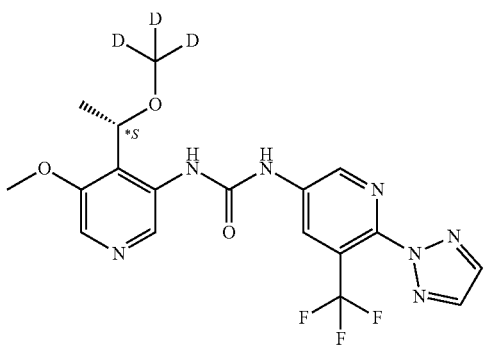 [SMILES: [2H]C([2H])([2H])O[C@@H](C)c1c(NC(=O)Nc2cnc(-n3nccn3)c(C(F)(F)F)c2)cncc1OC] | 1 4 2a 13 |
| 132 | 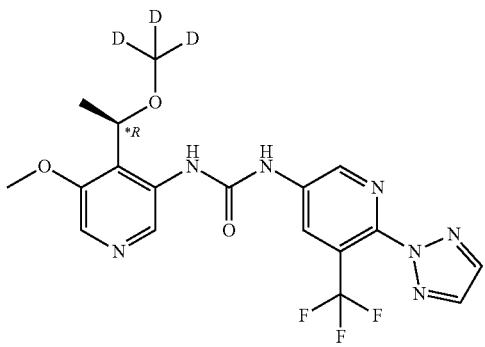 [SMILES: [2H]C([2H])([2H])O[C@H](C)c1c(NC(=O)Nc2cnc(-n3nccn3)c(C(F)(F)F)c2)cncc1OC] | 1 4 2a 13 |
| 133 | 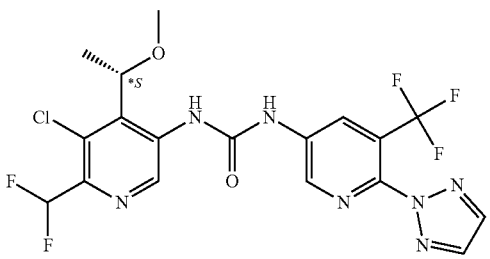 [SMILES: CO[C@@H](C)c1c(NC(=O)Nc2cnc(-n3nccn3)c(C(F)(F)F)c2)cnc(C(F)F)c1Cl] | 1 7 2b 13 |
| 134 | 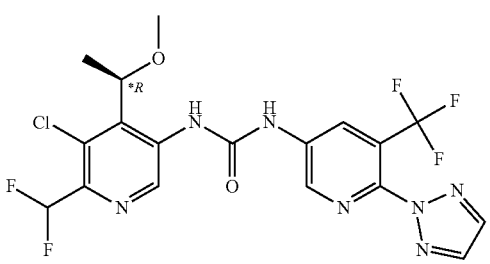 [SMILES: CO[C@H](C)c1c(NC(=O)Nc2cnc(-n3nccn3)c(C(F)(F)F)c2)cnc(C(F)F)c1Cl] | 1 7 2b 13 |

-continued

| Compound | Structure | Synthesis (ref to General Schemes) |
|---|---|---|
| 135 | 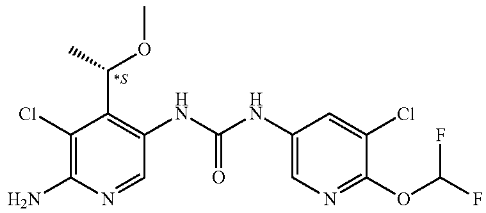 [SMILES: CO[C@@H](C)c1c(NC(=O)Nc2cnc(OC(F)F)c(Cl)c2)cnc(N)c1Cl] | 1 8 2b 13 |
| 136 | 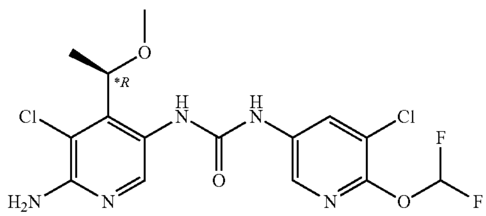 [SMILES: CO[C@H](C)c1c(NC(=O)Nc2cnc(OC(F)F)c(Cl)c2)cnc(N)c1Cl] | 1 8 2b 13 |
| 137 | 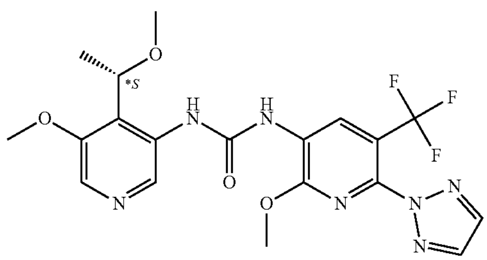 [SMILES: COc1cncc(NC(=O)Nc2cc(C(F)(F)F)c(-n3nccn3)nc2OC)c1[C@H](C)OC] | 1 4 2a 13 |
| 138 | 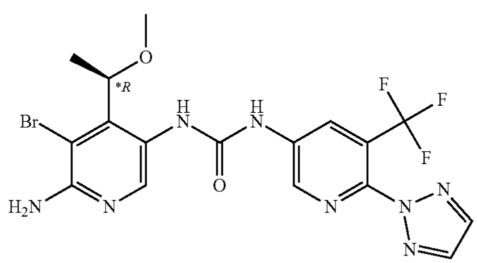 [SMILES: CO[C@H](C)c1c(NC(=O)Nc2cnc(-n3nccn3)c(C(F)(F)F)c2)cnc(N)c1Br] | 1 8 2b 13 |
| 139 | 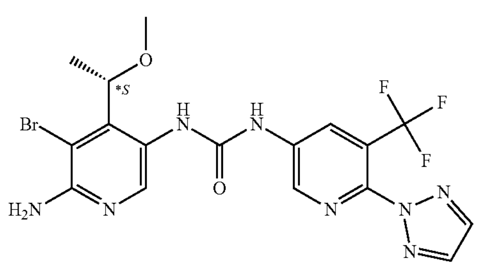 [SMILES: CO[C@@H](C)c1c(NC(=O)Nc2cnc(-n3nccn3)c(C(F)(F)F)c2)cnc(N)c1Br] | 1 8 2b 13 |
| 140 | 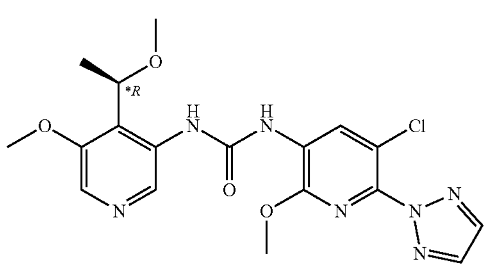 [SMILES: COc1cncc(NC(=O)Nc2cc(Cl)c(-n3nccn3)nc2OC)c1[C@@H](C)OC] | 1 4 2b 13 |

-continued

| Compound | Structure | Synthesis (ref to General Schemes) |
|---|---|---|
| 141 | 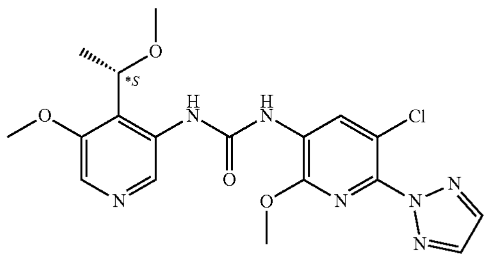 [SMILES: COc1cncc(NC(=O)Nc2cc(Cl)c(-n3nccn3)nc2OC)c1[C@H](C)OC] | 1 4 2b 13 |
| 142 | 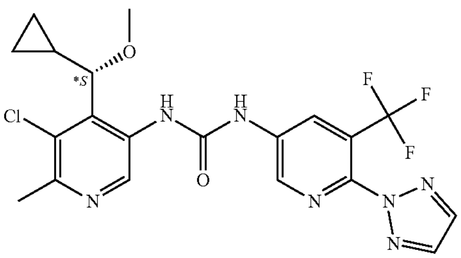 [SMILES: CO[C@H](c1c(NC(=O)Nc2cnc(-n3nccn3)c(C(F)(F)F)c2)cnc(C)c1Cl)C1CC1] | 1 2b 13 |
| 143 | 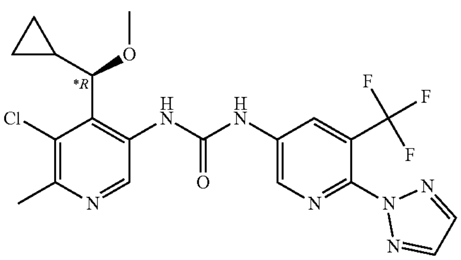 [SMILES: CO[C@@H](c1c(NC(=O)Nc2cnc(-n3nccn3)c(C(F)(F)F)c2)cnc(C)c1Cl)C1CC1] | 1 2b 13 |
| 144 | 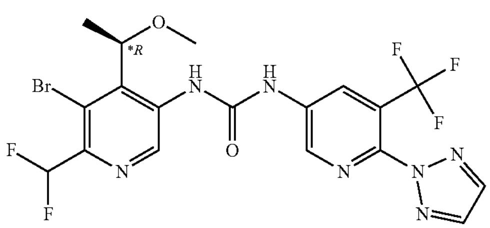 [SMILES: CO[C@H](C)c1c(NC(=O)Nc2cnc(-n3nccn3)c(C(F)(F)F)c2)cnc(C(F)F)c1Br] | 1 7 2b 13 |
| 145 | 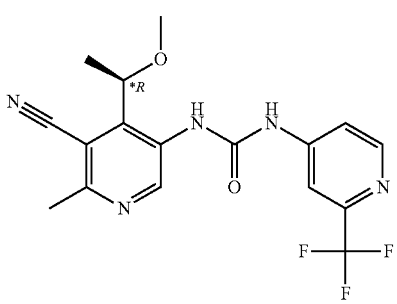 [SMILES: CO[C@H](C)c1c(NC(=O)Nc2ccnc(C(F)(F)F)c2)cnc(C)c1C#N] | 1 2a 3 13 |
| 146 | 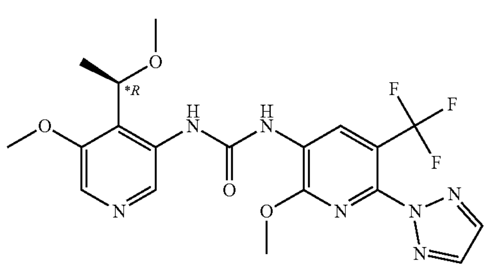 [SMILES: COc1cncc(NC(=O)Nc2cc(C(F)(F)F)c(-n3nccn3)nc2OC)c1[C@@H](C)OC] | 1 4 2a 13 |

| Compound | Structure | Synthesis (ref to General Schemes) |
|---|---|---|
| 147 | 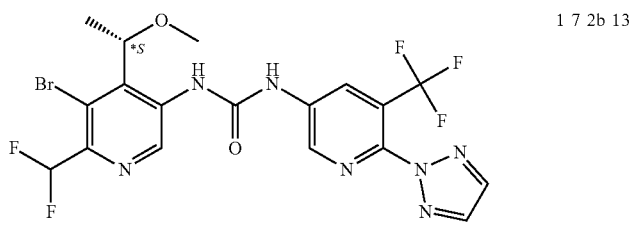 | 1 7 2b 13 |
| 148 | 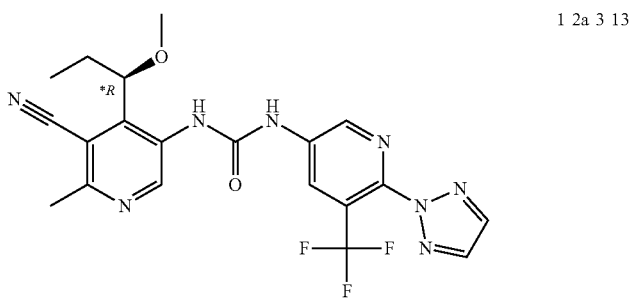 | 1 2a 3 13 |
| 149 | 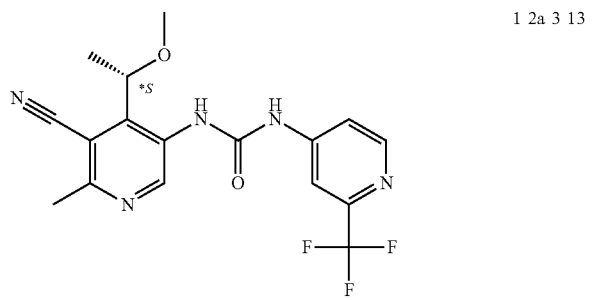 | 1 2a 3 13 |
| 150 | 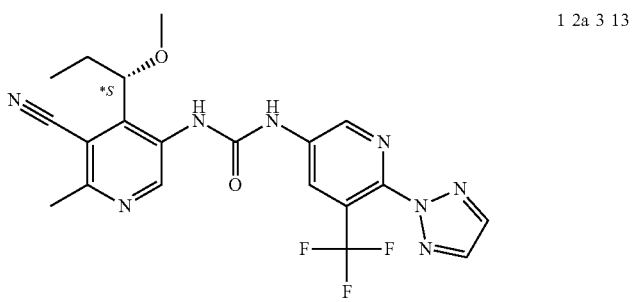 | 1 2a 3 13 |
| 151 | 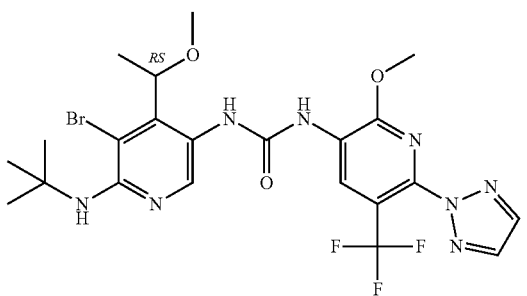 [SMILES: COc1nc(-n2nccn2)c(C(F)(F)F)cc1NC(=O)Nc1cnc(NC(C)(C)C)c(Br)c1C(C)OC] | 1 8 2b 13 |

| Compound | Structure | Synthesis (ref to General Schemes) |
|---|---|---|
| 152 | 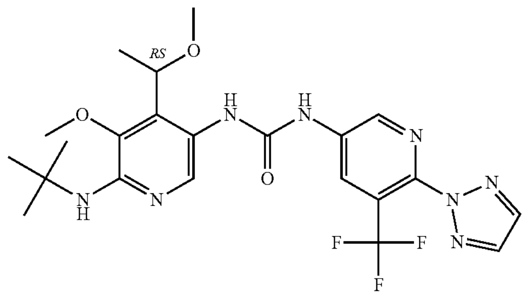 [SMILES: COc1c(NC(C)(C)C)ncc(NC(=O)Nc2cnc(-n3nccn3)c(C(F)(F)F)c2)c1C(C)OC] | 1 8 4 2b 13 |
| 153 | 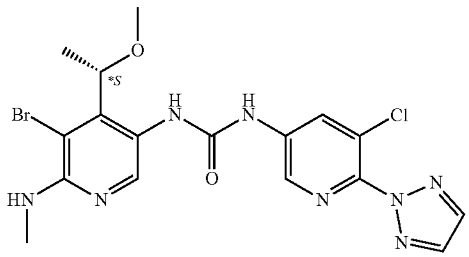 [SMILES: CNc1ncc(NC(=O)Nc2cnc(-n3nccn3)c(Cl)c2)c([C@H](C)OC)c1Br] | 1 8 2b 13 |
| 154 | 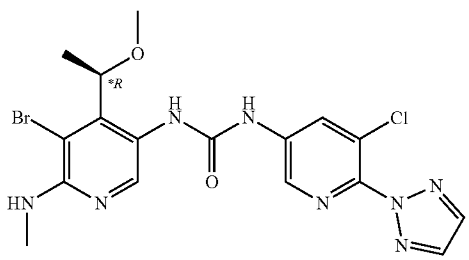 [SMILES: CNc1ncc(NC(=O)Nc2cnc(-n3nccn3)c(Cl)c2)c([C@@H](C)OC)c1Br] | 1 8 2b 13 |

Compound 130: ¹H NMR (400 MHz, DMSO-d₆) δ ppm 1.39 (d, J=6.8 Hz, 3H), 3.24 (s, 3H), 4.98 (d, J=6.4 Hz, 1H), 8.08 (s, 1H), 8.13 (s, 2H), 8.66 (d, J=2.4 Hz, 1H), 8.76 (s, 1H), 8.81 (d, J=2.4 Hz, 1H), 8.85 (s, 1H), 10.61 (br s, 1H);

HPLC/MS: m/z 441.1, [M+H]⁺, rt: 3.81 min. Purity: 100%, method: K.

SFC: purity: 99.48%, rt: 1.20 min, method: SFC30.

Compound 129:

HPLC/MS: m/z 441.1, [M+H]⁺, rt: 3.81 min. Purity: 100%, method: K;

SFC: purity: 100%, rt: 1.40 min, method: SFC30.

Compound 132: ¹H NMR (400 MHz, DMSO-d₆) δ ppm 1.39 (d, J=6.8 Hz, 3H), 3.28 (s, 3H), 3.88 (s, 3H), 4.97 (q, J=6.8 Hz, 1H), 8.08 (s, 1H), 8.13 (s, 2H), 8.66 (d, J=2.4 Hz, 1H), 8.77 (s, 1H), 8.81 (d, J=2.4 Hz, 1H), 8.85 (s, 1H), 10.61 (s, 1H);

HPLC/MS: m/z 441.1, [M+H]⁺, rt: 4.04 min, Purity: 100%, method: M;

SFC: purity: 99.72%, rt: 1.21 min, method: SFC30.

Compound 131:

HPLC/MS: m/z 441.1 [M+H]⁺, rt: 4.15 min, Purity: 100%, method: M;

SFC: purity: 99.69%, rt: 1.40 min, method: SFC30.

Compound 134:

LC/MS: m/z 492.1, 494.1 [M+H]⁺, rt 5.1 min. Purity 100%, method: K;

SFC: purity 99.9%, rt 5.3 min. method: SFC13.

Compound 133:

LC/MS: m/z 492.1, 494.1 [M+H]⁺, rt 5.1 min. Purity 100%, method: K;

SFC: purity 99.3%, rt 5.6 min. method: SFC13.

Compound 136:

HPLC/MS: m/z 422.1, 423.1, 424.1 [M+H]⁺, rt 4.2 min. Purity 98.6%, method: K;

SFC: purity 100%, rt 5.9 min. method: SFC1.

Compound 135:

HPLC/MS: m % z 422.1, 423.1, 424.1 [M+H]⁺, rt 4.2 min. Purity 98.6%, method: K;

SFC: purity 100%, rt 7.3 min. method: SFC1.

Compound 146:

LC/MS: m/z 468.2 [M+H]⁺, rt 4.0 min. Purity 99.6%, method: K;

SFC: purity 100%, rt 4.5 min. method: SFC25.

Compound 137:

LC/MS: m/z 468.2 [M+H]⁺, rt 4.0 min. Purity 99.8%, method: K;

SFC: purity 98%, rt 4.7 min. method: SFC25.

Compound 139: ¹H NMR (400 MHz, DMSO-d6) δ ppm 1.41 (d, J=6.8 Hz, 3H), 3.25 (s, 3H), 4.93 (q, J=6.8 Hz, 1H), 6.21 (s, 2H), 8.16 (s, 2H), 8.25 (s, 1H), 8.29 (s, 1H), 8.70 (d, J=2.4 Hz, 1H), 8.79 (d, J=2.4 Hz, 1H), 10.34 (br s, 1H);

HPLC/MS: m/z 501.1, 503.1 [M+H]⁺, rt: 3.875 min, Purity 99%, method: K;

SFC: purity 100%, rt: 0.666 min, method: SFC41.

Compound 138:
HPLC/MS: m/z 501.1, 503.1 [M+H]$^+$, rt: 3.877 min, Purity 98.7%, method: K;
SFC: purity 99.89%, rt: 1.128 min, method: SFC41.
Compound 140:
HPLC/MS: ml 434.2, 436.2 [M+H]$^+$, rt 3.8 min. Purity 99.9%, method: K.
SFC: purity 100%, rt 3.3 min. method: SFC25
Compound 141:
HPLC/MS: m/z 434.2, 436.2 [M+H]$^+$, rt 3.8 min. Purity 100%, method: K.
SFC: purity 100%, rt 5.0 min. method: SFC25
Compound 143:
HPLC/MS: m/z 482.2, 484.1 [M+H]$^+$, rt: 3.61 min. Purity: 100%, method: L;
SFC: purity 99.9%, rt: 3.51 min, method: SFC1.
Compound 142:
HPLC/MS: mi 482.1, 484.1 [M+H]$^+$, ii: 3.60 min. Purity: 100%, method: L;
SFC: purity 100%, rt: 4.40 min, method: SFC1.
Compound 144:
HPLC/MS: m % z 536.0, 538.0 [M+H]$^+$, rt: 5.29 min. Purity: 99%, method: K;
SFC: purity 100%, rt: 1.24 min, method: SFC33.
Compound 147:
HPLC/MS: m/z 535.9, 537.9 [M+H]$^+$, rt: 5.28 min. Purity: 98%, method: K;
SFC: purity 99.8%, rt: 1.34 min, method: SFC33.
Compound 145:
HPLC/MS: m/z 380.1 [M+H]$^+$, rt: 4.43 min. Purity 100%, method: K.
SFC: purity 100%, rt: 3.73 min, method: SFC39.
Compound 149:
HPLC/MS: m/z 380.2 [M+H]$^+$, rt: 4.43 min. Purity: 100%, method: K;
SFC: purity 99%, rt: 3.55 min, method: Method: SFC39.
Compound 148: $^1$H NMR (400 MHz, DMSO-d$_6$) δ ppm 0.89 (t, J=7.2 Hz, 3H), 1.69-1.81 (m, 1H), 1.94 (dt, J=14, 7.2 Hz, 1H), 2.64 (s, 3H), 3.26 (s, 3H), 4.56 (t, J 6.8 Hz, 1H), 8.13 (s, 2H), 8.65 (s, 2H), 8.80 (s, 1H), 9.09 (s, 1H), 10.46 (br s, 1H);
HPLC/MS: m/z 461.2, [M+H]$^+$, rt: 4.80 min, Purity: 100%, method: K;
SFC: purity 100%, rt: 1.45, min, method: SFC35.
Compound 150:
HPLC/MS: m/z 461.2, [M+H]$^+$, rt: 4.79 min, Purity: 100%, method: K;
SFC: purity 100%, rt: 1.58 min, method: SFC35.
Compound 151:
HPLC/MS: m/z 587.1, 589.1 [M+H]$^+$, rt: 4.649 min, Purity 96.77%, method: L
Compound 152:
HPLC/MS: m/z 509.3, [M+H]$^+$, rt: 3.06 min. Purity: 100%, method: L Compound 153:
LC/MS: m/z 481.1, 482.0, 483.1 [M+H]$^+$, rt 3.7 min. Purity 99.1%, method: K;
SFC: purity 100%, rt 4.0 min. method: SFC27
Compound 154:
LC/MS: m/z 481.1, 482.0, 483.1 [M+H]$^+$, rt 3.7 min. Purity 98%, method: K;
SFC: purity 100%, rt 2.1 min. method: SFC27

NMR Description

For some compounds, NMR experiments were carried out using a Bruker Avance III 400 spectrometer at ambient temperature (295 K), using internal deuterium lock and equipped with a 5 mm PABBO BB-1H/D probe head with z gradients and operating at 400 MHz for the proton and 100 MHz for carbon, or using a Varian VNMRS 400M spectrometer at ambient temperature (295 K), using internal deuterium lock and equipped with a 5 mm PFG 4Nuc Probe and operating at 400 MHz for the proton and 100 MHz for carbon. Chemical shifts (S) are reported in parts per million (ppm). J values are expressed in Hz.

Alternatively, some NMR experiments were carried out using a Varian MR 400 MHz spectrometer at ambient temperature (295 K), using internal deuterium lock and equipped with a 5 mm PFG 4Nuc Probe and operating at 400 MHz for the proton and 100 MHz for carbon. Chemical shifts (8) are reported in parts per million (ppm). J values are expressed in Hz.

LCMS (Liquid Chromatography/Mass Spectrometry) General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the [M+H]$^+$ (protonated molecule) and/or [M–H]$^-$ (deprotonated molecule). In case the compound was not directly ionizable the type of adduct is specified (i.e. [M+NH$_4$]$^+$, [M+HCOO]$^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE 1a

LCMS Method codes (Flow expressed in mL/min; column temperature (T) in ° C.; Run time in minutes).

| Method code | Instrument | column | mobile phase | gradient | Flow (ml/min) Col T (° C.) | Run time (min) |
|---|---|---|---|---|---|---|
| A | SHIMADZU LC20-MS2010 | MERCK, RP-18e (25*2 mm) | A: 0.04% TFA in H$_2$O | From 95% A to 5% A in 0.7 min | 1.5 50 | 1.5 min |

TABLE 1a-continued

LCMS Method codes (Flow expressed in mL/min; column temperature (T) in °C.; Run time in minutes).

| Method code | Instrument | column | mobile phase | gradient | Flow (ml/min) Col T (°C.) | Run time (min) |
|---|---|---|---|---|---|---|
| | UV 220, 254 nm | | B: 0.02% TFA in $CH_3CN$ | hold 0.4 min, back to 95% A in 0.01 min, hold 0.39 min | | |
| B | Agilent LC1200-MS6110 UV 220, 254 nm | MERCK,RP-18e (25*2 mm) | A: 0.04% TFA in $H_2O$ B: 0.02% TFA in $CH_3CN$ | From 95% A to 5% A in 0.7 min hold 0.4 min, back to 95% A in 0.01 min, hold 0.39 min | 1.5 50 | 1.5 min |
| C | SHIMADZU LC20-MS2020 UV 220, 254 nm | XBridge C18 (3.5 μm 2.1*30 mm) | A: 0.05% $NH_3$: $H_2O$ in $H_2O$ B: acetonitrile | From 90% A to 20% A in 2.0 min hold 0.48 min, back to 90% A in 0.01 min, hold 0.51 min | 1.0 50 | 3 min |
| D | Agilent LC1100-M51946D UV 220, 254 nm | Xbridge Shield RP-18 (5 μm, 2.1*50 mm) | A: 0.05% $NH_3H_2O$ in $H_2O$ B: acetonitrile | From 90% A to 20% A in 2.0 min, hold 0.48 min, back to 90% A in 0.01 min, hold 0.51 min | 1.0 30 | 3 min |
| E | Agilent LC1200-MS6110 UV 220, 254 nm | Xtimate C18 (3 μm, 2.1*30 mm) | A: 0.04% TFA in $H_2O$ B: 0.02% TFA in CH3CN | From 100% A to 40% A in 0.9 min hold 0.6 min, back to 100% A in 0.01 min, hold 0.49 min | 1.2 50 | 2 min |
| G | Agilent LC1200-MS6110, UV 220, 254 | Xtimate C18 (3 μm, 2.1*30 mm) | A: 0.04% TFA in $H_2O$ B: 0.02% TFA in $CH_3CN$ | From 90% A to 20% A in 0.9 min hold 0.6 min, back to 90% A in 0.01 min, hold 0.49 min | 1.2 50 | 2 min |
| K | Agilent LC1200-MSD6110 UV 220 nm | XBridge C18 (5 μm 2*50 mm) | A: $H_2O$ with 0.04% TFA B: acetonitrile with 0.02% TFA | 100% A hold 1 min, to 40% A in 4 min, to 15% A in 2.5 min, back to 100% A in 2 min, hold 0.5 min | 0.8 50 | 10 min |
| L | Agilent LC1200-MSD6110 UV 220 nm | XBridge C18 (5 μm 2*50 mm) | A: $H_2O$ with 0.04% TFA B: acetonitrile with 0.02% TFA | 90% A hold 0.8 min, to 20% A in 3.7 min, hold 3 min, back to 90% A in 2 min, hold 0.5 min | 0.8 50 | 10 min |
| M | Agilent LC1200-MSD6110 UV 220 nm | Waters XBridge ShieldRP18 column (5 μm, 2.1*50 mm) | A: $H_2O$ with 0.05% $NH_3 \cdot H_2O$ B: acetonitrile | 100% A hold 1 min, to 40% A in 4 min, to 5% A in 2.5 min, back to 100% A in 2 min, hold 0.5 min | 0.8 40 | 10 min |

Analytical SFC
General Procedure for SFC Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. Data acquisition was performed with appropriate software.

TABLE 2a

Analytical SFC Method Codes (Flow expressed in mL/min; column temperature (T) in ° C.; Run time in minutes, Backpressure (BPR) in bars. "ACN" means acetonitrile; "MeOH" means methanol; "EtOH" means ethanol; "DEA" means diethylamine; "HEP" means n-heptane. All other abbreviations used in the table below are as defined before.

| Method code | column | mobile phase | gradient | Flow Col T | Run time BPR |
|---|---|---|---|---|---|
| SFC1 | Brand Chiralpak ® AD-3 column (3.0 μm, 150 × 4.6 mm) | A: $CO_2$ B: EtOH + 0.05% DEA | 5% B to 40% in 5.5 min, 40% B hold 3 min, back to 5% B hold 1.5 min | 2.5 40 | 10 100 |
| SFC2 | Brand Chiralcel ® OJ-H column (5.0 μm, 150 × 4.6 mm) | A: $CO_2$ B: MeOH + 0.05% DEA | 5% B hold 0.5 min, 5% B to 40% in 3.5 min, 40% B hold 2.5 min, back to 5% B hold 1.5 min | 3.0 40 | 8 100 |
| SFC3 | Brand Chiralcel ® OJ-3 column (3.0 μm, 100 × 4.6 mm) | A: $CO_2$ B: EtOH + 0.05% DEA | 5% B to 40% in 4.5 min, 40% B hold 2.5 min, back to 5% B hold 1 min | 2.8 40 | 8 100 |
| SFC4 | Brand Chiralcel ® OJ-3 column (3.0 μm, 150 × 4.6 mm) | A: $CO_2$ B: EtOH + 0.05% DEA | 5% B to 40% in 5 min, 40% B to 5% in 0.5 min, 5% B hold 1.5 min | 2.5 35 | 7 100 |
| SFC5 | Brand Chiralpak ® AD-3 column (3.0 μm, 100 × 4.6 mm) | A: $CO_2$ B: EtOH + 0.05% DEA | 5% B to 40% in 4.5 min, 40% B hold 2.5 min, back to 5% B hold 1 min | 2.8 40 | 8 100 |
| SFC6 | Brand ChiralCel ® OD-3 column (3.0 μm, 150 × 4.6 mm) | A: $CO_2$ B: IPA + 0.1% Ethanolamine | 40% B hold 10 min | 2.5 40 | 10 100 |
| SFC7 | Brand Chiralcel ® OD-3 column (3.0 μm, 100 × 4.6 mm) | A: $CO_2$ B: EtOH + 0.05% DEA | 5% B to 40% in 4.5 min, 40% B hold 2.5 min, back to 5% B hold 1 min | 2.8 40 | 8 100 |
| SFC8 | Brand Chiralpak ® AS-3 column (3.0 μm, 150 × 4.6 mm) | A: $CO_2$ B: EtOH + 0.05% DEA | 5% B to 40% in 5 min, 40% B to 5% in 0.5 min, 5% B hold 1.5 min | 2.5 35 | 7 100 |
| SFC9 | Brand Chiralpak ® AD-3 column (3.0 μm, 50 × 3 mm) | A: $CO_2$ B: EtOH + 0.05% DEA | 5% B to 40% in 2.5 min, 40% B hold 0.35 min, 40% B to 5% in 0.15 min | 2.5 40 | 3 100 |
| SFC10 | Brand Chiralpak ® AD-3 column (3.0 μm, 150 × 4.6 mm) | A: $CO_2$ B: EtOH + 0.05% DEA | 5% B to 40% in 5.5 min, back to 5% B hold 1.5 min | 2.5 40 | 7 100 |
| SFC11 | Brand ChiralCel ® OD-3 column (3.0 μm, 150 × 4.6 mm) | A: $CO_2$ B: MeOH + 0.05% DEA | 5% B to 40% in 5 min, 40% B hold 2.5 min, back to 5% B hold 2.5 min | 2.5 35 | 10 100 |
| SFC12 | Brand ChiralCel ® OD-3 column (3.0 μm, 150 × 4.6 mm) | A: $CO_2$ B: MeOH + 0.05% DEA | 5% B to 40% in 5.5 min. back to5% B hold 1.5 min | 2.5 40 | 7 100 |
| SFC13 | Brand ChiralCel ® OD-3 column (3.0 μm, 150 × 4.6 mm) | A: $CO_2$ B: EtOH + 0.05% DEA | 5% B to 40% in 5 min, 40% B hold 2.5 min, back to 5% B hold 2.5 min | 2.5 35 | 10 100 |
| SFC14 | Brand Chiralpak ® AD-3 column (3.0 μm, 50 × 4.6 mm) | A: $CO_2$ B: MeOH + 0.05% DEA | 5% B to 40% in 2 min, 40% B hold 1.2 min, back to 5% B hold 0.8 min | 4 35 | 4 100 |
| SFC15 | Brand Chiralpak ® AD-3 column (3.0 μm, 150 × 4.6 mm) | A: $CO_2$ B: EtOH + 0.05% DEA | 40% B hold 4 min | 2.5 35 | 4 100 |
| SFC16 | Brand ChiralCel ® OJ-3 column (3.0 μm, 100 × 4.6 mm) | A: $CO_2$ B: MeOH + 0.05% DEA | 5% B to 40% in 4.5 min, back to 5% B hold 1 min | 2.8 40 | 5.5 100 |
| SFC17 | Brand ChiralCel ® OD-3 column (3.0 μm, 100 × 4.6 mm) | A: $CO_2$ B: MeOH + 0.05% DEA | 5% B to 40% in 4.5 min, 40% B hold 2.5 min, back to 5% B hold 1 min | 2.8 40 | 8 100 |
| SFC18 | Brand Chiralpak ® AD-3 column (3.0 μm, 50 × 4.6 mm) | A: $CO_2$ B: EtOH + 0.05% DEA | 40% B hold 3 min | 4 35 | 3 100 |
| SFC19 | Brand Chiralpak ® IC-3 column (3.0 μm, 100 × 4.6 mm) | A: $CO_2$ B: EtOH + 0.05% DEA | 5% B to 40% in 4 min, 40% B hold 2.5 min, back to 5% B hold 1.5 min | 2.8 35 | 8 100 |
| SFC20 | Brand Chiralpak ® AY-3 column (3.0 μm, 150 × 4.6 mm) | A: $CO_2$ B: EtOH + 0.05% DEA | 10% B hold 5 min | 2.5 40 | 5 100 |
| SFC21 | Brand Chiralpak ® IC-3 column (3.0 μm, 150 × 4.6 mm) | A: $CO_2$ B: IPA + 0.05% DEA | 40% B hold 9.5 min | 2.5 40 | 9.5 100 |

TABLE 2a-continued

Analytical SFC Method Codes (Flow expressed in mL/min; column temperature (T) in ° C.; Run time in minutes, Backpressure (BPR) in bars. "ACN" means acetonitrile; "MeOH" means methanol; "EtOH" means ethanol; "DEA" means diethylamine; "HEP" means n-heptane. All other abbreviations used in the table below are as defined before.

| Method code | column | mobile phase | gradient | Flow Col T | Run time BPR |
|---|---|---|---|---|---|
| SFC22 | Brand Chiralpak ® IC-3 column (3.0 μm, 150 × 4.6 mm) | A: $CO_2$ B: EtOH + 0.05% DEA | 40% B hold 12 min | 2.5 35 | 12 100 |
| SFC23 | Brand Chiralcel ® OD-3 column (3.0 μm, 150 × 4.6 mm) | A: $CO_2$ B: IPA + 0.05% DEA | 5% B to 40% in 5 min, 40% B hold 2.5 min, back to 5% B hold 2.5 min | 2.5 35 | 10 100 |
| SFC25 | Brand Chiralpak ® IC-3 column (3.0 μm, 100 × 4.6 mm) | A: $CO_2$ B: EtOH + 0.05% DEA | 5% B to 40% in 5 mi, 40% B hold 2.5 min, back to 5% B hold 2.5 min | 2.8 35 | 10 100 |
| SFC27 | Brand Chiralpak ® AD-3 column (3.0 μm, 150 × 4.6 mm) | A: $CO_2$ B: EtOH + 0.05% DEA | 40% B hold 6 min | 2.5 35 | 6 100 |
| SFC30 | Brand Chiralpak ® AD-3 column (3.0 μm, 50 × 4.6 mm) | A: $CO_2$ B: EtOH + 0.05% DEA | 5% B to 40% in 2 min, 40% B hold 1.2 min, back to 5% B hold 0.8 min | 4 35 | 4 100 |
| SFC33 | Brand Chiralpak ® IG-3 column (3.0 μm, 50 × 4.6 mm) | A: $CO_2$ B: MeOH + 0.05% DEA | 5% B to 40% in 2 min, 40% B hold 1.2 min, back to 5% B hold 0.8 min | 4 35 | 4 100 |
| SFC35 | Brand Chiralpak ® OD-3 column (3.0 μm, 50 × 4.6 mm) | A: $CO_2$ B: EtOH + 0.05% DEA | 5% B to 40% in 2 min, 40% B hold 1.2 min, back to 5% B hold 0.8 min | 4 35 | 4 100 |
| SFC39 | Brand Chiralpak ® (S,S)Whelk-01 100 × 4.6 mm I.D., 5.0 um | A: $CO_2$ B: EtOH + 0.05% DEA | 5% B to 40% in 5.5 min, back to 5% B hold 1.5 min | 2.5 40 | 7 100 |
| SFC41 | Brand Chiralpak ® AD-3 column (3.0 μm, 50 × 4.6 mm) | A: $CO_2$ B: EtOH + 0.05% DEA | 40% B hold 2 min | 4 35 | 2 100 |

BIOLOGICAL EXAMPLES

In vitro assays include assays that determine cell morphology, protein expression, and/or the cytotoxicity, enzyme inhibitory activity, and/or the subsequent functional consequences of treatment of cells with compounds of the invention. Alternate or additional in vitro assays may be used to quantitate the ability of the inhibitor to bind to protein or nucleic acid molecules within the cell.

Inhibitor binding may be measured by radiolabelling the inhibitor prior to binding, isolating the inhibitor/target molecule complex and determining the amount of radiolabel bound. Alternatively or additionally, inhibitor binding may be determined by running a competition experiment where new inhibitors are incubated with purified proteins or nucleic acids bound to known radioligands. Detailed conditions of exemplary systems for assaying a compound of Formula (I) of the present invention as MALT1 inhibitors are set forth in the Biological Examples below.

Such assays are exemplary and not intended to limit the scope of the invention. The skilled practitioner can appreciate that modifications can be made to conventional assays to develop equivalent or other assays that can be employed to comparably assess activity or otherwise characterize compounds and/or compositions as described herein.

The IC50 values reported in the tables below are subject to error margins associated with the assay used and the equipment.

In Vitro Assays

Biological Example 1

MALT1 Biochemical Protease Assay

MALT1 protease activity was assessed in an in vitro assay using a tetrapeptide as substrate and full-length MALT1 protein (Strep-MALT1(1-824)-His) purified from baculovirus-infected insect cells. The tetrapeptide LRSR is coupled to AMC (7-amino-4-methylcoumarin) and provides a quenched, fluorescent substrate for the MALT1 protease (SM Biochemicals). Cleavage of AMC from the Arginine residue results in an increase in coumarin fluorescence measured at 460 nm (excitation 355 nm). The final assay buffer consisted of 10 nM FL MALT1 protein, 200 μM Ac-LRSR-AMC, 50 mM Tris pH 7.5, 0.6 M Citrate, 1 mM DTT, 1 mM EDTA, 0.05% BSA and 1.5% DMSO. Test compounds were spotted at 50 nL in 100% DMSO per well of a black 384-Proxiplate (Perkin Elmer). Test compound concentrations ranged from 30 μM to 0.5 nM using 11 dilution steps (1:3). Background signal was measured from control wells containing assay buffer without enzyme which functions as low control (LC). High control (HC) values were generated using the reaction with enzyme but no compound treatment. Compounds were pre-incubated with MALT1 enzyme for 50 minutes at RT. Substrate was added subsequently and fluorescence was measured in Labsystems fluoroskan at excitation 355 nm and emission 460 nm to determine time 0. The reaction was subsequently incubated for 4 h at RT and fluorescence was measured. For $IC_{50}$ calculations, timepoint 0 was subtracted from the 4 h timepoint to correct for any potential autofluorescence of the compounds. The enzyme reaction was linear during the 4 h incubation period. Characterization of the substrate Ac-LRSR-AMC determined the Michaelis constant KM at 200 μM.

IC$_{50}$ values were calculated using the following formula (Z prime should be >0.5):

$LC$ = Median of the low control values
   = Low control: Reaction without enzyme
$HC$ = Median of the High control values
   = High Control: Reaction with enzyme % Effect = $100 - [(sample - LC)/(HC - LC) \times 100]$
% Control = $(sample/HC) \times 100$
% Controlmin = $(sample - LC)/(HC - LC) \times 100$ A best-fit curve was fitted by a minimum sum of squares method to the plot of % Controlmin vs. compound concentration. From this an IC$_{50}$ value (inhibitory concentration causing 50% inhibition) can be obtained. An estimate of the slope of the plot in terms of the Hill coefficient was also obtained.

IC$_{50}$ Calculation:

$$y = LB + \frac{UB - LB}{1 + 10^{(h(pConc - pIC50))}}$$

With y=estimated response
UB=upper bound
LB=lower bound
h=hill

Used in "Lexis Dose Response Curve Fitting" Version 1.0. Resultant data are shown in Table A.

TABLE A

| Cpd | MALT1_Biochemical activity (Ac-LRSR-amc) IC50 (μM) |
|---|---|
| Co. 7 | 0.17 |
| Co. 21 | 2.63 |
| Co. 19 | 2.75 |
| Co. 18 | 0.10 |
| Co. 2 | 2.40 |
| Co. 5 | 2.63 |
| Co. 6 | 23.99 |
| Co. 3 | >30.20 |
| Co. 10 | 3.02 |
| Co. 9 | 0.17 |
| Co. 20 | 4.17 |
| Co. 32 | 2.82 |
| Co. 11 | 1.74 |
| Co. 33 | 1.82 |
| Co. 29 | 0.98 |
| Co. 12 | 1.70 |
| Co. 28 | 0.60 |
| Co. 30 | 2.14 |
| Co. 47 | 8.71 |
| Co. 50 | 7.41 |
| Co. 31 | 1.23 |
| Co. 40 | 0.05 |
| Co. 49 | 0.62 |
| Co. 48 | >30.20 |
| Co. 13 | 0.85 |
| Co. 14 | 3.24 |
| Co. 36 | 0.23 |
| Co. 16 | 1.41 |
| Co. 37 | 1.48 |

TABLE A-continued

| Cpd | MALT1_Biochemical activity (Ac-LRSR-amc) IC50 (μM) |
|---|---|
| Co. 22 | 0.29 |
| Co. 25 | 0.24 |
| Co. 39 | 8.71 |
| Co. 24 | 4.57 |
| Co. 23 | 0.11 |
| Co. 27 | 2.10 |
| Co. 43 | 12.02 |
| Co. 42 | 0.54 |
| Co. 26 | 0.19 |
| Co. 46 | 0.58 |
| Co. 45 | 0.02 |
| Co. 53 | >30.20 |
| Co. 59 | 0.01 |
| Co. 61 | 0.04 |
| Co. 67 | 1.95 |
| Co. 56 | 2.51 |
| Co. 55 | 0.11 |
| Co. 52 | 1.02 |
| Co. 58 | 0.20 |
| Co. 68 | >30.20 |
| Co. 64 | 0.17 |
| Co. 62 | 0.22 |
| Co. 65 | 15.14 |
| Co. 105 | 0.04 |
| Co. 106 | 9.12 |
| Co. 101 | 0.21 |
| Co. 104 | 1.20 |
| Co. 100 | 0.03 |
| Co. 112 | 0.68 |
| Co. 103 | 0.04 |
| Co. 111 | 0.03 |
| Co. 71 | |
| Co. 70 | 0.05 |
| Co. 76 | 0.16 |
| Co. 97 | 0.08 |
| Co. 73 | 0.08 |
| Co. 98 | 5.89 |
| Co. 74 | 1.35 |
| Co. 77 | 8.32 |
| Co. 82 | 0.05 |
| Co. 91 | 0.02 |
| Co. 88 | 0.10 |
| Co. 89 | 0.11 |
| Co. 92 | 0.69 |
| Co. 85 | 0.03 |
| Co. 79 | 0.02 |
| Co. 83 | 0.35 |
| Co. 80 | 0.05 |
| Co. 115 | 0.06 |
| Co. 114 | 0.06 |
| Co. 124 | 0.08 |
| Co. 121 | 0.02 |
| Co. 119 | 0.02 |
| Co. 118 | 0.48 |
| Co. 127 | 0.03 |
| Co. 122 | 0.06 |
| Co. 125 | 1.45 |
| Co. 128 | 0.23 |
| Co. 129 | 1.38 |
| Co. 130 | 0.05 |
| Co. 131 | 1.02 |
| Co. 132 | 0.05 |
| Co. 133 | 0.55 |
| Co. 134 | 0.04 |
| Co. 135 | 2.00 |
| Co. 136 | 0.06 |
| Co. 137 | 0.04 |
| Co. 138 | 0.29 |
| Co. 139 | 0.02 |
| Co. 140 | ~0.62 |
| Co. 141 | 0.06 |
| Co. 142 | 0.79 |
| Co. 143 | 0.05 |
| Co. 144 | 0.04 |
| Co. 145 | 0.29 |
| Co. 146 | 0.27 |

TABLE A-continued

| Cpd | MALT1_Biochemical activity (Ac-LRSR-amc) IC50 (µM) |
|---|---|
| Co. 147 | 0.56 |
| Co. 148 | 0.03 |
| Co. 149 | 2.88 |
| Co. 150 | 0.10 |
| Co. 151 | >30 |
| Co. 152 | >30 |
| Co. 153 | 25 |
| Co. 154 | 2.69 |

Biological Example 2

Human IL6/IL10 Mesoscale Assay $NF_\kappa B$ signaling regulates the secretion of multiple cytokines, including IL6 and IL10. Secretion of the cytokines IL6 and IL10 by OCI-LY3 ABC-DLBCL cells was measured using a mesoscale assay. Inhibition of $NF_\kappa B$ signaling by MALT1 inhibitors results in a decrease of IL6/10 secretion.

OCI-LY3 cells were propagated in RPMI-1640 (Sigma Aldrich) supplemented with 10% fetal bovine serum (Hy-Clone), 1 mM sodium pyruvate (Invitrogen), 2 mM L-glutamine (Sigma Aldrich) and 1% PenStrep (Sigma Aldrich). Cell passage number should not exceed 30. Cells should be kept between 0.5-2.5 million cells per mL during culturing and cells should be supplemented every 2-3 days with fresh 50 µM beta-mercaptoethanol. No beta-mercaptoethanol was used during the mesoscale assay.

For the Mesoscale assay, 100,000 OCI-LY3 cells were seeded per well into black-colored 96-well plates with clear bottom (Corning #3904) and test compounds were added in 9 dilution steps (1:2) ranging from 15 µM to 58.6 nM (final DMSO concentration 0.3%). DMSO control wells were used to determine the maximum signal (High Control (HC)). Treatment with the BTK inhibitor RN486 in a dose range from 30 nM to 131 pM (9 dilutions of 1:2) served as a positive control for $NF_\kappa B$ pathway inhibition and was used to determine the maximum inhibition (Low Control (LC)). Compounds and cells were incubated for 24 h at 37° C. and 5% $CO_2$ (assay volume is 150 µL). After 24 h of incubation 50 µL of the supernatant was transferred to a MSD plate (V-Plex Proinflammation Panel 1 (human) kit, Mesoscale (MSD)) and incubated for 2 h with vigorous shaking (600 rpm) at room temperature. Following incubation, plates were washed 3× with PBS+0.05% Tween-20 and 25 µL detection antibody solution (IL6 & IL10 antibodies in diluent 3 (MSD)) was added per well followed by 2 h of incubation with vigorous shaking (600 rpm) at room temperature. After 3× washes with PBS+0.05% Tween-20, plates were incubated with 150 µL 2× Read Buffer T and read on SECTOR imager. Resultant data are shown in Table B.

TABLE B

| Cpd | Human IL10 Mesoscale assay (OCI-LY3) IC50 (µM) | Human IL6 Mesoscale assay (OCI-LY3) IC50 (µM) |
|---|---|---|
| Co. 7 | | |
| Co. 21 | | |
| Co. 19 | | |
| Co. 18 | 0.19 | 0.10 |
| Co. 2 | | |
| Co. 5 | | |
| Co. 6 | | |
| Co. 3 | | |
| Co. 10 | | |
| Co. 9 | 0.17 | 0.19 |
| Co. 20 | >3.02 | >3.02 |
| Co. 32 | | |
| Co. 11 | | |
| Co. 33 | | |
| Co. 29 | 1.78 | 1.82 |
| Co. 12 | | |
| Co. 28 | 1.10 | 1.95 |
| Co. 30 | | |
| Co. 47 | | |
| Co. 50 | | |
| Co. 31 | | |
| Co. 40 | 0.08 | 0.10 |
| Co. 49 | 1.70 | 2.34 |
| Co. 48 | | |
| Co. 13 | | |
| Co. 14 | 8.13 | 10.96 |
| Co. 36 | 0.14 | 0.22 |
| Co. 16 | | |
| Co. 37 | 1.66 | 2.75 |
| Co. 22 | 0.12 | 0.16 |
| Co. 25 | 0.18 | 0.22 |
| Co. 39 | 14.13 | >15.14 |
| Co. 24 | 3.98 | 5.62 |
| Co. 23 | 0.12 | 0.18 |
| Co. 27 | 1.60 | 2.80 |
| Co. 43 | >15 | >15 |
| Co. 42 | 0.98 | 1.10 |
| Co. 26 | 0.12 | 0.26 |
| Co. 46 | 0.85 | 0.75 |
| Co. 45 | 0.05 | 0.06 |
| Co. 53 | >15 | >15 |
| Co. 59 | 0.07 | 0.10 |
| Co. 61 | 0.09 | 0.13 |
| Co. 67 | 1.78 | 4.17 |
| Co. 56 | 9.33 | >15 |
| Co. 55 | 0.21 | 0.58 |
| Co. 52 | 0.71 | 1.45 |
| Co. 58 | 0.30 | 0.76 |
| Co. 68 | >15 | >15 |
| Co. 64 | 0.19 | 0.68 |
| Co. 62 | 0.45 | 0.75 |
| Co. 65 | 6.61 | >15 |
| Co. 105 | 0.06 | 0.12 |
| Co. 106 | 5.75 | 7.24 |
| Co. 101 | 0.15 | 0.24 |
| Co. 104 | 1.58 | 2.69 |
| Co. 100 | 0.06 | 0.09 |
| Co. 112 | 0.48 | 0.87 |
| Co. 103 | 0.10 | 0.15 |
| Co. 111 | 0.06 | 0.09 |
| Co. 71 | 0.15 | 0.32 |
| Co. 70 | 0.03 | 0.06 |
| Co. 76 | 0.11 | 0.13 |
| Co. 97 | 0.09 | 0.14 |
| Co. 73 | 0.06 | 0.11 |
| Co. 98 | 2.57 | 5.75 |
| Co. 74 | 0.65 | 0.93 |
| Co. 77 | 6.03 | 7.59 |
| Co. 82 | 0.09 | 0.12 |
| Co. 91 | 0.05 | 0.09 |
| Co. 88 | 0.17 | 0.29 |
| Co. 89 | 0.16 | 0.25 |
| Co. 92 | 1.51 | 3.02 |
| Co. 85 | 0.050 | 0.10 |
| Co. 79 | 0.06 | 0.11 |
| Co. 83 | 0.18 | 0.50 |
| Co. 80 | 0.09 | 0.15 |
| Co. 115 | 0.10 | 0.23 |
| Co. 114 | 0.17 | 0.40 |

TABLE B-continued

| Cpd | Human IL10 Mesoscale assay (OCI-LY3) IC50 (μM) | Human IL6 Mesoscale assay (OCI-LY3) IC50 (μM) |
|---|---|---|
| Co. 124 | 0.11 | 0.15 |
| Co. 121 | 0.04 | 0.06 |
| Co. 119 | 0.05 | 0.09 |
| Co. 118 | 1.51 | 2.75 |
| Co. 127 | 0.04 | 0.06 |
| Co. 122 | 0.13 | 0.14 |
| Co. 125 | 2.24 | 4.57 |
| Co. 128 | 0.21 | 0.46 |
| Co. 145 | 0.17 | 0.26 |
| Co. 149 | 1.32 | 1.91 |
| Co. 144 | ~0.045 | 0.06 |
| Co. 143 | 0.05 | 0.08 |
| Co. 142 | 0.78 | 1.20 |
| Co. 147 | 0.66 | 0.85 |
| Co. 141 | 0.14 | 0.13 |
| Co. 140 | 0.47 | 0.54 |
| Co. 139 | 0.07 | ~0.10 |
| Co. 138 | 0.38 | 0.60 |
| Co. 137 | 0.08 | 0.08 |
| Co. 146 | 0.16 | 0.32 |
| Co. 136 | 0.03 | 0.06 |
| Co. 135 | | |
| Co. 134 | 0.08 | 0.08 |
| Co. 133 | 0.31 | 0.93 |
| Co. 148 | ~0.06 | ~0.06 |
| Co. 150 | 0.14 | 0.15 |
| Co. 132 | 0.06 | 0.15 |
| Co. 131 | ~0.89 | 2.34 |
| Co. 130 | ~0.11 | 0.19 |
| Co. 129 | 1.02 | 2.29 |
| Co. 151 | >15 | >15 |
| Co. 152 | >15 | >15 |
| Co. 153 | 8.71 | 11.8 |
| Co. 154 | 0.71 | 1.10 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I)

Formula (I)

wherein
$R^x$ represents hydrogen, $C_{1-4}$alkyl, or $C_{3-6}$cycloalkyl;
$R^y$ represents hydrogen, $C_{1-4}$alkyl, or $C_{3-6}$cycloalkyl; and
$R^z$ represents hydrogen;
or
$R^x$ and $R^y$ are taken together to form a bivalent radical —$R^x$—$R^y$— wherein —$R^x$—$R^y$— represents —$(CH_2)_n$— or —$CH_2$—O—$(CH_2)_2$—; wherein n represents 2, 3, 4 or 5; and
$R^z$ represents hydrogen;

or
$R^y$ represents hydrogen, $C_{1-4}$alkyl, or $C_{3-6}$cycloalkyl;
$R^x$ and $R^z$ are taken together to form together with the carbon atom to which they are attached a $C_{3-6}$cycloalkyl;
$R^1$ is selected from the group consisting of hydrogen, —$OR^5$, $C_{1-4}$alkyl, $C_{2-4}$alkenyl, halo, —CN, $C_{3-6}$cycloalkyl, $Het^a$, —C(=O)—OH, —C(=O)—O—$C_{1-4}$ alkyl, —$NR^{6a}R^{7a}$ and —C(=O)—$NR^{6b}R^{7b}$;
$R^{2a}$ and $R^{2b}$ are each independently selected from the group consisting of hydrogen, —O—$C_{1-4}$alkyl, halo, —$NR^{6c}R^{7c}$, $C_{3-6}$cycloalkyl, $C_{1-4}$alkyl, and $C_{1-4}$alkyl substituted with 1, 2 or 3 halo atoms;
$X^1$ represents N or $CR^a$;
$X^2$ represents N or $CR^b$;
such that only one of $X^1$ and $X^2$ are N in any instance;
$R^3$ represents hydrogen, $C_{1-4}$alkyl or —O—$C_{1-4}$alkyl;
$R^4$ represents halo, cyano or trifluoromethyl;
$R^5$ is selected from the group consisting of hydrogen, $C_{1-4}$alkyl, $C_{3-6}$cycloalkyl, $Het^b$, and $C_{1-4}$alkyl substituted with one or two substituents each independently selected from the group consisting of —OH, halo, —C(=O)—$NR^8R^9$, —C(=O)—OH, —C(=O)—O—$C_{1-4}$alkyl, $C_{3-6}$cycloalkyl and phenyl;
$R^{6a}$, $R^{6b}$, $R^{6c}$, $R^{7a}$, $R^{7b}$, $R^{7c}$, $R^8$ and $R^9$ each independently are selected from the group consisting of hydrogen and $C_{1-4}$alkyl;
$Het^a$ represents a monocyclic 4- to 7-membered non-aromatic heterocyclyl containing one or two heteroatoms selected from nitrogen, oxygen and sulfur;
$Het^b$ represents a monocyclic 4- to 7-membered non-aromatic heterocyclyl containing one or two heteroatoms selected from nitrogen, oxygen and sulfur;
$R^a$ represents $C_{1-4}$alkyl or —O—$C_{1-4}$alkyl, each optionally substituted with one, two or three halo substituents;
or
$R^a$ represents 2H-1,2,3-triazol-2-yl or $C_{3-6}$cycloalkyl; each optionally substituted on one or two carbon atoms with a substituent each independently selected from the group consisting of $C_{1-4}$alkyl, and $C_{1-4}$alkyl substituted with one —OH;
$R^b$ represents hydrogen;
or an enantiomer, diastereomer, or pharmaceutically acceptable salt form thereof.

2. The compound of claim 1 wherein
$R^x$ represents hydrogen, $C_{1-4}$alkyl, or $C_{3-6}$cycloalkyl;
$R^y$ represents hydrogen, or $C_{1-4}$alkyl;
$R^z$ represents hydrogen;
$R^{2a}$ and $R^{2b}$ are each independently selected from the group consisting of hydrogen, —$NR^{6c}R^{7c}$, $C_{3-6}$cycloalkyl, $C_{1-4}$alkyl, and $C_{1-4}$alkyl substituted with 1, 2 or 3 halo atoms;
such that only one of $X^1$ and $X^2$ are N in any instance;
$R^5$ is selected from the group consisting of hydrogen, $C_{1-4}$alkyl, $C_{3-6}$cycloalkyl, $Het^b$, and $C_{1-4}$alkyl substituted with one or two substituents each independently selected from the group consisting of —C(=O)—$NR^8R^9$, —C(=O)—OH, —C(=O)—O—$C_{1-4}$alkyl, $C_{3-6}$cycloalkyl and phenyl;
$R^a$ represents —O—$C_{1-4}$alkyl optionally substituted with one, two or three halo substituents;
or
$R^a$ represents 2H-1,2,3-triazol-2-yl or $C_{3-6}$cycloalkyl; each optionally substituted on one carbon atom with a substituent each independently selected from the group consisting of $C_{1-4}$alkyl, and $C_{1-4}$alkyl substituted with one —OH.

3. The compound of claim 1 wherein
$R^x$ represents $C_{1-4}$alkyl;
$R^y$ represents $C_{1-4}$alkyl;
$R^z$ represents hydrogen;
$R^1$ is selected from the group consisting of —$OR^5$, halo, and —CN;
$R^{2a}$ represents hydrogen;
$R^{2b}$ is selected from the group consisting of hydrogen, —$NR^{6c}R^{7c}$, and $C_{1-4}$alkyl;
$X^1$ represents $CR^a$;
$X^2$ represents N;
$R^3$ represents hydrogen;
$R^4$ represents trifluoromethyl;
$R^5$ represents $C_{1-4}$alkyl;
$R^{6c}$ and $R^{7c}$ represent hydrogen; and
$R^a$ represents 2H-1,2,3-triazol-2-yl.

4. The compound of claim 1 wherein
$R^x$ represents hydrogen, $C_{1-4}$alkyl, or $C_{3-6}$cycloalkyl;
$R^y$ represents hydrogen, $C_{1-4}$alkyl, or $C_{3-6}$cycloalkyl; and
$R^z$ represents hydrogen.

5. The compound of claim 1 wherein
$X^1$ represents $CR^a$;
$X^2$ represents N.

6. The compound of claim 5 wherein $R^a$ represents 2H-1,2,3-triazol-2-yl.

7. A pharmaceutical composition comprising a compound of claim 1 and at least one of a pharmaceutically acceptable carrier, a pharmaceutically acceptable excipient, and a pharmaceutically acceptable diluent.

8. A method of treating a disease, syndrome, condition, or disorder, wherein said disease, syndrome, condition, or disorder is affected by the inhibition of MALT1, comprising administering to a subject in need thereof a therapeutically effective amount of the compound of claim 1.

9. The method of claim 8 wherein said disease, syndrome, condition, or disorder is selected from the group consisting of diffuse large B-cell lymphoma (DLBCL), mantle cell lymphoma (MCL), follicular lymphoma (FL), mucosa-associated lymphoid tissue (MALT) lymphoma, rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

* * * * *